US011662349B2

(12) United States Patent
Caron et al.

(10) Patent No.: US 11,662,349 B2
(45) Date of Patent: May 30, 2023

(54) CARBOHYDRATE SENSORS

(71) Applicant: Commonwealth Scientific and Industrial Research Organisation, Acton (AU)

(72) Inventors: Karine Caron, Acton (AU); Stephen Charles Trowell, Oxley (AU)

(73) Assignee: Commonwealth Scientific and Industrial Research Organisation, Acton (AU)

( * ) Notice: Subject to any disclaimer, the term of this patent is extended or adjusted under 35 U.S.C. 154(b) by 496 days.

(21) Appl. No.: 16/636,613

(22) PCT Filed: Aug. 7, 2018

(86) PCT No.: PCT/AU2018/050824
§ 371 (c)(1),
(2) Date: Feb. 4, 2020

(87) PCT Pub. No.: WO2019/028504
PCT Pub. Date: Feb. 14, 2019

(65) Prior Publication Data
US 2020/0319195 A1 Oct. 8, 2020

(30) Foreign Application Priority Data
Aug. 8, 2017 (AU) ................................ 2017903148

(51) Int. Cl.
| G01N 21/76 | (2006.01) |
| C12N 9/02 | (2006.01) |
| C12N 15/70 | (2006.01) |
| G01N 33/66 | (2006.01) |
| C07K 14/195 | (2006.01) |
| G01N 33/543 | (2006.01) |

(52) U.S. Cl.
CPC ........... *G01N 33/66* (2013.01); *C07K 14/195* (2013.01); *C12N 9/0069* (2013.01); *C12N 15/70* (2013.01); *C12Y 113/12007* (2013.01); *G01N 21/763* (2013.01); *G01N 33/54306* (2013.01); *C07K 2319/60* (2013.01); *C07K 2319/80* (2013.01); *G01N 2333/90241* (2013.01); *G01N 2400/00* (2013.01)

(58) Field of Classification Search
CPC ............. G01N 33/54306; G01N 33/66; G01N 21/763; C12Y 113/12007
See application file for complete search history.

(56) References Cited

U.S. PATENT DOCUMENTS

| 4,891,120 A | 1/1990 | Sethi et al. |
| 4,908,112 A | 3/1990 | Pace |
| 5,126,022 A | 6/1992 | Soane et al. |
| 5,196,524 A | 3/1993 | Gustafson et al. |
| 5,219,737 A | 6/1993 | Kajiyama et al. |
| 5,229,285 A | 7/1993 | Kajiyama et al. |
| 5,571,410 A | 11/1996 | Swedberg et al. |
| 5,580,523 A | 12/1996 | Bard |
| 5,670,356 A | 9/1997 | Sherf et al. |
| 5,750,015 A | 5/1998 | Soane et al. |
| 5,843,746 A | 12/1998 | Tatsumi et al. |
| 5,858,195 A | 1/1999 | Ramsey |
| 5,885,470 A | 3/1999 | Parce et al. |
| 6,228,604 B1 | 5/2001 | Escher et al. |
| 6,793,753 B2 | 9/2004 | Unger et al. |
| 6,949,377 B2 | 9/2005 | Ho |
| 10,473,665 B2 | 11/2019 | Trowell et al. |
| 11,385,234 B2* | 7/2022 | Trowell ............... G01N 33/542 |
| 2002/0123059 A1 | 9/2002 | Ho |
| 2003/0049799 A1* | 3/2003 | Schwartz ............. C12N 15/635 530/391.1 |
| 2003/0170915 A1 | 9/2003 | Singh et al. |
| 2007/0065818 A1 | 3/2007 | Foti et al. |
| 2008/0085552 A1 | 4/2008 | Larson et al. |
| 2010/0129820 A1 | 5/2010 | Kool et al. |
| 2011/0037077 A1 | 2/2011 | Ichimura et al. |
| 2011/0071045 A1 | 3/2011 | Patterson |
| 2012/0064587 A1* | 3/2012 | Papoutsakis ... C12Y 201/01013 435/140 |
| 2012/0077210 A1 | 3/2012 | Trowell et al. |
| 2012/0276548 A1 | 11/2012 | Schmidt |
| 2014/0001122 A1 | 1/2014 | Bhattacharyya et al. |
| 2014/0273038 A1 | 9/2014 | Thompson |
| 2015/0219654 A1 | 8/2015 | Naleway et al. |
| 2020/0103412 A1* | 4/2020 | Trowell ............... G01N 33/542 |

(Continued)

FOREIGN PATENT DOCUMENTS

| AU | 2015243093 | 11/2015 |
| EP | 2221606 | 8/2010 |

(Continued)

OTHER PUBLICATIONS

Majumdar D. S. et al: "Single-molecule FRET reveals sugar-induced conformational dynamics in LacY", Proceedings of the National Academy of Sciences, vol. 104, No. 31, Jul. 31, 2007 (Jul. 31, 2007), pp. 12640-12645.
Hartman Andrea H. et al: "Abstract", Applied and Environmental Microbiology, vol. 77, No. 2, Jan. 15, 2011 (Jan. 15, 2011), pp. 471-478.
18843350.2, Extended European Search Report, dated Jul. 8, 2021, 1-18.
2018315053, Examination Report No. 1, dated Jul. 26, 2021, 1-4.
Chabala, John C., (1995) "Solid-phase combinatorial chemistry and novel tagging methods for identifying leads", Current Opinion in Biotechnology, 6:632-639.
Walsh, Marie K. and Swaisgood, Harold E., (1996) "Investigating the use of the chymosin-sensitive sequence of K-casein as a cleavable linker site in fusion proteins", Jounral of Biotechnology, 45:235-241.

(Continued)

Primary Examiner — Maryam Monshipouri
(74) Attorney, Agent, or Firm — Shweta Chandra; Bozicevic, Field & Francis LLP

(57) ABSTRACT

The present invention relates to sensors and methods for detecting carbohydrates, such as lactose, in a sample. The sensors and methods may also be used to determine the amount of carbohydrate in the sample.

20 Claims, 6 Drawing Sheets

Figure 1:
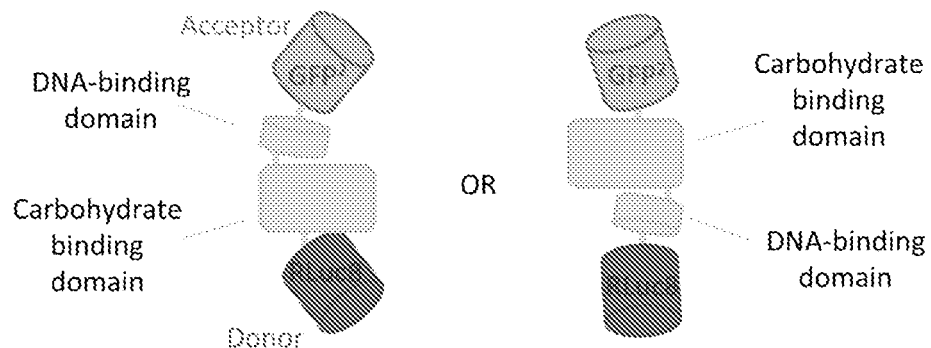

Specification includes a Sequence Listing.

(56) References Cited

U.S. PATENT DOCUMENTS

2020/0319195 A1  10/2020  Caron et al.
2021/0018497 A1  1/2021  Caron et al.

FOREIGN PATENT DOCUMENTS

| WO | WO1999049019 | 9/1999 |
|---|---|---|
| WO | WO2000024878 | 9/1999 |
| WO | 0003727 | 1/2000 |
| WO | WO2001001025 | 1/2001 |
| WO | WO200146694 | 6/2001 |
| WO | WO2001046691 | 6/2001 |
| WO | WO2002010433 | 2/2002 |
| WO | WO2003015923 | 2/2003 |
| WO | WO2003035229 | 5/2003 |
| WO | WO2006105616 | 10/2006 |
| WO | WO2007019634 | 2/2007 |
| WO | WO2007033385 | 3/2007 |
| WO | 2007059297 | 5/2007 |
| WO | WO2007092909 | 8/2007 |
| WO | WO 2008/083976 | 7/2008 |
| WO | WO2008083976 | 7/2008 |
| WO | WO2008131008 | 10/2008 |
| WO | WO2009018467 | 2/2009 |
| WO | WO2009020479 | 2/2009 |
| WO | WO2009044088 | 4/2009 |
| WO | WO2010052939 | 5/2010 |
| WO | WO2010085844 | 8/2010 |
| WO | WO2011091037 | 7/2011 |
| WO | WO2012074693 | 6/2012 |
| WO | WO2013155553 | 10/2013 |
| WO | WO2014207515 | 12/2014 |
| WO | WO2015007317 | 1/2015 |
| WO | WO2015153151 | 10/2015 |
| WO | WO2016131833 | 8/2016 |
| WO | 2017087912 | 5/2017 |

OTHER PUBLICATIONS

Zauner, Thomas, et al., (2011) "Highly Adaptable and Sensitive Protease Assay Based on Fluorescence Resonance Energy Transfer", Anal. Chem., 83:7356-7363.

Andreani, et al., (2016) "Characterisation of the thermostable protease AprX in strains of Pseudomonas fluorescens and impact on the shelf-life of dairy products: preliminary results", Italian Journal of Food Safety, vol. 5, No. 6175239-244.

Chandrapala, J., et al., (2012) "The effect of ultrasound on casein micelle integrity", Journal of Dairy Science., vol. 95, pp. 6882-6890.

Chyan et al., (2017) "Electronic and Steric Optimization of Fluorogenic Probes for Biomolecular Imaging", The Journal of Organic Chemistry, 82:4297-4304.

Chyan W. and Raines R.T., (2018) "Enzyme-Activated Fluorogenic Probes for Live-Cell and in Vivo Imaging", ACS Chemical Biology, 13:1810-1823.

Extended European Search Report, 18847441.5, dated Apr. 21, 2021, 1-9.

Gaucher, et al., (2011) "Proteolysis of casein micelles by Pseudomonas fluorescens CNRZ 798 contributes to the destabilisation of UHT milk during its storage", Dairy Science & Technology, vol. 91, No. 4, pp. 413-429.

Grimm et al., (2013) "The Chemistry of Small-Molecule Fluorogenic Probes", Progress in Molecular Biology and Translational Science, 113:1-34.

Hakamata et al., (2014) "Multicolor Imaging of Endoplasmic Reticulum-Located Esterase As a Prodrug Activation Enzyme", ACS Medicinal Chemistry Letters, 5:321-325.

Jensen, et al., (2015) "The function of the milk-clotting enzymes bovine and camel chymosin studied by a fluorescence resonance energy transfer Assay", Journal of Dairy Science, vol. 98, No. 5, pp. 2853-2860.

Mateos, et al. (2015) "Proteolysis of mild proteins by AprX, an extracellular protease identified in Pseudomonas LBSA1 isolated from bulk raw milk, and implications for the stability of UHT milk", International Dairy Journal, vol. 49, pp. 78-88.

Rauh, V.M. et al., (2014) "The determination of plasmin and plasminogen-derived activity in turbid samples from various dairy products using an optimised spectrophotometric method", International Dairy Journal., Vo. 38, pp. 74-80.

Rollema, H.S., et al., (1981) "On the determination, purification and characterization of the alkaline proteinase from bovine milk", Netherlands Milk and Dairy Journal., vol. 35, pp. 396-399.

Starovoitova, et al., (2006) "A Comparative Study of Functional Properties of Calf Chymosin and Its Recombinant Forms", Biochemistry, Vo. 71, No. 3, pp. 320-324.

Vavrusova, M., et al., (2015) "Characterisation of a whey protein hydrolysate as antioxidant", International Dairy Journal, vol. 47, pp. 86-93.

Wilkins, T.D., et al., (1992) "Isolation of recombinant proteins from milk", Journal of Cellular Biochemistry., vol. 49, pp. 333-338.

Wong, M.H-Y., et al., (2016) "IncHI2 plasmids are the key vectors responsible for oqxAB transmission among *Salmonella* species", Antimicrobial Agents and Chemotherapy, vol. 60, pp. 6911-6915.

Xia Z. and Rao J., (2009) "Biosensing and imaging based on bioluminescence resonance energy transfer", Current Opinion in Biotechnology, 20:37-44.

Yamakawa et al., (2002) "Rapid Homogeneous Immunoassay of Peptides Based on Bioluminescence Resonance Energy Transfer from Firefly Luciferase", Journal of Bioscience and Bioengineering, 93(6):537-542.

Bagshaw, Clive R (2001) "ATP analogues at a Glance", J. of Cell Science, 114:459-460.

Benslimane et al., (2009) "Variation with season and lactation of plasmin and plasminogen concentrations in Montbeliard cows' milk", Journal of Dairy Research, 57:423-435.

Button et al., (2011) "Improved Shelf Life Estimation of UHT Milk by Prediction of Proteolysis", Journal of Food Quality,34:229-235.

Datta and Deeth (2001) "Age Gelation of UHT Milk a Review", Transactions of the Institution of Chemical Engineers (Part C), 79:197-210.

Dupont et al. (2007) "ELISA To Detect Proteolysis of Ultrahigh-Temperature Milk upon Storage", Journal of Agriculture and Food Chemistry. 55: 6857-6862.

Dupont et al., (1997) "Differential titration of plasmin and plasminogen in milk using sandwich ELISA with monoclonal antibodies", Journal of Dairy Research., 64:77-86.

Eigel, W.N. (1977) "Effect of Bovine Plasmin on $\alpha_s$1-B and K-A Caseins" loumal of dairy science., 60:1399-1403.

Glusman et al. (2001) "The Complete Human Olfactory Subgenome" Genome Res. 11:685-702.

Guarise et al., (2006), "Gold nanoparticles-based protease assay", PNAS, 103:3978-3982.

Jones et al., (1997) "Quenched BODIPY Dye-Labeled Casein Substrates for the Assay of Protease Activity by Direct Fluorescence Measurement", Analytical Biochemistry, 251:144-152.

Kim and Kim (2012) "Analysis of Protease Activity Using Quantum Dots and Resonance Energy Transfer", Theranostics, 2:127-138.

Koka and Weimar (2000) "Isolation and characterization of a protease from Pseudomonas fluorescens RO98", Journal of Applied Microbiology., 89:280-288.

McSweeney et al., (1993) "Proteolytic specificity of plasmin on bovine $\alpha_s$1-Casein", Food Biotechnology., 7:143-158.

Mercier (1973) "Structure primaire de la caseine kB bovine", European Journal of Biochemistry, 35:222-235.

Saint-Denis et al., (2001) "Enzymatic assays for native plasmin, plasminogen and plasminogen activators in bovine milk", J. Dairy Res., 68:437-449.

Sapsford et al., (2006) "Materials for Fluorescence Resonance Energy Transfer Analysis: Beyond Traditional Donor-Acceptor Combinations**", Angew. Chemie. Int. Ed., 45:4562-4588.

Bajar et al., (2016) "A guide to fluorescent protection FRET pairs", Sensors, vol. 16, No. 1488, pp. 1-24.

(56) References Cited

OTHER PUBLICATIONS

Dacres et al., (2012) "Comparison of enhanced bioluminescence energy transfer donors for protease biosensors", Analytical Biochemistry, vol. 424, pp. 206-210.
Martins et al., (2015) "Milk-deteriorating exoenzymes from Pseudomonas fluorescens 041 isolated from refrigerated raw milk", Brazilian Journal of Microbiology, vol. 46, No. 1, pp. 207-217.
Zhang and Lv, (2014) "Purification and properties of heat-stable extracellular protease from pseudomonadas fluorescens BJ-10", J. Food Sci Technol, vol. 51, No. 6, pp. 1185-1190.
Caron et al., (2018) "Highly sensitive and selective biosensor for a disaccharide based on an AraC-like transcriptional regulator transduced with bioluminescence resonance energy transfer.", Analytical Chemistry, 12986-12993.
Deuschle et al., (2005) "Construction and optimization of a family of genetically encoded metabolite sensors by semirational protein engineering.", Protein Science, 14:2304-2314.
Le et al., (2014) "Real-time, continuous detection of maltose using bioluminescence resonance energy transfer (BRET) on a microfluidic system.", Biosensors and Bioelectronics, 62:177-181.
San Martin et al., (2013) "A genetically encoded FRET lactate sensor and its use to detect the Warburg effect in single cancer cells ", PLoS ONE, 8(2):e57712.
San Martin et al., (2014) "Imaging mitochondrial flux in single cells with a FRET sensor for pyruvate.", PLoS One, (9)1:e85780.
Wu et al., (2017) "Design and application of a lactulose biosensor.", Scientific Reports, 7(45994):1-8.
Berg et al., (2002) "Prokaryotic DNA-binding proteins bind specifically to regulatory sites in operons", Summary=Biochemistry, 1-3, XP55790699.
Brown and Shaw (2008) "Positive Transcription Control: The Glucose Effect", Nature Education, 1-3, XP55790707.
Newman et al., (2019) "Structures of the transcriptional regulator BgaR, a lactose sensor", Acta Cryst, 75(7):639-646.
PCT/AU2018/050824, Written Opinion of the International Preliminary Examining Authority, dated Jul. 3, 2019, 1-8.
Peroza et al., (2015) "A genetically encoded Forster resonance energy transfer sensor for monitoring in vivo trehalose-6-phosphate dynamics", Analytical Biochemistry, 474:1-7.
Salahpour et al., (2012) "BRET biosensors to study GPCR biology, pharmacology, and signal transduction", Frontiers in Endocrinology, 3(105):1-10.
18843350.2, Partial European Search Report, dated Apr. 14, 2021, 1-17.
Aloni et al. (2006) "Ancient genomic architecture for mammalian olfactory receptor clusters" Genome Biol. 7:R88.
Azuma et al., (1992) "Plasmin cleavage of human beta-casein", Biosci Biotechnol Biochem., 56(7)1140-1141.
Buck and Axel Cell (1991) "A novel multigene family may encode odorant receptors: A molecular basis for odor recognition" 65:175-187.
Dacres et al. (2009) "Direct comparison of bioluminescence-based resonance energy transfer methods for monitoring of proteolytic cleavage" Anal. Biochem. 385(2):194-202.
Dacres et al. (2009) "Direct comparison of fluorescence- and bioluminescence-based resonance energy transfer methods for real-time monitoring of thrombin-catalysed proteolytic cleavage" Biosensors and Bioelectronics 24(5):1164-1170.
Dacres et al. (2010) "Experimental Determination of the Förster Distance for Two Commonly Used Bioluminescent Resonance Energy Transfer Pairs" Anal. Chem. 82:432-435.
Dacres et al. (2011) "Greatly enhanced detection of a volatile ligand at femtomolar levels using bioluminescence resonance energy transfer (BRET)" Biosens. and Bioelectron. 29:119-124.
Dacres et al. (2012) "Effect of enhanced Renilla luciferase and fluorescent protein variants on the Förster distance of Bioluminescence resonance energy transfer (BRET)" Biochem. Biophys. Res. Commun. 425(3):625-629.
Day et al. (2004) "Evolution of beetle bioluminescence: the origin of beetle luciferin" Luminescence 19:8-20.

De et al. (2007) "An Improved Bioluminescence Resonance Energy Transfer Strategy for Imaging Intracellular Events in Single Cells and Living Subjects" Cancer Res. 67:7175-7183.
De et al. (2009) "BRET3: a red-shifted bioluminescence resonance energy transfer (BRET)-based integrated platform for imaging protein-protein interactions from single live cells and living animals" FASEB Journal 23(8):2702-2709.
De Wet et al. (1987) "Firefly luciferase gene: structure and expression in mammalian cells" Mol. Cell. Biol. 2987:725-737.
Doty Richard L. (2012) "Gustation" WOREs Cognitive Science 3:29-46.
Esch et al. (2011) "The Role of Body-on-a-Chip Devices in Drug and Toxicity Studies" Annu. Rev. Biomed. Eng. 13:55-72.
Fang et al. (2005) "Determination of Ribonuclease H Surface Enzyme Kinetics by Surface Plasmon Resonance Imaging and Surface Plasmon Fluorescence Spectroscopy" Anal. Chem. 77(20):6528-6534.
Fehr et al. (2002) "Visualization of maltose uptake in living yeast cells by fluorescent nanosensors" PNAS 99(15):9846-9851.
Feldmesser et al. (2006) "Widespread ectopic expression of olfactory receptor genes" BMC Genomics 7:121.
Fredriksson and Schioth (2005) "The Repertoire of G-Protein-Coupled Receptors in Fully Sequenced Genomes" Mol. Pharmacol. 67(5):1414-1425.
Frishman and Argos (1997) "Seventy-Five Percent Accuracy in Protein Secondary Structure Prediction" Proteins 27:329-335.
Fuchs et al. (2001) "The human olfactory subgenome: from sequence to structure and evolution" Human Genetics 108:1-13.
Gill and von Hippel (1989) "Calculation of protein extinction coefficients from amino acid sequence data" Anal. Biochem. 182(2):319-326.
Glusman et al. (2000) "The olfactory receptor gene superfamily: data mining classification and nomenclature" Mammalian Genome 11(11):1016-1023.
Glusman et al. (2000) "Sequence Structure and Evolution of a Complete Human Olfactory Receptor Gene Cluster" Genomics 63(2):227-245.
Godin et al. (2008) "Microfluidics and photonics for Bio-System-on-a-Chip: A review of advancements in technology towards a microfluidic flow cytometry chip" J. Biophotonics 1(5):355-376.
Greer and Szalay (2002) "Imaging of light emission from the expression of luciferases in living cells and organisms: a review" Luminescence 17:43-74.
Hall et al. (1997) "Two Modes of Ligand Binding in Maltose-binding Protein of *Escherichia coli* Functional Significance In Active Transport" J. Biol. Chem. 272:17615-17622.
Hastings (1996) "Chemistries and colors of bioluminescent reactions: a review" Gene 173:5-11.
Hofmann and Stoffel (1993) "MF C-35 A Database of Membrane Spanning Protein Segments" Biol. Chem. 374:166.
Holden and Cremer (2005) "Microfluidic Tools For Studying The Specific Binding Adsorption And Displacement Of Proteins At Interfaces" Annu. Rev. Phys. Chem. 56:369-387.
Hushpulian et al. (2007) "Biocatalytic properties of recombinant tobacco peroxidase in chemiluminescent reaction" Biotransformation 25:2-4.
Inouye and Shimomura (1997) "The Use of Renilla Luciferase Oplophorus Luciferase and Apoaequorin as Bioluminescent Reporter Protein in the Presence of Coelenterazine Analogues as Substrate" Biochem. J. 233(2):349-353.
Ismail et al., (2010) "Invited review: Plasmin protease in milk: current knowledge and relevance to dairy industry.", J Dairy Sci., 93(11)4999-5009.
Klein et al. (1984) "Prediction of protein function from sequence properties: Discriminant analysis of a data base" Biochim. Biophys. Acta 787(3):221-226.
Kocan et al. (2008) "Demonstration of Improvements to the Bioluminescence Resonance Energy Transfer (BRET) Technology for the Monitoring of G Protein-Coupled Receptors in Live Cells" Journal of Biomolecular Screening 13(9):888-898.

(56) References Cited

OTHER PUBLICATIONS

Kocan et al (2011) "Enhanced BRET technology for the monitoring of agonist-induced and agonist-independent interactions between GPCRs and β-arrestins" Frontiers in Endocrinology Cellular Endocrinology 1(12):1-9.
Lander et al. (2001) "Initial sequencing and analysis of the human genome" Nature 409:860-921.
Li and Lin (2008) "Applications of microfluidic systems in environmental analysis" Anal Bioanl. Chem. 393(2):555-567.
Loening et al. (2006) "Consensus guided mutagenesis of Renilla luciferase yields enhanced stability and light output" Protein Eng. Des. Sel. 19(9):391-400.
Loening et al. (2007) "Red-shifted Renilla reniformis luciferase variants for imaging in living subjects." Nature Methods 4(8):641-643.
Lorenz et al. (1991) "Isolation and expression of a cDNA encoding Renilla reniformis luciferase." Proc. Natl. Acad. Sci. USA 88(10):4438-4442.
Mark et al. (2010) "Microfluidic lab-on-a-chip platforms: requirements characteristics and applications" Chem. Soc. Rev. 39:1153-1182.
Medintz and Deschamps (2006) "Maltose-binding protein: a versatile platform for prototyping biosensing" Curr. Opin. Biotech. 17:17-27.
Mohammed and Desmulliez (2011) "Lab-on-a-chip based immunosensor principles and technologies for the detection of cardiac biomarkers: a review" Lab. Chip. 11:569-595.
Morin and Hastings (1971) "Energy transfer in a bioluminescent system" J. Cell. Physiol. 77(3):313-318.
Niimura and Nei (2003) "Evolution of olfactory receptor genes in the human genome" Proc. Natl. Acad. Sci. USA, 100(21):12235-12240.
Noh et al. (2011) "Biosensors in Microfluidic Chips" Top. Curr. Chem. 304:117-152.
Olender et al. (2004) "The olfactory receptor universe—from whole genome analysis to structure and evolution" Genet. Mol. Res. 3(4):545-553.
Olender et al. (2004) "The canine olfactory subgenome" Genomics. 83(3):361-372.
Park et al. (2009) "Detection of conformationally changed MBP using intramolecular FRET" Biochem. Biophys. Res. Commun. 388(3):560-564.
Persson and Argos (1994) "Prediction of Transmembrane Segments in Proteins Utilising Multiple Sequence Alignments" J. Mol. Biol. 237(2):182-192.
Pfleger and Eidne (2006) "Illuminating insights into protein-protein interactions using bioluminescence resonance energy transfer (BRET)" Nature Methods 3:165-174.
Pilpel and Lancet (1999) "The variable and conserved interfaces of modeled olfactory receptor proteins" Protein Science 8(5):969-977.
Remedios and Moens (1995) "Fluorescence Resonance Energy Transfer Spectroscopy Is a Reliable "Ruler" for Measuring Structural Changes in Proteins: Dispelling the Problem of the Unknown Orientation Factor" J. Structural Biol. 115(2): 175-185.
Robertson (1998) "Two Large Families of Chemoreceptor Genes in the Nematodes Caenorhabditis elegans and Caenorhabditis briggsae Reveal Extensive Gene Duplication Diversification Movement and Intron Loss" Genome Research 8:449-463.
Robertson (2001) "Updating the str and srj (stl) Families of Chemoreceptors in Caenorhabditis Nematodes Reveals Frequent Gene Movement Within and Between Chromosomes" Chem Senses 26(2):151-159.
Sengupta et al. (1996) "odr-10 Encodes a Seven Transmembrane Domain Olfactory Receptor Required for Responses to the Odorant Diacetyl" Cell 84(6):899-909.
Sharff et al. (1992) "Crystallographic evidence of a large ligand-induced hinge-twist motion between the two domains of the maltodextrin binding protein involved in active transport and chemotaxis" Biochemistry 31(44):10657-10663.

Sharff et al. (1993) "Refined 1.8-.ANG. structure reveals the mode of binding of .beta.-cyclodextrin to the maltodextrin binding protein" Biochemistry 32(40):10553-10559.
Sharon et al. (1998) "Genome Dynamics Evolution and Protein Modeling in the Olfactory Receptor Gene Superfamily" Ann. N Y Acad. Sci. 855:182-193.
Spurlino et al. (1991) "The 2.3-A resolution structure of the maltose- or maltodextrin-binding protein a primary receptor of bacterial active transport and chemotaxis." J. Biol. Chem. 266: 5202-5219.
Sun and Zhu, (2000) "Receptor-mediated endocytosis of uPA and its inhibitor complex and its application", Chemistry of Life, 20(4):151-153.
Theberge et al. (2010) "Microdroplets in Microfluidics: An Evolving Platform for Discoveries in Chemistry and Biology" Angew. Chem Int. Ed 49(34):5846-5868.
Tsien (1998) "The Green Fluorescent Protein" Ann. Rev. Biochem, 67:509-544.
Unger et al. (2000) "Monolithic Microfabricated Valves and Pumps by Multilayer Soft Lithography" Science 288(5463):113-116.
Verhaegen and Christopoulos (2002) "Recombinant Gaussia Luciferase. Overexpression Purification and Analytical Application of a Bioluminescent Reporter for DNA Hybridization" Anal. Chem. 74(17):4378-4385.
Viviani (2002) "The origin diversity and structure function relationships of insect luciferases" Cell. Mol. Life Sci. 59(11):1833-1850.
Von Heijne (1992) "Membrane protein structure prediction : Hydrophobicity analysis and the positive-inside rule" J. Mol. Biol. 225(2):487-494.
Xu et al. (1999) "A bioluminescence resonance energy transfer (BRET) system: Application to interacting circadian clock proteins" Proc. Natl. Acad. Sci. USA. 96:151-156.
Yeo et al. (2011) "Microfluidic Devices for Bioapplications" Small 7:12-48.
Young et al. (2002) "Different evolutionary processes shaped the mouse and human olfactory receptor gene families" J. Human Mol. Genet. 11(5):535-546.
Zhang and Firestein (2002) "The olfactory receptor gene superfamily of the mouse" Nat. Neurosci. 5:124-133.
Zozulya et al. (2001) "The human olfactory receptor repertoire" Genome Biol. 2(6):0018.1-0018.12.
Ansari et al., (2012) "Cost effective surface functionalization of silver nanoparticles for high yield immobilization of Aspergillus oryzae _-galactosidase and its application in lactose hydrolysis", Process Biochemistry. 47:2427-2433.
Chávez-Servín et al., (2004) "Analysis of mono- and disaccharides in milk-based formulae by high-performance liquid chromatography with refractive index detection", J. of Chromatography A, 1043:211-215.
Euber and Brunner (1979) "Determination of Lactose in Milk Products by High-Performance Liquid Chromatography", J. Dairy Sci., 62:685-690.
Franco et al., (2006) "Functional Domains of the Bacillus subtilis Transcription Factor AraR and Identification of Amino Acids Important for Nucleoprotein Complex Assembly and Effector Binding", Journal of Bacteriology, 188(8):3024-3036.
Franco et al., (2007) "Probing key DNA contacts in AraR-mediated transcriptional repression of the Bacillus subtilis arabinose regulon", Nucleic Acids Research, 35(14):4755-4766.
Kleyn (1985)., Symposium: Role and Significance of Enzymes in Dairy Processing, J. Dairy. Sci. 68:2791-2798.
Kolkof et al., (1992) "Lac repressor with the helix-turn-helix motif of lambda cro binds to lac operator", The EMBO Journal, 1(1):3031-3038.
Marconi et al., (2004) "Heat-treated milk differentiation by a sensitive lactulose assay", Food Chemistry, 84:447-450.
Montilla et al., (1996) "Correlation between Lactulose and Furosine in UHT-Heated Milk", Journal of Food Protection, 59:1061-1064.
Morales et al., (2000) "Characterization of industrial processed milk by analysis of heat-induced changes", International Journal of Food Science and Technology, 35:193-200.

(56) References Cited

OTHER PUBLICATIONS

Rigali et al., (2002) "Subdivision of the Helix-Turn-Helix GntR Family of Bacterial Regulators in the FadR, HutC, MocR, and YtrA Subfamilies*", Journal of Biological Chemistry, 277(15):12507-12515.
Rigali et al., (2004) "Extending the classification of bacterial transcription factors beyond the helix-turn-helix motif as an alternative approach to discover new cis/trans relationships", Nucleic Acid Research, 32(11):3418-3426.
Silveira et al., (2015) "Simultaneous Determination of Lactulose and Lactose in Conserved Milk by HPLC-RID", Journal of Chemistry, 1-7.
Southgate (1969)., "Determination of Carbohydrates in Foods 11. *-Unavailable carbohydrates", J. Sci. Food. Agric., 20:331-335.
Tsenkova et al., (1999) "Near-Infrared Spectroscopy for Dairy Management: Measurement of Unhomogenized Milk Composition", J. Dairy Sci., 82:2344-2351.
Woollard and Indyk et al., (1996) "High Performance Liquid Chromatographic Analysis of Lactose-Hydrolysed Milk", Food Chemistry, 57(4):575-580.
Xinmin et al., (2008) "Determination of glucosamine and lactose in milk-based formulae by high-performance liquid chromatography", J. Food Compos. Anal., 21:255-258.
Zhang et al., (2012) "Ribulokinase and Transcriptional Regulation of Arabinose Metabolism in Clostridium acetobutylicum", J. Bacteriol, 194:1055-1064.

* cited by examiner

LacB1   LacB2   LacB3   LacB4

FIGURE 8

A – LacB1 calibration curve for lactose with galactose and glucose in PBS

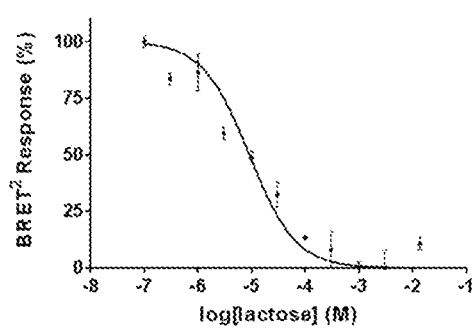

B – LacF1 calibration curve for lactose with galactose and glucose in PBS

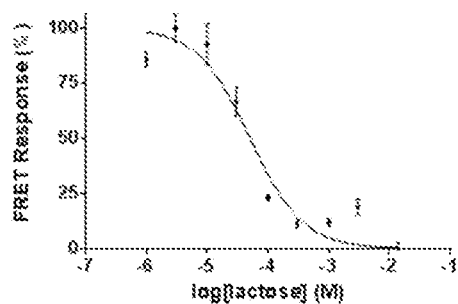

C – LacB1 calibration curve for lactose with galactose and glucose in dialysed milk

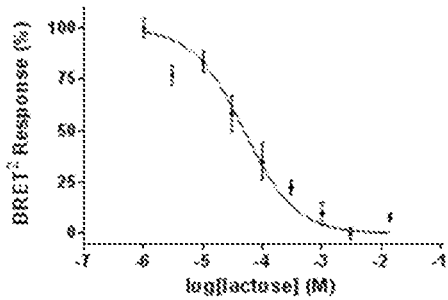

D – LacF1 calibration curve for lactose with galactose and glucose in dialysed milk

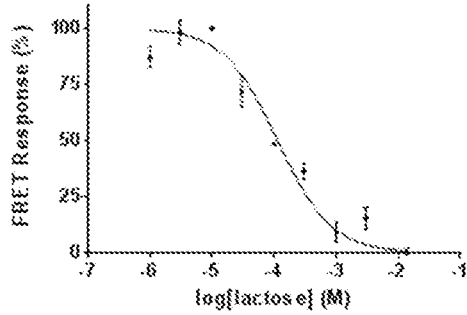

E – LacB1 calibration curve for lactose with galactose and glucose in dialysed milk (duplicate)

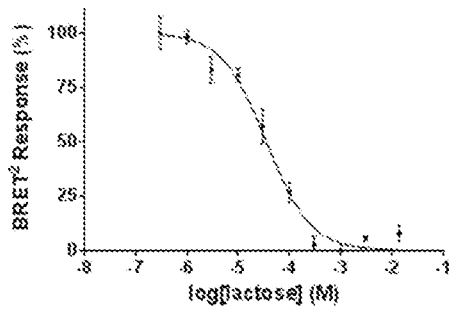

CARBOHYDRATE SENSORS

FIELD OF THE INVENTION

The present invention relates to sensors and methods for detecting carbohydrates, such as lactose, in a sample. The sensors and methods may also be used to determine the amount of carbohydrate in the sample.

BACKGROUND OF THE INVENTION

Assays for detecting carbohydrates, including sugars and sugar derivatives, are widely used in the food and medical industries. Of particular interest to the food industry are assays for detecting carbohydrates, such as lactose, in dairy products.

Currently, routine lactose analysis in dairy products is achieved with high-performance liquid chromatography (HPLC). This method yields accurate, sensitive and selective measurement of lactose but the analysis requires transport of samples to a laboratory facility with expensive apparatus operated by highly trained staff (Euber and Brunner, 1979; Indyk et al., 1996; Xinmin et al., 2008; Erich et al., 2012). Other technologies for detecting/measuring lactose use enzymatic cascades to indirectly measure the concentration of lactose in solution. These assays normally proceed through enzymatic hydrolysis of lactose to galactose and glucose with β-galactosidase, followed by oxidation of either of the monosaccharides (Kleyn, 1985; Ansari et al., 2012; Jia et al., 2014). Quantification of lactose is achieved through the measurement of the stoichiometric bi-products of the oxidation step, namely NADH or $H_2O_2$, using spectrophotometric, amperometric or colorimetric methods. These assays require a number of reagents and numerous steps making them too lengthy and cumbersome for routine use in a processing plant. They have inherently low selectivity. Alternatively, high levels of lactose (e.g. 3.9-4.8% (w/v)) may be measured by near infrared spectroscopy (Tsenkova et al., 1999). However, this method is inaccurate for measuring lower levels of lactose, such as below 1% (w/v) lactose, and requires expensive equipment.

Accordingly, there is a need for further methods of detecting and quantifying the amount of carbohydrates in a sample, preferably methods that can be performed in real time, with increased sensitivity and/or without having to send samples offsite for analysis.

SUMMARY OF THE INVENTION

The present inventors have identified sensors that can be used to detect carbohydrates in a sample. The present inventors have also identified an improved method of detecting the presence of carbohydrates in a sample using these sensors. In some embodiments, these sensors and methods can be used measure the concentration of carbohydrate in a sample. They have also identified an improved method of detecting lactose of a dairy product using these sensors. In some embodiments, the sensors and methods can be used to measure the lactose content of a dairy product. In some embodiments, the sensors and methods can be used to classify dairy products based on their lactose content.

In one aspect, there is provided a sensor molecule for detecting a carbohydrate, the sensor comprising:
i) a carbohydrate binding domain of a helix-turn-helix transcription factor, or a variant of the carbohydrate binding domain;
ii) a chemiluminescent donor domain; and
iii) an acceptor domain;
wherein the spatial location and/or dipole orientation of the chemiluminescent donor domain relative to the acceptor domain is altered when the carbohydrate binds to the carbohydrate binding domain.

In some embodiments, the helix-turn-helix transcription factor is a bacterial helix-turn-helix transcription factor, or a variant thereof. In some embodiments, the bacterial helix-turn-helix transcription factor is a $G_{NT}R$ transcription factor, or a variant thereof. In some embodiments, the bacterial helix-turn-helix transcription factor or variant thereof, has an amino acid sequence which is at least 60% identical to that provided in SEQ ID NO: 1. In another embodiment, the binding domain has an amino acid sequence which is at least 60% identical to that provided in SEQ ID NO: 9.

In a further embodiment, the binding domain has an amino acid sequence which is at least 30% identical to that provided in any one or more of SEQ ID NO's 9 and 56 to 74.

In some embodiments, the carbohydrate is a sugar or sugar derivative. In some embodiments, the carbohydrate is a sugar. In some embodiments, the sugar is a disaccharide. In preferred embodiments, the disaccharide is lactose. In another embodiment, the disaccharide is lactulose. In some embodiments, the carbohydrate is a sugar derivative. In some embodiments, the sugar derivative is selected from the group consisting of amino sugars, acidic sugars, deoxy sugars, sugar alcohols, glycosylamines and sugar phosphates.

In some embodiments, the chemiluminescent donor domain is a bioluminescent protein. In some embodiments, the bioluminescent protein is a luciferase, a β-galactosidase, a lactamase, a horseradish peroxidase, an alkaline phosphatase, a β-glucuronidase or a β-glucosidase. In some embodiments, the bioluminescent protein is a luciferase. In some embodiments, the luciferase is a *Renilla* luciferase, a Firefly luciferase, a Coelenterate luciferase, a North American glow worm luciferase, a click beetle luciferase, a railroad worm luciferase, a bacterial luciferase, a *Gaussia* luciferase, Aequorin, an *Arachnocampa* luciferase, an *Oplophorus gracilirostris* luciferase or a biologically active variant or fragment of any one, or chimera of two or more, thereof.

In some embodiments, the chemiluminescent donor domain is capable of modifying a substrate. In some embodiments, the substrate is luciferin, calcium, coelenterazine, furimazine or a derivative, analogue or stabilised derivative of coelenterazine, luciferin or furimazine.

In some embodiments, the acceptor domain is a fluorescent acceptor domain. In some embodiments, the fluorescent acceptor domain is selected from the group consisting of green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, tdimer2(12), mRFP1, pocilloporin, *Renilla* GFP, Monster GFP, paGFP, Kaede protein, tdTomato, mCherry, TagRFP, TurBoFB and a Phycobiliprotein, and a biologically active variant or fragment of any one thereof.

In some embodiments, the separation and relative orientation of the chemiluminescent donor domain and the acceptor domain, in the presence and/or the absence of carbohydrate, is within ±50% of the Förster distance. In some embodiments, the Förster distance of the chemiluminescent donor domain and the acceptor domain is at least 5.6 nm. In some embodiments, the Förster distance of the chemiluminescent donor domain and the acceptor domain is between about 7 nm and about 11 nm.

In another aspect there is also provided a method of detecting a carbohydrate in a sample, the method comprising i) contacting a sample with the sensor molecule defined herein; and ii) determining if the spatial location and/or dipole orientation of the chemiluminescent donor domain relative to the acceptor domain has been altered in the presence of the sample, wherein an alteration of the spatial location and/or dipole orientation of the chemiluminescent donor domain relative to the acceptor domain indicates the carbohydrate is present in the sample.

In some embodiments, the method further comprises determining the concentration of the carbohydrate in the sample. In some embodiments, the method is performed on a microfluidic device. In some embodiments, the sample is air, liquid, biological material or soil. In some embodiments, the sample comprises a dairy product. In preferred embodiments, the sample is milk.

In yet another aspect there is provided a sensor molecule for detecting lactose comprising a bacterial BgaR transcription factor or variant thereof, covalently joined to a resonance energy transfer donor domain and a resonance energy transfer acceptor domain, wherein the spatial location and/or dipole orientation of the donor domain relative to the acceptor domain is altered when lactose binds to the transcription factor.

Binding of lactose to the sensor molecule produces a change in resonance energy transfer (RET), for example a change in BRET or a change in FRET. Accordingly, the sensors can be used to detect the presence of lactose in a sample and/or to determine the concentration of lactose in a sample.

In yet another aspect there is provided a sensor molecule for detecting lactulose comprising a bacterial BgaR transcription factor or variant thereof, covalently joined to a resonance energy transfer donor domain and a resonance energy transfer acceptor domain, wherein the spatial location and/or dipole orientation of the donor domain relative to the acceptor domain is altered when lactulose binds to the transcription factor. Binding of lactulose to the sensor molecule produces a change in resonance energy transfer (RET), for example a change in BRET or a change in FRET. Accordingly, the sensors can be used to detect the presence of lactulose in a sample and/or to determine the concentration of lactose in a sample.

In some embodiments, the transcription factor or variant thereof, has an amino acid sequence which is at least 60%, 70%, 80%, 85%, 90%, 95%, 98%, 99% or 100% identical to that provided in SEQ ID NO: 1. In some embodiments, the transcription factor or variant thereof, has the amino acid sequence provided in SEQ ID NO: 1.

The sensor molecule can be a BRET or FRET based sensor. In some embodiments, the sensor molecule is a BRET based sensor such that binding of lactose to the sensor molecule produces a change in BRET. Accordingly, in some embodiments, the resonance energy transfer donor domain is a bioluminescent protein. Suitable bioluminescent proteins include a luciferase, a β-galactosidase, a lactamase, a horseradish peroxidase, an alkaline phosphatase, a β-glucuronidase or a β-glucosidase. In some embodiments, the bioluminescent protein is a luciferase. In some embodiments, luciferase is a *Renilla* luciferase, a Firefly luciferase, a Coelenterate luciferase, a North American glow worm luciferase, a click beetle luciferase, a railroad worm luciferase, a bacterial luciferase, a *Gaussia* luciferase, Aequorin, an *Arachnocampa* luciferase, an *Oplophorus gracilirostris* luciferase or a biologically active variant or fragment of any one, or chimera of two or more, thereof. In some embodiments, the donor domain is capable of modifying a substrate. Suitable substrates include luciferin, calcium, coelenterazine, furimazine or a derivative, analogue or stabilised derivative of coelenterazine, luciferin or furimazine.

In some embodiments, the sensor molecule is a FRET based sensor such that binding of lactose to the sensor molecule produces a change in FRET. Accordingly, in some embodiments, the resonance energy transfer donor domain is a fluorescent protein. In some embodiments, the fluorescent protein is selected from the group consisting of green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, tdimer2(12), mRFP1, pocilloporin, *Renilla* GFP, Monster GFP, paGFP, Kaede protein, tdTomato, mCherry, TagRFP, TurBoFB and a Phycobiliprotein, and a biologically active variant or fragment of any one thereof.

For both BRET and FRET based lactose sensors, the resonance energy transfer acceptor domain can be a fluorescent acceptor domain. In some embodiments, the fluorescent acceptor domain is a fluorescent protein. In some embodiments, the fluorescent acceptor domain is selected from the group consisting of green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, tdimer2(12), mRFP1, pocilloporin, *Renilla* GFP, Monster GFP, paGFP, Kaede protein, tdTomato, mCherry, TagRFP, TurBoFB and a Phycobiliprotein, and a biologically active variant or fragment of any one thereof.

In some embodiments, the resonance energy transfer donor domain is *Renilla* luciferase or a variant thereof and the resonance energy transfer acceptor domain is GFP or a variant thereof. In some embodiments, the present disclosure provides a sensor molecule having at least 60%, 70%, 80%, 85%, 90%, 95%, 98%, 99% or 100% sequence identity to a polypeptide sequence selected from the group consisting of SEQ ID NO: 15, SEQ ID NO: 16, SEQ ID NO: 17 and SEQ ID NO: 18. In these embodiments, binding of lactose to the sensor molecule produces a change in BRET.

In some embodiments, the resonance energy transfer donor domain is CFP or a variant thereof and the resonance energy transfer acceptor domain is YFP or a variant thereof. In some embodiments, the present disclosure provides a sensor molecule having at least 60%, 70%, 80%, 85%, 90%, 95%, 98%, 99% or 100% sequence identity to the polypeptide provided in SEQ ID NO: 23. In these embodiments, binding of lactose to the sensor molecule produces a change in FRET.

In some embodiments, the separation and relative orientation of the donor domain and the acceptor domain, in the presence and/or the absence of lactose, is within ±50% of the Förster distance. In some embodiments, the Förster distance of the donor domain and the acceptor domain is at least 5.6 nm. In some embodiments, the Förster distance of the donor domain and the acceptor domain is between about 5.6 nm and about 10 nm.

In another aspect there is also provided a method of detecting lactose in a sample, the method comprising
  i) contacting a sample with the sensor molecule for detecting lactose as defined herein; and
  ii) determining if the spatial location and/or dipole orientation of the donor domain relative to the acceptor domain has been altered in the presence of the sample,
  wherein an alteration of the spatial location and/or dipole orientation of the donor domain relative to the acceptor domain indicates that lactose is present in the sample. In some embodiments, the method further comprises determining the concentration of lactose in the sample. In some embodiments, the method is performed on a microfluidic device. In some embodiments, the sample is air, liquid, biological material or soil. In some embodiments, the sample comprises a dairy product. In some embodiments, the dairy product is milk.

In another aspect there is also provided a method of detecting lactulose in a sample, the method comprising
  i) contacting a sample with the sensor molecule as defined herein; and
  ii) determining if the spatial location and/or dipole orientation of the donor domain relative to the acceptor domain has been altered in the presence of the sample,
  wherein an alteration of the spatial location and/or dipole orientation of the donor domain relative to the acceptor domain indicates that lactulose is present in the sample. In some embodiments, the method further comprises determining the concentration of lactulose in the sample. In some embodiments, the method is performed on a microfluidic device. In some embodiments, the sample is air, liquid, biological material or soil. In some embodiments, the sample comprises a dairy product. In some embodiments, the dairy product is milk.

In some embodiments, the sensor molecule is a single polypeptide. In some embodiments, the chemiluminescent donor domain is at the N-terminus and the acceptor domain is at the C-terminus. In alternative embodiments, the acceptor domain is at the N-terminus and the chemiluminescent donor domain is at the C-terminus. In some embodiments, the resonance energy transfer donor domain is at the N-terminus and the resonance energy transfer acceptor domain is at the C-terminus. In alternative embodiments, the resonance energy transfer acceptor domain is at the N-terminus and the resonance energy transfer donor domain is at the C-terminus.

In some embodiments, the sensor molecule comprises at least one peptide linker.

In another aspect there is also provided a polynucleotide encoding a sensor molecule as defined herein. In another aspect there is also provided a vector comprising a polynucleotide encoding a sensor molecule as defined herein. In yet another aspect there is also provided a host cell comprising the polynucleotide and/or the vector defined herein. In yet another aspect there is also provided a process for producing a sensor molecule, the process comprising cultivating a host cell or a vector defined herein under conditions which allow expression of the polynucleotide encoding the polypeptide, and recovering the expressed polypeptide.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1—Schematic representation of an embodiment of the present disclosure. The illustrated sensor molecule, LacB1, comprises the BgaR transcriptional factor flanked with $GFP^2$ and RLuc8 at the N- and C-terminus, respectively.

Figure 2:
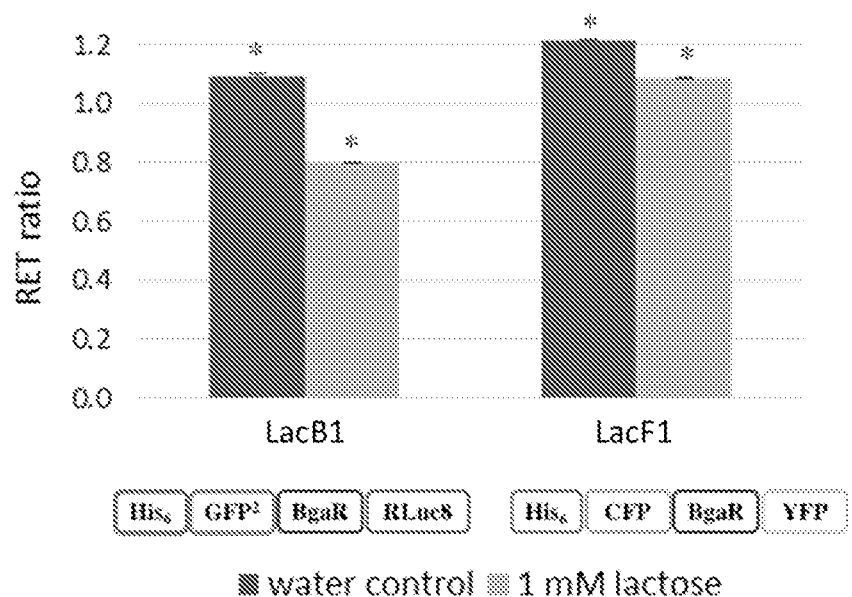

FIG. 2—RET ratios (means±SD, n=3) for 1 μM of LacB1 and LacF1 sensors in water (dark grey bars) or 1 mM lactose (light grey bars). $BRET^2$ scans were recorded following the addition of 17 μM coelenterazine 400a substrate. *P<0.0001.

Figure 3:
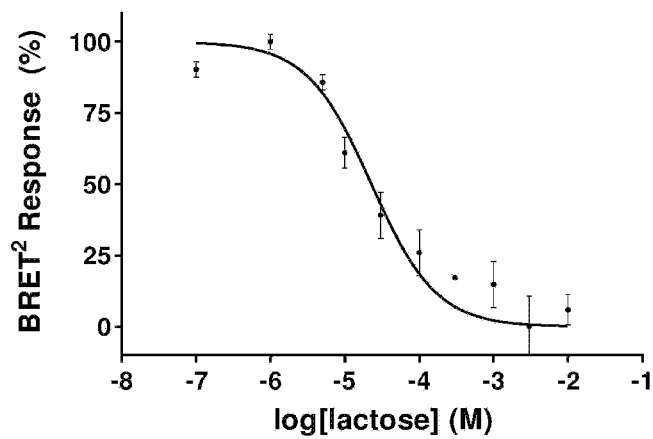

FIG. 3—$BRET^2$ response of LacB1 to 0.000034 w/v %-0.34% w/v of lactose.

Figure 4:
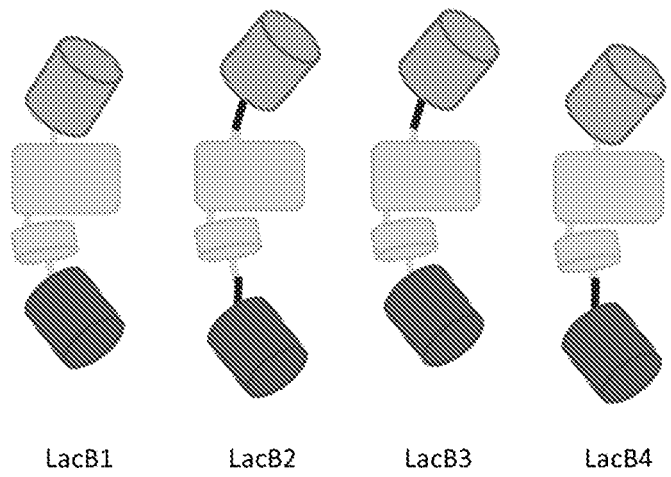

FIG. 4—Schematic representation of an embodiment of the present disclosure. LacB1 comprises the BgaR transcriptional factor (light grey) flanked with $GFP^2$ (mid grey) and RLuc8 (dark grey) at the N- and C-terminus, respectively. LacB2 comprises LacB1 with the amino acid linker -GGTGGG- inserted between BgaR and $GFP^2$ and BgaR and RLuc8. LacB3 comprises LacB1 with the linker -GGTGGG- inserted between BgaR and $GFP^2$. LacB4 comprises LacB1 with the linker -GGTGGG- inserted between BgaR and RLuc8. The location of the linker is represented by the black section joining BgaR and $GFP^2$ and/or BgaR and RLuc8.

Figure 5:
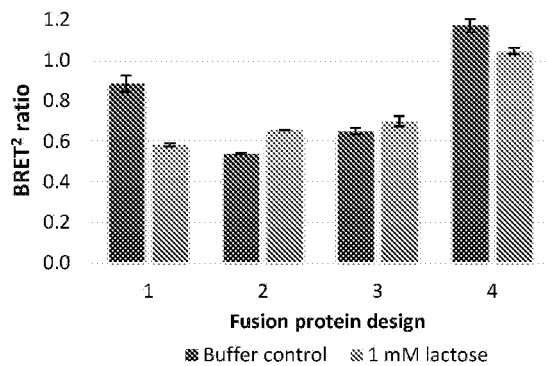

FIG. 5—$BRET^2$ response of LacB1 (1), LacB2 (2), LacB3 (3) and LacB4 (4) to the presence of 1 mM lactose.

Figure 6:
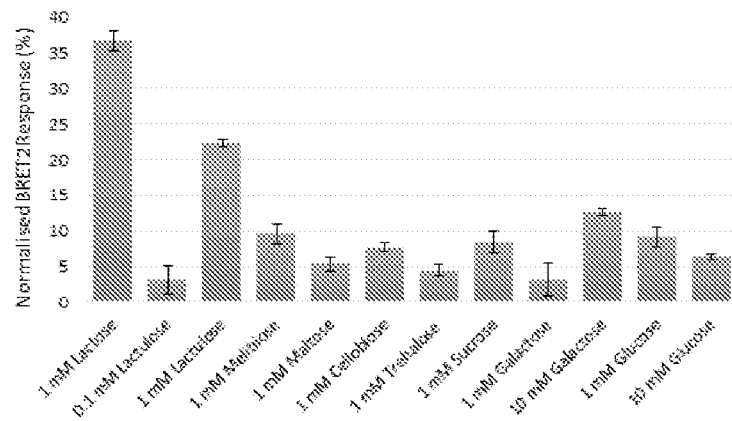

FIG. 6—Changes in $BRET^2$ ratio of the LacB1 sensor in the presence of the disaccharides, lactose, maltose and lactulose and the monosaccharides, galactose and glucose. $BRET^2$ ratios (mean±SD, n=3) were recorded following addition of 17 μM coelenterazine 400a to 1 μM of LacB1 after incubation with the specified sugars for 30 minutes at 30° C. $BRET^2$ ratios were normalized to the water response and expressed as percentages of $BRET^2$ change.

Figure 7:
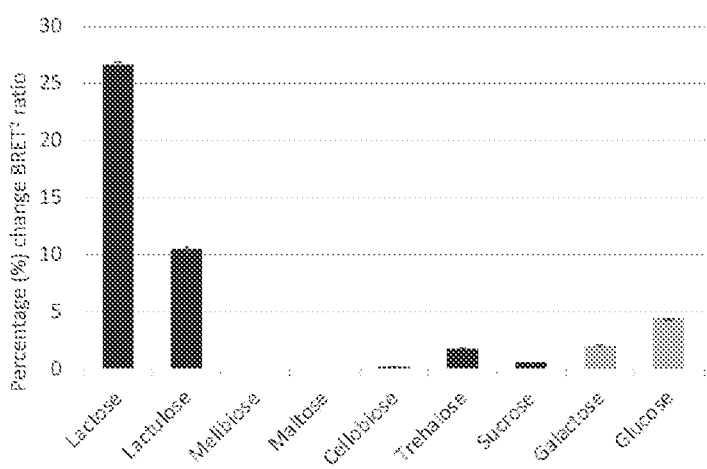

FIG. 7—Response of LacB1 to a range of di- and monosaccharides, all at 1 mM concentrations. $BRET^2$ ratios (mean±SD, n=3) were recorded following addition of 17 μM coelenterazine 400a to 1 μM of LacB1 after incubation with the specified sugars for 5 minutes at 30° C. $BRET^2$ ratios were normalized to the water response and expressed as percentages of $BRET^2$ change.

FIG. 8—Detection of lactose by the LacB1 sensor in the presence of galactose and glucose in PBS (A) and galactose and glucose in dialysed milk (C, E) (mean±S.D., n=3). Detection of lactose by the LacF1 sensor in the presence of galactose and glucose in PBS (B) and galactose and glucose in dialysed milk (D) (mean±S.D., n=3).

Figure 9:
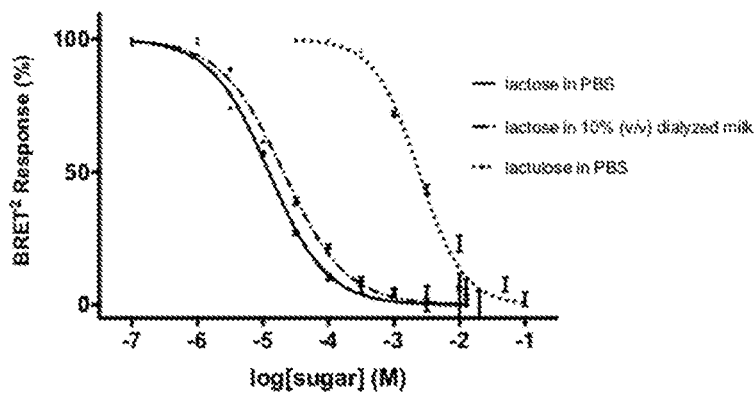

FIG. 9—Detection of lactose and lactulose by the LacB1 sensor in PBS and 10% (v/v) dialysed whole milk supplemented with lactose, galactose and glucose. Solid line: lactose concentration dependence of LacB1 in PBS. $EC_{50}=12\pm1$ µM, LOD=1 µM. Dashed line: lactose concentration dependence of LacB1 in 10% dialysed whole milk with lactose, galactose and glucose added such that ([lactose]+[galactose+glucose]/2=13.9 mM). $EC_{50}=21\pm2$ µM, LOD=0.2 µM. Dotted line: lactulose concentration dependence of LacB1 in PBS. $EC_{50}=2.4\pm0.2$ mM, LOD=0.1 mM.

Figure 10:
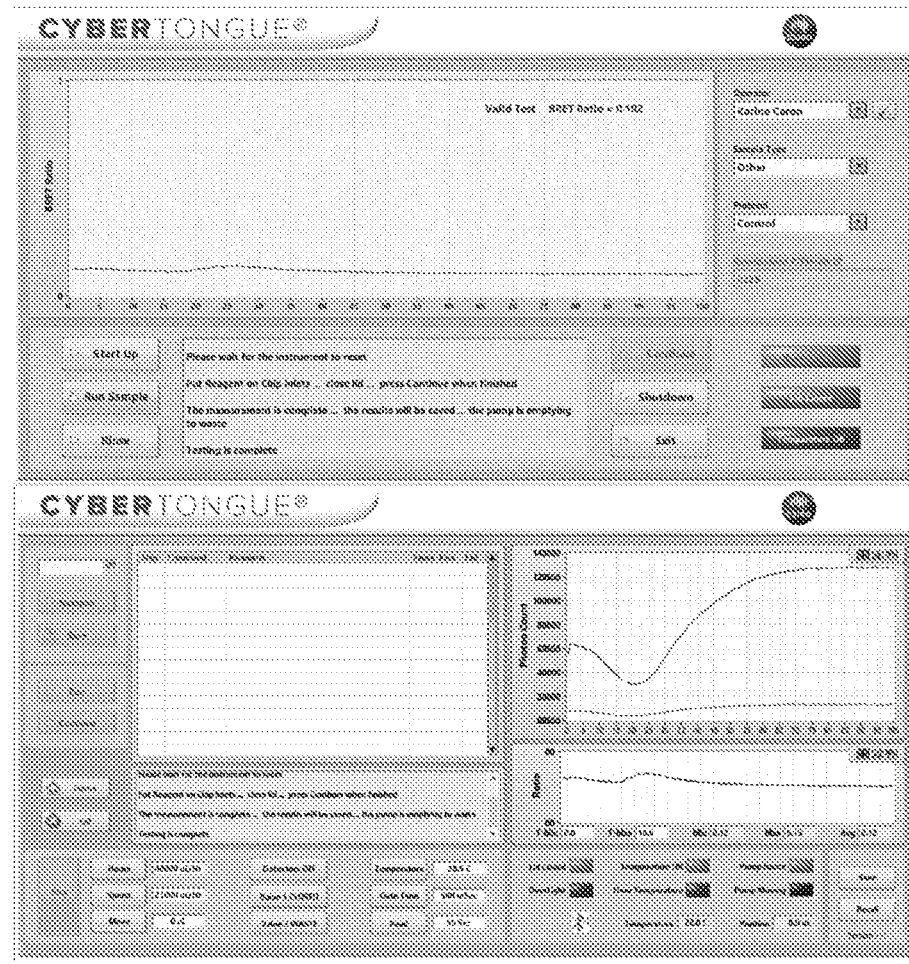

FIG. 10—(A) Example trace of $BRET^2$ ratio for the LacB1 sensor in the presence of 3 mM lactose in assay buffer (0.45% gelatine in phosphate buffer saline), determined using the CYBERTONGUE® device. (B) Example trace of donor emission (upper window, dark grey) and acceptor emission (upper window, light grey) intensities recorded by the CYBERTONGUE® device for LacB1 in the presence of 3 mM lactose in assay buffer.

Figure 11:
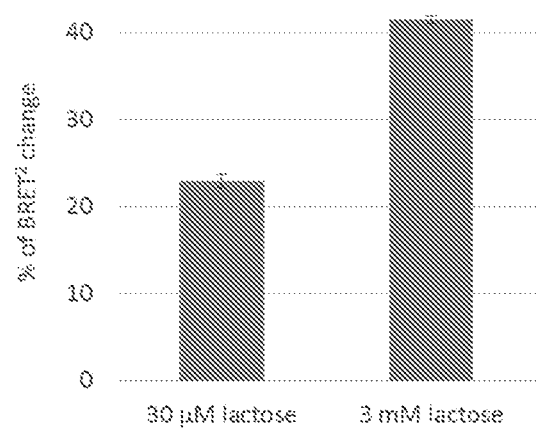

FIG. 11—Changes in the $BRET^2$ ratio of LacB1 determined with the CYBERTONGUE® device. $BRET^2$ ratios for LacB1 in the presence of 30 µM and 3 mM lactose were recorded with the CYBERTONGUE® device. The $BRET^2$ ratios were normalized to the assay buffer response and expressed as a percentage of $BRET^2$ change (mean±S.D., n=2 or 3).

KEY TO THE SEQUENCE LISTING

SEQ ID NO: 1—Amino acid sequence of the BgaR HTH transcription factor.
SEQ ID NO's: 2 to 8—Linker sequences.
SEQ ID NO: 9—BgaR HTH carbohydrate binding domain.
SEQ ID NO's: 10-14—Primer sequences.
SEQ ID NO: 15—Amino acid sequence of LacB1 ($GFP^2$-BgaR-RLuc8 fusion protein).
SEQ ID NO: 16—Amino acid sequence of LacB2 ($GFP^2$-BgaR-RLuc8 fusion protein).
SEQ ID NO: 17—Amino acid sequence of LacB3 ($GFP^2$-BgaR-RLuc8 fusion protein).
SEQ ID NO: 18—Amino acid sequence of LacB4 ($GFP^2$-BgaR-RLuc8 fusion protein).
SEQ ID NO: 19—Nucleotide sequence encoding LacB1 ($GFP^2$-BgaR-RLuc8 fusion protein).
SEQ ID NO: 20—Nucleotide sequence encoding LacB2 ($GFP^2$-BgaR-RLuc8 fusion protein).
SEQ ID NO: 21—Nucleotide sequence encoding LacB3 ($GFP^2$-BgaR-RLuc8 fusion protein).
SEQ ID NO: 22—Nucleotide sequence encoding LacB4 ($GFP^2$-BgaR-RLuc8 fusion protein).
SEQ ID NO: 23—Amino acid sequence of LacF1 ($His_6$-CFP-BgaR-YFP fusion protein).
SEQ ID NO: 24—Nucleotide sequence encoding LacF1 ($His_6$-CFP-BgaR-YFP fusion protein).
SEQ ID NO: 25—Amino acid sequence of LacB1 ($His_6$-$GFP^2$-BgaR-RLuc8 fusion protein).
SEQ ID NO: 26—Amino acid sequence of LacB2 ($His_6$-$GFP^2$-BgaR-RLuc8 fusion protein).
SEQ ID NO: 27—Amino acid sequence of LacB3 ($His_6$-$GFP^2$-BgaR-RLuc8 fusion protein).
SEQ ID NO: 28—Amino acid sequence of LacB4 ($His_6$-$GFP^2$-BgaR-RLuc8 fusion protein).
SEQ ID NO: 29—Nucleotide sequence encoding LacB1 ($His_6$-$GFP^2$-BgaR-RLuc8 fusion protein).
SEQ ID NO: 30—Nucleotide sequence encoding LacB2 ($His_6$-$GFP^2$-BgaR-RLuc8 fusion protein).
SEQ ID NO: 31—Nucleotide sequence encoding LacB3 ($His_6$-$GFP^2$-BgaR-RLuc8 fusion protein).
SEQ ID NO: 32—Nucleotide sequence encoding LacB4 ($His_6$-$GFP^2$-BgaR-RLuc8 fusion protein).
SEQ ID NO: 33—Amino acid sequence of $LacB1_{1-171}$ ($GFP^2$-$BgaR_{1-171}$-RLuc8 fusion protein). A sensor molecule according to an embodiment of the present disclosure comprising residues 1-171 of BgaR flanked by $GFP^2$ and RLuc8.
SEQ ID NO: 34—Amino acid sequence of $LacB_{1-150}$ ($GFP^2$-$BgaR_{1-150}$-RLuc8 fusion protein). A sensor molecule according to an embodiment of the present disclosure comprising residues 1-150 of BgaR flanked by $GFP^2$ and RLuc8.
SEQ ID NO: 35—Amino acid sequence of $LacB1_{12-171}$ ($GFP^2$-$BgaR_{12-171}$-RLuc8 fusion protein). A sensor molecule according to an embodiment of the present disclosure comprising residues 12-171 of BgaR flanked by $GFP^2$ and RLuc8.
SEQ ID NO: 36—Amino acid sequence of $LacB1_{12-150}$ ($GFP^2$-$BgaR_{12-150}$-RLuc8 fusion protein). A sensor molecule according to an embodiment of the present disclosure comprising residues 12-150 of BgaR flanked by $GFP^2$ and RLuc8.
SEQ ID NO: 37—Amino acid sequence of UniProt Accession No: A0A133MUX6.
SEQ ID NO: 38—Amino acid sequence of UniProt Accession No: B1V7N0.
SEQ ID NO: 39—Amino acid sequence of UniProt Accession No: A0A127EGD8.
SEQ ID NO: 40—Amino acid sequence of UniProt Accession No: A0A1C6JUB7.
SEQ ID NO: 41—Amino acid sequence of UniProt Accession No: A0A174HYB7.
SEQ ID NO: 42—Amino acid sequence of UniProt Accession No: A0A1C6KY47.
SEQ ID NO: 43—Amino acid sequence of UniProt Accession No: A0A174LZQ7.
SEQ ID NO: 44—Amino acid sequence of UniProt Accession No: N9YR91.
SEQ ID NO: 45—Amino acid sequence of UniProt Accession No: A0A174I591.
SEQ ID NO: 46—Amino acid sequence of UniProt Accession No: A0A2A7ME67.
SEQ ID NO: 47—Amino acid sequence of UniProt Accession No: A0A2K4AZL9.
SEQ ID NO: 48—Amino acid sequence of UniProt Accession No: A0A166PPM9.
SEQ ID NO: 49—Amino acid sequence of UniProt Accession No: A0A2T4R7G1.
SEQ ID NO: 50—Amino acid sequence of UniProt Accession No: A0A2A4HCU9.
SEQ ID NO: 51—Amino acid sequence of UniProt Accession No: A0A2T4MS83.
SEQ ID NO: 52—Amino acid sequence of UniProt Accession No: O33813.
SEQ ID NO: 53—Amino acid sequence of UniProt Accession No: A0A1D4LKB2.
SEQ ID NO: 54—Amino acid sequence of UniProt Accession No: A0A133QVV5.
SEQ ID NO: 55—Amino acid sequence of UniProt Accession No: A9QSR3.
SEQ ID NO: 56—Amino acid sequence of putative carbohydrate binding domain (CBD) of UniProt Accession No: A0A133MUX6.
SEQ ID NO: 57—Amino acid sequence of putative CBD of UniProt Accession No: B1V7N0.
SEQ ID NO: 58—Amino acid sequence of putative CBD of UniProt Accession No: A0A127EGD8.

SEQ ID NO: 59—Amino acid sequence of putative CBD of UniProt Accession No: A0A1C6JUB7.
SEQ ID NO: 60—Amino acid sequence of putative CBD of UniProt Accession No: A0A174HYB7.
SEQ ID NO: 61—Amino acid sequence of putative CBD of UniProt Accession No: A0A1C6KY47.
SEQ ID NO: 62—Amino acid sequence of putative CBD of UniProt Accession No: A0A174LZQ7.
SEQ ID NO: 63—Amino acid sequence of putative CBD of UniProt Accession No: N9YR91.
SEQ ID NO: 64—Amino acid sequence of putative CBD of UniProt Accession No: A0A174I591.
SEQ ID NO: 65—Amino acid sequence of putative CBD of UniProt Accession No: A0A2A7ME67.
SEQ ID NO: 66—Amino acid sequence of putative CBD of UniProt Accession No: A0A2K4AZL9.
SEQ ID NO: 67—Amino acid sequence of putative CBD of UniProt Accession No: A0A166PPM9.
SEQ ID NO: 68—Amino acid sequence of putative CBD of UniProt Accession No: A0A2T4R7G1.
SEQ ID NO: 69—Amino acid sequence of putative CBD of UniProt Accession No: A0A2A4HCU9.
SEQ ID NO: 70—Amino acid sequence of putative CBD of UniProt Accession No: A0A2T4MS83.
SEQ ID NO: 71—Amino acid sequence of putative CBD of UniProt Accession No: O33813.
SEQ ID NO: 72—Amino acid sequence of putative CBD of UniProt Accession No: A0A1D4LKB2.
SEQ ID NO: 73—Amino acid sequence of putative CBD of UniProt Accession No: A0A133QVV5.
SEQ ID NO: 74—Amino acid sequence of putative CBD of UniProt Accession No: A9QSR3.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in sensor technology, molecular biology, protein chemistry, dairy science, dairy technology, biochemistry and the like).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al., (editors) Current Protocols in Immunology, John Wiley & Sons (including all updates until present).

A polypeptide suitable for use in a method of the invention may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the query sequence is at least 450 amino acids in length and the GAP analysis aligns the two sequences over a region of at least 450 amino acids. Even more preferably, the GAP analysis aligns two sequences over their entire length.

The term "and/or", e.g., "X and/or Y" shall be understood to mean either "X and Y" or "X or Y" and shall be taken to provide explicit support for both meanings or for either meaning.

Unless the context suggests otherwise, the mention of a term in singular such as sensor and substrate clearly means the plural as well. For instance, logically many individual sensor molecules will be flowed through the device or contained within a well rather than a single molecule.

As used herein, the term about, unless stated to the contrary, refers to +/−10%, more preferably +/−5%, even more preferably +/−1%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Unless indicated or the context indicates otherwise, % concentration is weight/volume (% w/v).

Sensor

Throughout the specification "sensor" and "sensor molecule" are used interchangeably.

In one aspect the present disclosure provides a sensor molecule for detecting a carbohydrate, the sensor comprising
i) a carbohydrate binding domain of a helix-turn-helix transcription factor, or a variant of the carbohydrate binding domain;
ii) a chemiluminescent donor domain; and
iii) an acceptor domain;
wherein the spatial location and/or dipole orientation of the chemiluminescent donor domain relative to the acceptor domain is altered when the carbohydrate binds to the carbohydrate binding domain.

In some embodiments, the sensor is a continuous stretch of amino acids (in other words, the sensor is a single polypeptide). For example, the carbohydrate binding domain, chemiluminescent donor protein domain and acceptor domain are a single stretch of amino acids such as, but not limited to, a chemiluminescent donor protein domain covalently attached to the N-terminus of the carbohydrate binding domain and an acceptor protein domain covalently attached to the C-terminus of the carbohydrate binding domain, or an acceptor protein domain covalently attached to the N-terminus of the carbohydrate binding domain and a chemiluminescent donor protein domain covalently attached to the C-terminus of the carbohydrate binding domain. Examples are provided in FIG. 1.

For example, in some embodiments, the polypeptide has a sequence selected from the group consisting of SEQ ID NO: 15, SEQ ID NO: 16, SEQ ID NO: 17, SEQ ID NO: 18, SEQ ID NO: 25, SEQ ID NO: 26, SEQ ID NO: 27 and SEQ ID NO: 28 or a fragment or variant thereof. In some embodiments, the polypeptide can have a sequence at least 30%, 35%, 40%, 45%, 50%, 55%, 60%, 65%, 70%, 75%, 80%, 85%, 90%, 95%, 96%, 97%, 98%, 99% or 100% identical to the sequence shown in any one of SEQ ID NO: 15, SEQ ID NO: 16, SEQ ID NO: 17, SEQ ID NO: 18, SEQ ID NO: 25, SEQ ID NO: 26, SEQ ID NO: 27 and SEQ ID NO: 28 or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof. As used herein, a "portion" of a polypeptide retains the relevant activity of the polypeptide, for example, the portion of the polypeptide retains the ability to bind the carbohydrate.

For example, in some embodiments, the polypeptide has a sequence selected from the group consisting of SEQ ID NO: 15, SEQ ID NO: 16, SEQ ID NO: 17 and SEQ ID NO: 18 or a fragment or variant thereof. In some embodiments, the polypeptide can have a sequence at least 30%, 35%, 40%, 45%, 50%, 55%, 60%, 65%, 70%, 75%, 80%, 85%, 90%, 95%, 96%, 97%, 98%, 99% or 100% identical to the sequence shown in any one of SEQ ID NO: 15, SEQ ID NO: 16, SEQ ID NO: 17 and SEQ ID NO: 18, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof. In some embodiments, the polypeptide has a sequence selected from the group consisting of SEQ ID NO: 25, SEQ ID NO: 26, SEQ ID NO: 27 and SEQ ID NO: 28 or a fragment or variant thereof. In some embodiments, the polypeptide can have a sequence at least 30%, 35%, 40%, 45%, 50%, 55%, 60%, 65%, 70%, 75%, 80%, 85%, 90%, 95%, 96%, 97%, 98%, 99% or 100% identical to the sequence shown in any one of SEQ ID NO: 25, SEQ ID NO: 26, SEQ ID NO: 27 and SEQ ID NO: 28, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof.

In some embodiments, there is also provided a nucleic acid which comprises a polynucleotide sequence encoding a sensor as defined herein. In some embodiments, the nucleic acid is an isolated nucleic acid. For example, in some embodiments, the nucleic acid molecule comprises a sequence encoding a polypeptide sequence selected from the group consisting of SEQ ID NO: 15, SEQ ID NO: 16, SEQ ID NO: 17, SEQ ID NO: 18, SEQ ID NO: 25, SEQ ID NO: 26, SEQ ID NO: 27 and SEQ ID NO: 28. In some embodiments, the nucleic acid molecule comprises a sequence encoding a polypeptide sequence selected from the group consisting of SEQ ID NO: 15, SEQ ID NO: 16, SEQ ID NO: 17 and SEQ ID NO: 18. In some embodiments, the nucleic acid molecule comprises a sequence encoding a polypeptide sequence selected from the group consisting of SEQ ID NO: 25, SEQ ID NO: 26, SEQ ID NO: 27 and SEQ ID NO: 28. In some embodiments, the nucleic acid molecule comprises a sequence encoding the polypeptide sequence of SEQ ID NO: 15 or SEQ ID NO: 25. In some embodiments, the nucleic acid molecule comprises a sequence encoding the polypeptide sequence of SEQ ID NO: 15. In some embodiments, the nucleic acid molecule comprises a sequence encoding the polypeptide sequence of SEQ ID NO: 25. In some embodiments, the nucleic acid molecule comprises a sequence encoding the polypeptide having a sequence at least 30%, 35%, 40%, 45%, 50%, 55%, 60%, 65%, 70%, 75%, 80%, 85%, 90%, 95%, 96%, 97%, 98%, 99% or 100% identical to the sequence shown in any one of SEQ ID NO: 15, SEQ ID NO: 16, SEQ ID NO: 17, SEQ ID NO: 18, SEQ ID NO: 25, SEQ ID NO: 26, SEQ ID NO: 27 and SEQ ID NO: 28 or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof. In some embodiments, the nucleic acid molecule comprises a sequence encoding the polypeptide having a sequence at least 30%, 35%, 40%, 45%, 50%, 55%, 60%, 65%, 70%, 75%, 80%, 85%, 90%, 95%, 96%, 97%, 98%, 99% or 100% identical to the sequence shown in any one of SEQ ID NO: 15, SEQ ID NO: 16, SEQ ID NO: 17 and SEQ ID NO: 18, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof. In some embodiments, the nucleic acid molecule comprises a sequence encoding the polypeptide having a sequence at least 30%, 35%, 40%, 45%, 50%, 55%, 60%, 65%, 70%, 75%, 80%, 85%, 90%, 95%, 96%, 97%, 98%, 99% or 100% identical to the sequence shown in any one of SEQ ID NO: 25, SEQ ID NO: 26, SEQ ID NO: 27 and SEQ ID NO: 28, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof. In some embodiments, the nucleic acid molecule comprises a sequence selected from the group consisting of SEQ ID NO: 19, SEQ ID NO: 20, SEQ ID NO: 21, SEQ ID NO: 22, SEQ ID NO: 29, SEQ ID NO: 30, SEQ ID NO: 31 and SEQ ID NO: 32, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof of any one of SEQ ID NO: 19, SEQ ID NO: 20, SEQ ID NO: 21, SEQ ID NO: 22, SEQ ID NO: 29, SEQ ID NO: 30, SEQ ID NO: 31 and SEQ ID NO: 32. In some embodiments, the nucleic acid molecule comprises a sequence selected from the group consisting of SEQ ID NO: 19, SEQ ID NO: 20, SEQ ID NO: 21 and SEQ ID NO: 22, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof of any one of SEQ ID NO: 19, SEQ ID NO: 20, SEQ ID NO: 21 and SEQ ID NO: 22. In some embodiments, the nucleic acid molecule comprises a sequence selected from the group consisting of SEQ ID NO: 19, SEQ ID NO: 20, SEQ ID NO: 21 and SEQ ID NO: 22, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof of any one of SEQ ID NO: 29, SEQ ID NO: 30, SEQ ID NO: 31 and SEQ ID NO: 32.

In another aspect, the present disclosure provides a sensor molecule for detecting lactose or lactulose comprising a bacterial BgaR transcription factor or variant thereof, covalently joined to a resonance energy transfer donor domain and a resonance energy transfer acceptor domain, wherein the spatial location and/or dipole orientation of the donor domain relative to the acceptor domain is altered when lactose binds to the transcription factor. Binding of lactose or lactulose to the sensor molecules of this aspect produces a change in resonance energy transfer, for example a change in BRET or a change in FRET. In some embodiments, the present disclosure provides a sensor molecule for detecting lactose. In some embodiments, present disclosure provides a sensor molecule for detecting lactulose.

In some embodiments, the sensor is a continuous stretch of amino acids (in other words, the sensor is a single polypeptide). For example, the bacterial BgaR transcription factor or variant thereof, resonance energy transfer donor domain and resonance energy transfer acceptor domain are a single stretch of amino acids such as, but not limited to, a donor protein domain covalently attached to the N-terminus of the bacterial BgaR transcription factor and an acceptor protein domain covalently attached to the C-terminus of the bacterial BgaR transcription factor, or an acceptor protein domain covalently attached to the N-terminus of the bacterial BgaR transcription factor and a donor protein domain covalently attached to the C-terminus of the bacterial BgaR transcription factor.

For example, in some embodiments, the polypeptide has the sequence provided in SEQ ID NO: 23 or a fragment or variant thereof. In some embodiments, the polypeptide can have a sequence at least 30%, 35%, 40%, 45%, 50%, 55%, 60%, 65%, 70%, 75%, 80%, 85%, 90%, 95%, 96%, 97%, 98%, 99% or 100% identical to the sequence shown in SEQ ID NO: 23, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof.

In some embodiments, there is also provided a nucleic acid molecule which comprises a polynucleotide sequence encoding a sensor as defined herein. In some embodiments, the nucleic acid molecule is an isolated nucleic acid molecule. For example, in some embodiments, the nucleic acid molecule comprises a sequence encoding the polypeptide sequence provided in SEQ ID NO: 23 or a fragment or variant thereof. In some embodiments, the nucleic acid molecule comprises a sequence encoding the polypeptide having a sequence at least 30%, 35%, 40%, 45%, 50%, 55%, 60%, 65%, 70%, 75%, 80%, 85%, 90%, 95%, 96%, 97%, 98%, 99% or 100% identical to the sequence provided in SEQ ID NO: 23, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof. In some embodiments, the nucleic acid molecule comprises the sequence provided in SEQ ID NO: 24, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof.

The sensors, compositions, kits, methods and uses of the present disclosure encompass polypeptides and nucleic acids having the sequences specified, or sequences substantially identical or similar thereto, e.g., sequences at least 30%, 35%, 40%, 45%, 50%, 55%, 60%, 65%, 70%, 75%, 80%, 85%, 90%, 95%, 96%, 97%, 98%, 99% or 100% identical to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to the sequence specified are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to the sequence specified are termed substantially identical.

Calculations of homology or sequence identity between sequences (the terms are used interchangeably herein) are performed using techniques know to the person skilled in the art. For example, to determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch (1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet other embodiments, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6.

The percent identity between two amino acid or nucleotide sequences can be determined using the algorithm of Meyers and Miller (1989) which has been incorporated into the ALIGN program (version 2.0), using, for example, a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using, for example, the NBLAST and XBLAST programs (version 2.0) of Altschul, et al., (1990), as well as BLASTp. BLAST nucleotide searches can be performed with the NBLAST program, score=100, wordlength=12 to obtain nucleotide sequences homologous to nucleic acid molecules of some embodiments of the invention. BLAST protein searches can be performed with the XBLAST program, score=50, wordlength=3 to obtain amino acid sequences homologous to protein molecules of some embodiments of the invention. To obtain gapped alignments for comparison purposes, Gapped BLAST can be utilized as described in Altschul et al., (1997). When utilizing BLAST and Gapped BLAST programs, the default parameters of the respective programs (e.g., BLASTp, XBLAST and NBLAST) can be used. See http://_www_ncbi_nlm_nih_gov/BLAST.

Nucleic acid molecules corresponding to natural allelic variants, homologs, orthologs, or other related sequences (e.g., paralogs) of the sequences described herein can be isolated based on their homology to the nucleic acids encoding the amino acid sequences disclosed herein, for example by performing standard or stringent hybridization reactions using all or a portion of the known sequences as probes. Such methods for nucleic acid hybridization and cloning are well known in the art.

The homologs of the peptides as provided herein typically have structural similarity with such peptides. A homolog of a polypeptide includes one or more conservative amino acid substitutions, which may be selected from the same or different members of the class to which the amino acid belongs.

In some embodiments, the sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Some embodiments of the present invention also encompass conservative substitution (substitution and replacement are both used herein to mean the interchange of an existing amino acid residue with an alternative residue) that may occur e.g., like-for-like substitution such as basic for basic, acidic for acidic, polar for polar, etc. Non-conservative substitution may also occur e.g., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridyl-alanine, thienylalanine, naphthylalanine and phenylglycine. Conservative substitutions that may be made are, for example, within the groups of basic amino acids (arginine, lysine and histidine), acidic amino acids (glutamic acid and aspartic acid), aliphatic amino acids (alanine, valine, leucine, isoleucine), polar amino acids (glutamine, asparagine, serine, threonine), aromatic amino acids (phenylalanine, tryptophan and tyrosine), hydroxyl amino acids (serine, threonine), large amino acids (phenylalanine and tryptophan) and small amino acids (glycine, alanine).

In addition to the sequence encoding the sensor molecule of the invention, the nucleic acid molecule may contain other sequences such as primer sites, transcription factor binding sites, vector insertion sites and sequences which resist nucleolytic degradation (e.g. polyadenosine tails). The nucleic acid molecule may be DNA or RNA and may include synthetic nucleotides, provided that the polynucleotide is still capable of being translated in order to synthesize a protein of the invention.

In some embodiments, the nucleic acid forms part of a vector such as a plasmid. In addition to the nucleic acid sequence described above, the plasmid comprises other elements such as a prokaryotic origin of replication (for example, the *E. coli* OR1 origin of replication) an autonomous replication sequence, a centromere sequence; a promoter sequence capable of expressing the nucleic acid in the host cell which is operably linker to the nucleic acid, a terminator sequence located downstream of the nucleic acid sequence, an antibiotic resistance gene and/or a secretion signal sequence. A vector comprising an autonomous replication sequence is also a yeast artificial chromosome. In some alternative embodiments, the vector is a virus, such as a bacteriophage and comprises, in addition to the nucleic acid sequence of the invention, nucleic acid sequences for replication of the bacteriophage, such as structural proteins, promoters, transcription activators and the like.

The nucleic acid or vector of the invention may be used to transfect or transform host cells in order to synthesize the sensor molecule of the present disclosure. Suitable host cells include prokaryotic cells such as *E. coli* and eukaryotic cells such as yeast cells, or mammalian or plant cell lines. Host cells are transfected or transformed using techniques known in the art such as electroporation; calcium phosphate base methods; a biolistic technique or by use of a viral vector.

After transfection/transformation, the nucleic acid or vector of the invention is transcribed as necessary and translated. In some embodiments, the synthesized protein is extracted from the host cell, either by virtue of its being secreted from the cell due to, for example, the presence of secretion signal in the vector, or by lysis of the host cell and purification of the protein therefrom. In some embodiments, there is provided a process for producing a sensor molecule as defined herein, the process comprising cultivating a host cell or a vector as defined herein under conditions which allow expression of the polynucleotide encoding the polypeptide, and recovering the expressed polypeptide.

In some embodiments, the sensor is provided as a cell-free composition. As used herein, the term "cell free composition" refers to an isolated composition which contains few, if any, intact cells and which comprises the sensor. Examples of cell free compositions include cell (such as yeast cell) extracts and compositions containing an isolated and/or recombinant sensor molecules (such as proteins). Methods for preparing cell-free compositions from cells are well-known in the art.

The sensor molecules optionally comprise at least one linker. For example, the sensor may comprise a linker which connects the carbohydrate binding domain (or helix-turn-helix transcription factor comprising the carbohydrate binding domain) to the chemiluminescent donor domain and/or acceptor domain. In another example, the sensor molecule may comprise a linker at the N- and/or C-terminus of the sensor molecule. In some embodiments, the sensor molecule comprises at least one peptide linker. In some embodiments, a linker can be located at the N- and/or C-terminus of the carbohydrate binding domain (or helix-turn-helix transcription factor comprising the carbohydrate binding domain). Preferably the linker is a peptide or polypeptide. In some embodiments, the linker comprises one or more glycine, serine and/or threonine residues. For example, in some embodiments, the linker comprises an amino acid sequence selected from GSSGGS (SEQ ID NO: 2), GGSGGS (SEQ ID NO: 3), GGTGGG (SEQ ID NO: 4), GGGGGT (SEQ ID NO: 5) LQGGTGGG (SEQ ID NO: 6), FEGGTGGG (SEQ ID NO: 7) and GGSGGSL (SEQ ID NO: 8). In some embodiments, the linker is 25 amino acids or less, 20 amino acids or less, 15 amino acids or less, 10 amino acids or less, 8 amino acids or less, 6 amino acids or less, 4 amino acids or less, or 3 amino acids or less. In some embodiments, the linker is between 1 and 10 amino acids in length, between 2 and 9 amino acids in length or between 4 and 8 amino acids in length. The linker sequence can be located at the N-terminus of the carbohydrate binding domain, the C-terminus of the carbohydrate binding domain or both. When a linker is located at both the N- and C-terminus, the linker sequence can be the same or different. Without wishing to be bound by theory, the linker may serve one or more of the following purposes: (i) help ensure that the carbohydrate binding site is in a preferred conformation for binding; (ii) improve the accessibility of the carbohydrate binding site; (iii) increase the magnitude of the change in spatial location and/or dipole orientation of the chemiluminescent donor domain relative to the acceptor domain (for example, the linker sequence can function to increase the BRET ratio); and/or (iv) optimise the spatial location and/or dipole orientation of the chemiluminescent donor domain relative to the acceptor domain.

In some embodiments, the sensor further comprises protease cleavage sites and/or purification tags. In some embodiments, the linker comprises an amino acid or series of amino acids than can be used for purification and/or for attachment of the chemiluminescent donor domain and/or acceptor domain. For example, the linker can comprise a histidine tag for purification or self-assembly with the chemiluminescent donor domain and/or acceptor domain. In another example, the linker can comprise a reactive group (e.g. cysteine or lysine) for addition of the chemiluminescent donor domain and/or acceptor domain. In some embodiments, the sensor comprises a protease cleavage site. The protease cleavage site may be used to remove purification tags.

The polypeptides of the invention can be produced in a variety of ways, including production and recovery of natural polypeptides, production and recovery of recombinant polypeptides, and chemical synthesis of the polypeptides. In one embodiment, an isolated polypeptide is produced by culturing a cell capable of expressing the polypeptide under conditions effective to produce the polypeptide, and recovering the polypeptide. Effective culture conditions can be determined by the person skilled in the art include, but are not limited to, effective media, bioreactor, temperature, pH and oxygen conditions that permit polypeptide production. An effective medium refers to any medium in which a cell is cultured to produce a polypeptide. Such medium typically comprises an aqueous medium having assimilable carbon, nitrogen and phosphate sources, and appropriate salts, minerals, metals and other nutrients, such as vitamins. Cells can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

The polypeptides of the present invention may be extracted and purified from recombinant cells, such as plant, bacteria or yeast cells, producing said polypeptide by methods known to the person skilled in the art. In one embodiment, the method involves extracting total soluble proteins by homogenizing cells/tissues/plants and isolating the hexahistidine polypeptide using a Ni-NTA or Talon. Additional purification may be achieved with conventional gel or affinity chromatography.

Carbohydrate

The sensors of the present disclosure are capable of binding to carbohydrates. The term "carbohydrate" as used herein is defined broadly and refers to monosaccharides, oligosaccharides and polysaccharides as well as substances derived from monosaccharides, for example by reduction of the carbonyl group (forming alditols), by oxidation of one or more terminal groups to carboxylic acids, or by replacement of one or more hydroxy group(s) by a hydrogen atom, an amino group, thiol group or similar groups (forming a derivative). It also includes derivatives of these compounds (see IUPAC. Compendium of Chemical Terminology, 2nd ed. (the "Gold Book") compiled by A. D. McNaught and A. Wilkinson. Blackwell Scientific Publications, Oxford (1997)). As the person skilled in the art would be aware, carbohydrates can contain asymmetric centers and therefore have stereoisomers. The carbohydrates useful in the sensors, methods, kits and compositions of this disclosure may be in either the D-stereoisomeric and/or the L-forms (enantiomers) form. Both the open chain and closed ring structure fall within the definition of carbohydrate.

In some embodiments, the carbohydrate is a sugar or a sugar derivative.

In some embodiments, the carbohydrate is a sugar. As used herein, the term "sugar" includes both polyhydroxyaldehydes and polyhydroxyketones comprising at least one hydroxyl group and at least one aldehyde group or ketone group. In some embodiments, the sugar is a monosaccharide, oligosaccharide or polysaccharide. Suitable monosaccharides can include trioses (such as glyceraldehyde), tetroses (such as erythrose and threose), pentoses (such as ribulose, arabinose, xylose, ribose and lyxose), hexoses (such as glucose, mannose, galactose, idose, gulose, fructose, altrose, allose, fucose and talose), heptoses (such as sedoheptulose), octoses (such as glycero-D-manno-octulose) and pentose ring sugars (such as ribofuranose and ribopyranose). In some embodiments, the monosaccharide is selected from the group consisting of ribose, glucose, mannose, galactose, and fructose. As used herein, an "oligosaccharide" is a saccharide polymer containing between two to ten saccharides which are linked by a glycosidic bond. In some embodiments, the oligosaccharide comprises two, three, four, five, six, seven, eight, nine or ten saccharides. For example, oligosaccharides include, but are not limited to, disaccharides or trisaccharides. Suitable oligosaccharides include, but are not limited to, sucrose, lactose, lactulose, trehalose, gentiobiose, maltose, isomaltose, cellobiose melezitose, raffinose, stachyose, cellotriose, melibiose and verbascose. Suitable oligosaccharides include, but are not limited to, sucrose, lactose, trehalose, gentiobiose, maltose, isomaltose, cellobiose melezitose, raffinose, stachyose, cellotriose, melibiose and verbascose. In some embodiments, the carbohydrate is a disaccharide. In some embodiments, the carbohydrate is lactose or lactulose. In some embodiments, the carbohydrate is lactose. In some embodiements, the carbohydrate is lactulose. In preferred embodiments, the carbohydrate is lactose. Polysaccharides are sugars in which monosaccharides or oligosaccharides are chemically linked together via glycosidic bonds. Suitable polysaccharides include, but are not limited to, amylose, amylopectin and glycogen.

In some embodiments, the carbohydrate is a sugar derivative. As used herein, a "sugar derivative" refers to a sugar which has been modified to replace one or more hydroxy groups with a different substituent, or a sugar variant obtained by an oxidation-reduction reaction of a sugar. Suitable substituents include, but is not limited to, alkyl, substituted alkyl, cycloalkyl, substituted cycloalkyl, alkenyl, substituted alkenyl, cycloalkenyl, substituted cycloalkenyl, alkynyl, substituted alkynyl, alkoxy, substituted alkoxy, carbocyclic group, substituted carbocyclic group, heterocyclic group, substituted heterocyclic group, halogen, hydroxy, substituted hydroxy, thiol, substituted thiol, cyano, phospho, substituted phospho, nitro, amino, substituted amino, carboxy, substituted carboxy, acyl, substituted acyl, thiocarboxy, substituted thiocarboxy, amide, substituted amide, substituted carbonyl, substituted thiocarbonyl, substituted sulfonyl and substituted sulfinyl. In some embodiments, the sugar derivative is selected from the group consisting of a sugar alcohol (also referred to as an alditol or aldose alcohol), ketose, amino sugar (or glycosylamine), deoxy sugar, sugar phosphate, acidic sugar, glycoside, and lactone. Suitable sugar alcohols include, but are not limited to, erythritol, glucitol, sorbitol, or mannitol. Suitable ketoses include, but are not limited to, dihydroxyacetone, erythrulose, ribulose, xylulose, psicose, fructose, sorbose, and tagatose. Suitable amino sugars include, but are not limited to, glucosamine, galactosamine, N-acetylglucosamine, N-acetylgalactosamine, muramic acid, N-acetyl muramic acid, and N-acetylneuraminic acid (sialic acid). Suitable glycosides include, but are not limited to, glucopyranose and methyl-glucopyranose. Suitable lactones include, but are not limited to, gluconolactone. Suitable deoxy sugars, include but are not limited to, deoxyribose and rhamnose. Suitable sugar phosphates include, but are not limited to, glucose 6-phosphate, fructose 6-phosphate, erythrose 4 phosphate, ribose 5-phosphate, fructose-1,6-bisphosphate and xylulose 5-phosphate.

In some embodiments, the carbohydrate is a substance derived from a monosaccharide. In some embodiments, the carbohydrate is a substance derived from a monosaccharide by reduction of the carbonyl group or by oxidation of one or more terminal groups to carboxylic acids. For example the substance derived from a monosaccharide can be, but is not limited to, alditols (such as erythritol, glucitol, sorbitol, or mannitol) and sugar acids (such as gluconic acid, mannonic acid, threonic acid and glyceric acid). In some embodiments, the substance derived from a monosaccharide is selected from the group consisting of lactate and pyruvate.

Carbohydrate Binding Domains

As used herein, a "carbohydrate binding domain" is a polypeptide capable of binding to a carbohydrate. Carbohydrate binding domains comprise at least one binding site that binds to a carbohydrate. The term "binding to a carbohydrate" refers to non-covalent binding of a carbohydrate to a carbohydrate binding domain. Such binding may involve non-covalent interactions such as salt bridges, hydrogen bonds, van der Waal forces, stacking forces, complex formation or combinations thereof between the carbohydrate and the carbohydrate binding domain binding domain. It may also include interactions with water molecules in the binding site.

Suitable carbohydrate binding domains may be present on a polypeptide chain that consists solely of the binding domain amino acid sequence or may be present in the context of a larger polypeptide molecule (i.e., one which comprises amino acids other than those of the binding domain). Accordingly, the carbohydrate binding domain may be a full-length protein (for example, a full length helix-turn-helix transcription factor) or a fragment (for example, a fragment of a helix-turn-helix transcription factor comprising a carbohydrate binding domain) or variant thereof. The carbohydrate binding domain can comprise either natural or non-natural amino acid sequences. The minimum length of the carbohydrate binding domain which maintains binding to the carbohydrate and undergoes a conformational change which is sufficient and suitable for carbohydrate detection as described herein can be determined by the person skilled in the art.

In some embodiments, the carbohydrate binding domain is a naturally occurring polypeptide. In some embodiments, the carbohydrate binding domain is a variant of a naturally occurring polypeptide. For example, in some embodiments, the carbohydrate binding domain is an amino acid that is altered (i.e., by insertion, deletion or substitution of at least one amino acid or nucleotide, as the case may be) such that the carbohydrate binding domain sequence is no longer as found in nature. In some embodiments, the position of the variation is within the residues which form the carbohydrate binding domain. The variant may comprise either natural or non-natural amino acid sequences. In some embodiments, the variant carbohydrate binding domain comprises an amino acid sequence which at least 30% identical to a naturally occurring carbohydrate binding domain of a helix-turn-helix transcription factor. For example, in some embodiments, the variant carbohydrate binding domain comprises an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, or at least 99.5% identical to a naturally occurring carbohydrate binding domain of a helix-turn-helix transcription factor.

In some embodiments, the carbohydrate binding domain is a sugar or sugar derivative binding domain. In some embodiments, the carbohydrate binding domain is a sugar binding domain. In some embodiments, the carbohydrate binding domain is a sugar derivative binding domain.

In some embodiments, the carbohydrate binding domain binds to a carbohydrate with a high affinity. In some embodiments, the carbohydrate binding domain binds to a carbohydrate with half-maximal binding occurring at a carbohydrate concentration of 1 nM or below, 10 nM or below, 50 nM or below, 100 nM or below, 500 nM or below, 1 µM or below, 10 µM or below, 50 µM or below, 100 µM or below, 500 µM or below, 1 mM or below or 10 mM or below. For example, in some embodiments the $EC_{50}$ is between approximately 0.1 µM and 150 µM, between approximately 1 µM and 100 µM or between approximately 5 µM and 50 µM. In some embodiments, the $EC_{50}$ is between approximately 10 µM and 25 µM. Alternatively, in some embodiments the $EC_{50}$ is between approximately 0.1 mM and 150 mM, between approximately 1 mM and 100 mM, between approximately 2 mM and 50 mM or between approximately 2 mM and 5 mM.

Upon binding of a carbohydrate to the carbohydrate binding domain, a suitable carbohydrate binding domains undergo a conformational change which is sufficient and suitable for carbohydrate detection as described herein.

Carbohydrate binding domains useful in the sensors of the present disclosure are derived from transcription factors which contain a helix-turn-helix (HTH) domain (also referred to as a helix-turn-helix motif). That is, the sensors comprise a carbohydrate binding domain of a helix-turn-helix transcription factor, or a variant of the carbohydrate domain. In some embodiments, the sensor molecule comprises the carbohydrate binding domain of a helix-turn-helix transcription factor and one or more additional amino acids present in the helix-turn-helix transcription factor. For example, the sensor may also comprise one or more functional domains (for example, the DNA binding domain) also present in the helix-turn-helix transcription factor. In one embodiment, the polypeptide lacks the helix-turn-helix domain of the transcription factor. In an alternate embodiment, the polypeptide has the helix-turn-helix domain of the transcription factor. Any variant, portion or fragment useful in the sensors described herein retains the ability to bind to a carbohydrate. In some embodiments, the carbohydrate binding domain comprises a protein fold disclosed to bind to a carbohydrate. Non-limiting examples of protein folds which bind to a carbohydrate include the Nudix hydrolase fold, a carbohydrate-binding module, or the AraC carbohydrate recognition domain.

In some embodiments, the HTH transcription factor is a bacterial HTH transcription factor. In some embodiments, the HTH transcription factor may originate from gram-negative bacteria or gram-positive bacteria. Examples of such HTH transcription factors are shown in Table 1. Naturally occurring species variants of the HTH transcription factors listed in Table 1 can also be used, in addition to variants or fragments thereof as discussed herein. Homologues (such as orthologues originating from related species of bacteria) of the HTH transcription factors listed in Table 1 can also be used in the sensor molecules described herein. Moreover, it is contemplated that the term "HTH transcription factor" includes variants, portion, fragments or derivatives of any naturally occurring HTH transcription factor as long as the variant, portion, fragment or derivative retains the ability to bind a carbohydrate. It is also to be understood that the person skilled in the art is capable of modifying and optimizing naturally occurring HTH transcription factors by suitable techniques known in the art such as in vitro or in vivo mutagenesis, PCR shuffling mutagenesis, chemical modification and the like.

TABLE 1

Exemplary helix-turn-helix transcription factors

| Transcription Factor | Sugar or sugar derivative | Example Accession number (from UniProt) |
|---|---|---|
| YvoA/NgaR | N-acetylglucosamine (GlcNAc)/glucosamine-6-phosphate | O34817, Q795E9, |
| TrmB | maltose, trehalose, maltotriose, longer maltodextrins, sucrose, and glucose | Q7LYW4, Q9HGZ9, Q9HPW0 |
| AraR | arabinose | A2QJX5, Q5BGE2, P96711 |
| AraC | arabinose | P0A9E0, P96711 |
| TreR | trehalose-6-phosphate | P36673, P39796, P36674 |
| MurQ | N-acetylmuramic acid (MurNAc)-6-phosphate | P76535, Q45582, Q8ZN25 |
| LacI | allolactose | P03023, |
| BgaR | lactose | Q8XMB9, BAB80476, Q6PU53, O52846, A0A069CWF6, H1X564, Q6PU52 |
| EbgR | lactose | P06846 |
| CebR | cellobiose, cellotriose | D2Q7B0, A0A173WKF3 |
| CggR | fructose-1,6-biphosphate | O32253 |
| FruR | D-fructose | P0ACP1, O31713 |
| GalR | D-galactose | E1WAQ4, Q9ZB11 |
| GalS | galactose, D-fucose | P25748, P41030 |
| MalI | maltose | P18811, P96158 |
| MelR | melibiose | P0ACH8, P0ACH9 |
| RafR | raffinose | P21867, P43465 |
| RbtR | D-ribulose | P07760 |
| XylR | D-xylose | P06519 |
| ScrR | D-fructose | P37077, P37076 |
| MsmR | melibiose | O34829, Q00753 |
| XylS | D-xylose | P07859 |

In some embodiments, the HTH transcription factor is a member of the $G_{NT}R$ family of transcription factors. The $G_{NT}R$ family, named after the gluconate operon repressor in *Bacillus subtilis*, is one of the most prevalent superfamilies of HTH transcription factors (Haydon and Guest, 1991; Zheng et al., 2009). This family of HTH proteins generally has DNA-binding domain and an effector binding domain (Aravind and Anantharaman, 2003; Rigali et al., 2002; Rigali et al., 2004). The DNA-binding domain is relatively conserved amongst members of this superfamily with a central 0-sheet cluster and three α-helices, two of which, along with a connective loop, constitute the HTH motif (Zheng et al., 2009; Rigali et al., 2002; Kong et al., 2009). In contrast, the effector domain is diverse amongst the $G_{NT}R$ superfamily and their structural divergence leads to six subfamilies of $G_{NT}R$ transcriptional factors: four main subfamilies (FadR, HutC, MocR, YtrA) and two minor subfamilies (AraR and PlmA) (Zheng et al., 2009; Rigali et al., 2002; Rigali et al., 2004; Wiethaus et al., 2008; Lee et al., 2003; Zhang et al., 2012; Franco et al., 2006; Franco et al., 2007). The effector domain typically binds to molecules, for example carbohydrates. Typically, $G_{NT}R$ family members have an N-terminal DNA binding domain and a C-terminal effector binding. However, in the AraR subfamily the DNA-binding domain is typically located at the C-terminal end whereas the effector binding-domain is found at the N-terminal end.

One example of a suitable bacterial HTH transcription factor is BgaR. BgaR is a transcription factor from *Clostridium perfringins* strain 13 (CPE0770; UniProt Accession Number: Q8XMB9) and is a putative member of the AraR subfamily (Hartman et al., 2011). BgaR binds to lactose and forms part of a lactose-inducible regulatory system.

In some embodiments, the sensor comprises the helix-turn-helix transcription factor BgaR or a fragment or variant thereof. In some embodiments, the carbohydrate binding domain comprises an amino acid sequence provided as SEQ ID NO: 1 or is a fragment or variant thereof. In some embodiments, the carbohydrate binding domain has an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, at least 99.5% identical to that provided in SEQ ID NO: 1. In some embodiments, the carbohydrate binding domain has an amino acid sequence which is at least 30%, 35%, 40%, 45%, 50%, 55%, 60%, 65%, 70%, 75%, 80%, 85%, 90%, 95%, 96%, 97%, 98%, 99% or 100% identical to a portion thereof (e.g., a portion comprising amino acids 1-179, amino acids 1-171, 1-157, amino acids 1-150, amino acids 12-179, amino acids 12-171, amino acids 12-150, amino acids 16-179, amino acids 16-171, amino acids 16-151 or amino acids 16-129 of SEQ ID NO: 1). In some embodiments, the carbohydrate binding domain comprises an amino acid sequence provided as SEQ ID NO: 9 or is a fragment or variant thereof that retains carbohydrate binding activity. In some embodiments, the carbohydrate binding domain has an amino acid sequence which is at least 30%, 35%, 40%, 45%, 50%, 55%, 60%, 65%, 70%, 75%, 80%, 85%, 90%, 95%, 96%, 97%, 98%, 99% or 100% identical to SEQ ID NO: 9.

The minimum carbohydrate binding domain of BgaR (or another HTH transcription factor) can be determined using techniques known to the person skilled in the art. For example, the protein sequence described herein can be used as a "query sequence" to perform a search against the conserved domain database to, for example, identify the putative carbohydrate binding domain and/or HTH domain (Marchler-Bauer et al., 2017; Marchler-Bauer et al., 2015; Marchler-Bauer et al., 2011; Marchler-Bauer and Bryant, 2004). When searching for conserved domains using the conserved domain database, the default parameters can be used. See https://_www_ncbi_nlm_nih_gov/Structure/cdd/wrpsb_cgi. The ability of the predicted carbohydrate binding domain to bind carbohydrates can be confirmed using techniques known to the person skilled in the art.

In some embodiments, the carbohydrate binding domain of BgaR comprises amino acids 1-179, amino acids 1-171, amino acids 1-157, amino acids 1-150, amino amino acids 12-179, amino acids 12-171, amino acids 12-157, amino acids 12-150, amino acids 16-179, amino acids 16-171, amino acids 16-157, acids 16-151 or amino acids 16-129 of SEQ ID NO: 1. In some embodiments, the carbohydrate binding domain of BgaR comprises amino acids 1-150, amino acids 1-171, amino acids 1-179, amino acids 12-171 or amino acids 12-150 of SEQ ID NO: 1. In some embodiments, the carbohydrate binding domain has an amino acid sequence which is at least 30%, 35%, 40%, 45%, 50%, 55%, 60%, 65%, 70%, 75%, 80%, 85%, 90%, 95%, 96%, 97%, 98%, 99% or 100% identical to amino acids 1-157, amino acids 16-151 or amino acids 16-129 of SEQ ID NO: 1. In some embodiments, the carbohydrate binding domain has an amino acid sequence which is at least 30%, 35%, 40%, 45%, 50%, 55%, 60%, 65%, 70%, 75%, 80%, 85%, 90%, 95%, 96%, 97%, 98%, 99% or 100% identical to amino acids 1-150, amino acids 1-171, amino acids 12-150 or amino acids 12-171 of SEQ ID NO: 1. In some embodiments, the carbohydrate binding domain comprises an amino acid sequence provided as SEQ ID NO: 9. In some embodiments, the carbohydrate binding domain has an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, at least 99.5% identical, or 100% identical to that provided in SEQ ID NO: 9. In some embodiments, the carbohydrate binding domain has an amino acid sequence which is at least 30%, 35%, 40%, 45%, 50%, 55%, 60%, 65%, 70%, 75%, 80%, 85%, 90%, 95%, 96%, 97%, 98%, 99% or 100% identical to a portion of SEQ ID NO: 9 or at least 30%, 35%, 40%, 45%, 50%, 55%, 60%, 65%, 70%, 75%, 80%, 85%, 90%, 95%, 96%, 97%, 98%, 99% or 100% identical to a portion of SEQ ID NO: 9.

Other suitable transcription factors can be identified by the person skilled in the art using tools such as BLASTp. For example, in some embodiments the transcription factor comprises a carbohydrate binding domain that comprises an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, at least 99.5% identical to the carbohydrate binding domain of BgaR (for example, the amino acids in SEQ ID NO: 9 or to amino acids 1-179, amino acids 1-171, amino acids 1-150, amino acids 12-179, amino acids 12-171 or amino acids 12-150). Suitable transcription factors include, but are not limited to, putative lactose operon transcription activator from *Clostridium perfringens* (UniProt Accession No: A0A133MUX6), AraC family transcriptional regulator (*Clostridium perfringens* D str. JGS1721) (UniProt Accession No: B1V7NO), AraC family transcriptional regulator (*Clostridium perfringens*) (UniProt Accession No: A0A127EGD8), arabinose operon regulatory protein (uncultured *Clostridium* sp.) (UniProt Accession No: A0A1C6JUB7), transcriptional regulator (*Clostridium disporicum*) (UniProt Accession No: A0A174HYB7), arabinose operon regulatory protein (uncultured *Clostridium* sp.) (UniProt Accession No: A0A1C6KY47), transcriptional regulator (*Clostridium disporicum*) (UniProt Accession No: A0A174LZQ7), AraC family transcriptional regulator (*Clostridium paraputrificum*) (UniProt Accession No: A0A174I591), uncharacterized protein (*Clostridium butyricum* 60E.3) (UniProt Accession No: N9YR91), AraC family transcriptional regulator (*Clostridium neonatale*) (UniProt Accession No: A0A2A7ME67), AraC family transcriptional regulator (*Staphylococcus intermedius* NCTC 11048) (UniProt Accession No: A0A2K4AZL9). AraC family transcriptional regulator (*Staphylococcus pseudintermedius*) (UniProt Accession No: A0A166PPM9), AraC family transcriptional regulator (*Staphylococcus hyicus*) (UniProt Accession No: A0A2T4R7G1), AraC family transcriptional regulator (*Staphylococcus delphini*) (UniProt Accession No: A0A2A4HCU9), AraC family transcriptional regulator (*Staphylococcus agnetis*) (UniProt Accession No: A0A2T4MS83), Lactose operon transcription activator (*Staphylococcus xylosus*) (UniProt Accession No: O33813), Lactose operon transcription activator (*Staphylococcus saprophyticus*) (UniProt Accession No: A0A1D4LKB2), Putative lactose operon transcription activator (*Staphylococcus sinulans*) (UniProt Accession No: A0A133QVV5), Transcriptional regulator, AraC family (*Lactococcus lactis* subsp. *lactis* strain KF147) (UniProt Accession No: A9QSR3.

In some embodiments, the sensor comprises a transcription factor comprising an amino acid sequence selected from the group consisting of the amino acid sequence provided in SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 48, SEQ ID NO: 49, SEQ ID NO: 50, SEQ ID NO: 51, SEQ ID NO: 52, SEQ ID NO: 53, SEQ ID NO: 54 and SEQ ID NO: 55, or is a fragment or variant thereof. In some embodiments, the sensor comprises a transcription factor having an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, at least 99.5% identical to that provided in SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54 or SEQ ID NO: 55, or is a fragment or variant thereof.

In some embodiments, the carbohydrate binding domain comprises an amino acid sequence selected from the group consisting of the amino acid sequence provided in SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73 or SEQ ID NO: 74, or is a fragment or variant thereof. In some embodiments, the carbohydrate binding domain has an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, at least 99.5% identical to the amino acid sequence provided in SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73 or SEQ ID NO: 74, or is a fragment or variant thereof.

In some embodiments, the nucleic acid molecule comprises a sequence encoding the polypeptide having a sequence at least 30%, 35%, 40%, 45%, 50%, 55%, 60%, 65%, 70%, 75%, 80%, 85%, 90%, 95%, 96%, 97%, 98%, 99% or 100% identical to the sequence shown in any one of SEQ ID NO: 15, SEQ ID NO: 16, SEQ ID NO: 17, SEQ ID NO: 18, SEQ ID NO: 25, SEQ ID NO: 26, SEQ ID NO: 27 or SEQ ID NO: 28, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof (e.g., a portion comprising amino acids 11-349, amino acids 18-349, amino acids 28-349, amino acids 38-349, or amino acids 39-349 of any one of SEQ ID NO: 15, SEQ ID NO: 16, SEQ ID NO: 17, SEQ ID NO: 18, SEQ ID NO: 25, SEQ ID NO: 26, SEQ ID NO: 27 or SEQ ID NO: 28). In some embodiments, the nucleic acid molecule comprises a sequence encoding the polypeptide having a sequence at least 30%, 35%, 40%, 45%, 50%, 55%, 60%, 65%, 70%, 75%, 80%, 85%, 90%, 95%, 96%, 97%, 98%, 99% or 100% identical to the sequence shown in any one of SEQ ID NO: 15, SEQ ID NO: 16, SEQ ID NO: 17 or SEQ ID NO: 18, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof (e.g., a portion comprising amino acids 11-349, amino acids 18-349, amino acids 28-349, amino acids 38-349, or amino acids 39-349 of any one of SEQ ID NO: 15, SEQ ID NO: 16, SEQ ID NO: 17 or SEQ ID NO: 18). In some embodiments, the nucleic acid molecule comprises a sequence encoding the polypeptide having a sequence at least 50%, 55%, 60%, 65%, 70%, 75%, 80%, 85%, 90%, 95%, 96%, 97%, 98%, 99% or 100% identical to the sequence shown in any one of SEQ ID NO: 25, SEQ ID NO: 26, SEQ ID NO: 27 or SEQ ID NO: 28, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof (e.g., a portion comprising amino acids 11-349, amino acids 18-349, amino acids 28-349, amino acids 38-349, or amino acids 39-349 of any one of SEQ ID NO: 25, SEQ ID NO: 26, SEQ ID NO: 27 or SEQ ID NO: 28).

In some embodiments, the nucleic acid molecule comprises a sequence selected from the group consisting of SEQ ID NO: 19, SEQ ID NO: 20, SEQ ID NO: 21 and SEQ ID NO: 22 or a fragment or variant thereof. In some embodiments, the nucleic acid molecule comprises a sequence encoding the polypeptide having a sequence at least 50%, 55%, 60%, 65%, 70%, 75%, 80%, 85%, 90%, 95%, 96%, 97%, 98%, 99% or 100% identical to the sequence shown in any one of SEQ ID NO: 19, SEQ ID NO: 20, SEQ ID NO: 21 and SEQ ID NO: 22, or a sequence at least 50%, 55%, 60%, 65%, 70%, 75%, 80%, 85%, 90%, 95%, 96%, 97%, 98%, 99% or 100% identical to a portion thereof of any one of SEQ ID NO: 19, SEQ ID NO: 20, SEQ ID NO: 21, SEQ ID NO: 22, SEQ ID NO: 29, SEQ ID NO: 30, SEQ ID NO: 31 and SEQ ID NO: 32. In some embodiments, the nucleic acid molecule comprises a sequence selected from the group consisting of SEQ ID NO: 19, SEQ ID NO: 20, SEQ ID NO: 21, SEQ ID NO: 22, SEQ ID NO: 29, SEQ ID NO: 30, SEQ ID NO: 31 and SEQ ID NO: 32 or a fragment or variant thereof. In some embodiments, the nucleic acid molecule comprises a sequence encoding the polypeptide having a sequence at least 50%, 55%, 60%, 65%, 70%, 75%, 80%, 85%, 90%, 95%, 96%, 97%, 98%, 99% or 100% identical to the sequence shown in any one of SEQ ID NO: 19, SEQ ID NO: 20, SEQ ID NO: 21 and SEQ ID NO: 22, or a sequence at least 50%, 55%, 60%, 65%, 70%, 75%, 80%, 85%, 90%, 95%, 96%, 97%, 98%, 99% or 100% identical to a portion thereof of any one of SEQ ID NO: 29, SEQ ID NO: 30, SEQ ID NO: 31 and SEQ ID NO: 32.

The sensors, compositions, methods and uses of the present disclosure encompass polypeptides and nucleic acids having the sequences specified, or sequences substantially identical or similar thereto, e.g., sequences at least 30%, 35%, 40%, 45%, 50%, 55%, 60%, 65%, 70%, 75%, 80%, 85%, 90%, 95%, 96%, 97%, 98%, 99% or 100% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% or 100% identity to the sequence specified are termed substantially identical.

Resonance Energy Transfer

Binding of a carbohydrate, such as lactose, to the sensors of the present disclosure can result in a change in Resonance Energy Transfer (RET), including, but not limited to, bioluminescent resonance energy transfer ("BRET") and fluorescence resonance energy transfer ("FRET").

As used herein, "BRET" is a proximity assay based on the non-radiative transfer of energy between a bioluminescent protein donor and an acceptor molecule. "Bioluminescent resonance energy transfer" and "BRET" are used interchangeably.

As used herein, "FRET" is a proximity assay based on the non-radiative transfer of energy between two chromophores, for example, two fluorophores. "FRET" and "fluorescence resonance energy transfer" are used interchangeably.

In one aspect, the sensor molecule comprises a donor domain and an acceptor domain covalently attached to the transcription factor or fragment or variant thereof. In some embodiments, the donor domain is a chemiluminescent donor domain. In alternative embodiments, the donor domain is a fluorophore. In some embodiments, the acceptor domain is a fluorescent acceptor domain, such as a fluorophore.

In some embodiments, the donor domain is covalently attached to the N-terminus of the transcription factor or fragment or variant thereof and the acceptor domain is covalently attached to the C-terminus of the transcription factor or fragment or variant thereof. In alternative embodiments, the donor domain is covalently attached to the C-terminus of the transcription factor or fragment or variant thereof and the acceptor domain is covalently attached to the N-terminus of the transcription factor or fragment or variant thereof.

A. Donor Domain

The sensor molecules of the present disclosure comprise a donor domain. The donor domain is capable of serving as a donor domain in a resonance energy transfer pair (for example, in a BRET pair or a FRET pair) and, depending on context, is also referred to herein as a "resonance energy transfer donor domain". As used herein, the term "donor" means a molecule that emits light, for example a molecule which, when irradiated with light of a certain wavelength, emits light or a molecule which causes the emission of light as the result of a chemical reaction. Suitable donor domains include chemiluminescent domains and fluorescent domains.

In some preferred embodiments, the donor domain capable of serving as a donor domain in a BRET pair. For example, the donor domain can be a chemiluminescent donor domain. Chemiluminescence is the emission of energy with limited emission of heat (luminescence), as the result of a chemical reaction. The term "chemiluminescence" is used herein to encompass bioluminescence, which relies upon the activity of an enzyme. Non-enzymatic chemiluminescence is the result of chemical reactions between an organic dye and an oxidizing agent in the presence of a catalyst. Chemiluminescence emission occurs as the energy from the excited states of organic dyes, which are chemically induced, decays to ground state. The duration and the intensity of the chemiluminescence emission are mostly dependent on the extent of the chemical reagents present in the reaction solution.

In preferred embodiments, the chemiluminescent donor domain is a bioluminescent protein. As used herein, the term "bioluminescent protein" refers to any protein capable of acting on a suitable substrate to generate luminescence.

It is understood in the art that a bioluminescent protein is an enzyme which converts a substrate into an activated product which then releases energy as it relaxes. The activated product (generated by the activity of the bioluminescent protein on the substrate) is the source of the bioluminescent protein-generated luminescence that is transferred to the acceptor molecule.

There are a number of different bioluminescent proteins that can be employed in this invention (see, for example, Table 2). Light-emitting systems have been known and isolated from many luminescent organisms including bacteria, protozoa, coelenterates, molluscs, fish, millipedes, flies, fungi, worms, crustaceans, and beetles, particularly click beetles of genus Pyrophorus and the fire flies of the genera *Photinus, Photuris*, and *Luciola*. Additional organisms displaying bioluminescence are listed in WO 00/024878, WO 99/049019 and Viviani (2002).

TABLE 2

Exemplary bioluminescent proteins.

| Species | Name | Organism | MW kDa × $10^{-3}$ | Emission (nm) | Example of Substrate |
|---|---|---|---|---|---|
| Insect | FFluc | *Photinus pyralis* (North American Firefly) | ~61 | 560 | D-(−)-2-(6'-hydroxybenzothiazolyl)-$D^2$-thiazoline-4-carboxylic acid, HBTTCA ($C_{11}H_8N_2O_3S_2$) (luciferin) |
| Insect | FF'luc | *Luciola cruciata* (Japanese Firefly) | | 560-590 (many mutants) | Luciferin |
| Insect | | *Phengodid* beetles (railroad worms) | | | |
| Insect | | *Arachnocampa* spp. | | | Luciferin |
| Insect | | *Orphelia fultoni* (North American glow worm) | | | |
| Insect | Clluc | *Pyrophorus plagiophthalamus* (click beetle) | | 546, 560, 578 and 593 | Luciferin |
| Jellyfish | Aequorin | *Aequorea* | 44.9 | 460-470 | Coelenterazine |
| Sea pansy | RLuc | *Renilla reniformis* | 36 | 480 | Coelenterazine |
| Sea pansy (modified) | RLuc8 | *Renilla reniformis* (modified) | 36 | 487 (peak) | Coelenterazine/ Deep Blue C |
| Sea pansy (modified) | RLuc2 | *Renilla reniformis* (modified) M185V/Q235A | 36 | 480 | Coelenterazine |
| Sea pansy (modified) | RLuc 8.6-535 | *Renilla reniformis* (modified) | 36 | 535 | Coelenterazine |
| Sea pansy | Rmluc | *Renilla mullerei* | 36.1 | ~480 | Coelenterazine |
| Sea pansy | | *Renilla kollikeri* | | | |
| Crustacea (shrimp) | Vluc | *Vargula hilgendorfii* | ~62 | ~460 | Coelenterazine |
| Crustaeca | CLuc | *Cypridina* (sea firefly) | 75 | 465 | Coelenterazine/ Cypridina luciferin |

TABLE 2-continued

Exemplary bioluminescent proteins.

| Species | Name | Organism | MW kDa × 10⁻³ | Emission (nm) | Example of Substrate |
|---|---|---|---|---|---|
| Dinofagellate (marine alga) | | *Gonyaulax polyedra* | 130 | ~475 | Tetrapyrrole |
| Mollusc | | *Latia* (fresh water limpet) | 170 | 500 | Enol formate, terpene, aldehyde |
| Hydroid | | *Obelia biscuspidata* | ~20 | ~470 | Coelenterazine |
| Shrimp | | *Oplophorus gracilorostris* | 31 | 462 | Coelenterazine |
| Shrimp | | *Oplophorus gracilorostris* (NanoLuc) | 19 | ~460 | Furimazine |
| Others | Ptluc | *Ptilosarcus* | | ~490 | Coelenterazine |
| | Gluc | *Gaussia* | ~20 | ~475 | Coelenterazine |
| | Plluc | *Pleuromamma* | 22.6 | ~475 | Coelenterazine |

Any suitable bioluminescent protein can be used in the sensors of the present disclosure. One very well-known example is the class of proteins known as luciferases which catalyse an energy-yielding chemical reaction in which a specific biochemical substance, a luciferin (a naturally occurring fluorophore), is oxidized by an enzyme having a luciferase activity (Hastings, 1996). A great diversity of organisms, both prokaryotic and eukaryotic, including species of bacteria, algae, fungi, insects, fish and other marine forms can emit light energy in this manner and each has specific luciferase activities and luciferins which are chemically distinct from those of other organisms. Luciferin/luciferase systems are very diverse in form, chemistry and function. Bioluminescent proteins with luciferase activity are thus available from a variety of sources or by a variety of means. Examples of bioluminescent proteins with luciferase activity may be found in U.S. Pat. Nos. 5,229,285, 5,219,737, 5,843,746, 5,196,524, and 5,670,356. Two of the most widely used luciferases are: (i) *Renilla* luciferase (from *R. reniformis*), a 35 kDa protein, which uses coelenterazine as a substrate and emits light at 480 nm (Lorenz et al., 1991); and (ii) Firefly luciferase (from *Photinus pyralis*), a 61 kDa protein, which uses luciferin as a substrate and emits light at 560 nm (de Wet et al., 1987).

*Gaussia* luciferase (from *Gaussia princeps*) has been used in biochemical assays (Verhaegen et al., 2002). *Gaussia* luciferase is a 20 kDa protein that oxidises coelenterazine in a rapid reaction resulting in a bright light emission at 470 nm.

Luciferases useful for the present invention have also been characterized from Anachnocampa sp (WO 2007/019634). These enzymes are about 59 kDa in size and are ATP-dependent luciferases that catalyse luminescence reactions with emission spectra within the blue portion of the spectrum.

Biologically active variants or fragments of naturally occurring bioluminescent protein can readily be produced by those skilled in the art. Three examples of such variants useful for the invention are RLuc2 (Loening et al., 2006), RLuc8 (Loening et al., 2006) and RLuc8.6-535 (Loening et al., 2007) which are each variants of *Renilla* luciferase. In a further preferred embodiment, the sequence of the BRET chemiluminescent donor is chosen to have greater thermal stability than sensor molecules incorporating native *Renilla* luciferase sensors. RLuc2 or RLuc8 are convenient examples of suitable choices, which consequently exhibit ≥5× or ≥10× higher luminance than sensors incorporating the native *Renilla* luciferase sequence. Such enhanced luminance has significant benefits as it permits more economical use of reagents for any given time resolution.

Alternative, non-luciferase, bioluminescent proteins that can be employed in this invention are any enzymes which can act on suitable substrates to generate a luminescent signal. Specific examples of such enzymes are β-galactosidase, lactamase, horseradish peroxidase, alkaline phosphatase, β-glucuronidase and β-glucosidase. Synthetic luminescent substrates for these enzymes are well known in the art and are commercially available from companies, such as Tropix Inc. (Bedford, Mass., USA).

An example of a peroxidase useful for the present invention is described by Hushpulian et al., (2007).

In some embodiments, the bioluminescent protein is a luciferase, a (β-galactosidase, a lactamase, a horseradish peroxidase, an alkaline phosphatase, a β-glucuronidase or a β-glucosidase. In some embodiments, the bioluminescent protein is luciferase. Suitable luciferase include, but are not limited to a *Renilla* luciferase, a Firefly luciferase (e.g. PpyRE8, PpyRE10), a Coelenterate luciferase, a North American glow worm luciferase, a click beetle luciferase, a railroad worm luciferase, a bacterial luciferase, a *Gaussia* luciferase, Aequorin, an *Arachnocampa* luciferase, an *Oplophorus gracilirostris* luciferase or a biologically active variant or fragment of any one, or chimera of two or more, thereof. In one example, the preferred luciferase is RLuc8 or a variant thereof.

As used herein, a "biologically active fragment" is a portion of a polypeptide as described herein which maintains a defined activity of the full-length polypeptide. As used herein, a "biologically active variant" is a molecule which differs from a naturally occurring and/or defined molecule by one or more amino acids but maintains a defined activity, such as defined above for biologically active fragments. Biologically active variants are typically least 50%, more preferably at least 80%, more preferably at least 90%, more preferably at least 95%, more preferably at least 97%, and even more preferably at least 99% identical to the naturally occurring and/or defined molecule.

In a preferred embodiment, a bioluminescent protein with a small molecular weight is used to prevent an inhibition of the interaction due to steric hindrance. The bioluminescent protein preferably consists of a single polypeptide chain. Also the bioluminescent proteins preferably do not form oligomers or aggregates. The bioluminescent proteins *Renilla* luciferase, *Gaussia* luciferase and Firefly luciferase meet all or most of these criteria.

In some embodiments, the chemiluminescent donor domain is capable of modifying a substrate. As used herein, the term "substrate" refers to any molecule that can be used in conjunction with a chemiluminescent donor to generate or absorb luminescence. The choice of the substrate can impact on the wavelength and the intensity of the light generated by the chemiluminescent donor. In some embodiments, the bioluminescent protein has a substrate selected from luciferin, calcium, coelenterazine, furimazine or a derivative, analogue or stabilised derivative of coelenterazine, luciferin or furimazine.

Coelenterazine is a widely known substrate which occurs in cnidarians, copepods, chaetognaths, ctenophores, decapod shrimps, mysid shrimps, radiolarians and some fish taxa (Greer and Szalay, 2002). For *Renilla* luciferase for example, coelenterazine analogues/derivatives are available that result in light emission between 418 and 547 nm (Inouye et al., 1997, Loening et al., 2007). A coelenterazine analogue/derivative (400A, DeepBlueC) has been described emitting light at 400 nm with *Renilla* luciferase (WO 01/46691). Other examples of coelenterazine analogues/derivatives are EnduRen, Prolume purple, Prolume purple II, Prolume purple III, ViviRen and Furimazine. Other examples of coelenterazine analogues/derivatives include, but are not limited to, compounds disclosed in PCT/US2013057660 and US20140302539.

As used herein, the term "luciferin" is defined broadly and refers to a class of light-emitting biological pigments found in organisms capable of bioluminescence as well as synthetic analogues or functionally equivalent chemicals, which are oxidised in the presence of the enzyme luciferase to produce oxyluciferin and energy in the form of light. D-luciferin, or 2-(6-hydroxybenzothiazol-2-yl)-2-thiazoline-4-carboxylic acid, was first isolated from the firefly *Photinus pyralis*. Since then, various chemically distinct forms of luciferin have been discovered and studied from various different organisms, mainly from the ocean, for example fish and squid, however, many have been identified in land dwelling organisms, for example, worms, beetles and various other insects (Day et al., 2004; Viviani, 2002). As used herein, luciferin also includes derivatives or analogues of luciferin.

In addition to entirely synthetic luciferin, such as cyclic alkylaminoluciferin (CycLuc1), there are at least five general types of biologically evolved luciferin, which are each chemically different and catalysed by chemically and structurally different luciferases that employ a wide range of different cofactors. First, is firefly luciferin, the substrate of firefly luciferase, which requires ATP for catalysis (EC 1.13.12.7). Second, is bacterial luciferin, also found in some squid and fish, that consists of a long chain aldehyde and a reduced riboflavin phosphate. Bacterial luciferase is FMNH-dependent. Third, is dinoflagellate luciferin, a tetrapyrrolic chlorophyll derivative found in dinoflagellates (marine plankton), the organisms responsible for night-time ocean phosphorescence. Dinoflagellate luciferase catalyses the oxidation of dinoflagellate luciferin and consists of three identical and catalytically active domains. Fourth, is the imidazolopyrazine vargulin, which is found in certain ostracods and deep-sea fish, for example, Porichthys. Last, is coelenterazine (an imidazolpyrazine), the light-emitter of the protein Aequorin, found in radiolarians, ctenophores, cnidarians, squid, copepods, chaetognaths, fish and shrimp.

In some embodiments, the bioluminescent protein requires a co-factor. Examples of co-factors include, but are not necessarily limited to, ATP, magnesium, oxygen, $FMNH_2$, calcium, or a combination of any two or more thereof.

In a further embodiment, the resonance energy transfer donor domain is a fluorescent donor domain. The fluorescent donor domain can be a fluorescent protein or a non-protein. In some embodiments, the fluorescent donor domain is a non-protein. Non-limiting examples of fluorophores that are suitable for use as the donor domain include, but are not limited to, Alexa Fluor dye (e.g. AF680, AF750), Bodipy dye, Cy dye, fluorescein, dansyl, umbelliferone, fluorescent dye, fluorescent microsphere, luminescent microsphere, fluorescent nanocrystal, Marina Blue, Cascade Blue, Cascade Yellow, Pacific Blue, Oregon Green, Tetramethylrhodamine, Rhodamine, Texas Red, rare earth element chelates, or any combination or derivatives thereof.

In some embodiments the donor domain is a fluorescent protein. Non-limiting examples include proteins such as green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pocilloporin, *Renilla* GFP, Monster GFP, paGFP, TdTomato, mCherry, Kaede protein, TagRFP, TurBoFB or a Phycobiliprotein, or a biologically active variant or fragment of any one thereof. In some embodiments, the preferred fluorescent donor domain is CFP.

B. Acceptor Domain

The sensor molecules of the present disclosure also comprise an acceptor domain. The acceptor domain is capable of serving as an acceptor domain in a resonance energy transfer pair (for example, in a BRET pair or a FRET pair) and, depending on context, is also referred to herein as a "resonance energy transfer acceptor domain". As used herein, an "acceptor domain" is any molecule that is capable of accepting energy emitted as a result of the activity of the donor domain.

In some embodiments, the acceptor domain (also referred to herein as "acceptor molecule") is a fluorescent acceptor domain. As used herein, the term "fluorescent acceptor domain" (also referred herein to as "fluorescent acceptor molecule") refers to any compound which can accept energy emitted as a result of the activity of a donor domain, and re-emit it as light energy.

There are a number of different acceptor domains that can be employed in this invention. Suitable acceptor domains may be a protein or non-proteinaceous.

In some embodiments, the fluorescent acceptor domain is a fluorescent protein. One very well-known example is the group of fluorophores that includes the green fluorescent protein from the jellyfish *Aequorea victoria* and numerous other variants (GFPs) arising from the application of molecular biology, for example mutagenesis and chimeric protein technologies (Tsien, 1998). GFPs are classified based on the distinctive component of their chromophores, each class having distinct excitation and emission wavelengths: class 1, wild-type mixture of neutral phenol and anionic phenolate: class 2, phenolate anion: class 3, neutral phenol: class 4, phenolate anion with stacked s-electron system: class 5, indole: class 6, imidazole: and class 7, phenyl.

A naturally occurring acceptor molecule which has been mutated (variants) can also be useful for the present invention. One example of an engineered system which is suitable for BRET is a *Renilla* luciferase and enhanced yellow mutant of GFP (EYFP) pairing which do not directly interact to a significant degree with one another alone in the absence of a mediating protein(s) (in this case, the G protein coupled receptor) (Xu et al., 1999).

Examples include, but are not limited to, green fluorescent protein (GFP), blue fluorescent variant of GFP (BFP), cyan fluorescent variant of GFP (CFP), yellow fluorescent variant of GFP (YFP), enhanced GFP (EGFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pocilloporin, *Renilla* GFP, Monster GFP, paGFP, Kaede protein, TdTomato, mCherry, TagRFP, TurBoFB or a Phycobiliprotein, or a biologically active variant or fragment of any one thereof. In some embodiments, the preferred fluorescent acceptor domain is $GFP^2$. In other embodiments, the preferred fluorescent acceptor domain is YFP.

In some embodiments, the fluorescent acceptor domain is a non-protein. Examples of acceptor molecules that are not proteins include, but are not limited to, Alexa Fluor dye (e.g. AF680, AF750), Bodipy dye, Cy dye, fluorescein, dansyl, umbelliferone, fluorescent microsphere, luminescent microsphere, fluorescent nanocrystal, Marina Blue, Cascade Blue, Cascade Yellow, Pacific Blue, Oregon Green, Tetramethylrhodamine, Rhodamine, Texas Red, rare earth element chelates, or any combination or derivatives thereof.

C. Donor Domain and Acceptor Domain Pairs

Any number of donor-acceptor combinations can be used in the sensors of the present invention. The donor-acceptor combination should be capable of serving as a BRET pair or a FRET pair. A worker skilled in the art would be able to select a donor and acceptor pair which permits efficient energy transfer.

In preferred embodiments, the separation and relative orientation of the donor domain and the acceptor domain, in the presence and/or absence of the carbohydrate, is within ±50% of the Förster distance. As used herein, the term "the separation and relative orientation of the donor domain and the acceptor domain, in the presence and/or the absence of carbohydrate, is within ±50% of the Förster distance" refers to the steady state RET measurements which can be carried out within a range of ±50% of Ro. This phrase encompasses an efficiency of luminescence energy transfer from the donor domain to the acceptor domain in the range of 10-90%. In some embodiments, the Förster distance of the chemiluminescent donor domain and the acceptor domain is at least 4 nm, is at least 5.6 nm, or is at least 6 nm. In some embodiments, the Förster distance is less than 12 nm, less than 11 nm, less than 10 nm or less than 9 nm. In some embodiments, the Förster distance of the donor domain and the acceptor domain is between about 4 nm and about 11 nm, is between about 5.6 nm and about 11 nm or is between about 7 nm and about 11 nm. Without wishing to be bound by theory, the inventors believe that the Förster distance of the donor domain and the acceptor domain matches the size of the carbohydrate binding domain useful in the sensors of the present application. The carbohydrate binding domain may be, for example, a full length HTH transcription factor, a fragment thereof that retains carbohydrate binding activity, a carbohydrate binding domain of a HTH transcription factor, or a variant thereof.

A criterion which should be considered in determining suitable pairings is the relative emission/fluorescence spectrum of the acceptor molecule compared to that of the donor. The emission spectrum of the donor should overlap with the absorbance spectrum of the acceptor molecule such that the light energy from the donor emission is at a wavelength that is able to excite the acceptor molecule and thereby promote acceptor molecule fluorescence when the two molecules are in a proper proximity and orientation with respect to one another. For example, it has been demonstrated that a *Renilla* luciferase/EGFP pairing is not as good as a *Renilla* luciferase/EYEF pairing based on observable emission spectral peaks (Xu et al., 1999; Wang et al., (1997) in Bioluminescence and Chemiluminescence: Molecular Reporting with Photons, eds. Hastings et al., (Wiley, New York), pp. 419-422). To study potential pairing, protein fusions (for example) are prepared containing the selected donor and acceptor domains and are tested, in the presence of an appropriate substrate if required.

It should also be confirmed that the donor and acceptor domains do not spuriously associate with each other. For example, this can be accomplished by separate co-expression of a bioluminescent protein and acceptor molecule in the same cells and then monitoring the luminescence spectrum in order to determine if BRET occurs. This may be achieved, for example, using the method of Xu et al., (1999). The selected bioluminescent protein and acceptor molecule form a suitable BRET pair if little or no BRET is observed. Similar experiments can be performed for FRET pairs.

In some embodiments, the sensor molecules of the present disclosure comprise a chemiluminescent donor domain and fluorescent acceptor domain.

In some embodiments, the donor emission can be manipulated by modifications to the substrate. In the case of *Renilla* luciferases the substrate is coelenterazine. The rationale behind altering the donor emission is to improve the resolution between donor emission and acceptor emissions. The original BRET system uses the *Renilla* luciferase as donor, EYFP (or Topaz) as the acceptor and coelenterazine h derivative as the substrate. These components when combined in a BRET assay, generate light in the 475-480 nm range for the bioluminescent protein and the 525-530 nm range for the acceptor molecule, giving a spectral resolution of 45-55 nm.

Unfortunately, *Renilla* luciferase generates a broad emission peak overlapping substantially the GFP emission, which in turn contributes to decrease the signal to noise of the system. One BRET system for use in the present invention has coel400a as the *Renilla* luciferase substrate and provides broad spectral resolution between donor and acceptor emission wavelengths (~105 nm). *Renilla* luciferase with coe400a generates light between 390-400 nm and a GFP derivative ($GFP^2$) was prepared which absorbs light in this range and re-emits light at 505-508 nm. Because of this increase in spectral resolution between *Renilla* luciferase and GFP emissions, this BRET system provides an excellent biological tool to monitor binding of a carbohydrate to the sensors of the present application. However, smaller Stokes shift BRET systems would also allow sensitive measurement of carbohydrates.

Various coelenterazine derivatives are known in the art, including coel400a, that generate light at various wavelengths (distinct from that generated by the wild type coelenterazine) as a result of *Renilla* luciferase activity. A worker skilled in the art would appreciate that because the light emission peak of the donor has changed, it is necessary to select an acceptor molecule which will absorb light at this wavelength and thereby permit efficient energy transfer. This can be done, for example by altering a GFP class 4 such that it becomes a class 3 or 1 GFP. Spectral overlapping between light emission of the donor and the light absorption peak of the acceptor is one condition among others for an efficient energy transfer. Class 3 and 1 GFPs are known to absorb light at 400 nm and re-emit between 505-511 nm. This results in a wavelength difference between donor and acceptor emissions of approximately 111 nm.

Examples of further bioluminescent protein and acceptor molecule pairs are provided in Table 3.

TABLE 3

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| RLuc2 RLuc8 | Native coelenterazine | 470 nm | Venus | 515/528 nm |
| RLuc2 RLuc8 | Native coelenterazine | 470 nm | mOrange | 548/562 nm |
| RLuc2 RLuc8 | Native Coelenterazine | 470 nm | EYFP/Topaz | 514/527 nm |
| RLuc2 RLuc8 | Native Coelenterazine | 470 nm | mCitrine | 516/529 nm |
| RLuc RLuc2 RLuc8 | Native Coelenterazine | 470 nm | YPet | 517/530 nm |
| RLuc2 RLuc8 | Native Coelenterazine | 470 nm | Fluorescein | 495/519 nm |
| RLuc2 RLuc8 | Native Coelenterazine | 470 nm | Acridine yellow | 470/550 nm |
| RLuc2 RLuc8 | Native Coelenterazine | 470 nm | Nile red | 485/525 nm |
| RLuc2 RLuc8 | Native Coelenterazine | 470 nm | R-Phycoerythrin | 480/578 nm |
| RLuc2 RLuc8 | Native Coelenterazine | 470 nm | Red 613 | 480/613 nm |
| RLuc2 RLuc8 | Native Coelenterazine | 470 nm | TruRed | 490/695 nm |
| RLuc8.6-5.35 | Native Coelenterazine | 535 nm | mOrange | 548/562 nm |
| RLuc8.6-5.35 | Coelenterazine h | 535 nm | TagRFP | 555/584 nm |
| RLuc8.6-5.35 | Coelenterazine h | 535 nm | TurboRFP | 588/635 nm |
| RLuc RLuc2 RLuc8 | Coelenterazine v | 515 nm | mOrange | 548/562 nm |
| RLuc RLuc2 RLuc8 | Coelenterazine v | 515 nm | TagRFP | 555/584 nm |
| RLuc8.6-5.35 | Coelenterazine v | 570 nm | TurboRFP | 588/635 nm |
| RLuc2 RLuc8 | Coelenterazine h | 470 nm | Venus | 515/528 nm |
| RLuc2 RLuc8 | Coelenterazine h | 470 nm | mOrange | 548/528 nm |
| RLuc2 RLuc8 | Coelenterazine h | 470 nm | EYFP/Topaz | 514/527 nm |
| RLuc2 RLuc8 | Coelenterazine h | 470 nm | mCitrine | 516/529 nm |
| RLuc2 RLuc8 | Native Coelenterazine | 470 nm | YPet | 517/530 nm |
| RLuc RLuc2 RLuc8 | Coelenterazine h | 470 nm | Fluorescein | 490/525 nm |
| RLuc RLuc2 RLuc8 | Coelenterazine h | 470 nm | Acridine yellow | 470/550 nm |
| RLuc RLuc2 RLuc8 | Coelenterazine h | 470 nm | Nile red | 485/525 nm |
| RLuc RLuc2 RLuc8 | Coelenterazine h | 470 nm | R-Phycoerythrin | 480/578 nm |
| RLuc RLuc2 RLuc8 | Coelenterazine h | 470 nm | Red 613 | 480/613 nm |
| RLuc RLuc2 RLuc8 | Coelenterazine h | 470 nm | TruRed | 490/695 nm |
| RLuc8.6-5.35 | Coelenterazine h | 535 nm | mOrange | 548/562 nm |
| RLuc RLuc2 RLuc8 | Coelenterazine 400a | 400 nm | GFP$^2$ | 396/508 nm |
| RLuc RLuc2 RLuc8 | Coelenterazine 400a | 400 nm | GFP10 | 400/510 nm |

TABLE 3-continued

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| RLuc RLuc2 RLuc8 | Coelenterazine 400a | 400 nm | Wild type GFP | 396 (475)/508 nm |
| RLuc RLuc2 RLuc8 | Coelenterazine 400a | 400 nm | TagBFP | 402/457 nm |
| RLuc RLuc2 RLuc8 | Coelenterazine 400a | 400 nm | Cerulean/mCFP | 433/475 nm |
| RLuc RLuc2 RLuc8 | Coelenterazine 400a | 400 nm | ECFP/CyPet | 434/477 nm |
| RLuc RLuc2 RLuc8 | Coelenterazine 400a | 400 nm | Y66W | 436/485 nm |
| RLuc RLuc2 RLuc8 | Coelenterazine 400a | 400 nm | dKeima-Red | 440/616 nm |
| RLuc RLuc2 RLuc8 | Coelenterazine 400a | 400 nm | mKeima-Red | 440/620 nm |
| RLuc RLuc2 RLuc8 | Coelenterazine 400a | 400 nm | Quin-2 | 365/490 nm |
| RLuc RLuc2 RLuc8 | Coelenterazine 400a | 400 nm | Pacific blue | 403/551 nm |
| RLuc RLuc2 RLuc8 | Coelenterazine 400 | 400 nm | Dansychloride | 380/475 nm |
| Firefly luciferase | Luciferin | 560 nm | Cyanine Cy3 | 575/605 nm |
| Firefly luciferase | Luciferin | 560 nm | Texas red | 590/615 nm |
| Firefly luciferase | Luciferin | 560 nm | TurboRed | 553/574 nm |
| Firefly luciferase | Luciferin | 560 nm | tdTomato | 554/581 nm |
| Firefly luciferase | Luciferin | 560 nm | TagRFP | 555/584 nm |
| Firefly luciferase | Luciferin | 560 nm | DsRed | 557/592 nm |
| Firefly luciferase | Luciferin | 560 nm | mRFP1 | 584/607 nm |
| Firefly luciferase | Luciferin | 560 nm | mCherry | 587/610 nm |
| Beetle green luciferase | Luciferin | 560 nm | tdTomato | 554/581 nm |
| FFLuc PpyRE8 PpyRE10 | Luciferin | 560 nm | AF680 | 679/702 nm |
| FFLuc PpyRE8 PpyRE10 | Luciferin | 560 nm | AF750 | 749/775 nm |
| NanoLuc | Furimazine | 460 nm | Venus | 515/528 nm |
| NanoLuc | Furimazine | 460 nm | mOrange | 548/562 nm |
| NanoLuc | Furimazine | 460 nm | EYFP/Topaz | 514/527 nm |
| NanoLuc | Furimazine | 460 nm | mCitrine | 516/529 nm |
| NanoLuc | Furimazine | 460 nm | YPet | 517/530 nm |
| NanoLuc | Furimazine | 460 nm | Fluorescein | 495/519 nm |
| NanoLuc | Furimazine | 460 nm | Acridine yellow | 470/550 nm |
| NanoLuc | Furimazine | 460 nm | Nile red | 485/525 nm |
| NanoLuc | Furimazine | 460 nm | R-Phycoerythrin | 480/487 nm |
| NanoLuc | Furimazine | 460 nm | Red 613 | 480/613 nm |
| NanoLuc | Furimazine | 460 nm | TruRed | 490/695 nm |
| NanoLuc | Furimazine | 460 nm | Oregon Green | 496/516 nm |
| NanoLuc | Furimazine | 460 nm | diAcFAM | 494/526 nm |
| NanoLuc | Furimazine | 460 nm | AlexFluor488 | 494/517 nm |
| NanoLuc | Furimazine | 460 nm | TMR | 555/585 nm |
| NanoLuc | Furimazine | 460 nm | Halotag NCT | 595/635 nm |
| NanoLuc | Furimazine | 460 nm | HalotagBRET 618 | 525/618 nm |
| NanoLuc | Native Coelenterazine | 460 nm | Venus | 515/528 nm |
| NanoLuc | Native Coelenterazine | 460 nm | mOrange | 548/562 nm |

TABLE 3-continued

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| NanoLuc | Native Coelenterazine | 460 nm | EYFP/Topaz | 514/527 nm |
| NanoLuc | Native Coelenterazine | 460 nm | mCitrine | 516/529 nm |
| NanoLuc | Native Coelenterazine | 460 nm | YPet | 517/530 nm |
| NanoLuc | Native Coelenterazine | 460 nm | Fluorescein | 495/519 nm |
| NanoLuc | Native Coelenterazine | 460 nm | Acridine yellow | 470/550 nm |
| NanoLuc | Native Coelenterazine | 460 nm | Nile red | 485/525 nm |
| NanoLuc | Native Coelenterazine | 460 nm | R-Phycoerythrin | 480/487 nm |
| NanoLuc | Native Coelenterazine | 460 nm | Red 613 | 480/613 nm |
| NanoLuc | Native Coelenterazine | 460 nm | TruRed | 490/695 nm |
| NanoLuc | Native Coelenterazine | 460 nm | Oregon Green | 496/516 nm |
| NanoLuc | Native Coelenterazine | 460 nm | diAcFAM | 494/526 nm |
| NanoLuc | Native Coelenterazine | 460 nm | AlexFluor488 | 494/517 nm |
| NanoLuc | Native Coelenterazine | 460 nm | TMR | 555/585 nm |
| NanoLuc | Native Coelenterazine | 460 nm | Halotag NCT | 595/635 nm |
| NanoLuc | Native Coelenterazine | 460 nm | HalotagBRET 618 | 525/618 |
| NanoLuc | Native Coelenterazine | 460 nm | Oregon Green | 496/516 nm |
| NanoLuc | Native Coelenterazine | 460 nm | diAcFAM | 494/526 nm |
| NanoLuc | Native Coelenterazine | 460 nm | AlexFluor488 | 494/517 nm |
| NanoLuc | Native Coelenterazine | 460 nm | TMR | 555/585 nm |
| NanoLuc | Native Coelenterazine | 460 nm | Halotag NCT | 595/635 nm |
| NanoLuc | Native Coelenterazine | 460 nm | HalotagBRET 618 | 525/618 |
| NanoLuc | Coelenterazine h | 460 nm | Venus | 515/528 nm |
| NanoLuc | Coelenterazine h | 460 nm | mOrange | 548/562 nm |
| NanoLuc | Coelenterazine h | 460 nm | EYFP/Topaz | 514/527 nm |
| NanoLuc | Coelenterazine h | 460 nm | mCitrine | 516/529 nm |
| NanoLuc | Coelenterazine h | 460 nm | YPet | 517/530 nm |
| NanoLuc | Coelenterazine h | 460 nm | Fluorescein | 495/519 nm |
| NanoLuc | Coelenterazine h | 460 nm | Acridine yellow | 470/550 nm |
| NanoLuc | Coelenterazine h | 460 nm | Nile red | 485/525 nm |
| NanoLuc | Coelenterazine h | 460 nm | R-Phycoerythrin | 480/487 nm |
| NanoLuc | Coelenterazine h | 460 nm | Red 613 | 480/613 nm |
| NanoLuc | Coelenterazine h | 460 nm | TruRed | 490/695 nm |
| NanoLuc | Coelenterazine h | 460 nm | Oregon Green | 496/516 nm |
| NanoLuc | Coelenterazine h | 460 nm | diAcFAM | 494/526 nm |
| NanoLuc | Coelenterazine h | 460 nm | AlexFluor488 | 494/517 nm |
| NanoLuc | Coelenterazine h | 460 nm | TMR | 555/585 nm |
| NanoLuc | Coelenterazine h | 460 nm | Halotag NCT | 595/635 nm |
| NanoLuc | Coelenterazine h | 460 nm | HalotagBRET 618 | 525/618 |
| RLuc RLuc2 RLuc8 | Prolume Purple Substrate | 405 nm | GFP$^2$ | 396/508 nm |
| RLuc RLuc2 RLuc8 | Prolume Purple Substrate | 405 nm | GFP10 | 400/510 nm |
| RLuc RLuc2 RLuc8 | Prolume Purple Substrate | 405 nm | Wild type GFP | 396 (475)/508 nm |
| RLuc RLuc2 RLuc8 | Prolume Purple Substrate | 405 nm | TagBFP | 402/457 nm |
| RLuc RLuc2 RLuc8 | Prolume Purple Substrate | 405 nm | Cerulean/mCFP | 433/475 nm |

TABLE 3-continued

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| RLuc RLuc2 RLuc8 | Prolume Purple Substrate | 405 nm | ECFP/CyPet | 434/477 nm |
| RLuc RLuc2 RLuc8 | Prolume Purple Substrate | 405 nm | Y66W | 436/485 nm |
| RLuc RLuc2 RLuc8 | Prolume Purple Substrate | 405 nm | dKeima-Red | 440/616 nm |
| RLuc RLuc2 RLuc8 | Prolume Purple Substrate | 405 nm | mKeima-Red | 440/620 nm |
| RLuc RLuc2 RLuc8 | Prolume Purple Substrate | 405 nm | Quin-2 | 365/490 nm |
| RLuc RLuc2 RLuc8 | Prolume Purple Substrate | 405 nm | Pacific blue | 403/551 nm |
| RLuc RLuc2 RLuc8 | Prolume Purple Substrate | 405 nm | Dansychloride | 380/475 nm |
| RLuc RLuc2 RLuc8 | Prolume Purple Substrate II | 400 nm | GFP$^2$ | 396/508 nm |
| RLuc RLuc2 RLuc8 | Prolume Purple Substrate II | 400 nm | GFP10 | 400/510 nm |
| RLuc RLuc2 RLuc8 | Prolume Purple Substrate II | 400 nm | Wild type GFP | 396 (475)/508 nm |
| RLuc RLuc2 RLuc8 | Prolume Purple Substrate II | 400 nm | TagBFP | 402/457 nm |
| RLuc RLuc2 RLuc8 | Prolume Purple Substrate II | 400 nm | Cerulean/mCFP | 433/475 nm |
| RLuc RLuc2 RLuc8 | Prolume Purple Substrate II | 400 nm | ECFP/CyPet | 434/477 nm |
| RLuc RLuc2 RLuc8 | Prolume Purple Substrate II | 400 nm | Y66W | 436/485 nm |
| RLuc RLuc2 RLuc8 | Prolume Purple Substrate II | 400 nm | dKeima-Red | 440/616 nm |
| RLuc RLuc2 RLuc8 | Prolume Purple Substrate II | 400 nm | mKeima-Red | 440/620 nm |
| RLuc RLuc2 RLuc8 | Prolume Purple Substrate II | 400 nm | Quin-2 | 365/490 nm |
| RLuc RLuc2 RLuc8 | Prolume Purple Substrate II | 400 nm | Pacific blue | 403/551 nm |
| RLuc RLuc2 RLuc8 | Prolume Purple Substrate II | 400 nm | Dansychloride | 380/475 nm |
| RLuc RLuc2 RLuc8 | Prolume Purple Substrate III | 410 nm | GFP$^2$ | 396/508 nm |
| RLuc RLuc2 RLuc8 | Prolume Purple Substrate III | 410 nm | GFP10 | 400/510 nm |
| RLuc RLuc2 RLuc8 | Prolume Purple Substrate III | 410 nm | Wild type GFP | 396 (475)/508 nm |
| RLuc RLuc2 RLuc8 | Prolume Purple Substrate III | 410 nm | TagBFP | 402/457 nm |
| RLuc RLuc2 RLuc8 | Prolume Purple Substrate III | 410 nm | Cerulean/mCFP | 433/475 nm |
| RLuc RLuc2 RLuc8 | Prolume Purple Substrate III | 410 nm | ECFP/CyPet | 434/477 nm |

TABLE 3-continued

Exemplary BRET bioluminescent proteins and acceptor molecule pairs.

| BDP | Substrate | Substrate wavelength (peak) | Fluorescence acceptor molecule | Wavelength of acceptor (Ex/Em) |
|---|---|---|---|---|
| RLuc<br>RLuc2<br>RLuc8 | Prolume Purple<br>Substrate III | 410 nm | Y66W | 436/485 nm |
| RLuc<br>RLuc2<br>RLuc8 | Prolume Purple<br>Substrate III | 410 nm | dKeima-Red | 440/616 nm |
| RLuc<br>RLuc2<br>RLuc8 | Prolume Purple<br>Substrate III | 410 nm | mKeima-Red | 440/620 nm |
| RLuc<br>RLuc2<br>RLuc8 | Prolume Purple<br>Substrate III | 410 nm | Quin-2 | 365/490 nm |
| RLuc<br>RLuc2<br>RLuc8 | Prolume Purple<br>Substrate III | 410 nm | Pacific blue | 403/551 nm |
| RLuc<br>RLuc2<br>RLuc8 | Prolume Purple<br>Substrate III | 410 nm | Dansychloride | 380/475 nm |

In some embodiments, the preferred bioluminescent protein and acceptor domain pair is RLuc8 and GFP$^2$.

In some embodiments, the sensor molecules of the present disclosure comprise a fluorescent donor domain and a fluorescent acceptor domain.

Any appropriately selected fluorophore can be used as the donor and/or acceptor, provided that the emission spectrum of the donor overlaps sufficiently with the excitation spectrum of the acceptor. A criterion which should be considered in determining suitable pairings is the excitation spectrum of the acceptor molecule compared to that of the donor. As the person skilled in the art would appreciate there should be minimum direct excitation of the acceptor domain at the excitation maximum of the donor domain.

Examples of further fluorescent donor and acceptor domain pairs are provided in Table 4. Other examples of fluorescent donor and acceptor domain pairs are discussed in Bajar et al. (2016).

TABLE 4

Exemplary FRET fluorescent donor and acceptor domain pairs.

| Fluorescent donor | Wavelength of accentor (Em) | Fluorescence acceptor molecule | Wavelength of acceptor (Exc) |
|---|---|---|---|
| FITC | 520 nm | TRITC | 550 nm |
| Cy3 | 566 nm | Cy5 | 649 nm |
| EGFP | 508 nm | Cy3 | 554 nm |
| CFP | 477 nm | YFP | 514 nm |
| EGFP | 508 nm | YFP | 514 nm |
| GFP$^2$ | | YFP | 514 nm |
| ECFP | 475 nm | EYFP | 513 nm |
| mTurquioise2 | 474 nm | mCitrine | 516 nm |
| mClover3 | 518 nm | mRuby3 | 558 nm |
| eqFP650 | 650 nm | iRFP | 690 nm |
| mAmetrine | 526 nm | tdTomato | 554 nm |

In some embodiments, the preferred donor domain and acceptor domain pair is CFP and YFP.

Carbohydrate Binding

Binding of a carbohydrate to the carbohydrate binding domain of the sensors of the present disclosure alters the spatial location and/or dipole orientation of the donor domain relative to the acceptor domain. In some embodiments, the alteration in spatial location and/or dipole orientation results in a change in BRET. In some embodiments, the alteration in spatial location and/or dipole orientation results in a change in FRET.

As used herein, the term "spatial location" refers to the three dimensional positioning of the donor relative to the acceptor molecule which changes as a result of the analyte binding or releasing from the sensor molecule.

As used herein, the term "dipole orientation" refers to the direction in three-dimensional space of the dipole moment associated either with the donor and/or the acceptor molecule relative their orientation in three-dimensional space. The dipole moment is a consequence of a variation in electrical charge over a molecule.

Using BRET as an example, in an embodiment the energy transfer occurring between the bioluminescent protein and acceptor molecule is presented as calculated ratios from the emissions measured using optical filters (one for the acceptor molecule emission and the other for the bioluminescent protein emission) that select specific wavelengths (see equation 1).

$$E_a/E_d = \text{BRET ratio} \qquad (1)$$

where $E_a$ is defined as the acceptor molecule emission intensity (emission light is selected using a specific filter adapted for the emission of the acceptor) and $E_d$ is defined as the bioluminescent protein emission intensity (emission light is selected using a specific filter adapted for the emission of the bioluminescent protein).

It should be readily appreciated by those skilled in the art that the optical filters may be any type of filter that permits wavelength discrimination suitable for BRET. For example, optical filters used in accordance with the present invention can be interference filters, long pass filters, short pass filters, etc. Intensities (usually in counts per second (CPS) or relative luminescence units (RLU)) of the wavelengths passing through filters can be quantified using either a photo-multiplier tube (PMT), photodiode, including a cascade photodiode, photodiode array or a sensitive camera such as a charge coupled device (CCD) camera. The quantified signals are subsequently used to calculate BRET ratios and represent energy transfer efficiency. The BRET ratio increases with increasing intensity of the acceptor emission.

Generally, a ratio of the acceptor emission intensity over the donor emission intensity is determined (see equation 1), which is a number expressed in arbitrary units that reflects energy transfer efficiency. The ratio increases with an increase of energy transfer efficiency (see Xu et al., 1999). Energy transfer efficiencies can also be represented using the inverse ratio of donor emission intensity over acceptor emission intensity (see equation 2). In this case, ratios decrease with increasing energy transfer efficiency. Prior to performing this calculation the emission intensities are corrected for the presence of background light and auto-luminescence of the substrate. This correction is generally made by subtracting the emission intensity, measured at the appropriate wavelength, from a control sample containing the substrate but no bioluminescent protein, acceptor molecule or polypeptide of the invention.

$$E_d/E_a = \text{BRET ratio} \quad (2)$$

where $E_a$ and $E_d$ are as defined above.

The light intensity of the bioluminescent protein and acceptor molecule emission can also be quantified using a monochromator-based instrument such as a spectrofluorometer, a charged coupled device (CCD) camera or a diode array detector. Using a spectrofluorometer, the emission scan is performed such that both bioluminescent protein and acceptor molecule emission peaks are detected upon addition of the substrate. The areas under the peaks represent the relative light intensities and are used to calculate the ratios, as outlined above. Any instrument capable of measuring lights for the bioluminescent protein and acceptor molecule from the same sample, can be used to monitor the BRET system of the present invention.

In an alternative embodiment, the acceptor molecule emission alone is suitable for effective detection and/or quantification of BRET. In this case, the energy transfer efficiency is represented using only the acceptor emission intensity. It would be readily apparent to one skilled in the art that in order to measure energy transfer, one can use the acceptor emission intensity without making any ratio calculation. This is due to the fact that ideally the acceptor molecule will emit light only if it absorbs the light transferred from the bioluminescent protein. In this case only one light filter is necessary.

In a related embodiment, the bioluminescent protein emission alone is suitable for effective detection and/or quantification of BRET. In this case, the energy transfer efficiency is calculated using only the bioluminescent protein emission intensity. It would be readily apparent to one skilled in the art that in order to measure energy transfer, one can use the donor emission intensity without making any ratio calculation. This is due to the fact that as the acceptor molecule absorbs the light transferred from the bioluminescent protein there is a corresponding decrease in detectable emission from the bioluminescent protein. In this case only one light filter is necessary.

In an alternative embodiment, the energy transfer efficiency is represented using a ratiometric measurement which only requires one optical filter for the measurement. In this case, light intensity for the donor or the acceptor is determined using the appropriate optical filter and another measurement of the samples is made without the use of any filter (intensity of the open spectrum). In this latter measurement, total light output (for all wavelengths) is quantified. Ratio calculations are then made using either equation 3 or 4. For the equation 3, only the optical filter for the acceptor is required. For the equation 4, only the optical filter for the donor is required.

$$E_a/E_o - E_a = \text{BRET ratio or} = E_o - E_a/E_a \quad (3)$$

$$E_o - E_d/E_d = \text{BRET ratio or} = E_d/E_o - E_d \quad (4)$$

where $E_a$ and $E_d$ are as defined above and $E_o$ is defined as the emission intensity for all wavelengths combined (open spectrum).

It should be readily apparent to one skilled in the art that further equations can be derived from equations 1 through 4. For example, one such derivative involves correcting for background light present at the emission wavelength for bioluminescent protein and/or acceptor molecule.

In performing a BRET assay, light emissions can be determined from each well using the BRETCount. The BRETCount instrument is a modified TopCount, wherein the TopCount is a microtiterplate scintillation and luminescence counter sold by Packard Instrument (Meriden, Conn.). Unlike classical counters which utilise two photomultiplier tubes (PMTs) in coincidence to eliminate background noise, TopCount employs single-PMT technology and time-resolved pulse counting for noise reduction to allow counting in standard opaque microtiter plates. The use of opaque microtiterplates can reduce optical crosstalk to negligible level. TopCount comes in various formats, including 1, 2, 6 and 12 detectors (PMTs), which allow simultaneous reading of 1, 2, 6 or 12 samples, respectively. Beside the BRETCount, other commercially available instruments are capable of performing BRET: the Victor 2 (Wallac, Finland (Perkin Elmer Life Sciences)) and the Fusion (Packard Instrument, Meriden). BRET can be performed using readers that can detect at least the acceptor molecule emission and preferably two wavelengths (for the acceptor molecule and the bioluminescent protein) or more.

BRET is a ratiometric technique which can eliminate data variability caused by fluctuations in light output due to variations in assay volume, assay conditions and signal decay across different wells in a plate. RET-based reactions are homogeneous, generally occurring in solution without solid-phase attachment. This allows for detection of analytes in different forms such as liquid, gas and even particulates without separation.

Lactose Sensor Molecule

One non-limiting example of a sensor molecule as defined herein is a sensor molecule that can used to detect and/or measure lactose concentration. Accordingly, in some embodiments the present disclosure provides a sensor molecule for detecting lactose comprising a bacterial transcription factor which is capable of binding lactose or variant thereof, covalently joined to a resonance energy transfer donor domain and a resonance energy transfer acceptor domain, wherein the spatial location and/or dipole orientation of the donor domain relative to the acceptor domain is altered when lactose binds to the transcription factor. In some embodiments, the present disclosure provides a sensor molecule for detecting lactose comprising a bacterial BgaR transcription factor or variant thereof, covalently joined to a resonance energy transfer donor domain and a resonance energy transfer acceptor domain, wherein the spatial location and/or dipole orientation of the donor domain relative to the acceptor domain is altered when lactose binds to the transcription factor. Binding of lactose to the sensor produces a change in resonance energy transfer (RET) such that a change in RET indicates lactose is present. Depending on the chosen donor domain and acceptor domain the change in RET can be a change in BRET or a change in FRET.

In some embodiments, the BgaR transcription factor or variant thereof has an amino acid sequence which is at least 50%, 60%, 70%, 80%, 85%, 90%, 95%, 98%, 99% or 100% identical to that provided in SEQ ID NO: 1, or a sequence at least 30%, 35%, 40%, 45%, 50%, 55%, 60%, 65%, 70%, 75%, 80%, 85%, 90%, 95%, 96%, 97%, 98%, 99% or 100% identical to a portion thereof. In some embodiments, the BgaR transcription factor is 100% identical to that provided in SEQ ID NO: 1. In some embodiments, the BgaR transcription factor or variant thereof has an amino acid sequence which is at least 50%, 60%, 70%, 80%, 85%, 90%, 95%, 98%, 99% or 100% identical to that provided in SEQ ID NO: 9. In some embodiments, the BgaR transcription factor or variant thereof is 100% identical to that provided in SEQ ID NO: 9.

In some embodiments, the resonance energy transfer donor domain is a bioluminescent protein. Non-limiting examples of suitable bioluminescent proteins are described hereinabove and include luciferase, a β-galactosidase, a lactamase, a horseradish peroxidase, an alkaline phosphatase, a β-glucuronidase or a β-glucosidase. In some embodiments, the bioluminescent protein is a luciferase. The luciferase can be selected from the group consisting of *Renilla* luciferase, a Firefly luciferase, a Coelenterate luciferase, a North American glow worm luciferase, a click beetle luciferase, a railroad worm luciferase, a bacterial luciferase, a *Gaussia* luciferase, Aequorin, an *Arachnocampa* luciferase, and an *Oplophorus gracilirostris* luciferase or a biologically active variant or fragment of any one, or chimera of two or more, thereof. In some embodiments, the resonance energy transfer donor domain is a *Renilla* luciferase. In some embodiments, the resonance energy transfer donor domain is RLuc8. In some embodiments, the resonance energy transfer donor domain is capable of modifying a substrate. Non-limiting examples of substrates include luciferin, calcium, coelenterazine, furimazine or a derivative, analogue or stabilised derivative of coelenterazine, luciferin or furimazine. In these embodiments, binding of lactose to the sensor molecule results in a change in BRET.

In alternative embodiments, the resonance energy transfer donor domain is a fluorescent protein. Non-limiting examples of suitable fluorescent proteins include green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, tdimer2(12), mRFP1, pocilloporin, *Renilla* GFP, Monster GFP, paGFP, Kaede protein, tdTomato, mCherry, TagRFP, TurBoFB and a Phycobiliprotein, and a biologically active variant or fragment of any one thereof. In some embodiments, the donor domain is CFP. In these embodiments, binding of lactose to the sensor molecule results in a change in FRET.

In some embodiments, the resonance energy transfer acceptor domain is a fluorescent acceptor domain. In some embodiments, the fluorescent acceptor domain is a fluorescent protein. Non-limiting examples of suitable fluorescent proteins include green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Venus, mOrange, Topaz, GFPuv, destabilised EGFP (dEGFP), destabilised ECFP (dECFP), destabilised EYFP (dEYFP), HcRed, t-HcRed, DsRed, DsRed2, t-dimer2, tdimer2(12), mRFP1, pocilloporin, *Renilla* GFP, Monster GFP, paGFP, Kaede protein, tdTomato, mCherry, TagRFP, TurBoFB and a Phycobiliprotein, and a biologically active variant or fragment of any one thereof. In some embodiments, the acceptor domain is YFP. In other embodiments, the acceptor domain is GFP, preferably $GFP^2$.

In preferred embodiments, the donor domain is CFP or a variant thereof and the acceptor domain is YFP or a variant thereof. In some embodiments, the sensor further comprises a linker between YFP and BgaR and/or between CFP and BgaR. In some embodiments, the sensor further comprises protease cleavage sites and/or purification tags. In some embodiments, the sensor comprises an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, at least 99.5% identical to the amino acid sequence provided in SEQ ID NO: 23. In some embodiments, the sensor is 100% identical to that provided in SEQ ID NO: 23. In these embodiments, binding of lactose to the sensor molecule results in a change in FRET.

In other preferred embodiments, the donor domain is *Renilla* luciferase or a variant thereof and the acceptor domain is GFP or a variant thereof. For example, the donor domain can be RLuc8 and the acceptor domain can be $GFP^2$. In some embodiments, the sensor molecule is a single polypeptide comprising RLuc8-BgaR-$GFP^2$. In some embodiments, the sensor molecule is a single polypeptide comprising $GFP^2$-BgaR-RLuc8. In some embodiments, the sensor further comprises a linker between $GFP^2$ and BgaR and/or between RLuc8 and BgaR. In some embodiments, the sensor further comprises protease cleavage sites and/or purification tags. In some embodiments, the sensor comprises an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, at least 99.5% identical to an amino acid sequence selected from the group consisting of SEQ ID NO: 15, SEQ ID NO: 16, SEQ ID NO: 17, SEQ ID NO: 18, SEQ ID NO: 25, SEQ ID NO: 26, SEQ ID NO: 27, SEQ ID NO: 28. In some embodiments, the sensor comprises an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, at least 99.5% identical to an amino acid sequence selected from the group consisting of SEQ ID NO: 33, SEQ ID NO: 34, SEQ ID NO: 35 and SEQ ID NO: 36. In some embodiments, the sensor comprises an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, at least 99.5% identical to an amino acid sequence selected from the group consisting of SEQ ID NO: 15, SEQ ID NO: 16, SEQ ID NO: 17 and SEQ ID NO: 18. In some embodiments, the sensor comprises an amino acid sequence which is at least 30% identical, at least 35% identical, at least 40% identical, at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 98% identical, at least 99% identical, at least 99.5% identical to an amino acid sequence selected from the group consisting of SEQ ID NO: 25, SEQ ID NO: 26, SEQ ID NO: 27 and SEQ ID NO: 28. In some embodiments, the sensor has an amino acid sequence which is 100% identical to an amino acid sequence selected from the group consisting of SEQ ID NO: 15, SEQ ID NO: 16, SEQ ID NO: 17, SEQ ID NO: 18, SEQ ID NO: 25, SEQ ID NO: 26, SEQ ID NO: 27 and SEQ ID NO: 28. In some embodiments, the sensor has an amino acid sequence which is 100% identical to an amino acid sequence selected from the group consisting of SEQ ID NO: 15, SEQ ID NO: 16, SEQ ID NO: 17 and SEQ ID NO: 18. In some embodiments, the sensor has an amino acid sequence which is 100% identical to an amino acid sequence selected from the group consisting of SEQ ID NO: 25, SEQ ID NO: 26, SEQ ID NO: 27 and SEQ ID NO: 28. In some embodiments, the sensor has an amino acid sequence which is 100% identical to an amino acid sequence selected from the group consisting of SEQ ID NO: 33, SEQ ID NO: 34, SEQ ID NO: 35 and SEQ ID NO: 36. In some embodiments, the sensor comprises an amino acid sequence selected from the group consisting of SEQ ID NO: 15, SEQ ID NO: 16, SEQ ID NO: 17, SEQ ID NO: 18, SEQ ID NO: 25, SEQ ID NO: 26, SEQ ID NO: 27 and SEQ ID NO: 28 or is a fragment or variant thereof. In some embodiments, the sensor comprises an amino acid sequence selected from the group consisting of SEQ ID NO: 15, SEQ ID NO: 16, SEQ ID NO: 17 and SEQ ID NO: 18 or is a fragment or variant thereof. In some embodiments, the sensor comprises an amino acid sequence selected from the group consisting of SEQ ID NO: 25, SEQ ID NO: 26, SEQ ID NO: 27 and SEQ ID NO: 28 or is a fragment or variant thereof. In these embodiments, binding of lactose to the sensor molecule results in a change in BRET.

A sensor molecule that can be used to detect and/or measure lactose concentration is of particular interest for use in determining residual lactose in lactose-free products. High levels of lactose (5%) are found in milk and milk products (cream, butter, ice cream, cheese, powdered milk) (Fernandes Silveira et al., 2015). There is a growing market for lactose-free and lactose-reduced products, but there is no cheap, fast, sensitive method to measure residual amounts of lactose in dairy following treatment to remove or reduce the amounts of lactose. According to Food Standards Australia New Zealand (FSANZ), lactose-reduced dairy products must contain no more than 0.3% lactose. Lactose-free products are defined as having undetectable levels of the disaccharide, a definition which is subject to interpretation. However, levels of lactose below 0.01% are required for the European and Chinese markets.

Although the enzymatic process leading to the reduction/elimination of lactose in milk is well established, there are no established means for those carrying out the enzymatic process to verify the degree of lactose reduction at the time of processing. Currently, lactose-reduced and lactose-free milk samples are sent away from the processing plant to specialised laboratories for analysis. This incurs additional costs, due to logistics, need for specialised laboratory equipment and expertise, and the need for additional holding of the goods being assessed. In addition to the costs associated with current analysis methods and storage, not all lactose-free milk is tested, leading to an uneven treatment of milk and potential unreliability of products for the consumer. Accordingly, there is a need for alternative methods and sensors for measuring the concentration of lactose in food products, for example lactose reduced and lactose free dairy products. Preferably, the methods and sensors would provide dairy processors with a fast, sensitive, selective, inline method for the measurement of low levels of lactose in milk at the processing plant.

Measurement of residual lactose in milk represents a challenge on at least two levels: i) the amount of lactose in milk following enzymatic treatment to degrade the lactose is approximately 0.01% w/v; ii) selectivity due to the presence of high concentrations of lactose-derived monosaccharides that might interfere with the measurement of lactose. Preferably, the methods and sensors described in some embodiments will be able to detect lactose at a concentration of approximately 0.0001% w/v or more, approximately 0.0003% w/v or more, approximately 0.0005% w/v or more, approximately 0.0007% w/v or more, approximately 0.001% w/v or more, approximately 0.003% w/v or more, approximately 0.005% w/v or more, approximately 0.007% w/v or more, approximately 0.01% w/v or more, approximately 0.03% w/v or more, approximately 0.05% w/v or more, approximately 0.07% w/v or more, or approximately 0.1% w/v or more. Preferably, the methods and sensors described in some embodiments will be able to detect lactose in the presence of other carbohydrates, for example lactose-derived monosaccharides and/or lactulose. In some embodiments, the methods and sensors described can detect lactose in the presence of at least 0.1 mM, at least 1 mM, at least 10 mM, at least 20 mM, at least 50 mM, at least 100 mM, at least 130 mM, at least 200 mM, at least 260 mM carbohydrate, at least 300 mM, or at least 350 mM total carbohydrate. As the person skilled in the art would understand, the total carbohydrate concentrations exclude lactose (for example, if the sample comprises lactose, galactose and glucose, the concentration refers to the concentration of glucose and galactose). In some embodiments, the methods and sensors described can detect lactose in the presence of at least 0.1 mM, at least 1 mM, at least 10 mM, at least 20 mM, at least 50 mM, at least 100 mM, at least 130 mM, at least 200 mM, at least 260 mM carbohydrate, at least 300 mM, or at least 350 mM glucose and galactose.

In some embodiments, there is provided a sensor molecule for detecting lactose, the sensor comprising
i) a lactose binding domain of a helix-turn-helix transcription factor, or a variant of the carbohydrate binding domain;
ii) a chemiluminescent donor domain; and
iii) an acceptor domain;
wherein the spatial location and/or dipole orientation of the chemiluminescent donor domain relative to the acceptor domain is altered when lactose binds to the carbohydrate binding domain.

In some embodiments, there is provided a sensor molecule for detecting lactose, the sensor comprising
i) a bacterial BgaR transcription factor;
ii) a resonance energy transfer donor domain; and
iii) a resonance energy transfer acceptor domain;
wherein the spatial location and/or dipole orientation of the chemiluminescent donor domain relative to the acceptor domain is altered when lactose binds to the transcription factor. The resonance energy transfer donor domain and resonance energy transfer acceptor domain are as defined herein.

Lactulose Sensor Molecule

A further non-limiting example of a sensor molecule as defined herein is a sensor molecule that can used to detect and/or measure lactulose concentration. Accordingly, in some embodiments the present disclosure provides a sensor molecule as defined herein for detecting lactulose. In some embodiments, the methods and sensors described herein will be able to detect lactulose at a concentration of approximately 0.05 mM or more, approximately 0.1 mM or more, approximately 0.5 mM or more, approximately 1 mM or more, approximately 1.5 mM or more, approximately 1.8 mM or more or approximately 2 mM or more. In some embodiments, the methods and sensors described in some embodiments will be able to detect lactulose at a concentration of approximately 0.1 mM or more.

Compositions, Kits, Methods and Uses

The sensors described herein may be included in compositions for use in detecting carbohydrates. For example, the sensors described herein may be included in compositions for use in detecting sugars or sugar derivatives. In one embodiment, the sensors described herein may be included in compositions for use in detecting lactose. In one embodiment, the sensors described herein may be included in compositions for use in detecting lactulose. In some embodiments, there is provided a composition comprising a sensor in accordance with the present invention and an acceptable carrier. As used herein, the term "acceptable carrier" includes any and all solids or solvents (such as phosphate buffered saline buffers, water, saline) dispersion media, coatings, and the like, compatible with the methods and uses of the present invention. The acceptable carriers must be 'acceptable' in the sense of being compatible with the other ingredients of the composition, not damaging the carbohydrates being tested for and not inhibiting binding of the carbohydrate to the carbohydrate binding domain. Generally, suitable acceptable carriers are known in the art and are selected based on the end use application.

As the skilled person would appreciate, the sensors of the present application can be used to detect the presence or absence of a carbohydrate in a sample, and if present may also be used to determine the amount of the carbohydrate present in the sample. Therefore, in some embodiments there is provided a method of detecting a carbohydrate in a sample, the method comprising i) contacting a sample with the sensor molecule of the present invention; and ii) determining if the spatial location and/or dipole orientation of the chemiluminescent donor domain relative to the acceptor domain has been altered in the presence of the sample, wherein an alteration of the spatial location and/or dipole orientation of the chemiluminescent donor domain relative to the acceptor domain indicates the carbohydrate is present in the sample. In some embodiments, determining if the spatial location and/or dipole orientation of the chemiluminescent donor domain relative to the acceptor domain has been altered in the presence of the sample comprises measuring the BRET ratio before and after addition of the sample.

In some embodiments, the method further comprises determining the concentration of the carbohydrate in the sample.

In some embodiments, the carbohydrate is selected from the group consisting of lactose and lactulose. In some embodiments, the carbohydrate is lactose. In some embodiments, the carbohydrate is lactulose.

The sensors can be used to detect and quantify carbohydrates in a sample. The "sample" can be any substance or composition that has the potential to contain a carbohydrate.

In some embodiments, the sample is air, liquid, biological material or soil. In some embodiments, the sample is selected from the group consisting of a dairy product or an extract thereof, soil or an extract thereof, biological materials or an extract thereof and the like. The sample may be obtained directly from the environment or source, or may be extracted and/or at least partially purified by a suitable procedure before a method of the invention is performed.

In some examples, the sample comprises a biological material. As used herein, "biological materials" is defined broadly and includes any material derived in whole or in part from an organism. Biological materials include, but are not limited to, bodily fluids, cells, soft tissues (such as connective and non-connective tissue) and hard tissues (such as bone and cartilage). In some embodiments, the bodily fluids are blood, serum, sputum, mucus, pus, peritoneal fluid, urine or other bodily fluids. In some embodiments, such materials may have been harvested from a living organism and then subjected to further processing and/or chemical treatment. In an embodiment, the sensor is not used to detect a carbohydrate within a living cell. In some embodiments, the sensor is used ex vivo.

In some examples, the sample comprises a dairy product. As used herein, the term "dairy product" includes milk and products derived partially or in full from milk. The milk may be obtained from any mammal, for example cow, sheep, goat, horse, camel, buffalo, human and the like. Dairy products include, but are not limited to, raw milk, low fat milk, skim milk, pasteurized milk, extended shelf life milk, UHT milk, lactose-modified UHT milk, fortified UHT milk, flavoured UHT milk, and combinations of these products as well as UHT infant formula, cheese, yoghurt, whey, buttermilk, cream, milk powder, powdered infant formula, ice-cream and butter and the like. In some examples, the sample is milk or diluted milk. The dairy product may also be an extract, such as a partially purified portion, of dairy product comprising, or suspected of comprising, the carbohydrate of interest.

In some embodiments, the sensors of the present invention can be used to detect lactose in a dairy product. Accordingly, there is provided a method of detecting lactose in a dairy product, the method comprising i) contacting a sample with the sensor molecule of the present invention; and ii) determining if the spatial location and/or dipole orientation of the chemiluminescent donor domain relative to the acceptor domain has been altered in the presence of the sample, wherein an alteration of the spatial location and/or dipole orientation of the chemiluminescent donor domain relative to the acceptor domain indicates that lactose is present in the sample.

The sensors of the present invention can also be used to monitor the concentrations of carbohydrate in a sample.

In some embodiments, the sensors of the present invention can be used to detect lactulose in a dairy product. Accordingly, there is provided a method of detecting lactulose in a dairy product, the method comprising i) contacting a sample with the sensor molecule of the present invention; and ii) determining if the spatial location and/or dipole orientation of the chemiluminescent donor domain relative to the acceptor domain has been altered in the presence of the sample, wherein an alteration of the spatial location and/or dipole orientation of the chemiluminescent donor domain relative to the acceptor domain indicates that lactulose is present in the sample. In some embodiments, the method further comprises determining the concentration of lactulose in the sample.

Lactulose has been proposed by the International Dairy Federation and the European Union as an indicator of milk damage caused by heat-treatment and as a criterion to distinguish between pasteurized milk ([lactulose]<10 µM), ultra-high temperature (UHT)-treated milk ([lactulose]<1.8 mM) and in-container sterilized milk ([lactulose]>1.8 mM) (Marconi et al., 2004; Montilla et al., 1996). In some embodiments, the sensors of the present invention can be used to monitor the concentrations of lactulose in a sample. In some embodiments, the sensors of the present invention can be used to provide an indication of milk damage caused by heat-treatment. In some embodiments, the sensors of the present invention can be used to distinguish between various forms of milk, such as pasteurized milk, ultra-high temperature (UHT)-treated milk and in-container sterilized milk.

In some embodiments, there is also provided use of a sensor molecule for detecting carbohydrate, the sensor molecule comprising:

i) a carbohydrate binding domain of a helix-turn-helix transcription factor, or a variant of the carbohydrate binding domain;

ii) a chemiluminescent donor domain; and iii) an acceptor domain;

wherein the spatial location and/or dipole orientation of the chemiluminescent donor domain relative to the acceptor domain is altered when the carbohydrate binds to the carbohydrate binding domain. In some embodiments, the use further comprises determining the concentration of carbohydrate in the sample.

In some embodiments, there is also provided use of a sensor molecule for detecting lactose, the sensor molecule comprising a bacterial BgaR transcription factor or variant thereof, covalently joined to a resonance energy transfer donor domain and a resonance energy transfer acceptor domain, wherein the spatial location and/or dipole orientation of the donor domain relative to the acceptor domain is altered when lactose binds to the transcription factor. In some embodiments, the use further comprises determining the concentration of lactose in the sample.

In some embodiments, there is also provided use of a sensor molecule for detecting lactulose, the sensor molecule comprising a bacterial BgaR transcription factor or variant thereof, covalently joined to a resonance energy transfer donor domain and a resonance energy transfer acceptor domain, wherein the spatial location and/or dipole orientation of the donor domain relative to the acceptor domain is altered when lactulose binds to the transcription factor. In some embodiments, the use further comprises determining the concentration of lactulose in the sample.

As the skilled person would be aware, the sensors of the present invention can also be multiplexed. In this system, two or more different sensor molecules are provided which detect different carbohydrates. For example, a sensor molecule of the present invention that detects lactose can be multiplexed with sensors that detect other carbohydrates such as lactulose, galactose and/or glucose. In some embodiments, each different sensor molecule may include a different donor and/or acceptor molecule such that they emit at different wavelengths to enable the detection and quantification of different target compounds. In some embodiments, each different sensor molecule may comprise the same donor and/or acceptor molecule. In some embodiments, a single fluidic detection chamber is used. In some embodiments, a multi-channel detection device may be used.

In some embodiments, the sample is an aqueous liquid. For example, the sample includes but is not limited to, milk, fruit juices, other beverages and bodily fluids including blood serum.

The methods of the present invention can be performed on any system suitable for measuring a detectable change.

As the person skilled in the art will appreciate the methods of the present invention can be performed in a batch (for example batch format using a plate reader) or flow format. For example, the methods of the present invention can be performed in a microplate format using a microplate reader equipped with the appropriate filters. The methods of the present invention can also be performed on a microfluidic device, such as described in WO2013/155553.

In another aspect, the present invention provides a kit comprising the sensor as described herein. In some embodiments, the kit further comprises a standard (such as a lactose and/or a lactulose standard).

EXAMPLES

Example 1—Construction of LacB1 and LacF1 Sensors

DNA constructs encoding BgaR (codon optimized for expression in *E. coli*) were synthesised by GenScript (USA). If required, linker sequences were added to the DNA construct by PCR using BgaR synthesised by GenScript as the template and the appropriate primers (Table 5). The primers included the linker sequence (if required) and restriction sites for PstI or BstBI. The amplified PCR product was digested with PstI and BstBI and cloned into pRSET vector (BioLabs, Australia), previously cloned with $GFP^2$ and RLuc8 (for the LacB sensors) or CFP and YFP (for the LacF sensors), using the PstI/BstBI restriction sites, such that the expressed fusion protein had an N-terminal histidine tag.

TABLE 5

Oligonucleotides used in the preparation of the lactose sensors

| | Orientation | Sequence |
|---|---|---|
| P1 | Forward | AAAAAACTGCAGATGCAGATTCTGTG (SEQ ID NO: 10) |
| P2 | Reverse | ACACACTTCGAAAATGCTCGGTTTAT (SEQ ID NO: 11) |
| P3 | Forward | AAAAAACTGCAGGGTGGTACCGGAGG CGGCATGCAGATTCTGTGGAAAAA (SEQ ID NO: 12) |
| P4 | Reverse | AAAAAATTCGAAGCCGCCTCCGGTA CCACCAATGCTCGGTTTATTAACTT (SEQ ID NO: 13) |
| P5 | Reverse | AAAAAACTGCAGAATGCTCGGTTTAT (SEQ ID NO: 14) |

Cells of *Escherichia coli* strain BL21(DE3) (New England BioLabs) were transformed with pRSET vector encoding the sensor. The sensors were expressed in *E. coli* strain BL21(DE3) using protocols known to the person skilled in the art.

For expression of the sensors, 50 mL of LB (10 g tryptone, 5 g yeast extract, 5 g NaCl per L of water (pH 7.4)) supplemented with 2% (v/v) glucose and 100 µg/mL ampicillin was inoculated with a single colony and incubated at 37° C., 200 rpm until it reached an $Abs_{600\ nm}$ of 0.8. 250 mL LB, supplemented with 100 µg/mL ampicillin, was inoculated using the starter culture to an $Abs_{600\ nm}$ of 0.05 and incubated at 28° C., 200 rpm for 16 hours and the cells were harvested.

Alternatively, 200 mL LB containing 100 µg/mL ampicillin was inoculated with a single colony and the culture was incubated at 28° C. for 48 h with shaking at 200 rpm and the cells were harvested.

Cells were harvested by centrifugation at 5000×g (4° C.) for 10 minutes, washed with phosphate buffered saline (PBS; 137 mM NaCl, 2.7 mM KCl, 10 mM $Na_2HPO_4$, 1.8 mM $KH_2PO_4$, pH 7.4) and resuspended in sodium phosphate buffer (50 mM $Na_2HPO_4$, 300 mM NaCl, pH 7.0). The cells suspension was passed through a homogenizer (Microfluidics M-110P (Newton, Mass., USA)) at a pressure of 20,000 psi and the soluble protein fraction was isolated by centrifugation at 15,000×g (4° C.) for 15 minutes. Proteins were purified using cobalt affinity chromatography (TALON® Superflow Metal Affinity Resin (Takara Clontech, Australia)) according to the manufacturer's instructions. Following elution of the purified protein with 150 mM imidazole, the sample was dialysed against Tris buffer (50 mM Tris, 100 mM NaCl, 0.1 mM EDTA, pH 8.0) using a dialysis unit (GE Healthcare, Vivaspin 6, 10 kDa MWCO). Aliquots of 500 µL of the purified protein were snap-frozen in liquid nitrogen and stored at −80° C. Protein concentrations were determined by absorbance at 280 nm.

The purified LacB1 sensor is a polypeptide having the sequence SEQ ID NO: 15. The LacB1 sensor contains GFP2-BgaR-RLuc8. The purified LacF1 sensor is a polypeptide having the sequence SEQ ID NO: 23. The LacF1 sensor contains CFP-BgaR-YFP. A schematic of the His tagged LacB1 and LacF1 sensors is shown in FIG. 2.

Example 2—Lactose Binding by LacB1 and LacF1

Materials and Methods

BRET assays were carried out in 96-well plates with a final volume of 100 µL. The purified sensor and lactose were diluted to the desired concentration using PBS (58 mM $Na_2H_2PO_4$, 17 mM $NaH_2PO_4$, 68 mM NaCl, pH 7.4). The LacB1 sensor was incubated for 5 minutes at 30° C. with 1 mM lactose or water. At the end of the incubation time, 5 µL of coelenterazine 400a in EtOH was added (to a final coelenterazine 400a concentration of 17 µM) and the spectral scans were recorded immediately.

FRET measurements were carried out in a similar manner to the $BRET^2$ assays, with the following modifications. The LacF1 sensor was incubated for 5 minutes at 30° C. with 1 mM lactose. Spectral scans were recorded in fluorescence mode ($\lambda_{ex}$=435 nm, 455 nm cut-off, 20 nm increments).

Spectral scans were recorded with a SpectraMax M3 plate-reading spectrofluorimeter (Molecular Devices) in luminescence mode (20 nm increments) in white 96-well plates (Opti-Plate™-96, PerkinElmer).

Data Analysis $BRET^2$ ratio was calculated as the ratio of acceptor emission intensity at 500 nm to donor emission intensity at 420 nm.

FRET ratio was calculated as the ratio of acceptor emission intensity at 520 nm to donor emission intensity at 480 nm.

Results

RET ratios were measured for both the LacB1 sensor and the LacF1 sensor in the presence of water or 1 mM lactose (FIG. 2). For both sensors, the presence of 1 mM lactose resulted in a decrease in the RET ratio. For LacB1 the change was from 1.09±0.01 to 0.800±0.003. For LacF1, the change was from 1.216±0.004 to 1.089±0.004. Therefore 1 mM lactose caused a 27% drop in the RET ratio for the LacB1 sensor compared with a 10% decrease for LacF1 sensor.

Example 3—BRET Assays for Detecting Lactose Binding by LacB1

Materials and Methods

BRET assays were carried out in 96-well plates with a final volume of 100 µL. The purified sensor and lactose were diluted to the desired concentration using PBS (58 mM $Na_2H_2PO_4$, 17 mM $NaH_2PO_4$, 68 mM NaCl, pH 7.4). Purified sensor (1 µM) was incubated for 30 minutes at 30° C. with varying amounts of lactose (0.000036%-0.36% w/v) or other carbohydrate. For BRET measurement, 5 µL coelenterazine 400a substrate (final [coel 400a]=16.7 µM)) was added following the incubation period. Spectral scans were recorded immediately after the addition of the substrate. Spectral scans were recorded with a Spectramax M2 plate-reading spectrofluorimeter (Molecular Devices).

Data Analysis $BRET^2$ ratios were calculated as the ratio of the maximum acceptor emission intensity (500 nm) to maximum donor emission intensity (420 nm).

Results

The $BRET^2$ ratio for the LacB1 sensor in the presence of increasing amounts of lactose is shown in FIG. 3.

Example 4—the Effect of Linker Length on Lactose Binding

Materials and Methods

To investigate the effect varying the length of the linker connecting the carbohydrate binding domain to the chemiluminescent donor domain and/or acceptor domain, lactose sensors were constructed in which the linker sequence -GGTGGG- was included before and after BgaR (LacB2; SEQ ID NO: 16), before BgaR (LacB3; SEQ ID NO: 17) and after BgaR (LacB4; SEQ ID NO: 18). The LacB2 sensor contains RLuc8-GGTGGG-BgaR-GGTGGG-$GFP^2$. The LacB3 sensor contains RLuc8-GGTGGG-BgaR-$GFP^2$. The LacB4 sensor contains RLuc8-BgaR-GGTGGG-$GFP^2$. A schematic representation of the lactose sensors is shown in FIG. 4. The linker location is indicated by a darkened section compared to the same area of LacB1. Binding of these sensors to 1 mM lactose was assessed using the BRET assay described in Example 3.

Results

The $BRET^2$ ratio for the LacB2, LacB3 and LacB4 sensors in the presence and absence of 1 mM lactose is shown in FIG. 5. The $BRET^2$ ratio for the LacB1 sensor in the presence and absence of 1 mM Lactose is included as a comparison. While all sensors exhibited a change in the $BRET^2$ ratio in the presence of 1 mM Lactose, LacB1 (no linkers) gave the most substantial change in $BRET^2$ ratio in the presence of 1 mM lactose.

Example 5—Sensitivity of the LacB1 and LacF1 Sensors

The process used to generate lactose-free and lactose reduced milk uses β galactosidase (also referred to as lactase) to break the disaccharide lactose into its two component monosaccharides, galactose and glucose. Galactose and glucose remain in the final milk product in high concentrations. Due to their structural similarities with lactose, galactose and glucose have the potential to competitively bind to a lactose biosensor, interfering with the measurement of trace levels of lactose. In addition, the heat treatment of milk to yield long-life product (such as UHT or milk powder, but not pasteurised 'fresh' milk) results in partial isomerization of the disaccharide lactose to lactulose. Typically levels of lactulose reach 0.32 to 2.16 mM (0.011 to 0.074% (w/v)) in UHT milk (Morales et al., 2000; Marconi et al., 2004). Lactulose is not hydrolysed to its component monosaccharides by β-galactosidase treatment. Similarly to the monosaccharides galactose and glucose, the presence of lactulose in heat treated milk has the potential to interfere with measurement of low levels of lactose in dairy products.

Materials and Methods

In order to determine whether the LacB1 sensor has sufficient specificity and sensitivity to avoid interference by sugars such as galactose, glucose and lactulose, the ability of the LacB1 sensor to bind a range of disaccharides that are structurally related to lactose (β-D-galactosyl-(1→4)-D-glucose), namely lactulose (4-O-β-D-galactosyl-D-fructose), melibiose (D-galactosyl-α(1→6)-D-glucose), maltose (4-O-α-D-glucosyl-D-glucose), cellobiose (4-O-β-D-glucosyl-D-glucose), trehalose (α-D-glucosyl-(1→1)-α-D-glucose) and sucrose (β-D-Fructosyl α-D-glucose), as well as the monosaccharides, galactose and glucose was assessed using the BRET assay described in Examples 2 and 3.

Briefly, the LacB1 sensor was incubated separately with 0.1 mM or 1 mM lactose, 1 mM lactulose, melibiose, maltose, cellobiose, trehalose or sucrose or 1 mM or 10 mM galactose or glucose.

Next, a 'corrected' calibration curve for the LacB1 and LacF1 sensors in the presence of glucose and galactose was generated following the protocol detailed in Example 3, however to simulate a 1 in 10 dilution of treated milk in phosphate buffer saline (PBS) glucose and galactose were included at a concentration such that [lactose]+0.5×[galactose]+0.5×[glucose]=13.9 mM and [galactose]=[glucose]. For example, if 139 mM of lactose is found in milk prior to treatment by lactase, following lactase treatment to a residual [lactose] of 1 mM, galactose and glucose would be present at concentrations of 138 mM. In the case of a 1 in 10 dilution of such a lactase treated milk sample in PBS, the diluted sample would contain 0.1 mM of residual lactose and 13.8 mM of both galactose and glucose. Therefore, when the reaction mix contained 0.1 mM lactose, 13.8 mM glucose and 13.8 mM galactose were also added.

A 'corrected' calibration curve was also constructed for the LacB1 and LacF1 sensors in the presence of glucose and galactose using lactose-free full fat milk which had been dialysed to remove low molecular weight components, particularly lactose, galactose and glucose, as the diluent. To remove, full cream lactose-free milk was dialysed according to the following protocol. 10 mL of lactose-free full-fat milk was dialysed twice against 1000 mL PBS at 4° C. for 24 h to remove any residual lactose present in lactose-free milk. 1 mL aliquots of the dialysed milk were frozen on dry ice and stored at −80° C. The dialysed milk was used as the 'milk matrix' at a 1 in 10 dilution in PBS.

Results and Discussion

The changes in BRET$^2$ ratio for the LacB1 sensor in the presence of lactose, lactulose, melibiose, maltose, cellobiose, trehalose, sucrose, galactose and glucose for 30 minutes is shown in FIG. 6.

Incubation of the LacB1 sensor with 1 mM (0.034% w/v) of the disaccharide lactulose resulted in a change in BRET$^2$ ratio of approximately 21%, whereas the other disaccharides led to BRET$^2$ ratio changes between 3 and 10%. In comparison, the change in BRET$^2$ ratio upon the addition of 1 mM (0.034%) lactose was approximately 35%. This indicates that the LacB1 sensor is selective for lactose over other saccharides.

Incubation of the LacB1 sensor with 1 and 10 mM (0.018% and 0.18%) galactose or glucose resulted in 3 and 13% changes in the BRET$^2$ ratios with the galactose and 9 and 6% changes with the glucose.

Similar results were obtained when the LacB1 sensor was incubated in the presence of lactose, lactulose, melibiose, maltose, cellobiose, trehalose, sucrose, galactose and glucose for 5 minutes before coelenterazine 400a was added (FIG. 7).

Corrected calibration curves for the LacB1 and LacF1 sensors in PBS and 10% dialysed milk in PBS are shown in FIG. 8. FIGS. 8A and 8B shows the corrected calibration curves in PBS. FIGS. 8C, 8D and 8E shows the corrected calibration curves in 10% dialysed milk in PBS. The corrected calibration curves are linear over at least 2 log units to allow lactose quantification. Samples with higher lactose content can be analysed using the same method by diluting the sampling 10:90 with buffer (see FIG. 8).

Example 6—LacB1 Binding to Lactose and Lactulose

Of the sugars tested in Example 5, lactose caused the largest change in BRET$^2$ ratio, followed by lactulose. Since LacB1 exhibited the largest responses to lactose and lactulose, the affinity of the biosensor for each respective sugar was investigated further.

Materials and Methods

Spectral scans were recorded with a SpectraMax M3 plate-reading spectrofluorimeter (Molecular Devices) in luminescence mode (20 nm increments) in white 96-well plates (Opti-Plate™-96, PerkinElmer). 1 μM of purified protein was used for the BRET assay, in a final volume of 100 μL, where the protein and analyte were diluted in phosphate-buffered saline (PBS; 10 mM phosphate, 137 mM NaCl, 2.7 mM KCl, pH 7.3) or 10% (v/v) dialysed lactose-free, full cream milk in PBS. The purified protein was incubated for 5 minutes at 30° C. with lactose or lactulose. At the end of the incubation time, 5 μL of coelenterazine 400a in EtOH was added (to a final coelenterazine 400a concentration of 17 μM) and the spectral scans were recorded immediately.

Data Analysis

BRET$^2$ ratio was calculated as the ratio of acceptor emission intensity at 500 nm to donor emission intensity at 420 nm.

Results and Discussion

The changes in BRET$^2$ ratio for the LacB1 sensor in the presence of lactose or lactulose is shown in FIG. 9. The response of LacB1 to lactose and lactulose (in PBS) was concentration dependent. The response of LacB1 to lactose was quasi-linear over almost 3 log units with an EC$_{50}$ of 12±1 μM and a limit of detection of 1 μM. The affinity of LacB1 for lactulose was approximately 150 fold weaker, with an EC$_{50}$ of 2.4±0.2 mM. The limit of detection for lactulose was 0.1 mM i.e. 100 fold higher than for lactose. The lactulose response was quasi-linear over almost 2 log units. The limit of detection of LacB1 for lactulose (0.1 mM) is 10-fold higher than the lactulose levels found in pasteurized milk (10 μM), which means it could be used to determine any relevant level of lactose in lactase treated pasteurized milk.

The response of the LacB1 sensor to lactose in 10% (v/v) dialysed milk is concentration dependent with an $EC_{50}$ of 21±2 µM, linearity over almost 3 log units and a limit of detection of 1 µM. The sensitivity of LacB1 to lactose in 10% (v/v) dialysed milk and saturating concentrations of galactose and glucose is statistically different from that observed in PBS only (11-14 µM & 18-23 µM). However, the affinity of LacB1 for lactose was not decreased dramatically by the presence of either 10% (v/v) dialysed milk or high concentrations of glucose and galactose. Without wishing to be bound by theory, it is thought that this is due to the high selectivity of the sensor for lactose and/or due to the efficiency of the $BRET^2$ transduction mechanism in complex media.

The characterization of LacB1 binding with lactose and lactulose highlights the intrinsic power of using binding proteins as analyte recognition elements for biosensing, particularly when coupled with the $BRET^2$ transduction mechanism for detecting the change. The lactose binding transcriptional regulator, BgaR, used to construct LacB1 yielded sensitivity in the low micromolar range, with the ability to discriminate between structurally related disaccharides, as demonstrated by the 200-fold difference in $EC_{50}$ observed between lactose and the second most potent sugar tested, lactulose.

Example 7—LacB1 Binding to Lactose in a Simulated Milk System

To investigate the effects of measuring the lactose concentrations in a simulated milk system, a dialysed milk sample was used where the total concentration of sugars was held constant by adding compensating amounts of glucose and galactose as the lactose concentration was reduced from 13.9 mM (equivalent to unmodified 10% (v/v) whole milk) to zero.

Materials and Methods

Full cream milk was dialysed against water to eliminate small molecules. Briefly, 20 mL of full cream lactose-free milk was dialysed twice against 1 L of water at 4° C. for 90 minutes in a D-Tube™ Dialyzer (Merck, 3.5 kDa MWCO). 1 mL aliquots of the dialysed milk were frozen on dry ice and stored at −80° C.

The dialysed milk was used to reconstitute a 10% (v/v) milk matrix with a range of precisely defined levels of lactose, galactose and glucose where ([lactose]+[galactose+glucose]/2=13.9 mM. The ten-fold dilution factor was chosen to accurately simulate assay conditions when measuring lactose in samples at or below the 300 µM 'lactose-free' threshold, i.e. following lactase treatment. The BRET assays was performed as described in Example 6.

Results and Discussion

The changes in $BRET^2$ ratio for the LacB1 sensor in a simulated milk system is shown in FIG. 9. Under these conditions, which closely mimic the situation in milk samples, the LOD for lactose was 0.2 µM (0.00003% w/v). The $EC_{50}$ for lactose changed marginally under these conditions, from 12 to 21 µM, but the difference was not statistically different. The $EC_{50}$ for lactose is approximately 15 fold lower than the most stringent objective regulatory standard (0.01% w/v) for "lactose free" dairy products. The similarity of the log concentration-response functions in the presence or absence of 10% (w/v) full cream milk is remarkable because in the latter case, at lower concentrations of lactose, the measurements are made in the presence of 13.9 mM glucose and galactose. Without wishing to be bound by theory, it is thought that the strong ability of the biosensor to "ignore" potentially interfering substances arises from the selectivity of the sensor, the robust ratiometric nature of the $BRET^2$ transduction mechanism and/or the absence of an external source of illumination, which would cause light scattering and increase noise in a turbid medium such as milk, even when diluted tenfold.

Example 8—CYBERTONGUE® Assay for Lactose

Materials and Methods

LacB1 was diluted to 1200 µM in assay buffer (0.45% gelatine in phosphate buffer saline: 0.45% (w/v) gelatine from fresh water fish skin (Sigma Aldrich), 58 mM $Na_2H_2PO_4$, 17 mM $NaH_2PO_4$, 68 mM NaCl, pH 7.4). 35 µL of analyte (30 µM or 3 mM lactose in assay buffer or assay buffer alone), LacB1 (1200 µM) and coelenterazine 400a (30 µM in 15% EtOH/assay buffer) were placed one in each of the three inlets of the CYBERTONGUE® microfluidic chip and the assay was performed at a flow rate of 1200 µL/h for 100 sec.

BRET ratios were recorded using the CYBERTONGUE® device with a flow rate of 1200 µL/h and the donor and acceptor luminescence intensities averaged between 80 and 100 sec. $BRET^2$ ratios were calculated by the CYBERTONGUE® device software program as the ratio of the maximum acceptor emission intensity (green filter) to maximum donor emission intensity (blue filter).

Results

An example CYBERTONGUE® device trace for assay buffer with 3 mM lactose is shown in FIG. 10. As is shown in FIG. 11, the CYBERTONGUE® assay can be used to detect lactose at both 30 µM and 3 mM. The addition of 30 µM and 3 mM lactose resulted in approximately 22% and 41% changes in the $BRET^2$ ratios, respectively.

Example 9—Estimation of Lactose in Whole Milk

Engineering a sensor to quantify an analyte in a defined buffer under controlled laboratory conditions is of itself a challenge but accurately quantifying an analyte under real world conditions is even more challenging. In particular, complex and interfering sample matrices, such as milk, dairy and other biological samples, can complicate and degrade biosensor performance. One use of the sensors described herein would be to quantify lactose levels, which range from approximately 4.5 to 7.0% (w/v), depending on species, in unmodified milk. The present inventors compared the lactose estimates obtained with using the sensor described herein, calibrated against known amounts of lactose in PBS or 10% of a dialysed milk matrix with two methods currently in commercial use, a coupled-enzyme lactose assay kit (BioVision) and HPLC with refractive index detector performed in a NATA accredited analytical laboratory.

Materials and Methods

The concentration of lactose in whole milk was estimated using a commercial kit (The BioVision lactose colorimetric/fluorometric assay kit (San Francisco, USA, #K624-100)), by HPLC with refractive index (RI) detection and using the LacB1 sensor described herein.

The sample used in these assays was whole pasteurized cow's milk purchased from a supermarket. The nutritional panel on the carton of milk stated a representative value for lactose of 137 mM.

The BioVision lactose colorimetric/fluorometric assay kit was used in accordance with the manufacturer's instructions to estimate lactose and galactose concentration. Briefly, a standard curve was prepared using 0, 2, 4, 6, 8 or 10 µL of a lactose standard (1 mM in the provided lactose assay buffer). The required volume was pipetted into individual wells of a clear 96-well plate (UV-star microplate, Greiner). Whole pasteurized cow's milk purchased was diluted approximately $10^4$ fold in water and 10 μL was used for the assay. In addition, 2 μL of the chromogenic probe, 2 μL of enzyme mix, and 2 μL of horseradish oxidase (HRP) were added to each well and volumes were made up to 100 μL with lactose assay buffer and mixed well. The reaction mixtures were incubated at 37° C. for 60 minutes and protected from light. $Abs_{570\ nm}$ was recorded with a SpectraMax M3 plate-reading spectrofluorimeter (Molecular Devices) in the absorbance mode (end-point measurement $Abs_{570\ nm}$). The assay was performed in triplicate.

HPLC estimation of lactose concentration was performed by a commercial laboratory. Briefly, 200 mL of whole milk was frozen and stored at −80° C. and shipped on dry ice to a commercial NATA-accredited testing laboratory (DTS/Asure Quality, Melbourne, Australia). Analysis was performed according to the laboratory's standard commercial protocol, using HPLC and RI detection (Chaves-Servin et al., 2004; Southgate, 1969). Results were reported as g of sugar per 100 mL of milk, using 1.033 g/mL as the density of full cream whole milk. No error values were reported.

Estimation of lactose concentration was performed using the LacB1 sensor, calibrated against known amounts of lactose in PBS or 10% of a dialysed milk matrix, as described herein. The $EC_{50}$ of LacB1 for lactose is 12 μM, i.e. approximately $10^4$-fold lower than the lactose concentration found in unmodified cow's milk. Consequently, whole milk samples were diluted 3200 fold in water prior to lactose estimation.

Results

The lactose concentration of pasteurized whole cow's determined using the LacB1 sensor, the BioVision kit and HPLC is presented in Table 6.

Using the BioVision coupled-enzyme kit and following the manufacturer's protocol the inventors estimated the lactose concentration of the whole milk sample to be 129±1 mM.

A sample of the same milk was submitted to a NATA accredited laboratory for lactose estimation by HPLC/refractive index (RI) analysis. The laboratory reported a lactose concentration of 134 mM. In this case, no error value was reported.

Using the LacB1 sensor as described herein the inventors estimated that the lactose concentration in the whole milk sample was 157±6 mM.

TABLE 6

Comparison of lactose concentration in pasteurized whole cow's determined using the LacB1 sensor and two independent methods.

|  | [Lactose] (mM) | [Lactose] (% w/v) |
| --- | --- | --- |
| LacB1 sensor | 157 ± 6 | 5.4 ± 0.2 |
| Coupled enzyme assay (BioVision) | 129 ± 1 | 4.4 ± 0.03 |
| HPLC with RI detection* | 134* | 4.6 |

Example 10—Estimation of Lactose in Lactase-Treated Milk

A further use of a lactose biosensor is to measure lactose in different grades of lactase treated milk, characterized as "reduced lactose" or "lactose-free". Estimation of lactose in lactase-treated milk is challenging due to the low level of the analyte, the complexity of the milk medium and the presence of high levels of glucose and galactose that can interfere with the measurement of lactose itself. Food Standards Australia and New Zealand (FSANZ) specifies lactose-reduced dairy as containing no more than 0.3% (8.8 mM) lactose whereas lactose-free products should contain "no detectable lactose", a subjective, method-dependent definition. European authorities specify an objective threshold for lactose-free foods at 0.01% (w/v) (0.3 mM).

Milk is a complex matrix comprising proteins and lipids each at concentrations of approximately 3% (w/v) (Kailasapathy, 2009). To minimize interference, analytical laboratories routinely precipitate fats and proteins from milk samples before analyzing the sugar content by HPLC or colorimetric coupled-enzyme assays. In addition to being time consuming and incurring extra cost, work-up of samples prior to analysis increases the risk of error due to yield variation and modification of sample volumes. There is a need for an improved method of determining the concentration of a carbohydrate, for example lactose, in a sample that avoids at least some of the disadvantages associated with HPLC or colorimetric coupled-enzyme assays.

Materials and Methods

The concentration of lactose in commercially obtained full cream, "lactose-free" cow's milk was estimated using a commercial kit (The BioVision lactose colorimetric/fluorometric assay kit (San Francisco, USA, #K624-100)), by HPLC with refractive index (RI) detection and using the LacB1 sensor as described for Example 9.

The sample used in these assays was commercially obtained full cream, "lactose-free" cow's milk. A ten-fold dilution of the "lactose-free" cow's milk was used for the LacB1 assay.

The concentration of galactose in the sample was also determined using the commercial kit (The BioVision lactose colorimetric/fluorometric assay kit (San Francisco, USA, #K624-100)) and by HPLC with refractive index (RI) detection using standard protocols.

Results

The LacB1 sensor was used to estimate lactose concentration in a ten-fold dilution of commercially obtained full cream, "lactose-free" cow's milk. The $BRET^2$ ratio was decreased by 16%, equivalent to a concentration of 2.7±0.1 μM, corresponding to 27±1 μM lactose in the original milk sample (Table 7).

Attempts to estimate the lactose concentration of full cream, "lactose-free" cow's milk using the BioVision lactose colorimetric/fluorometric assay kit described in Example 9 were unsuccessful. It was thought that this was a result of the high concentrations of galactose present in the "lactose-free" cow's milk. The concentration of galactose in the sample was estimated to be 163±2 mM.

Samples of the same full cream, lactose-free milk were submitted to a NATA accredited analytical laboratory for analysis by HPLC-refractive index detection. No lactose was detected, with a limit of detection of 0.1% (w/v) or approximately 3 mM (Table 7).

TABLE 7

Comparison of lactose concentration in fresh "lactose free" full cream cow's milk using the LacB1 sensor and two independent methods.

| | [Lactose] (mM) | [Lactose] (% w/v) | [Galactose] (mM) |
|---|---|---|---|
| LacB1 sensor | 0.027 ± 0.001 | 0.00092 ± 0.00003 | NA |
| Coupled enzyme assay (BioVision) | NA | NA | 163 ± 2 |
| HPLC with RI detection* | <3 | <0.1 | 124 |

*No error quoted

Therefore, the LacB1 sensor appears to be suitable for directly determining the concentration of residual lactose in lactose free commercial dairy products.

This application claims priority from Australian application no. 2017903148 filed 8 Aug. 2017, the entire contents of which are incorporated by reference herein.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Ansari et al. (2012) Process Biochem. 47:2427-2433.
Aravind and Anantharaman (2003) FEMS Microbiol. Rev. 222:17-23.
Aravind et al. (2005) FEMS Microbiol. Rev. 29:231-262.
Altschul et al. (1990) J. Mol. Biol. 215:403-10.
Altschul et al. (1997) Nucleic Acids Res. 25:3389-402.
Bajar et al. (2016) Sensors. 16:1488-1512.
Chávez-Servin et al. (2004) J. of Chromatogr. A. 1043:211-215.
Dacres et al. (2009a) Anal. Biochem. 385:194-202.
Dacres et al. (2009b) Biosensors and Bioelectronics 24:1164-1170.
Dacres et al. (2010) Anal. Chem. 82: 432-435.
Dacres et al. (2011) Biosens. Bioelectron. 29: 119-124.
Dacres et al. (2012) Biochem. Biophys. Res. Commun. 425:625-629.
Dacres et al. (2014) Poster presentation. Biosensors 2014, May 27-30$^{th}$, Melbourne.
Day et al. (2004) Luminescence 19:8-20.
de Wet et al. (1987) Mol. Cell. Biol. 2987:725-737.
Euber and Brunner (1979) J. Dairy Sci. 62:685-690.
Erich et al. (2012) Food Chem. 135:2393-2396.
Fernandes Silveira et al. (2015) J. Chem. id185967, 6 pages.
Förster (1948) Ann. Physik. 2:55.
Förster (1959) Discuss. Faraday Soc. 27:7-17.
Förster (1960) Rad. Res. Suppl. 2:326.
Franco et al. (2006) J. Bacteriol. 188:3024-3036.
Franco et al. (2007) Nucleic Acids Res. 35:4755-4766.
Greer and Szalay (2002) Luminescence 17:43-74.
Hartman et al. (2011) Appl. Environ. Microbiol. 77: 471-8.
Haydon and Guest (1991) FEMS Microbiol. Lett. 63:291-295.
Hastings (1996) Gene 173:5-11.
Hushpulian et al. (2007) Biotransformation 25:2-4.
Indyk et al. (1996) Food Chem. 57:575-580.
Inouye et al. (1997) Biochem. J. 233:349-353.
Jia et al. (2014) Biotechnol. Bioeng. 111:209-222.
Kailasapathy, K. (2009) "Chemical Composition, Physical and Functional Properties of Milk and Milk Ingredients; Dairy Processing & Quality Assurance", Wiley-Blackwell, chapter 4.
Kim and Kim (2012) Theranostics 2:127-138.
Kleyn (1985) J. Dairy. Sci. 68:2791-2798.
Kong et al. (2009) Nucleic Acids Res. 37:1915-1924.
Lee et al. (2003) J. Bacteriol. 185:4315-4325.
Loening et al. (2006) Protein Eng. Des. Sel. 19:391-400.
Loening et al. (2007) Nature Methods 4:641-643.
Lorenz et al. (1991) Proc. Natl. Acad. Sci. USA 88:4438-4442.
Marchler-Bauer et al. (2017), Nucleic Acids Res. 45:D200-3.
Marchler-Bauer et al. (2015), Nucleic Acids Res. 43:D222-6.
Marchler-Bauer et al. (2011), Nucleic Acids Res. 39:D225-9.
Marchler-Bauer and Bryant (2004), Nucleic Acids Res. 32:W327-331.
Marconi et al. (2004) Food Chem. 84:447-450.
McSweeney et al. (1993) Food Biotechnology. 7:143-158.
Milk and Milk Products—Determination of Lactose Content by High Performance Liquid Chromatography (Reference method)—ISO 22622:2007.
Montilla et al. (1996) J. Food Prot. 59:1061-1064.
Morales et al. (2000) Int. J. Food Sci. Tech. 35:193-200.
Myers and Miller (1988), Comput. Appl. Biosci. 4:11-7.
Needleman and Wunsch (1970) J. Mol. Biol. 48:443-53.
Pabo and Sauer (1992) Annu. Rev. Biochem. 61:1053-95.
Pfleger and Eidne (2006) Nature Methods 3:165-174.
Rigali et al. (2002) J. Biol. Chem. 15:12507-12515.
Rigali et al. (2004) Nuc. Acids Res. 32:3418-3426.
Southgate (1969) J. Sci. Food. Agric. 20:326.
Tsenkova et al. (1999). J. Dairy Sci. 82:2344-2351.
Tsien (1998) Ann. Rev. Biochem. 63:509-544.
Verhaegen et al. (2002) Anal. Chem. 74:4378-4385.
Viviani (2002) Cell. Mol. Life Sci. 59:1833-1850.
Wang et al. (1997) "Bioluminescence and Chemiluminescence: Molecular Reporting with Photons", Wiley, 419-422.
Wiethaus et al. (2008) J. Bacteriol. 190:487-93.
Xinmin et al. (2008) J. Food Compos. Anal. 21:255-258.
Xu et al. (1999) Proc. Natl. Acad. Sci. USA. 96:151-156.
Zhang et al. (2012) J. Bacteriol. 194:1055-64.
Zheng et al. (2009) Acta Crystallogr. D Biol. Crystallogr. D65:356-365.

The invention claimed is:

1. A sensor molecule for detecting lactose or lactulose comprising:
   a bacterial BgaR transcription factor or variant thereof, covalently joined to a resonance energy transfer donor domain and a resonance energy transfer acceptor domain, wherein the spatial location and/or dipole orientation of the donor domain relative to the acceptor domain is altered when lactose or lactulose binds to the transcription factor,
   wherein the sensor molecule has at least 80% sequence identity to the polypeptide provided in SEQ ID NO: 15, SEQ ID NO: 16, SEQ ID NO: 17, or SEQ ID NO: 18, and
   wherein the sensor molecule binds to lactose or lactulose.

2. The sensor molecule of claim 1, wherein the BgaR transcription factor or variant thereof, has an amino acid sequence which is at least 80% identical to that provided in SEQ ID NO: 1.

3. A method of detecting lactose or lactulose in a sample, the method comprising
   i) contacting a sample with the sensor molecule of claim 1; and
   ii) determining if the spatial location and/or dipole orientation of the donor domain relative to the acceptor domain has been altered in the presence of the sample,
   wherein an alteration of the spatial location and/or dipole orientation of the chemiluminescent donor domain relative to the acceptor domain indicates that lactose is present in the sample.

4. The method of claim 3, which further comprises determining the concentration of lactose or lactulose in the sample.

5. The method according to claim 4, wherein the sample comprises a dairy product.

6. The sensor molecule of claim 1, wherein the resonance energy transfer donor domain is RLuc8 and the resonance energy transfer acceptor domain is GFP$^2$.

7. The sensor molecule of claim 1, wherein the separation and relative orientation of the chemiluminescent donor domain and the acceptor domain, in the presence and/or the absence of carbohydrate, is within ±50% of the Förster distance.

8. The sensor molecule of claim 1, wherein the BgaR transcription factor or variant thereof comprises an amino acid sequence which is at least 90% identical to that provided in SEQ ID NO: 1.

9. The sensor molecule of claim 1, wherein the BgaR transcription factor or variant thereof comprises an amino acid sequence which is at least 95% identical to that provided in SEQ ID NO: 1.

10. The sensor molecule of claim 1, wherein the BgaR transcription factor or variant thereof comprises the amino acid sequence provided in SEQ ID NO: 1.

11. The sensor molecule of claim 1, wherein the sensor molecule has at least 90% sequence identity to the polypeptide provided in SEQ ID NO: 15.

12. The sensor molecule of claim 1, wherein the sensor molecule has at least 90% sequence identity to the polypeptide provided in SEQ ID NO: 16.

13. The sensor molecule of claim 1, wherein the sensor molecule has at least 95% sequence identity to the polypeptide provided in SEQ ID NO: 15.

14. The sensor molecule of claim 1, wherein the sensor molecule has at least 95% sequence identity to the polypeptide provided in SEQ ID NO: 16.

15. The sensor molecule of claim 1, wherein the sensor molecule has at least 95% sequence identity to the polypeptide provided in SEQ ID NO: 17.

16. The sensor molecule of claim 1, wherein the sensor molecule has at least 95% sequence identity to the polypeptide provided in SEQ ID NO: 18.

17. The sensor molecule of claim 1, wherein the sensor molecule is the polypeptide provided in SEQ ID NO: 15.

18. The sensor molecule of claim 1, wherein the sensor molecule is the polypeptide provided in SEQ ID NO: 16.

19. The sensor molecule of claim 1, wherein the sensor molecule is the polypeptide provided in SEQ ID NO: 17.

20. The sensor molecule of claim 1, wherein the sensor molecule is the polypeptide provided in SEQ ID NO: 18.

* * * * *

SEQUENCE LISTING

<160> NUMBER OF SEQ ID NOS: 74

<210> SEQ ID NO 1
<211> LENGTH: 279
<212> TYPE: PRT
<213> ORGANISM: Artificial Sequence
<220> FEATURE:
<223> OTHER INFORMATION: BgaR

<400> SEQUENCE: 1

```
Met Gln Ile Leu Trp Lys Lys Tyr Val Lys Glu Asn Phe Glu Met Asn
1               5                   10                  15

Val Asp Glu Cys Gly Ile Glu Gln Gly Ile Pro Gly Leu Gly Tyr Asn
            20                  25                  30

Tyr Glu Val Leu Lys Asn Ala Val Ile His Tyr Val Thr Lys Gly Tyr
        35                  40                  45

Gly Thr Phe Lys Phe Asn Gly Lys Val Tyr Asn Leu Lys Gln Gly Asp
    50                  55                  60

Ile Phe Ile Leu Leu Lys Gly Met Gln Val Glu Tyr Val Ala Ser Ile
65                  70                  75                  80

Asp Asp Pro Trp Glu Tyr Tyr Trp Ile Gly Phe Ser Gly Ser Asn Ala
                85                  90                  95

Asn Glu Tyr Leu Asn Arg Thr Ser Ile Thr Asn Ser Cys Val Ala Asn
            100                 105                 110

Cys Glu Glu Asn Ser Lys Ile Pro Gln Ile Ile Leu Asn Met Cys Glu
        115                 120                 125

Ile Ser Lys Thr Tyr Asn Pro Ser Arg Ser Asp Asp Ile Leu Leu Leu
    130                 135                 140

Lys Glu Leu Tyr Ser Leu Leu Tyr Ala Leu Ile Glu Glu Phe Pro Lys
145                 150                 155                 160

Pro Phe Glu Tyr Lys Asp Lys Glu Leu His Thr Tyr Ile Gln Asp Ala
                165                 170                 175

Leu Asn Phe Ile Asn Ser Asn Tyr Met His Ser Ile Thr Val Gln Glu
            180                 185                 190

Ile Ala Asp Tyr Val Asn Leu Ser Arg Ser Tyr Leu Tyr Lys Met Phe
        195                 200                 205

Ile Lys Asn Leu Gly Ile Ser Pro Gln Arg Tyr Leu Ile Asn Leu Arg
    210                 215                 220

Met Tyr Lys Ala Thr Leu Leu Leu Lys Ser Thr Lys Leu Pro Ile Gly
225                 230                 235                 240

Glu Val Ala Ser Ser Val Gly Tyr Ser Asp Ser Leu Leu Phe Ser Lys
                245                 250                 255

Thr Phe Ser Lys His Phe Ser Met Ser Pro Leu Asn Tyr Arg Asn Asn
            260                 265                 270

Gln Val Asn Lys Pro Ser Ile
        275
```

<210> SEQ ID NO 2
<211> LENGTH: 6
<212> TYPE: PRT
<213> ORGANISM: Artificial Sequence
<220> FEATURE:
<223> OTHER INFORMATION: Linker sequence

<400> SEQUENCE: 2

```
Gly Ser Ser Gly Gly Ser
1               5
```

```
<210> SEQ ID NO 3
<211> LENGTH: 6
<212> TYPE: PRT
<213> ORGANISM: Artificial Sequence
<220> FEATURE:
<223> OTHER INFORMATION: Linker sequence

<400> SEQUENCE: 3

Gly Gly Ser Gly Gly Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Linker sequence

<400> SEQUENCE: 4

Gly Gly Thr Gly Gly Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Linker sequence

<400> SEQUENCE: 5

Gly Gly Gly Gly Gly Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Linker sequence

<400> SEQUENCE: 6

Leu Gln Gly Gly Thr Gly Gly Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Linker sequence

<400> SEQUENCE: 7

Phe Glu Gly Gly Thr Gly Gly Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Linker sequence

<400> SEQUENCE: 8

Gly Gly Ser Gly Gly Ser Leu
1               5
```

```
<210> SEQ ID NO 9
<211> LENGTH: 157
<212> TYPE: PRT
<213> ORGANISM: Artificial Sequence
<220> FEATURE:
<223> OTHER INFORMATION: BgaR putative CBD

<400> SEQUENCE: 9
```

Met Gln Ile Leu Trp Lys Lys Tyr Val Lys Glu Asn Phe Glu Met Asn
1               5                   10                  15

Val Asp Glu Cys Gly Ile Glu Gln Gly Ile Pro Gly Leu Gly Tyr Asn
            20                  25                  30

Tyr Glu Val Leu Lys Asn Ala Val Ile His Tyr Val Thr Lys Gly Tyr
        35                  40                  45

Gly Thr Phe Lys Phe Asn Gly Lys Val Tyr Asn Leu Lys Gln Gly Asp
    50                  55                  60

Ile Phe Ile Leu Leu Lys Gly Met Gln Val Glu Tyr Val Ala Ser Ile
65                  70                  75                  80

Asp Asp Pro Trp Glu Tyr Tyr Trp Ile Gly Phe Ser Gly Ser Asn Ala
                85                  90                  95

Asn Glu Tyr Leu Asn Arg Thr Ser Ile Thr Asn Ser Cys Val Ala Asn
            100                 105                 110

Cys Glu Glu Asn Ser Lys Ile Pro Gln Ile Ile Leu Asn Met Cys Glu
        115                 120                 125

Ile Ser Lys Thr Tyr Asn Pro Ser Arg Ser Asp Asp Ile Leu Leu Leu
    130                 135                 140

Lys Glu Leu Tyr Ser Leu Leu Tyr Ala Leu Ile Glu Glu
145                 150                 155

```
<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
aaaaaactgc agatgcagat tctgtg                                        26

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
acacacttcg aaaatgctcg gtttat                                        26

<210> SEQ ID NO 12
<211> LENGTH: 50
<212> TYPE: DNA
<213> ORGANISM: Artificial Sequence
<220> FEATURE:
<223> OTHER INFORMATION: primer

<400> SEQUENCE: 12
aaaaaactgc agggtggtac cggaggcggc atgcagattc tgtggaaaaa              50

<210> SEQ ID NO 13
<211> LENGTH: 50
<212> TYPE: DNA
```

<213> ORGANISM: Artificial Sequence
<220> FEATURE:
<223> OTHER INFORMATION: primer

<400> SEQUENCE: 13
aaaaaattcg aagccgcctc cggtaccacc aatgctcggt ttattaactt    50

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
aaaaaactgc agaatgctcg gtttat    26

<210> SEQ ID NO 15
<211> LENGTH: 833
<212> TYPE: PRT
<213> ORGANISM: Artificial Sequence
<220> FEATURE:
<223> OTHER INFORMATION: LacB1

<400> SEQUENCE: 15

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Leu
225                 230                 235                 240

Gln Met Gln Ile Leu Trp Lys Lys Tyr Val Lys Glu Asn Phe Glu Met
                245                 250                 255
```

```
Asn Val Asp Glu Cys Gly Ile Glu Gln Gly Ile Pro Gly Leu Gly Tyr
            260                 265                 270

Asn Tyr Glu Val Leu Lys Asn Ala Val Ile His Tyr Thr Lys Gly
        275                 280                 285

Tyr Gly Thr Phe Lys Phe Asn Gly Lys Val Tyr Asn Leu Lys Gln Gly
    290                 295                 300

Asp Ile Phe Ile Leu Leu Lys Gly Met Gln Val Glu Tyr Val Ala Ser
305                 310                 315                 320

Ile Asp Asp Pro Trp Glu Tyr Tyr Trp Ile Gly Phe Ser Gly Ser Asn
                325                 330                 335

Ala Asn Glu Tyr Leu Asn Arg Thr Ser Ile Thr Asn Ser Cys Val Ala
                340                 345                 350

Asn Cys Glu Glu Asn Ser Lys Ile Pro Gln Ile Ile Leu Asn Met Cys
                355                 360                 365

Glu Ile Ser Lys Thr Tyr Asn Pro Ser Arg Ser Asp Asp Ile Leu Leu
    370                 375                 380

Leu Lys Glu Leu Tyr Ser Leu Tyr Ala Leu Ile Glu Glu Phe Pro
385                 390                 395                 400

Lys Pro Phe Glu Tyr Lys Asp Lys Glu Leu His Thr Tyr Ile Gln Asp
                405                 410                 415

Ala Leu Asn Phe Ile Asn Ser Asn Tyr Met His Ser Ile Thr Val Gln
                420                 425                 430

Glu Ile Ala Asp Tyr Val Asn Leu Ser Arg Ser Tyr Leu Tyr Lys Met
        435                 440                 445

Phe Ile Lys Asn Leu Gly Ile Ser Pro Gln Arg Tyr Leu Ile Asn Leu
    450                 455                 460

Arg Met Tyr Lys Ala Thr Leu Leu Leu Lys Ser Thr Lys Leu Pro Ile
465                 470                 475                 480

Gly Glu Val Ala Ser Ser Val Gly Tyr Ser Asp Ser Leu Leu Phe Ser
                485                 490                 495

Lys Thr Phe Ser Lys His Phe Ser Met Ser Pro Leu Asn Tyr Arg Asn
                500                 505                 510

Asn Gln Val Asn Lys Pro Ser Ile Phe Glu Met Ala Ser Lys Val Tyr
        515                 520                 525

Asp Pro Glu Gln Arg Lys Arg Met Ile Thr Gly Pro Gln Trp Trp Ala
    530                 535                 540

Arg Cys Lys Gln Met Asn Val Leu Asp Ser Phe Ile Asn Tyr Tyr Asp
545                 550                 555                 560

Ser Glu Lys His Ala Glu Asn Ala Val Ile Phe Leu His Gly Asn Ala
                565                 570                 575

Thr Ser Ser Tyr Leu Trp Arg His Val Val Pro His Ile Glu Pro Val
                580                 585                 590

Ala Arg Cys Ile Ile Pro Asp Leu Ile Gly Met Gly Lys Ser Gly Lys
    595                 600                 605

Ser Gly Asn Gly Ser Tyr Arg Leu Leu Asp His Tyr Lys Tyr Leu Thr
    610                 615                 620

Ala Trp Phe Glu Leu Leu Asn Leu Pro Lys Lys Ile Ile Phe Val Gly
625                 630                 635                 640

His Asp Trp Gly Ala Ala Leu Ala Phe His Tyr Ala Tyr Glu His Gln
                645                 650                 655

Asp Arg Ile Lys Ala Ile Val His Met Glu Ser Val Val Asp Val Ile
                660                 665                 670
```

```
Glu Ser Trp Asp Glu Trp Pro Asp Ile Glu Glu Asp Ile Ala Leu Ile
            675                 680                 685
Lys Ser Glu Glu Gly Lys Met Val Leu Glu Asn Asn Phe Phe Val
690                 695                 700
Glu Thr Val Leu Pro Ser Lys Ile Met Arg Lys Leu Glu Pro Glu Glu
705                 710                 715                 720
Phe Ala Ala Tyr Leu Glu Pro Phe Lys Glu Lys Gly Glu Val Arg Arg
                725                 730                 735
Pro Thr Leu Ser Trp Pro Arg Glu Ile Pro Leu Val Lys Gly Gly Lys
                740                 745                 750
Pro Asp Val Val Gln Ile Val Arg Asn Tyr Asn Ala Tyr Leu Arg Ala
                755                 760                 765
Ser Asp Asp Leu Pro Lys Leu Phe Ile Glu Ser Asp Pro Gly Phe Phe
                770                 775                 780
Ser Asn Ala Ile Val Glu Gly Ala Lys Lys Phe Pro Asn Thr Glu Phe
785                 790                 795                 800
Val Lys Val Lys Gly Leu His Phe Leu Gln Glu Asp Ala Pro Asp Glu
                805                 810                 815
Met Gly Lys Tyr Ile Lys Ser Phe Val Glu Arg Val Leu Lys Asn Glu
                820                 825                 830
Gln

<210> SEQ ID NO 16
<211> LENGTH: 845
<212> TYPE: PRT
<213> ORGANISM: Artificial Sequence
<220> FEATURE:
<223> OTHER INFORMATION: LacB2

<400> SEQUENCE: 16

Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
                20                  25                  30
Glu Gly Glu Gly Asp Ala Thr Tyr Gly Lys Leu Thr Leu Lys Phe Ile
            35                  40                  45
Cys Thr Thr Gly Lys Leu Pro Val Pro Trp Pro Thr Leu Val Thr Thr
50                  55                  60
Leu Ser Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
            115                 120                 125
Ile Asp Phe Lys Glu Asp Gly Asn Ile Leu Gly His Lys Leu Glu Tyr
130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
```

-continued

```
Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Leu
225                 230                 235                 240

Gln Gly Gly Thr Gly Gly Met Gln Ile Leu Trp Lys Lys Tyr Val
                245                 250                 255

Lys Glu Asn Phe Glu Met Asn Val Asp Glu Cys Gly Ile Glu Gln Gly
                260                 265                 270

Ile Pro Gly Leu Gly Tyr Asn Tyr Glu Val Leu Lys Asn Ala Val Ile
            275                 280                 285

His Tyr Val Thr Lys Gly Tyr Gly Thr Phe Lys Phe Asn Gly Lys Val
            290                 295                 300

Tyr Asn Leu Lys Gln Gly Asp Ile Phe Ile Leu Leu Lys Gly Met Gln
305                 310                 315                 320

Val Glu Tyr Val Ala Ser Ile Asp Asp Pro Trp Glu Tyr Tyr Trp Ile
                325                 330                 335

Gly Phe Ser Gly Ser Asn Ala Asn Glu Tyr Leu Asn Arg Thr Ser Ile
            340                 345                 350

Thr Asn Ser Cys Val Ala Asn Cys Glu Glu Asn Ser Lys Ile Pro Gln
            355                 360                 365

Ile Ile Leu Asn Met Cys Glu Ile Ser Lys Thr Tyr Asn Pro Ser Arg
370                 375                 380

Ser Asp Asp Ile Leu Leu Leu Lys Glu Leu Tyr Ser Leu Leu Tyr Ala
385                 390                 395                 400

Leu Ile Glu Glu Phe Pro Lys Pro Phe Glu Tyr Lys Asp Lys Glu Leu
                405                 410                 415

His Thr Tyr Ile Gln Asp Ala Leu Asn Phe Ile Asn Ser Asn Tyr Met
            420                 425                 430

His Ser Ile Thr Val Gln Glu Ile Ala Asp Tyr Val Asn Leu Ser Arg
            435                 440                 445

Ser Tyr Leu Tyr Lys Met Phe Ile Lys Asn Leu Gly Ile Ser Pro Gln
    450                 455                 460

Arg Tyr Leu Ile Asn Leu Arg Met Tyr Lys Ala Thr Leu Leu Leu Lys
465                 470                 475                 480

Ser Thr Lys Leu Pro Ile Gly Glu Val Ala Ser Ser Val Gly Tyr Ser
                485                 490                 495

Asp Ser Leu Leu Phe Ser Lys Thr Phe Ser Lys His Phe Ser Met Ser
            500                 505                 510

Pro Leu Asn Tyr Arg Asn Asn Gln Val Asn Lys Pro Ser Ile Phe Glu
            515                 520                 525

Gly Gly Thr Gly Gly Met Ala Ser Lys Val Tyr Asp Pro Glu Gln
                530                 535                 540

Arg Lys Arg Met Ile Thr Gly Pro Gln Trp Trp Ala Arg Cys Lys Gln
545                 550                 555                 560

Met Asn Val Leu Asp Ser Phe Ile Asn Tyr Tyr Asp Ser Glu Lys His
                565                 570                 575

Ala Glu Asn Ala Val Ile Phe Leu His Gly Asn Ala Thr Ser Ser Tyr
            580                 585                 590

Leu Trp Arg His Val Val Pro His Ile Glu Pro Val Ala Arg Cys Ile
    595                 600                 605
```

-continued

```
Ile Pro Asp Leu Ile Gly Met Gly Lys Ser Gly Lys Ser Gly Asn Gly
610                 615                 620

Ser Tyr Arg Leu Leu Asp His Tyr Lys Tyr Leu Thr Ala Trp Phe Glu
625                 630                 635                 640

Leu Leu Asn Leu Pro Lys Lys Ile Ile Phe Val Gly His Asp Trp Gly
                645                 650                 655

Ala Ala Leu Ala Phe His Tyr Ala Tyr Glu His Gln Asp Arg Ile Lys
                660                 665                 670

Ala Ile Val His Met Glu Ser Val Asp Val Ile Glu Ser Trp Asp
            675                 680                 685

Glu Trp Pro Asp Ile Glu Glu Asp Ile Ala Leu Ile Lys Ser Glu Glu
690                 695                 700

Gly Glu Lys Met Val Leu Glu Asn Asn Phe Phe Val Glu Thr Val Leu
705                 710                 715                 720

Pro Ser Lys Ile Met Arg Lys Leu Glu Pro Glu Phe Ala Ala Tyr
                725                 730                 735

Leu Glu Pro Phe Lys Glu Lys Gly Glu Val Arg Arg Pro Thr Leu Ser
                740                 745                 750

Trp Pro Arg Glu Ile Pro Leu Val Lys Gly Gly Lys Pro Asp Val Val
            755                 760                 765

Gln Ile Val Arg Asn Tyr Asn Ala Tyr Leu Arg Ala Ser Asp Asp Leu
770                 775                 780

Pro Lys Leu Phe Ile Glu Ser Asp Pro Gly Phe Phe Ser Asn Ala Ile
785                 790                 795                 800

Val Glu Gly Ala Lys Lys Phe Pro Asn Thr Glu Phe Val Lys Val Lys
                805                 810                 815

Gly Leu His Phe Leu Gln Glu Asp Ala Pro Asp Glu Met Gly Lys Tyr
                820                 825                 830

Ile Lys Ser Phe Val Glu Arg Val Leu Lys Asn Glu Gln
                835                 840                 845

<210> SEQ ID NO 17
<211> LENGTH: 839
<212> TYPE: PRT
<213> ORGANISM: Artificial Sequence
<220> FEATURE:
<223> OTHER INFORMATION: LacB3

<400> SEQUENCE: 17

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

-continued

```
Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Leu
225                 230                 235                 240

Gln Gly Gly Thr Gly Gly Met Gln Ile Leu Trp Lys Lys Tyr Val
                245                 250                 255

Lys Glu Asn Phe Glu Met Asn Val Asp Glu Cys Gly Ile Glu Gln Gly
                260                 265                 270

Ile Pro Gly Leu Gly Tyr Asn Tyr Glu Val Leu Lys Asn Ala Val Ile
            275                 280                 285

His Tyr Val Thr Lys Gly Tyr Gly Thr Phe Lys Phe Asn Gly Lys Val
        290                 295                 300

Tyr Asn Leu Lys Gln Gly Asp Ile Phe Ile Leu Leu Lys Gly Met Gln
305                 310                 315                 320

Val Glu Tyr Val Ala Ser Ile Asp Asp Pro Trp Glu Tyr Tyr Trp Ile
                325                 330                 335

Gly Phe Ser Gly Ser Asn Ala Asn Glu Tyr Leu Asn Arg Thr Ser Ile
                340                 345                 350

Thr Asn Ser Cys Val Ala Asn Cys Glu Glu Asn Ser Lys Ile Pro Gln
            355                 360                 365

Ile Ile Leu Asn Met Cys Glu Ile Ser Lys Thr Tyr Asn Pro Ser Arg
        370                 375                 380

Ser Asp Asp Ile Leu Leu Leu Lys Glu Leu Tyr Ser Leu Leu Tyr Ala
385                 390                 395                 400

Leu Ile Glu Glu Phe Pro Lys Pro Phe Glu Tyr Lys Asp Lys Glu Leu
                405                 410                 415

His Thr Tyr Ile Gln Asp Ala Leu Asn Phe Ile Asn Ser Asn Tyr Met
                420                 425                 430

His Ser Ile Thr Val Gln Glu Ile Ala Asp Tyr Val Asn Leu Ser Arg
            435                 440                 445

Ser Tyr Leu Tyr Lys Met Phe Ile Lys Asn Leu Gly Ile Ser Pro Gln
        450                 455                 460

Arg Tyr Leu Ile Asn Leu Arg Met Tyr Lys Ala Thr Leu Leu Leu Lys
465                 470                 475                 480

Ser Thr Lys Leu Pro Ile Gly Glu Val Ala Ser Ser Val Gly Tyr Ser
                485                 490                 495

Asp Ser Leu Leu Phe Ser Lys Thr Phe Ser Lys His Phe Ser Met Ser
            500                 505                 510

Pro Leu Asn Tyr Arg Asn Asn Gln Val Asn Lys Pro Ser Ile Phe Glu
        515                 520                 525

Met Ala Ser Lys Val Tyr Asp Pro Glu Gln Arg Lys Arg Met Ile Thr
530                 535                 540
```

Gly Pro Gln Trp Trp Ala Arg Cys Lys Gln Met Asn Val Leu Asp Ser
545                 550                 555                 560

Phe Ile Asn Tyr Tyr Asp Ser Glu Lys His Ala Glu Asn Ala Val Ile
                565                 570                 575

Phe Leu His Gly Asn Ala Thr Ser Ser Tyr Leu Trp Arg His Val Val
            580                 585                 590

Pro His Ile Glu Pro Val Ala Arg Cys Ile Ile Pro Asp Leu Ile Gly
        595                 600                 605

Met Gly Lys Ser Gly Lys Ser Gly Asn Gly Ser Tyr Arg Leu Leu Asp
610                 615                 620

His Tyr Lys Tyr Leu Thr Ala Trp Phe Glu Leu Leu Asn Leu Pro Lys
625                 630                 635                 640

Lys Ile Ile Phe Val Gly His Asp Trp Gly Ala Ala Leu Ala Phe His
                645                 650                 655

Tyr Ala Tyr Glu His Gln Asp Arg Ile Lys Ala Ile Val His Met Glu
            660                 665                 670

Ser Val Val Asp Val Ile Glu Ser Trp Asp Glu Trp Pro Asp Ile Glu
        675                 680                 685

Glu Asp Ile Ala Leu Ile Lys Ser Glu Glu Gly Glu Lys Met Val Leu
690                 695                 700

Glu Asn Asn Phe Phe Val Glu Thr Val Leu Pro Ser Lys Ile Met Arg
705                 710                 715                 720

Lys Leu Glu Pro Glu Glu Phe Ala Ala Tyr Leu Glu Pro Phe Lys Glu
                725                 730                 735

Lys Gly Glu Val Arg Arg Pro Thr Leu Ser Trp Pro Arg Glu Ile Pro
            740                 745                 750

Leu Val Lys Gly Gly Lys Pro Asp Val Val Gln Ile Val Arg Asn Tyr
        755                 760                 765

Asn Ala Tyr Leu Arg Ala Ser Asp Asp Leu Pro Lys Leu Phe Ile Glu
770                 775                 780

Ser Asp Pro Gly Phe Phe Ser Asn Ala Ile Val Glu Gly Ala Lys Lys
785                 790                 795                 800

Phe Pro Asn Thr Glu Phe Val Lys Val Lys Gly Leu His Phe Leu Gln
                805                 810                 815

Glu Asp Ala Pro Asp Glu Met Gly Lys Tyr Ile Lys Ser Phe Val Glu
            820                 825                 830

Arg Val Leu Lys Asn Glu Gln
        835

<210> SEQ ID NO 18
<211> LENGTH: 839
<212> TYPE: PRT
<213> ORGANISM: Artificial Sequence
<220> FEATURE:
<223> OTHER INFORMATION: LacB4

<400> SEQUENCE: 18

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

```
Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Leu
225                 230                 235                 240

Gln Met Gln Ile Leu Trp Lys Lys Tyr Val Lys Glu Asn Phe Glu Met
                245                 250                 255

Asn Val Asp Glu Cys Gly Ile Glu Gln Gly Ile Pro Gly Leu Gly Tyr
            260                 265                 270

Asn Tyr Glu Val Leu Lys Asn Ala Val Ile His Tyr Val Thr Lys Gly
        275                 280                 285

Tyr Gly Thr Phe Lys Phe Asn Gly Lys Val Tyr Asn Leu Lys Gln Gly
    290                 295                 300

Asp Ile Phe Ile Leu Leu Lys Gly Met Gln Val Glu Tyr Val Ala Ser
305                 310                 315                 320

Ile Asp Asp Pro Trp Glu Tyr Tyr Trp Ile Gly Phe Ser Gly Ser Asn
                325                 330                 335

Ala Asn Glu Tyr Leu Asn Arg Thr Ser Ile Thr Asn Ser Cys Val Ala
            340                 345                 350

Asn Cys Glu Glu Asn Ser Lys Ile Pro Gln Ile Ile Leu Asn Met Cys
        355                 360                 365

Glu Ile Ser Lys Thr Tyr Asn Pro Ser Arg Ser Asp Ile Leu Leu
370                 375                 380

Leu Lys Glu Leu Tyr Ser Leu Leu Tyr Ala Leu Ile Glu Glu Phe Pro
385                 390                 395                 400

Lys Pro Phe Glu Tyr Lys Asp Lys Glu Leu His Thr Tyr Ile Gln Asp
                405                 410                 415

Ala Leu Asn Phe Ile Asn Ser Asn Tyr Met His Ser Ile Thr Val Gln
            420                 425                 430

Glu Ile Ala Asp Tyr Val Asn Leu Ser Arg Ser Tyr Leu Tyr Lys Met
        435                 440                 445

Phe Ile Lys Asn Leu Gly Ile Ser Pro Gln Arg Tyr Leu Ile Asn Leu
    450                 455                 460

Arg Met Tyr Lys Ala Thr Leu Leu Leu Lys Ser Thr Lys Leu Pro Ile
465                 470                 475                 480
```

```
Gly Glu Val Ala Ser Ser Val Gly Tyr Ser Asp Ser Leu Leu Phe Ser
                485                 490                 495
Lys Thr Phe Ser Lys His Phe Ser Met Ser Pro Leu Asn Tyr Arg Asn
            500                 505                 510
Asn Gln Val Asn Lys Pro Ser Ile Phe Glu Gly Gly Thr Gly Gly Gly
            515                 520                 525
Met Ala Ser Lys Val Tyr Asp Pro Glu Gln Arg Lys Arg Met Ile Thr
530                 535                 540
Gly Pro Gln Trp Trp Ala Arg Cys Lys Gln Met Asn Val Leu Asp Ser
545                 550                 555                 560
Phe Ile Asn Tyr Tyr Asp Ser Glu Lys His Ala Glu Asn Ala Val Ile
                565                 570                 575
Phe Leu His Gly Asn Ala Thr Ser Ser Tyr Leu Trp Arg His Val Val
            580                 585                 590
Pro His Ile Glu Pro Val Ala Arg Cys Ile Ile Pro Asp Leu Ile Gly
            595                 600                 605
Met Gly Lys Ser Gly Lys Ser Gly Asn Gly Ser Tyr Arg Leu Leu Asp
            610                 615                 620
His Tyr Lys Tyr Leu Thr Ala Trp Phe Glu Leu Leu Asn Leu Pro Lys
625                 630                 635                 640
Lys Ile Ile Phe Val Gly His Asp Trp Gly Ala Ala Leu Ala Phe His
                645                 650                 655
Tyr Ala Tyr Glu His Gln Asp Arg Ile Lys Ala Ile Val His Met Glu
            660                 665                 670
Ser Val Val Asp Val Ile Glu Ser Trp Asp Glu Trp Pro Asp Ile Glu
            675                 680                 685
Glu Asp Ile Ala Leu Ile Lys Ser Glu Glu Gly Glu Lys Met Val Leu
            690                 695                 700
Glu Asn Asn Phe Phe Val Glu Thr Val Leu Pro Ser Lys Ile Met Arg
705                 710                 715                 720
Lys Leu Glu Pro Glu Glu Phe Ala Ala Tyr Leu Glu Pro Phe Lys Glu
                725                 730                 735
Lys Gly Glu Val Arg Arg Pro Thr Leu Ser Trp Pro Arg Glu Ile Pro
            740                 745                 750
Leu Val Lys Gly Gly Lys Pro Asp Val Gln Ile Val Arg Asn Tyr
            755                 760                 765
Asn Ala Tyr Leu Arg Ala Ser Asp Asp Leu Pro Lys Leu Phe Ile Glu
            770                 775                 780
Ser Asp Pro Gly Phe Phe Ser Asn Ala Ile Val Glu Gly Ala Lys Lys
785                 790                 795                 800
Phe Pro Asn Thr Glu Phe Val Lys Val Lys Gly Leu His Phe Leu Gln
                805                 810                 815
Glu Asp Ala Pro Asp Glu Met Gly Lys Tyr Ile Lys Ser Phe Val Glu
            820                 825                 830
Arg Val Leu Lys Asn Glu Gln
        835

<210> SEQ ID NO 19
<211> LENGTH: 2502
<212> TYPE: DNA
<213> ORGANISM: Artificial Sequence
<220> FEATURE:
<223> OTHER INFORMATION: Nucleotide sequence encoding LacB1
```

<400> SEQUENCE: 19

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgagcta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagctg    720
cagatgcaga ttctgtggaa aaaatacgtc aaagaaaact ttgaaatgaa cgtggatgaa    780
tgcggcattg aacaaggcat tccgggcctg ggttataact acgaagttct gaaaaatgca    840
gtcatccatt atgtgaccaa aggctatggt acgtttaaat caacggcaa agtctataat     900
ctgaaacagg gtgacatttt catcctgctg aaaggcatgc aagtggaata cgttgcgagc    960
attgatgacc cgtgggaata ttactggatc ggctttagtg gttccaacgc gaatgaatat   1020
ctgaaccgta ccagcattac caacagctgc gtggccaact gtgaagaaaa tagcaaaatt   1080
ccgcagatta tcctgaacat gtgtgaaatc tctaaaaacct acaacccgtc acgctcggat   1140
gacattctgc tgctgaaaga actgtattcc ctgctgtacg cactgatcga agaatttccg   1200
aaaccgtttg aatacaaaga taaagaactg catacctaca ttcaggacgc gctgaacttc   1260
atcaactcaa attatatgca ctcgattacg gtgcaagaaa tcgccgatta cgttaatctg   1320
agccgttctt acctgtacaa aatgttcatc aaaaacctgg gtatcagtcc gcagcgttat   1380
ctgattaatc tgcgcatgta caaagcaacc ctgctgctga atctacgaa actgccgatc     1440
ggcgaagttg cgagcagcgt gggttatagt gattccctgc tgtttagtaa aaccttctcc   1500
aaacactttt caatgtcgcc gctgaactac cgcaacaatc aagttaataa accgagcatt   1560
ttcgaaatgg cttccaaggt gtacgacccc gagcaacgca aacgcatgat cactgggcct   1620
cagtggtggg ctcgctgcaa gcaaatgaac gtgctggact ccttcatcaa ctactatgat   1680
tccgagaagc acgccgagaa cgccgtgatt tttctgcatg gtaacgctac ctccagctac   1740
ctgtggaggc acgtcgtgcc tcacatcgag cccgtggcta gatgcatcat ccctgatctg   1800
atcggaatgg gtaagtccgg caagagcggg aatggctcat atcgcctcct ggatcactac   1860
aagtacctca ccgcttggtt cgagctgctg aaccttccaa agaaaatcat ctttgtgggc   1920
cacgactggg gggctgctct ggcctttcac tacgcctacg agcaccaaga caggatcaag   1980
gccatcgtcc atatggagag tgtcgtggac gtgatcgagt cctgggacga gtggcctgac   2040
atcgaggagg atatcgccct gatcaagagc gaagagggcg agaaaatggt gcttgagaat   2100
aacttcttcg tcgagaccgt gctcccaagc aagatcatgc ggaaactgga gcctgaggag   2160
ttcgctgcct acctggagcc attcaaggag aagggcgagg ttagacggcc taccctctcc   2220
tggcctcgcg agatccctct cgttaaggga ggcaagcccg acgtcgtcca gattgtccgc   2280
```

```
aactacaacg cctaccttcg ggccagcgac gatctgccta agctgttcat cgagtccgac    2340
cctgggttct tttccaacgc tattgtcgag ggagctaaga agttccctaa caccgagttc    2400
gtgaaggtga agggcctcca cttcctccag gaggacgctc cagatgaaat gggtaagtac    2460
atcaagagct tcgtggagcg cgtgctgaag aacgagcagt aa                      2502

<210> SEQ ID NO 20
<211> LENGTH: 2538
<212> TYPE: DNA
<213> ORGANISM: Artificial Sequence
<220> FEATURE:
<223> OTHER INFORMATION: Nucleotide sequence encoding LacB2

<400> SEQUENCE: 20
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgagcta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagctg     720
cagggtggta ccggaggcgg catgcagatt ctgtggaaaa aatacgtcaa gaaaacttt     780 gaaatgaacg tggatgaatg cggcattgaa caaggcattc cgggcctggg ttataactac     840
gaagttctga aaaatgcagt catccattat gtgaccaaag gctatggtac gtttaaattc     900
aacggcaaag tctataatct gaaacagggt gacattttca tcctgctgaa aggcatgcaa     960
gtggaatacg ttgcgagcat tgatgacccg tgggaatatt actggatcgg ctttagtggt    1020
tccaacgcga tgaatatctc gaaccgtacc agcattacca acagctgcgt ggccaactgt    1080
gaagaaaata gcaaaattcc gcagattatc ctgaacatgt gtgaaatctc taaaacctac    1140
aacccgtcac gctcggatga cattctgctg ctgaaagaac tgtattccct gctgtacgca    1200
ctgatcgaag aatttccgaa accgtttgaa tacaaagata agaactgca tacctacatt    1260 caggacgcgc tgaacttcat caactcaaat tatatgcact cgattacggt gcaagaaatc    1320
gccgattacg ttaatctgag ccgttcttac ctgtacaaaa tgttcatcaa aaacctgggt    1380
atcagtccgc agcgttatct gattaatctg cgcatgtaca agcaacccct gctgctgaaa    1440
tctacgaaac tgccgatcgg cgaagttgcg agcagcgtgg ttatagtga ttccctgctg    1500 tttagtaaaa ccttctccaa acactttca atgtcgccgc tgaactaccg caacaatcaa    1560
gttaataaac cgagcatttt cgaaggtggt accggaggcg gcatggcttc caaggtgtac    1620
gaccccgagc aacgcaaacg catgatcact gggcctcagt ggtgggctcg ctgcaagcaa    1680
atgaacgtgc tggactcctt catcaactac tatgattccg agaagcacgc cgagaacgcc    1740
gtgatttttc tgcatggtaa cgctacctcc agctacctgt ggaggcacgt cgtgcctcac    1800
atcgagcccg tggctagatg catcatccct gatctgatcg gaatgggtaa gtccggcaag    1860
```

```
agcgggaatg gctcatatcg cctcctggat cactacaagt acctcaccgc ttggttcgag   1920
ctgctgaacc ttccaaagaa aatcatcttt gtgggccacg actggggggc tgctctggcc   1980
tttcactacg cctacgagca ccaagacagg atcaaggcca tcgtccatat ggagagtgtc   2040
gtggacgtga tcgagtcctg ggacgagtgg cctgacatcg aggaggatat cgccctgatc   2100
aagagcgaag agggcgagaa aatggtgctt gagaataact tcttcgtcga ccgtgctc     2160 ccaagcaaga tcatgcggaa actggagcct gaggagttcg ctgcctacct ggagccattc   2220
aaggagaagg gcgaggttag acggcctacc ctctcctggc ctcgcgagat ccctctcgtt   2280
aagggaggca agcccgacgt cgtccagatt gtccgcaact acaacgccta ccttcgggcc   2340
agcgacgatc tgcctaagct gttcatcgag tccgaccctg ggttcttttc caacgctatt   2400
gtcgagggag ctaagaagtt ccctaacacc gagttcgtga aggtgaaggg cctccacttc   2460
ctccaggagg acgctccaga tgaaatgggt aagtacatca agagcttcgt ggagcgcgtg   2520
ctgaagaacg agcagtaa                                                 2538
```

<210> SEQ ID NO 21
<211> LENGTH: 2520
<212> TYPE: DNA
<213> ORGANISM: Artificial Sequence
<220> FEATURE:
<223> OTHER INFORMATION: Nucleotide sequence encoding LacB3

<400> SEQUENCE: 21

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgagcta cggcgtgcag tgcttcagcc gctacccgga ccacatgaag   240
cagcacgact cttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagctg   720
cagggtggta ccggaggcgg catgcagatt ctgtggaaaa aatacgtcaa agaaaacttt   780
gaaatgaacg tggatgaatg cggcattgaa caaggcattc cgggcctggg ttataactac   840
gaagttctga aaaatgcagt catccattat gtgaccaaag ctatggtac gtttaaattc   900 aacggcaaag tctataatct gaaacagggt gacattttca tcctgctgaa aggcatgcaa   960
gtggaatacg ttgcgagcat tgatgacccg tgggaatatt actggatcgg ctttagtggt  1020
tccaacgcga tgaatatct gaaccgtacc agcattacca acagctgcgt ggccaactgt  1080
gaagaaaata gcaaaattcc gcagattatc ctgaacatgt gtgaaatctc taaaacctac  1140
aacccgtcac gctcggatga cattctgctg ctgaaagaac tgtattccct gctgtacgca  1200
ctgatcgaag aatttccgaa accgtttgaa tacaaagata agaactgca tacctacatt  1260 caggacgcgc tgaacttcat caactcaaat tatatgcact cgattacggt gcaagaaatc  1320
```

| | |
|---|---|
| gccgattacg ttaatctgag ccgttcttac ctgtacaaaa tgttcatcaa aaacctgggt | 1380 |
| atcagtccgc agcgttatct gattaatctg cgcatgtaca aagcaaccct gctgctgaaa | 1440 |
| tctacgaaac tgccgatcgg cgaagttgcg agcagcgtgg gttatagtga ttccctgctg | 1500 |
| tttagtaaaa ccttctccaa acactttca atgtcgccgc tgaactaccg caacaatcaa | 1560 |
| gttaataaac cgagcatttt cgaaatggct tccaaggtgt acgaccccga gcaacgcaaa | 1620 |
| cgcatgatca ctgggcctca gtggtgggct cgctgcaagc aaatgaacgt gctggactcc | 1680 |
| ttcatcaact actatgattc cgagaagcac gccgagaacg ccgtgatttt tctgcatggt | 1740 |
| aacgctacct ccagctacct gtggaggcac gtcgtgcctc acatcgagcc cgtggctaga | 1800 |
| tgcatcatcc ctgatctgat cggaatgggt aagtccggca agagcgggaa tggctcatat | 1860 |
| cgcctcctgg atcactacaa gtacctcacc gcttggttcg agctgctgaa ccttccaaag | 1920 |
| aaaatcatct ttgtgggcca cgactggggg gctgctctgg cctttcacta cgcctacgag | 1980 |
| caccaagaca ggatcaaggc catcgtccat atggagagtg tcgtggacgt gatcgagtcc | 2040 |
| tgggacgagt ggcctgacat cgaggaggat atcgccctga tcaagagcga agagggcgag | 2100 |
| aaaatggtgc ttgagaataa cttcttcgtc gagaccgtgc tcccaagcaa gatcatgcgg | 2160 |
| aaactggagc ctgaggagtt cgctgcctac ctggagccat tcaaggagaa gggcgaggtt | 2220 |
| agacggccta ccctctcctg gcctcgcgag atccctctcg ttaagggagg caagcccgac | 2280 |
| gtcgtccaga ttgtccgcaa ctacaacgcc taccttcggg ccagcgacga tctgcctaag | 2340 |
| ctgttcatcg agtccgaccc tgggttcttt tccaacgcta ttgtcgaggg agctaagaag | 2400 |
| ttccctaaca ccgagttcgt gaaggtgaag ggcctccact tcctccagga ggacgctcca | 2460 |
| gatgaaatgg gtaagtacat caagagcttc gtggagcgcg tgctgaagaa cgagcagtaa | 2520 |

<210> SEQ ID NO 22
<211> LENGTH: 2520
<212> TYPE: DNA
<213> ORGANISM: Artificial Sequence
<220> FEATURE:
<223> OTHER INFORMATION: Nucleotide sequence encoding LacB4

<400> SEQUENCE: 22

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgagcta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacacctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagctg | 720 |
| cagatgcaga ttctgtggaa aaaatacgtc aaagaaaact ttgaaatgaa cgtggatgaa | 780 |
| tgcggcattg aacaaggcat tccgggcctg gttataact acgaagttct gaaaaatgca | 840 |
| gtcatccatt atgtgaccaa aggctatggt acgtttaaat tcaacggcaa agtctataat | 900 |

```
ctgaaacagg gtgacatttt catcctgctg aaaggcatgc aagtggaata cgttgcgagc    960
attgatgacc cgtgggaata ttactggatc ggctttagtg gttccaacgc gaatgaatat   1020
ctgaaccgta ccagcattac caacagctgc gtggccaact gtgaagaaaa tagcaaaatt   1080
ccgcagatta tcctgaacat gtgtgaaatc tctaaaacct acaacccgtc acgctcggat   1140
gacattctgc tgctgaaaga actgtattcc ctgctgtacg cactgatcga agaatttccg   1200
aaaccgtttg aatacaaaga taagaactg catacctaca ttcaggacgc gctgaacttc   1260
atcaactcaa attatatgca ctcgattacg gtgcaagaaa tcgccgatta cgttaatctg   1320
agccgttctt acctgtacaa aatgttcatc aaaaacctgg gtatcagtcc gcagcgttat   1380
ctgattaatc tgcgcatgta caaagcaacc ctgctgctga atctacgaa actgccgatc   1440
ggcgaagttg cgagcagcgt gggttatagt gattccctgc tgtttagtaa aaccttctcc   1500
aaacactttt caatgtcgcc gctgaactac cgcaacaatc aagttaataa accgagcatt   1560
ttcgaaggtg gtaccggagg cggcatggct tccaaggtgt acgacccga gcaacgcaaa    1620
cgcatgatca ctgggcctca gtggtgggct cgctgcaagc aaatgaacgt gctggactcc   1680
ttcatcaact actatgattc cgagaagcac gccgagaacg ccgtgatttt tctgcatggt   1740
aacgctacct ccagctacct gtggaggcac gtcgtgcctc acatcgagcc cgtggctaga   1800
tgcatcatcc ctgatctgat cggaatgggt aagtccggca agagcgggaa tggctcatat   1860
cgcctcctgg atcactacaa gtacctcacc gcttggttcg agctgctgaa ccttccaaag   1920
aaaatcatct ttgtgggcca cgactggggg gctgctctgg cctttcacta cgcctacgag   1980
caccaagaca ggatcaaggc catcgtccat atggagagtg tcgtggacgt gatcgagtcc   2040
tgggacgagt ggcctgacat cgaggaggat atcgccctga tcaagagcga agagggcgag   2100
aaaatggtgc ttgagaataa cttcttcgtc gagaccgtgc tcccaagcaa gatcatgcgg   2160
aaactggagc tgaggagtt cgctgcctac ctggagccat tcaaggagaa gggcgaggtt   2220
agacggccta ccctctcctg gcctcgcgag atccctctcg ttaagggagg caagcccgac   2280
gtcgtccaga ttgtccgcaa ctacaacgcc taccttcggg ccagcgacga tctgcctaag   2340
ctgttcatcg agtccgaccc tgggttcttt tccaacgcta ttgtcgaggg agctaagaag   2400
ttccctaaca ccgagttcgt gaaggtgaag ggcctccact cctccagga ggacgctcca    2460
gatgaaatgg gtaagtacat caagagcttc gtggagcgcg tgctgaagaa cgagcagtaa   2520
```

<210> SEQ ID NO 23
<211> LENGTH: 799
<212> TYPE: PRT
<213> ORGANISM: Artificial Sequence
<220> FEATURE:
<223> OTHER INFORMATION: LacF1

<400> SEQUENCE: 23

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Phe Met Val Ser Lys Gly Glu Glu Leu Phe Thr
        35                  40                  45

Gly Val Val Pro Ile Leu Val Glu Leu Asp Gly Asp Val Asn Gly His
    50                  55                  60

Arg Phe Ser Val Ser Gly Glu Gly Glu Gly Asp Ala Thr Tyr Gly Lys
65                  70                  75                  80

```
Leu Thr Leu Lys Phe Ile Cys Thr Thr Gly Lys Leu Pro Val Pro Trp
                85                  90                  95
Pro Thr Leu Val Thr Thr Leu Thr Trp Gly Val Gln Cys Phe Ser Arg
                100                 105                 110
Tyr Pro Asp His Met Lys Gln His Asp Phe Phe Lys Ser Ala Met Pro
                115                 120                 125
Glu Gly Tyr Val Gln Glu Arg Thr Ile Phe Phe Lys Asp Asp Gly Asn
                130                 135                 140
Tyr Lys Thr Arg Ala Glu Val Lys Phe Glu Gly Asp Thr Leu Val Asn
145                 150                 155                 160
Arg Ile Glu Leu Lys Gly Ile Asp Phe Lys Glu Asp Gly Asn Ile Leu
                165                 170                 175
Gly His Lys Leu Glu Tyr Asn Tyr Ile Ser His Asn Val Tyr Ile Thr
                180                 185                 190
Ala Asp Lys Gln Lys Asn Gly Ile Lys Ala His Phe Lys Ile Arg His
                195                 200                 205
Asn Ile Glu Asp Gly Ser Val Gln Leu Ala Asp His Tyr Gln Gln Asn
                210                 215                 220
Thr Pro Ile Gly Asp Gly Pro Val Leu Leu Pro Asp Asn His Tyr Leu
225                 230                 235                 240
Ser Thr Gln Ser Ala Leu Ser Lys Asp Pro Asn Glu Lys Arg Asp His
                245                 250                 255
Met Val Leu Leu Glu Phe Val Thr Ala Ala Gly Ile Thr Leu Gly Met
                260                 265                 270
Asp Glu Leu Tyr Lys Leu Gln Met Gln Ile Leu Trp Lys Lys Tyr Val
                275                 280                 285
Lys Glu Asn Phe Glu Met Asn Val Asp Glu Cys Gly Ile Glu Gln Gly
                290                 295                 300
Ile Pro Gly Leu Gly Tyr Asn Tyr Glu Val Leu Lys Asn Ala Val Ile
305                 310                 315                 320
His Tyr Val Thr Lys Gly Tyr Gly Thr Phe Lys Phe Asn Gly Lys Val
                325                 330                 335
Tyr Asn Leu Lys Gln Gly Asp Ile Phe Ile Leu Lys Gly Met Gln
                340                 345                 350
Val Glu Tyr Val Ala Ser Ile Asp Asp Pro Trp Glu Tyr Tyr Trp Ile
                355                 360                 365
Gly Phe Ser Gly Ser Asn Ala Asn Glu Tyr Leu Asn Arg Thr Ser Ile
                370                 375                 380
Thr Asn Ser Cys Val Ala Asn Cys Glu Glu Asn Ser Lys Ile Pro Gln
385                 390                 395                 400
Ile Ile Leu Asn Met Cys Glu Ile Ser Lys Thr Tyr Asn Pro Ser Arg
                405                 410                 415
Ser Asp Asp Ile Leu Leu Leu Lys Glu Leu Tyr Ser Leu Leu Tyr Ala
                420                 425                 430
Leu Ile Glu Glu Phe Pro Lys Pro Phe Glu Tyr Lys Asp Lys Glu Leu
                435                 440                 445
His Thr Tyr Ile Gln Asp Ala Leu Asn Phe Ile Asn Ser Asn Tyr Met
                450                 455                 460
His Ser Ile Thr Val Gln Glu Ile Ala Asp Tyr Val Asn Leu Ser Arg
465                 470                 475                 480
Ser Tyr Leu Tyr Lys Met Phe Ile Lys Asn Leu Gly Ile Ser Pro Gln
                485                 490                 495
```

```
Arg Tyr Leu Ile Asn Leu Arg Met Tyr Lys Ala Thr Leu Leu Lys
                500                 505                 510

Ser Thr Lys Leu Pro Ile Gly Glu Val Ala Ser Ser Val Gly Tyr Ser
            515                 520                 525

Asp Ser Leu Leu Phe Ser Lys Thr Phe Ser Lys His Phe Ser Met Ser
        530                 535                 540

Pro Leu Asn Tyr Arg Asn Asn Gln Val Asn Lys Pro Ser Ile Phe Glu
545                 550                 555                 560

Met Val Ser Lys Gly Glu Glu Leu Phe Thr Gly Val Val Pro Ile Leu
                565                 570                 575

Val Glu Leu Asp Gly Asp Val Asn Gly His Lys Phe Ser Val Ser Gly
            580                 585                 590

Glu Gly Glu Gly Asp Ala Thr Tyr Gly Lys Leu Thr Leu Lys Phe Ile
        595                 600                 605

Cys Thr Thr Gly Lys Leu Pro Val Pro Trp Pro Thr Leu Val Thr Thr
610                 615                 620

Phe Gly Tyr Gly Val Gln Cys Phe Ala Arg Tyr Pro Asp His Met Arg
625                 630                 635                 640

Gln His Asp Phe Phe Lys Ser Ala Met Pro Glu Gly Tyr Val Gln Glu
                645                 650                 655

Arg Thr Ile Phe Phe Lys Asp Asp Gly Asn Tyr Lys Thr Arg Ala Glu
            660                 665                 670

Val Lys Phe Glu Gly Asp Thr Leu Val Asn Arg Ile Glu Leu Lys Gly
        675                 680                 685

Ile Asp Phe Lys Glu Asp Gly Asn Ile Leu Gly His Lys Leu Glu Tyr
690                 695                 700

Asn Tyr Asn Ser His Asn Val Tyr Ile Met Ala Asp Lys Gln Lys Asn
705                 710                 715                 720

Gly Ile Lys Val Asn Phe Lys Ile Arg His Asn Ile Glu Asp Gly Ser
                725                 730                 735

Val Gln Leu Ala Asp His Tyr Gln Gln Asn Thr Pro Ile Gly Asp Gly
            740                 745                 750

Pro Val Leu Leu Pro Asp Asn His Tyr Leu Ser Tyr Gln Ser Ala Leu
        755                 760                 765

Ser Lys Asp Pro Asn Glu Lys Arg Asp His Met Val Leu Leu Glu Phe
770                 775                 780

Val Thr Ala Ala Gly Ile Thr Leu Gly Met Asp Glu Leu Tyr Lys
785                 790                 795

<210> SEQ ID NO 24
<211> LENGTH: 2397
<212> TYPE: DNA
<213> ORGANISM: Artificial Sequence
<220> FEATURE:
<223> OTHER INFORMATION: Nucleotide sequence encoding LacF1

<400> SEQUENCE: 24
atgcggggtt ctcatcatca tcatcatcat ggtatggcta gcatgactgg tggacagcaa      60
atgggtcggg atctgtacga cgatgacgat aaggatcgat ggggatccga attcatggtg     120
agcaagggcg aggagctgtt caccggggtg gtgcccatcc tggtcgagct ggacggcgac     180
gtaaacggcc acaggttcag cgtgtccggc gagggcgagg gcgatgccac ctacggcaag     240
ctgaccctga agttcatctg caccaccggc aagctgcccg tgccctggcc caccctcgtg     300
accaccctga cctggggcgt gcagtgcttc agccgctacc ccgaccacat gaagcagcac     360
```

```
gacttcttca agtccgccat gcccgaaggc tacgtccagg agcgtaccat cttcttcaag    420
gacgacggca actacaagac ccgcgccgag gtgaagttcg agggcgacac cctggtgaac    480
cgcatcgagc tgaagggcat cgacttcaag gaggacggca acatcctggg gcacaagctg    540
gagtacaact acatcagcca caacgtctat atcaccgccg acaagcagaa gaacggcatc    600
aaggcccact tcaagatccg ccacaacatc gaggacggca cgtgcagct cgccgaccac    660 taccagcaga cacccccat cggcgacggc cccgtgctgc tgcccgacaa ccactacctg    720
agcacccagt ccgccctgag caaagacccc aacgagaagc gcgatcacat ggtcctgctg    780
gagttcgtga ccgccgccgg gatcactctc ggcatggacg agctgtacaa gctgcagatg    840
cagattctgt ggaaaaaata cgtcaaagaa actttgaaa tgaacgtgga tgaatgcggc    900
attgaacaag gcattccggg cctgggttat aactacgaag ttctgaaaaa tgcagtcatc    960
cattatgtga ccaaaggcta tggtacgttt aaattcaacg gcaaagtcta taatctgaaa   1020
cagggtgaca ttttcatcct gctgaaaggc atgcaagtgg aatacgttgc gagcattgat   1080
gacccgtggg aatattactg gatcggcttt agtggttcca acgcgaatga atatctgaac   1140
cgtaccagca ttaccaacag ctgcgtggcc aactgtgaag aaaatagcaa aattccgcag   1200
attatcctga acatgtgtga aatctctaaa acctacaacc cgtcacgctc ggatgacatt   1260
ctgctgctga agaactgta ttccctgctg tacgcactga tcgaagaatt tccgaaaccg   1320
tttgaataca agataaaga actgcatacc tacattcagg acgcgctgaa cttcatcaac   1380
tcaaattata tgcactcgat tacggtgcaa gaaatcgccg attacgttaa tctgagccgt   1440
tcttacctgt acaaaatgtt catcaaaaac ctgggtatca gtccgcagcg ttatctgatt   1500
aatctgcgca tgtacaaagc aaccctgctg ctgaaatcta cgaaactgcc gatcggcgaa   1560
gttgcgagca gcgtgggtta tagtgattcc ctgctgttta gtaaaaccct ctccaaacac   1620
ttttcaatgt cgccgctgaa ctaccgcaac aatcaagtta ataaaccgag cattctgcag   1680
atggtgagca gggcgagga gctgttcacc ggggtggtgc ccatcctggt cgagctggac   1740
ggcgacgtaa acgccacaa gttcagcgtg tccggcgagg gcgagggcga tgccacctac   1800
ggcaagctga ccctgaagtt catctgcacc accggcaagc tgcccgtgcc ctggcccacc   1860
ctcgtgacca ccttcggcta cggcgtgcag tgcttcgccc gctaccccga ccacatgcgc   1920
cagcacgact tcttcaagtc cgccatgccc gaaggctacg tccaggagcg caccatcttc   1980
ttcaaggacg acggcaacta caagacccgc gccgaggtga agttcgaggg cgacaccctg   2040
gtgaaccgca tcgagctgaa gggcatcgac ttcaaggagg acggcaacat cctggggcac   2100
aagctggagt acaactacaa cagccacaac gtctatatca tggccgacaa gcagaagaac   2160
ggcatcaagg tgaacttcaa gatccgccac aacatcgagg acggcagcgt gcagctcgcc   2220
gaccactacc agcagaacac ccccatcggc gacggccccg tgctgctgcc cgacaaccac   2280
tacctgagct accagtccgc cctgagcaaa gaccccaacg agaagcgcga tcacatggtc   2340
ctgctggagt tcgtgaccgc cgccgggatc actctcggca tggacgagct gtacaag       2397
```

<210> SEQ ID NO 25
<211> LENGTH: 873
<212> TYPE: PRT
<213> ORGANISM: Artificial Sequence
<220> FEATURE:
<223> OTHER INFORMATION: LacB1

<400> SEQUENCE: 25

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Phe Met Val Ser Lys Gly Glu Glu Leu Phe Thr
        35                  40                  45

Gly Val Val Pro Ile Leu Val Glu Leu Asp Gly Asp Val Asn Gly His
    50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Ser Tyr Gly Val Gln Cys Phe Ser Arg
            100                 105                 110

Tyr Pro Asp His Met Lys Gln His Asp Phe Phe Lys Ser Ala Met Pro
            115                 120                 125

Glu Gly Tyr Val Gln Glu Arg Thr Ile Phe Phe Lys Asp Asp Gly Asn
130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
            195                 200                 205

Asn Ile Glu Asp Gly Ser Val Gln Leu Ala Asp His Tyr Gln Gln Asn
210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Tyr Lys Leu Gln Met Gln Ile Leu Trp Lys Lys Tyr Val
            275                 280                 285

Lys Glu Asn Phe Glu Met Asn Val Asp Glu Cys Gly Ile Glu Gln Gly
290                 295                 300

Ile Pro Gly Leu Gly Tyr Asn Tyr Glu Val Leu Lys Asn Ala Val Ile
305                 310                 315                 320

His Tyr Val Thr Lys Gly Tyr Gly Thr Phe Lys Phe Asn Gly Lys Val
                325                 330                 335

Tyr Asn Leu Lys Gln Gly Asp Ile Phe Ile Leu Lys Gly Met Gln
            340                 345                 350

Val Glu Tyr Val Ala Ser Ile Asp Asp Pro Trp Glu Tyr Trp Ile
            355                 360                 365

Gly Phe Ser Gly Ser Asn Ala Asn Glu Tyr Leu Asn Arg Thr Ser Ile
        370                 375                 380

Thr Asn Ser Cys Val Ala Asn Cys Glu Glu Asn Ser Lys Ile Pro Gln
385                 390                 395                 400
```

-continued

```
Ile Ile Leu Asn Met Cys Glu Ile Ser Lys Thr Tyr Asn Pro Ser Arg
            405                 410                 415

Ser Asp Asp Ile Leu Leu Lys Glu Leu Tyr Ser Leu Leu Tyr Ala
            420                 425                 430

Leu Ile Glu Glu Phe Pro Lys Pro Phe Glu Tyr Lys Asp Lys Glu Leu
            435                 440                 445

His Thr Tyr Ile Gln Asp Ala Leu Asn Phe Ile Asn Ser Asn Tyr Met
            450                 455                 460

His Ser Ile Thr Val Gln Glu Ile Ala Asp Tyr Val Asn Leu Ser Arg
465                 470                 475                 480

Ser Tyr Leu Tyr Lys Met Phe Ile Lys Asn Leu Gly Ile Ser Pro Gln
            485                 490                 495

Arg Tyr Leu Ile Asn Leu Arg Met Tyr Lys Ala Thr Leu Leu Leu Lys
            500                 505                 510

Ser Thr Lys Leu Pro Ile Gly Glu Val Ala Ser Ser Val Gly Tyr Ser
            515                 520                 525

Asp Ser Leu Leu Phe Ser Lys Thr Phe Ser Lys His Phe Ser Met Ser
            530                 535                 540

Pro Leu Asn Tyr Arg Asn Asn Gln Val Asn Lys Pro Ser Ile Phe Glu
545                 550                 555                 560

Leu Gln Met Ala Ser Lys Val Tyr Asp Pro Glu Gln Arg Lys Arg Met
            565                 570                 575

Ile Thr Gly Pro Gln Trp Trp Ala Arg Cys Lys Gln Met Asn Val Leu
            580                 585                 590

Asp Ser Phe Ile Asn Tyr Tyr Asp Ser Glu Lys His Ala Glu Asn Ala
            595                 600                 605

Val Ile Phe Leu His Gly Asn Ala Thr Ser Ser Tyr Leu Trp Arg His
            610                 615                 620

Val Val Pro His Ile Glu Pro Val Ala Arg Cys Ile Ile Pro Asp Leu
625                 630                 635                 640

Ile Gly Met Gly Lys Ser Gly Lys Ser Gly Asn Gly Ser Tyr Arg Leu
            645                 650                 655

Leu Asp His Tyr Lys Tyr Leu Thr Ala Trp Phe Glu Leu Leu Asn Leu
            660                 665                 670

Pro Lys Lys Ile Ile Phe Val Gly His Asp Trp Gly Ala Ala Leu Ala
            675                 680                 685

Phe His Tyr Ala Tyr Glu His Gln Asp Arg Ile Lys Ala Ile Val His
            690                 695                 700

Met Glu Ser Val Val Asp Val Ile Glu Ser Trp Asp Glu Trp Pro Asp
705                 710                 715                 720

Ile Glu Glu Asp Ile Ala Leu Ile Lys Ser Glu Glu Gly Glu Lys Met
            725                 730                 735

Val Leu Glu Asn Asn Phe Phe Val Glu Thr Val Leu Pro Ser Lys Ile
            740                 745                 750

Met Arg Lys Leu Glu Pro Glu Glu Phe Ala Ala Tyr Leu Glu Pro Phe
            755                 760                 765

Lys Glu Lys Gly Glu Val Arg Arg Pro Thr Leu Ser Trp Pro Arg Glu
            770                 775                 780

Ile Pro Leu Val Lys Gly Gly Lys Pro Asp Val Val Gln Ile Val Arg
785                 790                 795                 800

Asn Tyr Asn Ala Tyr Leu Arg Ala Ser Asp Asp Leu Pro Lys Leu Phe
            805                 810                 815
```

-continued

```
Ile Glu Ser Asp Pro Gly Phe Phe Ser Asn Ala Ile Val Glu Gly Ala
            820                 825                 830

Lys Lys Phe Pro Asn Thr Glu Phe Val Lys Val Lys Gly Leu His Phe
835                 840                 845

Leu Gln Glu Asp Ala Pro Asp Glu Met Gly Lys Tyr Ile Lys Ser Phe
    850                 855                 860

Val Glu Arg Val Leu Lys Asn Glu Gln
865                 870

<210> SEQ ID NO 26
<211> LENGTH: 885
<212> TYPE: PRT
<213> ORGANISM: Artificial Sequence
<220> FEATURE:
<223> OTHER INFORMATION: LacB2

<400> SEQUENCE: 26

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Arg Trp Gly Ser Glu Phe Met Val Ser Lys Gly Glu Glu Leu Phe Thr
        35                  40                  45

Gly Val Val Pro Ile Leu Val Glu Leu Asp Gly Asp Val Asn Gly His
    50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Ser Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Tyr Lys Leu Gln Gly Gly Thr Gly Gly Met Gln Ile
        275                 280                 285

Leu Trp Lys Lys Tyr Val Lys Glu Asn Phe Glu Met Asn Val Asp Glu
    290                 295                 300
```

-continued

Cys Gly Ile Glu Gln Gly Ile Pro Gly Leu Gly Tyr Asn Tyr Glu Val
305                 310                 315                 320

Leu Lys Asn Ala Val Ile His Tyr Val Thr Lys Gly Tyr Gly Thr Phe
            325                 330                 335

Lys Phe Asn Gly Lys Val Tyr Asn Leu Lys Gln Gly Asp Ile Phe Ile
            340                 345                 350

Leu Leu Lys Gly Met Gln Val Glu Tyr Val Ala Ser Ile Asp Asp Pro
            355                 360                 365

Trp Glu Tyr Tyr Trp Ile Gly Phe Ser Gly Ser Ala Asn Glu Tyr
            370                 375                 380

Leu Asn Arg Thr Ser Ile Thr Asn Ser Cys Val Ala Asn Cys Glu Glu
385                 390                 395                 400

Asn Ser Lys Ile Pro Gln Ile Ile Leu Asn Met Cys Glu Ile Ser Lys
            405                 410                 415

Thr Tyr Asn Pro Ser Arg Ser Asp Asp Ile Leu Leu Leu Lys Glu Leu
            420                 425                 430

Tyr Ser Leu Leu Tyr Ala Leu Ile Glu Glu Phe Pro Lys Pro Phe Glu
            435                 440                 445

Tyr Lys Asp Lys Glu Leu His Thr Tyr Ile Gln Asp Ala Leu Asn Phe
            450                 455                 460

Ile Asn Ser Asn Tyr Met His Ser Ile Thr Val Gln Glu Ile Ala Asp
465                 470                 475                 480

Tyr Val Asn Leu Ser Arg Ser Tyr Leu Tyr Lys Met Phe Ile Lys Asn
            485                 490                 495

Leu Gly Ile Ser Pro Gln Arg Tyr Leu Ile Asn Leu Arg Met Tyr Lys
            500                 505                 510

Ala Thr Leu Leu Leu Lys Ser Thr Lys Leu Pro Ile Gly Glu Val Ala
            515                 520                 525

Ser Ser Val Gly Tyr Ser Asp Ser Leu Leu Phe Ser Lys Thr Phe Ser
            530                 535                 540

Lys His Phe Ser Met Ser Pro Leu Asn Tyr Arg Asn Asn Gln Val Asn
545                 550                 555                 560

Lys Pro Ser Ile Gly Gly Thr Gly Gly Phe Glu Leu Gln Met Ala
            565                 570                 575

Ser Lys Val Tyr Asp Pro Glu Gln Arg Lys Arg Met Ile Thr Gly Pro
            580                 585                 590

Gln Trp Trp Ala Arg Cys Lys Gln Met Asn Val Leu Asp Ser Phe Ile
            595                 600                 605

Asn Tyr Tyr Asp Ser Glu Lys His Ala Glu Asn Ala Val Ile Phe Leu
            610                 615                 620

His Gly Asn Ala Thr Ser Ser Tyr Leu Trp Arg His Val Val Pro His
625                 630                 635                 640

Ile Glu Pro Val Ala Arg Cys Ile Ile Pro Asp Leu Ile Gly Met Gly
            645                 650                 655

Lys Ser Gly Lys Ser Gly Asn Gly Ser Tyr Arg Leu Leu Asp His Tyr
            660                 665                 670

Lys Tyr Leu Thr Ala Trp Phe Glu Leu Leu Asn Leu Pro Lys Lys Ile
            675                 680                 685

Ile Phe Val Gly His Asp Trp Gly Ala Ala Leu Ala Phe His Tyr Ala
            690                 695                 700

Tyr Glu His Gln Asp Arg Ile Lys Ala Ile Val His Met Glu Ser Val
705                 710                 715                 720

-continued

```
Val Asp Val Ile Glu Ser Trp Asp Glu Trp Pro Asp Ile Glu Glu Asp
            725                 730                 735
Ile Ala Leu Ile Lys Ser Glu Glu Gly Lys Met Val Leu Glu Asn
            740                 745                 750
Asn Phe Phe Val Glu Thr Val Leu Pro Ser Lys Ile Met Arg Lys Leu
            755                 760                 765
Glu Pro Glu Glu Phe Ala Ala Tyr Leu Glu Pro Phe Lys Glu Lys Gly
            770                 775                 780
Glu Val Arg Arg Pro Thr Leu Ser Trp Pro Arg Glu Ile Pro Leu Val
785                 790                 795                 800
Lys Gly Gly Lys Pro Asp Val Val Gln Ile Val Arg Asn Tyr Asn Ala
                805                 810                 815
Tyr Leu Arg Ala Ser Asp Asp Leu Pro Lys Leu Phe Ile Glu Ser Asp
                820                 825                 830
Pro Gly Phe Phe Ser Asn Ala Ile Val Glu Gly Ala Lys Lys Phe Pro
                835                 840                 845
Asn Thr Glu Phe Val Lys Val Lys Gly Leu His Phe Leu Gln Glu Asp
            850                 855                 860
Ala Pro Asp Glu Met Gly Lys Tyr Ile Lys Ser Phe Val Glu Arg Val
865                 870                 875                 880
Leu Lys Asn Glu Gln
                885

<210> SEQ ID NO 27
<211> LENGTH: 879
<212> TYPE: PRT
<213> ORGANISM: Artificial Sequence
<220> FEATURE:
<223> OTHER INFORMATION: LacB3

<400> SEQUENCE: 27

Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Arg Trp Gly Ser Glu Phe Met Val Ser Lys Gly Glu Glu Leu Phe Thr
            35                  40                  45
Gly Val Val Pro Ile Leu Val Glu Leu Asp Gly Asp Val Asn Gly His
        50                  55                  60
Lys Phe Ser Val Ser Gly Glu Gly Glu Gly Asp Ala Thr Tyr Gly Lys
65              70                  75                  80
Leu Thr Leu Lys Phe Ile Cys Thr Thr Gly Lys Leu Pro Val Pro Trp
                85                  90                  95
Pro Thr Leu Val Thr Thr Leu Ser Tyr Gly Val Gln Cys Phe Ser Arg
            100                 105                 110
Tyr Pro Asp His Met Lys Gln His Asp Phe Phe Lys Ser Ala Met Pro
            115                 120                 125
Glu Gly Tyr Val Gln Glu Arg Thr Ile Phe Phe Lys Asp Asp Gly Asn
        130                 135                 140
Tyr Lys Thr Arg Ala Glu Val Lys Phe Glu Gly Asp Thr Leu Val Asn
145                 150                 155                 160
Arg Ile Glu Leu Lys Gly Ile Asp Phe Lys Glu Asp Gly Asn Ile Leu
                165                 170                 175
Gly His Lys Leu Glu Tyr Asn Tyr Asn Ser His Asn Val Tyr Ile Met
            180                 185                 190
```

```
Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
                260                 265                 270

Asp Glu Leu Tyr Lys Leu Gln Gly Gly Thr Gly Gly Gly Met Gln Ile
            275                 280                 285

Leu Trp Lys Lys Tyr Val Lys Glu Asn Phe Glu Met Asn Val Asp Glu
        290                 295                 300

Cys Gly Ile Glu Gln Gly Ile Pro Gly Leu Gly Tyr Asn Tyr Glu Val
305                 310                 315                 320

Leu Lys Asn Ala Val Ile His Tyr Val Thr Lys Gly Tyr Gly Thr Phe
                325                 330                 335

Lys Phe Asn Gly Lys Val Tyr Asn Leu Lys Gln Gly Asp Ile Phe Ile
            340                 345                 350

Leu Leu Lys Gly Met Gln Val Glu Tyr Val Ala Ser Ile Asp Asp Pro
        355                 360                 365

Trp Glu Tyr Tyr Trp Ile Gly Phe Ser Gly Ser Asn Ala Asn Glu Tyr
        370                 375                 380

Leu Asn Arg Thr Ser Ile Thr Asn Ser Cys Val Ala Asn Cys Glu Glu
385                 390                 395                 400

Asn Ser Lys Ile Pro Gln Ile Ile Leu Asn Met Cys Glu Ile Ser Lys
                405                 410                 415

Thr Tyr Asn Pro Ser Arg Ser Asp Asp Ile Leu Leu Leu Lys Glu Leu
            420                 425                 430

Tyr Ser Leu Leu Tyr Ala Leu Ile Glu Glu Phe Pro Lys Pro Phe Glu
        435                 440                 445

Tyr Lys Asp Lys Glu Leu His Thr Tyr Ile Gln Asp Ala Leu Asn Phe
        450                 455                 460

Ile Asn Ser Asn Tyr Met His Ser Ile Thr Val Gln Glu Ile Ala Asp
465                 470                 475                 480

Tyr Val Asn Leu Ser Arg Ser Tyr Leu Tyr Lys Met Phe Ile Lys Asn
                485                 490                 495

Leu Gly Ile Ser Pro Gln Arg Tyr Leu Ile Asn Leu Arg Met Tyr Lys
            500                 505                 510

Ala Thr Leu Leu Lys Ser Thr Lys Leu Pro Ile Gly Glu Val Ala
        515                 520                 525

Ser Ser Val Gly Tyr Ser Asp Ser Leu Leu Phe Ser Lys Thr Phe Ser
    530                 535                 540

Lys His Phe Ser Met Ser Pro Leu Asn Tyr Arg Asn Asn Gln Val Asn
545                 550                 555                 560

Lys Pro Ser Ile Phe Glu Leu Gln Met Ala Ser Lys Val Tyr Asp Pro
                565                 570                 575

Glu Gln Arg Lys Arg Met Ile Thr Gly Pro Gln Trp Trp Ala Arg Cys
            580                 585                 590

Lys Gln Met Asn Val Leu Asp Ser Phe Ile Asn Tyr Tyr Asp Ser Glu
        595                 600                 605
```

Lys His Ala Glu Asn Ala Val Ile Phe Leu His Gly Asn Ala Thr Ser
610                 615                 620

Ser Tyr Leu Trp Arg His Val Pro His Ile Glu Pro Val Ala Arg
625                 630                 635                 640

Cys Ile Ile Pro Asp Leu Ile Gly Met Gly Lys Ser Gly Lys Ser Gly
                645                 650                 655

Asn Gly Ser Tyr Arg Leu Leu Asp His Tyr Lys Tyr Leu Thr Ala Trp
                660                 665                 670

Phe Glu Leu Leu Asn Leu Pro Lys Lys Ile Ile Phe Val Gly His Asp
                675                 680                 685

Trp Gly Ala Ala Leu Ala Phe His Tyr Ala Tyr Glu His Gln Asp Arg
690                 695                 700

Ile Lys Ala Ile Val His Met Glu Ser Val Val Asp Val Ile Glu Ser
705                 710                 715                 720

Trp Asp Glu Trp Pro Asp Ile Glu Asp Ile Ala Leu Ile Lys Ser
                725                 730                 735

Glu Glu Gly Glu Lys Met Val Leu Glu Asn Asn Phe Phe Val Glu Thr
                740                 745                 750

Val Leu Pro Ser Lys Ile Met Arg Lys Leu Glu Pro Glu Glu Phe Ala
                755                 760                 765

Ala Tyr Leu Glu Pro Phe Lys Glu Lys Gly Glu Val Arg Arg Pro Thr
770                 775                 780

Leu Ser Trp Pro Arg Glu Ile Pro Leu Val Lys Gly Gly Lys Pro Asp
785                 790                 795                 800

Val Val Gln Ile Val Arg Asn Tyr Asn Ala Tyr Leu Arg Ala Ser Asp
                805                 810                 815

Asp Leu Pro Lys Leu Phe Ile Glu Ser Asp Pro Gly Phe Phe Ser Asn
                820                 825                 830

Ala Ile Val Glu Gly Ala Lys Lys Phe Pro Asn Thr Glu Phe Val Lys
                835                 840                 845

Val Lys Gly Leu His Phe Leu Gln Glu Asp Ala Pro Asp Glu Met Gly
                850                 855                 860

Lys Tyr Ile Lys Ser Phe Val Glu Arg Val Leu Lys Asn Glu Gln
865                 870                 875

<210> SEQ ID NO 28
<211> LENGTH: 879
<212> TYPE: PRT
<213> ORGANISM: Artificial Sequence
<220> FEATURE:
<223> OTHER INFORMATION: LacB4

<400> SEQUENCE: 28

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Glu Phe Met Val Ser Lys Gly Glu Glu Leu Phe Thr
                35                  40                  45

Gly Val Val Pro Ile Leu Val Glu Leu Asp Gly Asp Val Asn Gly His
                50                  55                  60

Lys Phe Ser Val Ser Gly Glu Gly Glu Gly Asp Ala Thr Tyr Gly Lys
65              70                  75                  80

Leu Thr Leu Lys Phe Ile Cys Thr Thr Gly Lys Leu Pro Val Pro Trp
                85                  90                  95

```
Pro Thr Leu Val Thr Thr Leu Ser Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Tyr Lys Leu Gln Met Gln Ile Leu Trp Lys Lys Tyr Val
        275                 280                 285

Lys Glu Asn Phe Glu Met Asn Val Asp Glu Cys Gly Ile Glu Gln Gly
    290                 295                 300

Ile Pro Gly Leu Gly Tyr Asn Tyr Glu Val Leu Lys Asn Ala Val Ile
305                 310                 315                 320

His Tyr Val Thr Lys Gly Tyr Gly Thr Phe Lys Phe Asn Gly Lys Val
                325                 330                 335

Tyr Asn Leu Lys Gln Gly Asp Ile Phe Ile Leu Leu Lys Gly Met Gln
            340                 345                 350

Val Glu Tyr Val Ala Ser Ile Asp Asp Pro Trp Glu Tyr Tyr Trp Ile
        355                 360                 365

Gly Phe Ser Gly Ser Asn Ala Asn Glu Tyr Leu Asn Arg Thr Ser Ile
    370                 375                 380

Thr Asn Ser Cys Val Ala Asn Cys Glu Glu Asn Ser Lys Ile Pro Gln
385                 390                 395                 400

Ile Ile Leu Asn Met Cys Glu Ile Ser Lys Thr Tyr Asn Pro Ser Arg
                405                 410                 415

Ser Asp Asp Ile Leu Leu Lys Glu Leu Tyr Ser Leu Leu Tyr Leu Ala
            420                 425                 430

Leu Ile Glu Glu Phe Pro Lys Pro Phe Glu Tyr Lys Asp Lys Glu Leu
        435                 440                 445

His Thr Tyr Ile Gln Asp Ala Leu Asn Phe Ile Asn Ser Asn Tyr Met
    450                 455                 460

His Ser Ile Thr Val Gln Glu Ile Ala Asp Tyr Val Asn Leu Ser Arg
465                 470                 475                 480

Ser Tyr Leu Tyr Lys Met Phe Ile Lys Asn Leu Gly Ile Ser Pro Gln
                485                 490                 495

Arg Tyr Leu Ile Asn Leu Arg Met Tyr Lys Ala Thr Leu Leu Leu Lys
            500                 505                 510
```

```
Ser Thr Lys Leu Pro Ile Gly Glu Val Ala Ser Ser Val Gly Tyr Ser
        515                 520                 525

Asp Ser Leu Leu Phe Ser Lys Thr Phe Ser Lys His Phe Ser Met Ser
    530                 535                 540

Pro Leu Asn Tyr Arg Asn Asn Gln Val Asn Lys Pro Ser Ile Gly Gly
545                 550                 555                 560

Thr Gly Gly Gly Phe Glu Leu Gln Met Ala Ser Lys Val Tyr Asp Pro
                565                 570                 575

Glu Gln Arg Lys Arg Met Ile Thr Gly Pro Gln Trp Trp Ala Arg Cys
                580                 585                 590

Lys Gln Met Asn Val Leu Asp Ser Phe Ile Asn Tyr Tyr Asp Ser Glu
            595                 600                 605

Lys His Ala Glu Asn Ala Val Ile Phe Leu His Gly Asn Ala Thr Ser
        610                 615                 620

Ser Tyr Leu Trp Arg His Val Val Pro His Ile Glu Pro Val Ala Arg
625                 630                 635                 640

Cys Ile Ile Pro Asp Leu Ile Gly Met Gly Lys Ser Gly Lys Ser Gly
                645                 650                 655

Asn Gly Ser Tyr Arg Leu Leu Asp His Tyr Lys Tyr Leu Thr Ala Trp
                660                 665                 670

Phe Glu Leu Leu Asn Leu Pro Lys Lys Ile Ile Phe Val Gly His Asp
            675                 680                 685

Trp Gly Ala Ala Leu Ala Phe His Tyr Ala Tyr Glu His Gln Asp Arg
        690                 695                 700

Ile Lys Ala Ile Val His Met Glu Ser Val Val Asp Val Ile Glu Ser
705                 710                 715                 720

Trp Asp Glu Trp Pro Asp Ile Glu Glu Asp Ile Ala Leu Ile Lys Ser
                725                 730                 735

Glu Glu Gly Glu Lys Met Val Leu Glu Asn Asn Phe Phe Val Glu Thr
                740                 745                 750

Val Leu Pro Ser Lys Ile Met Arg Lys Leu Glu Pro Glu Glu Phe Ala
            755                 760                 765

Ala Tyr Leu Glu Pro Phe Lys Glu Lys Gly Glu Val Arg Arg Pro Thr
770                 775                 780

Leu Ser Trp Pro Arg Glu Ile Pro Leu Val Lys Gly Gly Lys Pro Asp
785                 790                 795                 800

Val Val Gln Ile Val Arg Asn Tyr Asn Ala Tyr Leu Arg Ala Ser Asp
                805                 810                 815

Asp Leu Pro Lys Leu Phe Ile Glu Ser Asp Pro Gly Phe Phe Ser Asn
            820                 825                 830

Ala Ile Val Glu Gly Ala Lys Lys Phe Pro Asn Thr Glu Phe Val Lys
        835                 840                 845

Val Lys Gly Leu His Phe Leu Gln Glu Asp Ala Pro Asp Glu Met Gly
    850                 855                 860

Lys Tyr Ile Lys Ser Phe Val Glu Arg Val Leu Lys Asn Glu Gln
865                 870                 875

<210> SEQ ID NO 29
<211> LENGTH: 2622
<212> TYPE: DNA
<213> ORGANISM: Artificial Sequence
<220> FEATURE:
<223> OTHER INFORMATION: Nucleotide sequence encoding LacB1
```

<400> SEQUENCE: 29

```
atgcggggtt ctcatcatca tcatcatcat ggtatggcta gcatgactgg tggacagcaa    60
atgggtcggg atctgtacga cgatgacgat aaggatcgat ggggatccga attcatggtg   120
agcaagggcg aggagctgtt caccggggtg gtgcccatcc tggtcgagct ggacggcgac   180
gtaaacggcc acaagttcag cgtgtccggc gagggcgagg gcgatgccac ctacggcaag   240
ctgaccctga agttcatctg caccaccggc aagctgcccg tgccctgccc cacccttgtg   300
accaccctga gctacggcgt gcagtgcttc agccgctacc ccgaccacat gaagcagcac   360
gacttcttca gtccgccat gcccgaaggc tacgtccagg agcgcaccat cttcttcaag   420
gacgacggca actacaagac ccgcgccgag gtgaagttcg agggcgacac cctggtgaac   480
cgcatcgagc tgaagggcat cgacttcaag gaggacggca acatcctggg gcacaagctg   540
gagtacaact acaacagcca caacgtctat atcatggccg acaagcagaa gaacggcatc   600
aaggtgaact tcaagatccg ccacaacatc gaggacggca cgtgcagct cgccgaccac   660
taccagcaga cacccccat cggcgacggc ccgtgctgc tgcccgacaa ccactacctg   720
agcacccagt ccgccctgag caaagacccc aacgagaagc gcgatcacat ggtcctgctg   780
gagttcgtga ccgccgccgg gatcactctc ggcatggacg agctgtacaa gctgcagatg   840
cagattctgt ggaaaaaata cgtcaaagaa aactttgaaa tgaacgtgga tgaatgcggc   900
attgaacaag gcattccggg cctgggttat aactacgaag ttctgaaaaa tgcagtcatc   960
cattatgtga ccaaaggcta tggtacgttt aaattcaacg gcaaagtcta taatctgaaa  1020
cagggtgaca ttttcatcct gctgaaaggc atgcaagtgg aatacgttgc gagcattgat  1080
gacccgtggg aatattactg gatcggcttt agtggttcca acgcgaatga atatctgaac  1140
cgtaccagca ttaccaacag ctgcgtggcc aactgtgaag aaaatagcaa aattccgcag  1200
attatcctga acatgtgtga aatctctaaa acctacaacc cgtcacgctc ggatgacatt  1260
ctgctgctga agaactgta ttccctgctg tacgcactga tcgaagaatt ccgaaaccg  1320
tttgaataca agataaaga actgcatacc tacattcagg acgcgctgaa cttcatcaac  1380
tcaaattata tgcactcgat tacggtgcaa gaaatcgccg attacgttaa tctgagccgt  1440
tcttacctgt acaaaatgtt catcaaaaac ctgggtatca gtccgcagcg ttatctgatt  1500
aatctgcgca tgtacaaagc aaccctgctg ctgaaatcta cgaaactgcc gatcggcgaa  1560
gttgcgagca gcgtgggtta tagtgattcc ctgctgttta gtaaaacctt ctccaaacac  1620
ttttcaatgt cgccgctgaa ctaccgcaac aatcaagtta taaaaccgag cattttcgaa  1680
cttcagatgg cttccaaggt gtacgacccc gagcaacgca aacgcatgat cactgggcct  1740
cagtggtggg ctcgctgcaa gcaaatgaac gtgctggact ccttcatcaa ctactatgat  1800
tccgagaagc acgccgagaa cgccgtgatt tttctgcatg gtaacgctac ctccagctac  1860
ctgtggaggc acgtcgtgcc tcacatcgag cccgtggcta gatgcatcat ccctgatctg  1920
atcggaatgg gtaagtccgg caagagcggg aatggctcat atcgcctcct ggatcactac  1980
aagtacctca ccgcttggtt cgagctgctg aaccttccaa agaaaatcat ctttgtgggc  2040
cacgactggg ggctgctctc ggcctttcac tacgcctacg agcaccaaga caggatcaag  2100
gccatcgtcc atatggagag tgtcgtggac gtgatcgagt cctgggacga gtggcctgac  2160
atcgaggagg atatcgccct gatcaagagc gaagagggcg agaaaatggt gcttgagaat  2220
aacttcttcg tcgagaccgt gctcccaagc aagatcatgc ggaaactgga gcctgaggag  2280
```

-continued

| | |
|---|---|
| ttcgctgcct acctggagcc attcaaggag aagggcgagg ttagacggcc taccctctcc | 2340 |
| tggcctcgcg agatccctct cgttaaggga ggcaagcccg acgtcgtcca gattgtccgc | 2400 |
| aactacaacg cctaccttcg ggccagcgac gatctgccta agctgttcat cgagtccgac | 2460 |
| cctgggttct tttccaacgc tattgtcgag ggagctaaga agttccctaa caccgagttc | 2520 |
| gtgaaggtga agggcctcca cttcctccag gaggacgctc cagatgaaat gggtaagtac | 2580 |
| atcaagagct cgtggagcg cgtgctgaag aacgagcagt aa | 2622 |

<210> SEQ ID NO 30
<211> LENGTH: 2658
<212> TYPE: DNA
<213> ORGANISM: Artificial Sequence
<220> FEATURE:
<223> OTHER INFORMATION: Nucleotide sequence encoding LacB2

<400> SEQUENCE: 30

| | |
|---|---|
| atgcggggtt ctcatcatca tcatcatcat ggtatggcta gcatgactgg tggacagcaa | 60 |
| atgggtcggg atctgtacga cgatgacgat aaggatcgat ggggatccga attcatggtg | 120 |
| agcaagggcg aggagctgtt caccggggtg gtgcccatcc tggtcgagct ggacggcgac | 180 |
| gtaaacggcc acaagttcag cgtgtccggc gagggcgagg gcgatgccac ctacggcaag | 240 |
| ctgaccctga agttcatctg caccaccggc aagctgcccg tgccctggcc caccctcgtg | 300 |
| accaccctga gctacggcgt gcagtgcttc agccgctacc ccgaccacat gaagcagcac | 360 |
| gacttcttca gtccgccat gcccgaaggc tacgtccagg agcgcaccat cttcttcaag | 420 |
| gacgacggca actacaagac ccgcgccgag gtgaagttcg agggcgacac cctggtgaac | 480 |
| cgcatcgagc tgaagggcat cgacttcaag gaggacggca acatcctggg cacaagctg | 540 |
| gagtacaact acaacagcca caacgtctat atcatggccg acaagcagaa gaacggcatc | 600 |
| aaggtgaact tcaagatccg ccacaacatc gaggacggca gcgtgcagct cgccgaccac | 660 |
| taccagcaga cacccccat cggcgacggc cccgtgctgc tgcccgacaa ccactacctg | 720 |
| agcacccagt ccgccctgag caaagacccc aacgagaagc gcgatcacat ggtcctgctg | 780 |
| gagttcgtga ccgccgccgg gatcactctc ggcatggacg agctgtacaa gctgcagggt | 840 |
| ggtaccggag gcggcatgca gattctgtgg aaaaaatacg tcaaagaaaa ctttgaaatg | 900 |
| aacgtggatg aatgcggcat tgaacaaggc attccgggcc tgggttataa ctacgaagtt | 960 |
| ctgaaaaatg cagtcatcca ttatgtgacc aaaggctatg gtacgtttaa attcaacggc | 1020 |
| aaagtctata atctgaaaca gggtgacatt ttcatcctgc tgaaaggcat gcaagtggaa | 1080 |
| tacgttgcga gcattgatga cccgtgggaa tattactgga tcggctttag tggttccaac | 1140 |
| gcgaatgaat atctgaaccg taccagcatt accaacagct gcgtggccaa ctgtgaagaa | 1200 |
| aatagcaaaa ttccgcagat tatcctgaac atgtgtgaaa tctctaaaac ctacaacccg | 1260 |
| tcacgctcgg atgacattct gctgctgaaa gaactgtatt ccctgctgta cgcactgatc | 1320 |
| gaagaatttc gaaaccgtt tgaatacaaa gataaagaac tgcatacctg cattcaggac | 1380 |
| gcgctgaact tcatcaactc aaattatatg cactcgatta cggtgcaaga aatcgccgat | 1440 |
| tacgttaatc tgagccgttc ttacctgtac aaaatgttca tcaaaaacct gggtatcagt | 1500 |
| ccgcagcgtt atctgattaa tctgcgcatg tacaaagcaa ccctgctgct gaaatctacg | 1560 |
| aaactgccga tcggcgaagt tgcgagcagc gtgggttata gtgattccct gctgtttagt | 1620 |
| aaaaccttct ccaaacactt ttcaatgtcg ccgctgaact accgcaacaa tcaagttaat | 1680 |
| aaaccgagca ttggtggtac cggaggcggc ttcgaacttc agatggcttc caaggtgtac | 1740 |

```
gaccccgagc aacgcaaacg catgatcact gggcctcagt ggtgggctcg ctgcaagcaa    1800
atgaacgtgc tggactcctt catcaactac tatgattccg agaagcacgc cgagaacgcc    1860
gtgatttttc tgcatggtaa cgctacctcc agctacctgt ggaggcacgt cgtgcctcac    1920
atcgagcccg tggctagatg catcatccct gatctgatcg gaatgggtaa gtccggcaag    1980
agcgggaatg gctcatatcg cctcctggat cactacaagt acctcaccgc ttggttcgag    2040
ctgctgaacc ttccaaagaa aatcatcttt gtgggcacg actgggggc tgctctggcc    2100 tttcactacg cctacgagca ccaagacagg atcaaggcca tcgtccatat ggagagtgtc    2160
gtggacgtga tcgagtcctg ggacgagtgg cctgacatcg aggaggatat cgccctgatc    2220
aagagcgaag agggcgagaa aatggtgctt gagaataact tcttcgtcga ccgtgctc    2280 ccaagcaaga tcatgcggaa actggagcct gaggagttcg ctgcctacct ggagccattc    2340
aaggagaagg gcgaggttag acggcctacc ctctcctggc ctcgcgagat ccctctcgtt    2400
aagggaggca agcccgacgt cgtccagatt gtccgcaact acaacgccta ccttcgggcc    2460
agcgacgatc tgcctaagct gttcatcgag tccgaccctg ggttcttttc caacgctatt    2520
gtcgagggag ctaagaagtt ccctaacacc gagttcgtga aggtgaaggg cctccacttc    2580
ctccaggagg acgctccaga tgaaatgggt aagtacatca agagcttcgt ggagcgcgtg    2640
ctgaagaacg agcagtaa                                                   2658

<210> SEQ ID NO 31
<211> LENGTH: 2640
<212> TYPE: DNA
<213> ORGANISM: Artificial Sequence
<220> FEATURE:
<223> OTHER INFORMATION: Nucleotide sequence encoding LacB3

<400> SEQUENCE: 31
atgcggggtt ctcatcatca tcatcatcat ggtatggcta gcatgactgg tggacagcaa      60
atgggtcggg atctgtacga cgatgacgat aaggatcgat ggggatccga attcatggtg     120
agcaagggcg aggagctgtt caccggggtg gtgcccatcc tggtcgagct ggacggcgac     180
gtaaacggcc acaagttcag cgtgtccggc gagggcgagg gcgatgccac ctacggcaag     240
ctgaccctga agttcatctg caccaccggc aagctgcccg tgccctggcc caccctcgtg     300
accaccctga gctacggcgt gcagtgcttc agccgctacc ccgaccacat gaagcagcac     360
gacttcttca gtccgccat gcccgaaggc tacgtccagg agcgcaccat cttcttcaag     420
gacgacggca actacaagac ccgcgccgag gtgaagttcg agggcgacac cctggtgaac     480
cgcatcgagc tgaagggcat cgacttcaag gaggacggca acatcctggg gcacaagctg     540
gagtacaact acaacagcca caacgtctat atcatggccg acaagcagaa gaacggcatc     600
aaggtgaact tcaagatccg ccacaacatc gaggacggca gcgtgcagct cgccgaccac     660
taccagcaga cacccccat cggcgacggc ccgtgctgc tgcccgacaa ccactacctg     720
agcacccagt ccgccctgag caaagacccc aacgagaagc gcgatcacat ggtcctgctg     780
gagttcgtga ccgccgccgg gatcactctc ggcatggacg agctgtacaa gctgcagggt     840
ggtaccggag gcggcatgca gattctgtgg aaaaaatacg tcaaagaaaa ctttgaaatg     900
aacgtggatg aatgcggcat tgaacaaggc attccgggcc tgggttataa ctacgaagtt     960
ctgaaaaatg cagtcatcca ttatgtgacc aaaggctatg gtacgtttaa attcaacggc    1020
aaagtctata atctgaaaca gggtgacatt ttcatcctgc tgaaaggcat gcaagtggaa    1080
```

| | |
|---|---|
| tacgttgcga gcattgatga cccgtgggaa tattactgga tcggctttag tggttccaac | 1140 |
| gcgaatgaat atctgaaccg taccagcatt accaacagct gcgtggccaa ctgtgaagaa | 1200 |
| aatagcaaaa ttccgcagat tatcctgaac atgtgtgaaa tctctaaaac ctacaacccg | 1260 |
| tcacgctcgg atgacattct gctgctgaaa gaactgtatt ccctgctgta cgcactgatc | 1320 |
| gaagaatttc cgaaaccgtt tgaatacaaa gataaagaac tgcatacctu cattcaggac | 1380 |
| gcgctgaact tcatcaactc aaattatatg cactcgatta cggtgcaaga atcgccgat | 1440 |
| tacgttaatc tgagccgttc ttacctgtac aaaatgttca tcaaaaacct gggtatcagt | 1500 |
| ccgcagcgtt atctgattaa tctgcgcatg tacaaagcaa ccctgctgct gaaatctacg | 1560 |
| aaactgccga tcggcgaagt tgcgagcagc gtgggttata gtgattccct gctgtttagt | 1620 |
| aaaaccttct ccaaacactt ttcaatgtcg ccgctgaact accgcaacaa tcaagttaat | 1680 |
| aaaccgagca ttttcgaact tcagatggct tccaaggtgt acgaccccga gcaacgcaaa | 1740 |
| cgcatgatca ctgggcctca gtggtgggct cgctgcaagc aaatgaacgt gctggactcc | 1800 |
| ttcatcaact actatgattc cgagaagcac gccgagaacg ccgtgatttt tctgcatggt | 1860 |
| aacgctacct ccagctacct gtggaggcac gtcgtgcctc acatcgagcc cgtggctaga | 1920 |
| tgcatcatcc ctgatctgat cggaatgggt aagtccggca gagcgggaa tggctcatat | 1980 |
| cgcctcctgg atcactacaa gtacctcacc gcttggttcg agctgctgaa ccttccaaag | 2040 |
| aaaatctctc ttgtgggcca cgactggggg gctgctctgg cctttcacta cgcctacgag | 2100 |
| caccaagaca ggatcaaggc catcgtccat atggagagtg tcgtggacgt gatcgagtcc | 2160 |
| tgggacgagt ggcctgacat cgaggaggat atcgccctga tcaagagcga agagggcgag | 2220 |
| aaaatggtgc ttgagaataa cttcttcgtc gagaccgtgc tcccaagcaa gatcatgcgg | 2280 |
| aaactggagc ctgaggagtt cgctgcctac ctggagccat tcaaggagaa gggcgaggtt | 2340 |
| agacggccta ccctctcctg gcctcgcgag atccctctcg ttaagggagg caagcccgac | 2400 |
| gtcgtccaga ttgtccgcaa ctacaacgcc taccttcggg ccagcgacga tctgcctaag | 2460 |
| ctgttcatcg agtccgaccc tgggttctttu tccaacgcta ttgtcgaggg agctaagaag | 2520 |
| ttccctaaca ccgagttcgt gaaggtgaag ggcctccact tcctccagga ggacgctcca | 2580 |
| gatgaaatgg gtaagtacat caagagcttc gtggagcgcg tgctgaagaa cgagcagtaa | 2640 |

<210> SEQ ID NO 32
<211> LENGTH: 2640
<212> TYPE: DNA
<213> ORGANISM: Artificial Sequence
<220> FEATURE:
<223> OTHER INFORMATION: Nucleotide sequence encoding LacB4

<400> SEQUENCE: 32

| | |
|---|---|
| atgcggggtt ctcatcatca tcatcatcat ggtatggcta gcatgactgg tggacagcaa | 60 |
| atgggtcggg atctgtacga cgatgacgat aaggatcgat ggggatccga attcatggtg | 120 |
| agcaagggcg aggagctgtt caccggggtg gtgcccatcc tggtcgagct ggacggcgac | 180 |
| gtaaacggcc acaagttcag cgtgtccggc gagggcgagg gcgatgccac ctacggcaag | 240 |
| ctgaccctga agttcatctg caccaccggc aagctgcccg tgccctggcc caccctcgtg | 300 |
| accaccctga gctacggcgt gcagtgcttc agccgctacc ccgaccacat gaagcagcac | 360 |
| gacttcttca gtccgccat gcccgaaggc tacgtccagg agcgcaccat cttcttcaag | 420 |
| gacgacggca actacaagac ccgcgccgag gtgaagttcg agggcgacac cctggtgaac | 480 |
| cgcatcgagc tgaagggcat cgacttcaag gaggacggca acatcctggg gcacaagctg | 540 |

```
gagtacaact acaacagcca caacgtctat atcatggccg acaagcagaa gaacggcatc      600
aaggtgaact tcaagatccg ccacaacatc gaggacggca gcgtgcagct cgccgaccac      660
taccagcaga acacccccat cggcgacggc cccgtgctgc tgcccgacaa ccactacctg      720
agcacccagt ccgccctgag caagaccccc aacgagaagc gcgatcacat ggtcctgctg      780
gagttcgtga ccgccgccgg gatcactctc ggcatggacg agctgtacaa gctgcagatg      840
cagattctgt ggaaaaaata cgtcaaagaa actttgaaaa tgaacgtgga tgaatgcggc      900
attgaacaag gcattccggg cctgggttat aactacgaag ttctgaaaaa tgcagtcatc      960
cattatgtga ccaaaggcta tggtacgttt aaattcaacg gcaaagtcta taatctgaaa     1020
cagggtgaca ttttcatcct gctgaaaggc atgcaagtgg aatacgttgc gagcattgat     1080
gacccgtggg aatattactg gatcggcttt agtggttcca acgcgaatga atatctgaac     1140
cgtaccagca ttaccaacag ctgcgtggcc aactgtgaag aaaatagcaa aattccgcag     1200
attatcctga acatgtgtga aatctctaaa acctacaacc cgtcacgctc ggatgacatt     1260
ctgctgctga agaactgta ttccctgctg tacgcactga tcgaagaatt tccgaaaccg     1320
tttgaataca agataaaga actgcatacc tacattcagg acgcgctgaa cttcatcaac     1380
tcaaattata tgcactcgat tacggtgcaa gaaatcgccg attacgttaa tctgagccgt     1440
tcttacctgt acaaaatgtt catcaaaaac ctgggtatca gtccgcagcg ttatctgatt     1500
aatctgcgca tgtacaaagc aaccctgctg ctgaaatcta cgaaactgcc gatcggcgaa     1560
gttgcgagca gcgtgggtta tagtgattcc ctgctgttta gtaaaacctt ctccaaacac     1620
ttttcaatgt cgccgctgaa ctaccgcaac aatcaagtta ataaaccgag cattggtggt     1680
accggaggcg gcttcgaact tcagatggct tccaaggtgt acgaccccga gcaacgcaaa     1740
cgcatgatca ctgggcctca gtggtgggct cgctgcaagc aaatgaacgt gctggactcc     1800
ttcatcaact actatgattc cgagaagcac gccgagaacg ccgtgatttt tctgcatggt     1860
aacgctacct ccagctacct gtggaggcac gtcgtgcctc acatcgagcc cgtggctaga     1920
tgcatcatcc ctgatctgat cggaatgggg aagtccggca agagcgggaa tggctcatat     1980
cgcctcctgg atcactacaa gtacctcacc gcttggttcg agctgctgaa ccttccaaag     2040
aaaatcatct ttgtgggcca cgactggggg gctgctctgg cctttcacta cgcctacgag     2100
caccaagaca ggatcaaggc catcgtccat atggagagtg tcgtggacgt gatcgagtcc     2160
tgggacgagt ggcctgacat cgaggaggat atcgccctga tcaagagcga gagggcgag     2220 aaaatggtgc ttgagaataa cttcttcgtc gagaccgtgc tcccaagcaa gatcatgcgg     2280
aaactggagc ctgaggagtt cgctgcctac ctggagccat tcaaggagaa gggcgaggtt     2340
agacggccta ccctctcctg gcctcgcgag atccctctcg ttaagggagg caagcccgac     2400
gtcgtccaga ttgtccgcaa ctacaacgcc taccttcggg ccagcgacga tctgcctaag     2460
ctgttcatcg agtccgaccc tgggttcttt tccaacgcta ttgtcgaggg agctaagaag     2520
ttccctaaca ccgagttcgt gaaggtgaag gcctccact tcctccagga ggacgctcca     2580
gatgaaatgg gtaagtacat caagagcttc gtggagcgcg tgctgaagaa cgagcagtaa     2640
```

<210> SEQ ID NO 33
<211> LENGTH: 765
<212> TYPE: PRT
<213> ORGANISM: Artificial Sequence
<220> FEATURE:
<223> OTHER INFORMATION: GFP2-BgaR1-171-RLuc8

<400> SEQUENCE: 33

```
Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Arg Trp Gly Ser Glu Phe Met Val Ser Lys Gly Glu Glu Leu Phe Thr
            35                  40                  45
Gly Val Val Pro Ile Leu Val Glu Leu Asp Gly Asp Val Asn Gly His
        50                  55                  60
Lys Phe Ser Val Ser Gly Glu Gly Glu Gly Asp Ala Thr Tyr Gly Lys
65                  70                  75                  80
Leu Thr Leu Lys Phe Ile Cys Thr Thr Gly Lys Leu Pro Val Pro Trp
                85                  90                  95
Pro Thr Leu Val Thr Thr Leu Ser Tyr Gly Val Gln Cys Phe Ser Arg
            100                 105                 110
Tyr Pro Asp His Met Lys Gln His Asp Phe Phe Lys Ser Ala Met Pro
        115                 120                 125
Glu Gly Tyr Val Gln Glu Arg Thr Ile Phe Phe Lys Asp Asp Gly Asn
    130                 135                 140
Tyr Lys Thr Arg Ala Glu Val Lys Phe Glu Gly Asp Thr Leu Val Asn
145                 150                 155                 160
Arg Ile Glu Leu Lys Gly Ile Asp Phe Lys Glu Asp Gly Asn Ile Leu
                165                 170                 175
Gly His Lys Leu Glu Tyr Asn Tyr Asn Ser His Asn Val Tyr Ile Met
            180                 185                 190
Ala Asp Lys Gln Lys Asn Gly Ile Lys Val Asn Phe Lys Ile Arg His
        195                 200                 205
Asn Ile Glu Asp Gly Ser Val Gln Leu Ala Asp His Tyr Gln Gln Asn
    210                 215                 220
Thr Pro Ile Gly Asp Gly Pro Val Leu Leu Pro Asp Asn His Tyr Leu
225                 230                 235                 240
Ser Thr Gln Ser Ala Leu Ser Lys Asp Pro Asn Glu Lys Arg Asp His
                245                 250                 255
Met Val Leu Leu Glu Phe Val Thr Ala Ala Gly Ile Thr Leu Gly Met
            260                 265                 270
Asp Glu Leu Tyr Lys Leu Gln Met Gln Ile Leu Trp Lys Lys Tyr Val
        275                 280                 285
Lys Glu Asn Phe Glu Met Asn Val Asp Glu Cys Gly Ile Glu Gln Gly
    290                 295                 300
Ile Pro Gly Leu Gly Tyr Asn Tyr Glu Val Leu Lys Asn Ala Val Ile
305                 310                 315                 320
His Tyr Val Thr Lys Gly Tyr Gly Thr Phe Lys Phe Asn Gly Lys Val
                325                 330                 335
Tyr Asn Leu Lys Gln Gly Asp Ile Phe Ile Leu Leu Lys Gly Met Gln
            340                 345                 350
Val Glu Tyr Val Ala Ser Ile Asp Asp Pro Trp Glu Tyr Tyr Trp Ile
        355                 360                 365
Gly Phe Ser Gly Ser Asn Ala Asn Glu Tyr Leu Asn Arg Thr Ser Ile
    370                 375                 380
Thr Asn Ser Cys Val Ala Asn Cys Glu Glu Asn Ser Lys Ile Pro Gln
385                 390                 395                 400
Ile Ile Leu Asn Met Cys Glu Ile Ser Lys Thr Tyr Asn Pro Ser Arg
                405                 410                 415
```

```
Ser Asp Asp Ile Leu Leu Lys Glu Leu Tyr Ser Leu Leu Tyr Ala
        420                 425                 430

Leu Ile Glu Glu Phe Pro Lys Pro Phe Glu Tyr Lys Asp Lys Glu Leu
        435                 440                 445

His Thr Phe Glu Leu Gln Met Ala Ser Lys Val Tyr Asp Pro Glu Gln
450                 455                 460

Arg Lys Arg Met Ile Thr Gly Pro Gln Trp Trp Ala Arg Cys Lys Gln
465                 470                 475                 480

Met Asn Val Leu Asp Ser Phe Ile Asn Tyr Tyr Asp Ser Glu Lys His
                485                 490                 495

Ala Glu Asn Ala Val Ile Phe Leu His Gly Asn Ala Thr Ser Ser Tyr
            500                 505                 510

Leu Trp Arg His Val Val Pro His Ile Glu Pro Val Ala Arg Cys Ile
        515                 520                 525

Ile Pro Asp Leu Ile Gly Met Gly Lys Ser Gly Lys Ser Gly Asn Gly
        530                 535                 540

Ser Tyr Arg Leu Leu Asp His Tyr Lys Tyr Leu Thr Ala Trp Phe Glu
545                 550                 555                 560

Leu Leu Asn Leu Pro Lys Lys Ile Ile Phe Val Gly His Asp Trp Gly
                565                 570                 575

Ala Ala Leu Ala Phe His Tyr Ala Tyr Glu His Gln Asp Arg Ile Lys
            580                 585                 590

Ala Ile Val His Met Glu Ser Val Val Asp Val Ile Glu Ser Trp Asp
        595                 600                 605

Glu Trp Pro Asp Ile Glu Glu Asp Ile Ala Leu Ile Lys Ser Glu Glu
        610                 615                 620

Gly Glu Lys Met Val Leu Glu Asn Asn Phe Phe Val Glu Thr Val Leu
625                 630                 635                 640

Pro Ser Lys Ile Met Arg Lys Leu Glu Pro Glu Glu Phe Ala Ala Tyr
                645                 650                 655

Leu Glu Pro Phe Lys Glu Lys Gly Glu Val Arg Arg Pro Thr Leu Ser
            660                 665                 670

Trp Pro Arg Glu Ile Pro Leu Val Lys Gly Gly Lys Pro Asp Val Val
        675                 680                 685

Gln Ile Val Arg Asn Tyr Asn Ala Tyr Leu Arg Ala Ser Asp Asp Leu
690                 695                 700

Pro Lys Leu Phe Ile Glu Ser Asp Pro Gly Phe Phe Ser Asn Ala Ile
705                 710                 715                 720

Val Glu Gly Ala Lys Lys Phe Pro Asn Thr Glu Phe Val Lys Val Lys
                725                 730                 735

Gly Leu His Phe Leu Gln Glu Asp Ala Pro Asp Glu Met Gly Lys Tyr
            740                 745                 750

Ile Lys Ser Phe Val Glu Arg Val Leu Lys Asn Glu Gln
        755                 760                 765

<210> SEQ ID NO 34
<211> LENGTH: 744
<212> TYPE: PRT
<213> ORGANISM: Artificial Sequence
<220> FEATURE:
<223> OTHER INFORMATION: GFP2-BgaR1-150-RLuc8

<400> SEQUENCE: 34

Met Arg Gly Ser His His His His His His Gly Met Ala Ser Met Thr
1               5                   10                  15
```

Gly Gly Gln Gln Met Gly Arg Asp Leu Tyr Asp Asp Asp Lys Asp
            20                  25                  30

Arg Trp Gly Ser Glu Phe Met Val Ser Lys Gly Glu Glu Leu Phe Thr
        35                  40                  45

Gly Val Val Pro Ile Leu Val Glu Leu Asp Gly Asp Val Asn Gly His
    50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Ser Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Tyr Lys Leu Gln Met Gln Ile Leu Trp Lys Lys Tyr Val
        275                 280                 285

Lys Glu Asn Phe Glu Met Asn Val Asp Glu Cys Gly Ile Glu Gln Gly
290                 295                 300

Ile Pro Gly Leu Gly Tyr Asn Tyr Glu Val Leu Lys Asn Ala Val Ile
305                 310                 315                 320

His Tyr Val Thr Lys Gly Tyr Gly Thr Phe Lys Phe Asn Gly Lys Val
                325                 330                 335

Tyr Asn Leu Lys Gln Gly Asp Ile Phe Ile Leu Leu Lys Gly Met Gln
            340                 345                 350

Val Glu Tyr Val Ala Ser Ile Asp Asp Pro Trp Glu Tyr Tyr Trp Ile
        355                 360                 365

Gly Phe Ser Gly Ser Asn Ala Asn Glu Tyr Leu Asn Arg Thr Ser Ile
370                 375                 380

Thr Asn Ser Cys Val Ala Asn Cys Glu Glu Asn Ser Lys Ile Pro Gln
385                 390                 395                 400

Ile Ile Leu Asn Met Cys Glu Ile Ser Lys Thr Tyr Asn Pro Ser Arg
                405                 410                 415

Ser Asp Asp Ile Leu Leu Leu Lys Glu Leu Tyr Ser Leu Phe Glu Leu
            420                 425                 430

Gln Met Ala Ser Lys Val Tyr Asp Pro Glu Gln Arg Lys Arg Met Ile
            435                 440                 445

Thr Gly Pro Gln Trp Trp Ala Arg Cys Lys Gln Met Asn Val Leu Asp
    450                 455                 460

Ser Phe Ile Asn Tyr Tyr Asp Ser Glu Lys His Ala Glu Asn Ala Val
465                 470                 475                 480

Ile Phe Leu His Gly Asn Ala Thr Ser Ser Tyr Leu Trp Arg His Val
                485                 490                 495

Val Pro His Ile Glu Pro Val Ala Arg Cys Ile Ile Pro Asp Leu Ile
            500                 505                 510

Gly Met Gly Lys Ser Gly Lys Ser Gly Asn Gly Ser Tyr Arg Leu Leu
        515                 520                 525

Asp His Tyr Lys Tyr Leu Thr Ala Trp Phe Glu Leu Leu Asn Leu Pro
    530                 535                 540

Lys Lys Ile Ile Phe Val Gly His Asp Trp Gly Ala Ala Leu Ala Phe
545                 550                 555                 560

His Tyr Ala Tyr Glu His Gln Asp Arg Ile Lys Ala Ile Val His Met
                565                 570                 575

Glu Ser Val Val Asp Val Ile Glu Ser Trp Asp Glu Trp Pro Asp Ile
            580                 585                 590

Glu Glu Asp Ile Ala Leu Ile Lys Ser Glu Glu Gly Glu Lys Met Val
        595                 600                 605

Leu Glu Asn Asn Phe Phe Val Glu Thr Val Leu Pro Ser Lys Ile Met
    610                 615                 620

Arg Lys Leu Glu Pro Glu Glu Phe Ala Ala Tyr Leu Glu Pro Phe Lys
625                 630                 635                 640

Glu Lys Gly Glu Val Arg Arg Pro Thr Leu Ser Trp Pro Arg Glu Ile
                645                 650                 655

Pro Leu Val Lys Gly Gly Lys Pro Asp Val Val Gln Ile Val Arg Asn
            660                 665                 670

Tyr Asn Ala Tyr Leu Arg Ala Ser Asp Asp Leu Pro Lys Leu Phe Ile
        675                 680                 685

Glu Ser Asp Pro Gly Phe Phe Ser Asn Ala Ile Val Glu Gly Ala Lys
    690                 695                 700

Lys Phe Pro Asn Thr Glu Phe Val Lys Val Lys Gly Leu His Phe Leu
705                 710                 715                 720

Gln Glu Asp Ala Pro Asp Glu Met Gly Lys Tyr Ile Lys Ser Phe Val
                725                 730                 735

Glu Arg Val Leu Lys Asn Glu Gln
            740

<210> SEQ ID NO 35
<211> LENGTH: 754
<212> TYPE: PRT
<213> ORGANISM: Artificial Sequence
<220> FEATURE:
<223> OTHER INFORMATION: GFP2-BgaR12-171-RLuc8

<400> SEQUENCE: 35

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Glu Phe Met Val Ser Lys Gly Glu Glu Leu Phe Thr
            35                  40                  45

-continued

Gly Val Val Pro Ile Leu Val Glu Leu Asp Gly Asp Val Asn Gly His
    50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Ser Tyr Gly Val Gln Cys Phe Ser Arg
                100                 105                 110

Tyr Pro Asp His Met Lys Gln His Asp Phe Phe Lys Ser Ala Met Pro
            115                 120                 125

Glu Gly Tyr Val Gln Glu Arg Thr Ile Phe Phe Lys Asp Asp Gly Asn
130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
            195                 200                 205

Asn Ile Glu Asp Gly Ser Val Gln Leu Ala Asp His Tyr Gln Gln Asn
210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Tyr Lys Leu Gln Asn Phe Glu Met Asn Val Asp Glu Cys
            275                 280                 285

Gly Ile Glu Gln Gly Ile Pro Gly Leu Gly Tyr Asn Tyr Glu Val Leu
290                 295                 300

Lys Asn Ala Val Ile His Tyr Val Thr Lys Gly Tyr Gly Thr Phe Lys
305                 310                 315                 320

Phe Asn Gly Lys Val Tyr Asn Leu Lys Gln Gly Asp Ile Phe Ile Leu
                325                 330                 335

Leu Lys Gly Met Gln Val Glu Tyr Val Ala Ser Ile Asp Asp Pro Trp
            340                 345                 350

Glu Tyr Tyr Trp Ile Gly Phe Ser Gly Ser Asn Ala Asn Glu Tyr Leu
            355                 360                 365

Asn Arg Thr Ser Ile Thr Asn Ser Cys Val Ala Asn Cys Glu Glu Asn
370                 375                 380

Ser Lys Ile Pro Gln Ile Ile Leu Asn Met Cys Glu Ile Ser Lys Thr
385                 390                 395                 400

Tyr Asn Pro Ser Arg Ser Asp Asp Ile Leu Leu Leu Lys Glu Leu Tyr
                405                 410                 415

Ser Leu Leu Tyr Ala Leu Ile Glu Glu Phe Pro Lys Pro Phe Glu Tyr
            420                 425                 430

Lys Asp Lys Glu Leu His Thr Phe Glu Leu Gln Met Ala Ser Lys Val
            435                 440                 445

Tyr Asp Pro Glu Gln Arg Lys Arg Met Ile Thr Gly Pro Gln Trp Trp
450                 455                 460

-continued

```
Ala Arg Cys Lys Gln Met Asn Val Leu Asp Ser Phe Ile Asn Tyr Tyr
465                 470                 475                 480

Asp Ser Glu Lys His Ala Glu Asn Ala Val Ile Phe Leu His Gly Asn
            485                 490                 495

Ala Thr Ser Ser Tyr Leu Trp Arg His Val Pro His Ile Glu Pro
        500                 505                 510

Val Ala Arg Cys Ile Ile Pro Asp Leu Ile Gly Met Gly Lys Ser Gly
            515                 520                 525

Lys Ser Gly Asn Gly Ser Tyr Arg Leu Leu Asp His Tyr Lys Tyr Leu
        530                 535                 540

Thr Ala Trp Phe Glu Leu Leu Asn Leu Pro Lys Lys Ile Ile Phe Val
545                 550                 555                 560

Gly His Asp Trp Gly Ala Ala Leu Ala Phe His Tyr Ala Tyr Glu His
                565                 570                 575

Gln Asp Arg Ile Lys Ala Ile Val His Met Glu Ser Val Val Asp Val
            580                 585                 590

Ile Glu Ser Trp Asp Glu Trp Pro Asp Ile Glu Glu Asp Ile Ala Leu
                595                 600                 605

Ile Lys Ser Glu Glu Gly Glu Lys Met Val Leu Glu Asn Asn Phe Phe
610                 615                 620

Val Glu Thr Val Leu Pro Ser Lys Ile Met Arg Lys Leu Glu Pro Glu
625                 630                 635                 640

Glu Phe Ala Ala Tyr Leu Glu Pro Phe Lys Glu Lys Gly Glu Val Arg
                645                 650                 655

Arg Pro Thr Leu Ser Trp Pro Arg Glu Ile Pro Leu Val Lys Gly Gly
            660                 665                 670

Lys Pro Asp Val Val Gln Ile Val Arg Asn Tyr Asn Ala Tyr Leu Arg
            675                 680                 685

Ala Ser Asp Asp Leu Pro Lys Leu Phe Ile Glu Ser Asp Pro Gly Phe
        690                 695                 700

Phe Ser Asn Ala Ile Val Glu Gly Ala Lys Lys Phe Pro Asn Thr Glu
705                 710                 715                 720

Phe Val Lys Val Lys Gly Leu His Phe Leu Gln Glu Asp Ala Pro Asp
                725                 730                 735

Glu Met Gly Lys Tyr Ile Lys Ser Phe Val Glu Arg Val Leu Lys Asn
            740                 745                 750

Glu Gln
```

<210> SEQ ID NO 36
<211> LENGTH: 733
<212> TYPE: PRT
<213> ORGANISM: Artificial Sequence
<220> FEATURE:
<223> OTHER INFORMATION: GFP2-BgaR12-150-RLuc8

<400> SEQUENCE: 36

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Phe Met Val Ser Lys Gly Glu Glu Leu Phe Thr
            35                  40                  45

Gly Val Val Pro Ile Leu Val Glu Leu Asp Gly Asp Val Asn Gly His
        50                  55                  60
```

```
Lys Phe Ser Val Ser Gly Glu Gly Glu Gly Asp Ala Thr Tyr Gly Lys
 65                  70                  75                  80

Leu Thr Leu Lys Phe Ile Cys Thr Thr Gly Lys Leu Pro Val Pro Trp
                 85                  90                  95

Pro Thr Leu Val Thr Thr Leu Ser Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Tyr Lys Leu Gln Asn Phe Glu Met Asn Val Asp Glu Cys
        275                 280                 285

Gly Ile Glu Gln Gly Ile Pro Gly Leu Gly Tyr Asn Tyr Glu Val Leu
    290                 295                 300

Lys Asn Ala Val Ile His Tyr Val Thr Lys Gly Tyr Gly Thr Phe Lys
305                 310                 315                 320

Phe Asn Gly Lys Val Tyr Asn Leu Lys Gln Gly Asp Ile Phe Ile Leu
                325                 330                 335

Leu Lys Gly Met Gln Val Glu Tyr Val Ala Ser Ile Asp Asp Pro Trp
            340                 345                 350

Glu Tyr Tyr Trp Ile Gly Phe Ser Gly Ser Asn Ala Asn Glu Tyr Leu
        355                 360                 365

Asn Arg Thr Ser Ile Thr Asn Ser Cys Val Ala Asn Cys Glu Glu Asn
    370                 375                 380

Ser Lys Ile Pro Gln Ile Ile Leu Asn Met Cys Glu Ile Ser Lys Thr
385                 390                 395                 400

Tyr Asn Pro Ser Arg Ser Asp Ile Leu Leu Leu Lys Glu Leu Tyr
                405                 410                 415

Ser Leu Phe Glu Leu Gln Met Ala Ser Lys Val Tyr Asp Pro Glu Gln
            420                 425                 430

Arg Lys Arg Met Ile Thr Gly Pro Gln Trp Trp Ala Arg Cys Lys Gln
        435                 440                 445

Met Asn Val Leu Asp Ser Phe Ile Asn Tyr Tyr Asp Ser Glu Lys His
    450                 455                 460

Ala Glu Asn Ala Val Ile Phe Leu His Gly Asn Ala Thr Ser Ser Tyr
465                 470                 475                 480
```

```
Leu Trp Arg His Val Pro His Ile Glu Pro Val Ala Arg Cys Ile
                485                 490                 495

Ile Pro Asp Leu Ile Gly Met Gly Lys Ser Gly Lys Ser Gly Asn Gly
            500                 505                 510

Ser Tyr Arg Leu Leu Asp His Tyr Lys Tyr Leu Thr Ala Trp Phe Glu
            515                 520                 525

Leu Leu Asn Leu Pro Lys Lys Ile Ile Phe Val Gly His Asp Trp Gly
            530                 535                 540

Ala Ala Leu Ala Phe His Tyr Ala Tyr Glu His Gln Asp Arg Ile Lys
545                 550                 555                 560

Ala Ile Val His Met Glu Ser Val Val Asp Val Ile Glu Ser Trp Asp
                565                 570                 575

Glu Trp Pro Asp Ile Glu Glu Asp Ile Ala Leu Ile Lys Ser Glu Glu
            580                 585                 590

Gly Glu Lys Met Val Leu Glu Asn Asn Phe Phe Val Glu Thr Val Leu
            595                 600                 605

Pro Ser Lys Ile Met Arg Lys Leu Glu Pro Glu Glu Phe Ala Ala Tyr
            610                 615                 620

Leu Glu Pro Phe Lys Glu Lys Gly Glu Val Arg Arg Pro Thr Leu Ser
625                 630                 635                 640

Trp Pro Arg Glu Ile Pro Leu Val Lys Gly Gly Lys Pro Asp Val Val
                645                 650                 655

Gln Ile Val Arg Asn Tyr Asn Ala Tyr Leu Arg Ala Ser Asp Asp Leu
            660                 665                 670

Pro Lys Leu Phe Ile Glu Ser Asp Pro Gly Phe Phe Ser Asn Ala Ile
            675                 680                 685

Val Glu Gly Ala Lys Lys Phe Pro Asn Thr Glu Phe Val Lys Val Lys
            690                 695                 700

Gly Leu His Phe Leu Gln Glu Asp Ala Pro Asp Glu Met Gly Lys Tyr
705                 710                 715                 720

Ile Lys Ser Phe Val Glu Arg Val Leu Lys Asn Glu Gln
                725                 730

<210> SEQ ID NO 37
<211> LENGTH: 279
<212> TYPE: PRT
<213> ORGANISM: Artificial Sequence
<220> FEATURE:
<223> OTHER INFORMATION: A0A133MUX6

<400> SEQUENCE: 37

Met Gln Ile Leu Trp Lys Lys Tyr Val Lys Glu Asn Phe Glu Met Asn
1               5                   10                  15

Val Asp Glu Cys Gly Ile Glu Gln Gly Ile Pro Gly Leu Gly Tyr Asn
            20                  25                  30

Tyr Glu Val Leu Lys Asn Ala Val Ile His Tyr Val Thr Lys Gly Tyr
        35                  40                  45

Gly Thr Phe Lys Phe Asn Gly Lys Val Tyr Asn Leu Lys Gln Gly Asp
    50                  55                  60

Ile Phe Ile Leu Leu Lys Gly Met Gln Val Glu Tyr Val Ala Ser Ile
65                  70                  75                  80

Asp Asp Pro Trp Glu Tyr Tyr Trp Ile Gly Phe Ser Gly Ser Asn Ala
                85                  90                  95

Asn Glu Tyr Leu Asn Arg Thr Ser Ile Thr Asp Ser Cys Val Ala Asn
            100                 105                 110
```

```
Cys Glu Glu Asn Ser Lys Ile Pro Gln Ile Ile Leu Asn Met Cys Glu
            115                 120                 125

Ile Ser Lys Thr Tyr Asn Pro Ser Arg Ser Asp Asp Ile Leu Leu Leu
        130                 135                 140

Lys Glu Leu Tyr Ser Leu Leu Tyr Ala Leu Ile Glu Glu Phe Pro Lys
145                 150                 155                 160

Pro Phe Glu Tyr Lys Asp Lys Glu Leu His Thr Tyr Ile Gln Asp Ala
                165                 170                 175

Leu Asn Phe Ile Asn Ser Asn Tyr Met His Ser Ile Thr Val Gln Glu
            180                 185                 190

Ile Ala Asp Tyr Val Asn Leu Ser Arg Ser Tyr Leu Tyr Lys Met Phe
        195                 200                 205

Ile Lys Asn Leu Gly Ile Ser Pro Gln Arg Tyr Leu Ile Asn Leu Arg
    210                 215                 220

Met Tyr Lys Ala Thr Leu Leu Lys Gly Thr Lys Leu Pro Ile Gly
225                 230                 235                 240

Glu Val Ala Ser Ser Val Gly Tyr Ser Asp Ser Leu Leu Phe Ser Lys
                245                 250                 255

Thr Phe Ser Lys His Phe Ser Met Ser Pro Leu Asn Tyr Arg Asn Asn
            260                 265                 270

Gln Val Asn Lys Pro Asn Ile
        275

<210> SEQ ID NO 38
<211> LENGTH: 279
<212> TYPE: PRT
<213> ORGANISM: Artificial Sequence
<220> FEATURE:
<223> OTHER INFORMATION: B1V7N0

<400> SEQUENCE: 38

Met Gln Ile Leu Trp Lys Lys Tyr Val Lys Glu Asn Phe Glu Met Asn
1               5                   10                  15

Val Asp Glu Cys Gly Ile Glu Gln Gly Ile Pro Gly Leu Gly Tyr Lys
            20                  25                  30

Tyr Glu Val Leu Lys Asn Ala Val Ile His Tyr Val Thr Lys Gly Tyr
        35                  40                  45

Gly Thr Phe Lys Phe Asn Gly Lys Val Tyr Thr Leu Lys Gln Gly Asp
    50                  55                  60

Ile Phe Ile Leu Leu Lys Gly Met Gln Val Asp Tyr Val Ala Ser Ile
65                  70                  75                  80

Asp Asp Pro Trp Glu Tyr Tyr Trp Ile Gly Phe Ser Gly Ser Asn Ala
                85                  90                  95

Asn Glu Tyr Leu Asn Arg Thr Ser Ile Thr Asn Ser Cys Val Ala Asn
            100                 105                 110

Cys Glu Glu Asn Ser Lys Ile Pro Gln Ile Ile Leu Asn Met Cys Glu
        115                 120                 125

Ile Ser Lys Thr Tyr Asn Pro Ser Arg Ser Asp Asp Ile Leu Leu Leu
    130                 135                 140

Lys Glu Leu Tyr Ser Leu Leu Tyr Ala Leu Ile Glu Glu Phe Pro Lys
145                 150                 155                 160

Pro Phe Glu Tyr Lys Asp Lys Glu Leu His Thr Tyr Ile Gln Asp Ala
                165                 170                 175

Leu Asn Phe Ile Asn Ser Asn Tyr Met His Ser Ile Thr Val Gln Glu
            180                 185                 190
```

```
Ile Ala Asp Tyr Val Asn Leu Ser Arg Ser Tyr Leu Tyr Lys Met Phe
        195                 200                 205

Ile Lys Asn Leu Gly Ile Ser Pro Gln Arg Tyr Leu Ile Asn Leu Arg
        210                 215                 220

Met Tyr Lys Ala Thr Leu Leu Lys Gly Thr Lys Leu Pro Ile Gly
225                 230                 235                 240

Glu Val Ala Ser Ser Val Gly Tyr Ser Asp Ser Leu Leu Phe Ser Lys
                245                 250                 255

Thr Phe Ser Lys His Phe Ser Met Ser Pro Leu Asn Tyr Arg Asn Asn
                260                 265                 270

Gln Val Tyr Lys Ser Ser Ile
            275
```

<210> SEQ ID NO 39
<211> LENGTH: 279
<212> TYPE: PRT
<213> ORGANISM: Artificial Sequence
<220> FEATURE:
<223> OTHER INFORMATION: A0A127EGD8

<400> SEQUENCE: 39

```
Met Gln Ile Leu Trp Lys Lys Tyr Ile Lys Glu Asn Phe Glu Met Asn
1               5                   10                  15

Val Asp Glu Cys Gly Ile Glu Gln Gly Ile Pro Gly Leu Gly Tyr Lys
                20                  25                  30

Tyr Glu Val Leu Lys Asn Ala Val Ile His Tyr Val Thr Lys Gly Tyr
            35                  40                  45

Gly Thr Phe Lys Phe Asn Gly Lys Val Tyr Thr Leu Lys Gln Gly Asp
        50                  55                  60

Ile Phe Ile Leu Leu Lys Gly Met Lys Val Glu Tyr Val Ala Ser Ile
65                  70                  75                  80

Asp Asp Pro Trp Glu Tyr Tyr Trp Ile Gly Phe Ser Gly Ser Asn Ala
                85                  90                  95

Asn Glu Tyr Leu Asn Arg Thr Ser Ile Thr Asn Ser Tyr Val Ala Asn
            100                 105                 110

Cys Glu Lys Asn Ser Lys Ile Pro Gln Ile Ile Leu Asn Met Cys Glu
        115                 120                 125

Ile Ser Lys Thr Tyr Asn Pro Ser Ser Ser Asp Asp Ile Leu Leu Leu
    130                 135                 140

Lys Glu Leu Tyr Ser Leu Leu Tyr Thr Leu Ile Glu Glu Phe Pro Lys
145                 150                 155                 160

Pro Phe Asp Tyr Lys Asp Lys Glu Leu His Thr Tyr Ile Gln Asp Ala
                165                 170                 175

Leu Asn Phe Ile Asn Ser Asn Tyr Met Asn Ser Ile Thr Val Gln Glu
            180                 185                 190

Ile Ala Asp Tyr Val Asn Leu Ser Arg Ser Tyr Leu Tyr Lys Met Phe
        195                 200                 205

Ile Lys Asn Leu Gly Ile Ser Pro Gln Arg Tyr Leu Ile Asn Leu Arg
    210                 215                 220

Met Tyr Lys Ala Thr Leu Leu Lys Gly Thr Lys Leu Pro Ile Gly
225                 230                 235                 240

Glu Val Ala Ser Arg Ile Gly Tyr Ser Asp Ser Leu Leu Phe Ser Lys
                245                 250                 255

Thr Phe Ser Lys His Phe Ser Met Ser Pro Leu Asn Tyr Arg Asn Asn
                260                 265                 270
```

-continued

Gln Val Asn Lys Pro Ser Ile
        275

<210> SEQ ID NO 40
<211> LENGTH: 278
<212> TYPE: PRT
<213> ORGANISM: Artificial Sequence
<220> FEATURE:
<223> OTHER INFORMATION: A0A1C6JUB7

<400> SEQUENCE: 40

Met Gln Ile Leu Trp Lys Lys Tyr Thr Lys Glu Asn Phe Glu Met Asn
1               5                   10                  15

Val Asp Glu Cys Gly Ile Glu Gln Gly Ile Pro Gly Phe Gly Tyr Lys
            20                  25                  30

Tyr Glu Val Leu Lys Asn Ala Val Ile His Tyr Ile Ser Lys Gly Asn
        35                  40                  45

Gly Thr Phe Lys Phe Asn Asp Lys Val Tyr Asn Leu Lys Gln Gly Asp
    50                  55                  60

Val Phe Ile Leu Leu Lys Gly Met Lys Val Glu Tyr Ile Ala Ser Ile
65                  70                  75                  80

Asp Asp Pro Trp Glu Tyr Tyr Trp Ile Gly Phe Ser Gly Ser Asn Ala
                85                  90                  95

Asn Glu Tyr Leu Asn Arg Thr Ser Ile Ile Asp Ser Tyr Ala Ala Asn
            100                 105                 110

Cys Lys Glu Asp Ser Lys Ile Pro Asp Ile Ile Ser Asn Met Cys Glu
        115                 120                 125

Ile Ser Lys Thr Tyr Asn Pro Ser Arg Ser Asp Asp Ile Leu Leu Leu
    130                 135                 140

Lys Glu Leu Tyr Ser Leu Leu Tyr Ala Phe Ile Glu Glu Phe Pro Lys
145                 150                 155                 160

Ala Phe Glu Tyr Lys Asp Lys Glu Leu His Thr Tyr Ile Gln Glu Ala
                165                 170                 175

Ile Asp Phe Ile Asn Ser Asn Tyr Met Asn Ser Ile Thr Val Asn Asp
            180                 185                 190

Ile Ala Glu His Val Asn Leu Ser Arg Ser Tyr Leu Tyr Lys Met Phe
        195                 200                 205

Met Lys Asn Leu Lys Val Ser Pro Gln Lys Tyr Leu Ile Asn Leu Arg
    210                 215                 220

Met Tyr Lys Ala Thr Leu Leu Leu Lys Asn Thr Arg Ile Pro Ile Gly
225                 230                 235                 240

Glu Val Ala Ser Lys Val Gly Tyr Ser Asp Ser Leu Leu Phe Ser Lys
                245                 250                 255

Thr Phe Ser Lys Tyr Phe Ser Met Ser Pro Leu Asn Tyr Arg Asn Asn
            260                 265                 270

Gln Met Asn Gly Asn Lys
        275

<210> SEQ ID NO 41
<211> LENGTH: 278
<212> TYPE: PRT
<213> ORGANISM: Artificial Sequence
<220> FEATURE:
<223> OTHER INFORMATION: A0A174HYB7

<400> SEQUENCE: 41

Met Gln Ile Leu Trp Lys Lys Tyr Thr Lys Glu Asn Phe Glu Met Asn
1               5                   10                  15

Val Asp Glu Cys Gly Ile Glu Gln Gly Ile Pro Gly Phe Gly Tyr Lys
            20                  25                  30

Tyr Glu Val Leu Lys Asn Ala Val Ile His Tyr Ile Ser Lys Gly Asn
        35                  40                  45

Gly Thr Phe Lys Phe Asn Asp Lys Val Tyr Asn Leu Lys Gln Gly Asp
    50                  55                  60

Val Phe Ile Leu Lys Gly Met Lys Val Glu Tyr Ile Ala Ser Ile
65                  70                  75                  80

Asp Asp Pro Trp Glu Tyr Tyr Trp Ile Gly Phe Ser Gly Ser Asn Ala
                85                  90                  95

Asn Glu Tyr Leu Asn Arg Thr Ser Ile Ile Asp Ser Tyr Ala Ala Lys
            100                 105                 110

Cys Lys Gly Asp Ser Lys Ile Pro Asp Ile Ile Ser Asn Met Cys Glu
        115                 120                 125

Ile Ser Lys Thr Tyr Asn Pro Ser Arg Ser Asp Asp Ile Leu Leu Leu
    130                 135                 140

Lys Glu Leu Tyr Ser Leu Leu Tyr Ala Phe Ile Glu Glu Phe Pro Lys
145                 150                 155                 160

Ala Phe Glu Tyr Lys Asp Lys Glu Leu His Thr Tyr Ile Gln Glu Ala
                165                 170                 175

Ile Asp Phe Ile Asn Ser Asn Tyr Met Asn Ser Ile Thr Val Asn Asp
            180                 185                 190

Ile Ala Glu His Ile Asn Leu Ser Arg Ser Tyr Leu Tyr Lys Met Phe
        195                 200                 205

Met Lys Asn Leu Lys Val Ser Pro Gln Lys Tyr Leu Ile Asn Leu Arg
    210                 215                 220

Met Tyr Lys Ala Thr Leu Leu Lys Gly Thr Arg Ile Pro Ile Gly
225                 230                 235                 240

Glu Val Ala Ser Lys Val Gly Tyr Ser Asp Ser Leu Leu Phe Ser Lys
                245                 250                 255

Thr Phe Ser Lys Tyr Phe Ser Met Ser Pro Leu Asn Tyr Arg Asn Asn
            260                 265                 270

Gln Thr Ser Asp Asn Lys
        275

<210> SEQ ID NO 42
<211> LENGTH: 278
<212> TYPE: PRT
<213> ORGANISM: Artificial Sequence
<220> FEATURE:
<223> OTHER INFORMATION: A0A1C6KY47

<400> SEQUENCE: 42

Met Gln Ile Leu Trp Lys Lys Tyr Ile Lys Glu Asn Phe Glu Met Asn
1               5                   10                  15

Val Asp Glu Cys Gly Ile Glu Gln Gly Ile Pro Gly Phe Gly Tyr Lys
            20                  25                  30

Tyr Glu Val Leu Lys Asn Ser Val Ile His Tyr Ile Thr Lys Gly His
        35                  40                  45

Gly Thr Phe Lys Ile Asn Asp Lys Leu Tyr Asn Leu Gly Gln Gly Asp
    50                  55                  60

Val Phe Ile Leu Leu Lys Gly Met Lys Val Glu Tyr Met Ala Ser Ile
65                  70                  75                  80

Asp Asp Pro Trp Glu Tyr Tyr Trp Ile Gly Phe Ser Gly Ser Asn Ala
            85                  90                  95

Asn Glu Tyr Leu Asn Arg Thr Ser Ile Ile Asp Ser Tyr Ala Ala Thr
            100                 105                 110

Cys Lys Glu Asp Ser Lys Ile Pro Cys Ile Ile Ser Asn Met Cys Glu
            115                 120                 125

Ile Ser Lys Thr Tyr Asn Pro Ser Cys Cys Asp Asp Ile Leu Leu Leu
            130                 135                 140

Lys Glu Leu Tyr Ser Leu Leu Tyr Ala Phe Ile Glu Glu Phe Pro Lys
145                 150                 155                 160

Ala Phe Glu Tyr Lys Asp Lys Glu Leu His Thr Tyr Ile Gln Glu Ala
            165                 170                 175

Ile Asn Phe Ile Asn Ser Asn Tyr Met Lys Ser Ile Thr Val Asn Asp
            180                 185                 190

Ile Ala Glu His Val Asn Leu Ser Arg Ser Tyr Leu Tyr Lys Met Phe
            195                 200                 205

Met Lys Asn Leu Lys Val Ser Pro Gln Lys Tyr Leu Ile Asn Leu Arg
210                 215                 220

Met Tyr Lys Ala Thr Leu Leu Lys Gly Thr Arg Ile Pro Ile Gly
225                 230                 235                 240

Glu Val Ala Ser Lys Val Gly Tyr Ser Asp Ser Leu Leu Phe Ser Lys
            245                 250                 255

Thr Phe Ser Lys Tyr Phe Ser Met Ser Pro Leu Asn Tyr Arg Asn Asn
            260                 265                 270

Gln Thr Ser Asp Asn Lys
            275

<210> SEQ ID NO 43
<211> LENGTH: 277
<212> TYPE: PRT
<213> ORGANISM: Artificial Sequence
<220> FEATURE:
<223> OTHER INFORMATION: A0A174LZQ7

<400> SEQUENCE: 43

Met Gln Ile Leu Trp Arg Lys Tyr Lys Lys Glu Asn Phe Asp Ile Asn
1               5                   10                  15

Leu Asp Glu Cys Gly Ile Glu His Gly Ile Pro Gly Phe Gly Tyr Arg
            20                  25                  30

Tyr Lys Val Leu Lys Asn Ser Val His Tyr Val Ile Arg Gly Tyr
            35                  40                  45

Gly Thr Phe Lys Val Asn Asp Lys Val Tyr Asn Leu Lys Glu Gly Asp
50                  55                  60

Ile Phe Ile Leu Leu Lys Gly Met Asp Val Glu Tyr Met Ala Ser Met
65                  70                  75                  80

Asp Asn Pro Trp Glu Tyr Cys Trp Ile Gly Phe Ser Gly Ser Lys Ala
            85                  90                  95

Asp Glu Tyr Leu Asn Arg Thr Ser Ile Ile Asp Ser His Val Ala Asn
            100                 105                 110

Cys Asn Glu Asn Ser Lys Ile Pro Cys Ile Ile Leu Asn Ile Cys Glu
            115                 120                 125

Ile Ser Lys Asn Tyr Asn Pro Ser Asn Ser Asp Asp Ile Leu Leu Leu
            130                 135                 140

Asn Glu Leu Tyr Ser Leu Leu Tyr Glu Leu Ile Gly Glu Phe Pro Lys
145                 150                 155                 160

Pro Phe Glu Tyr Lys Asp Lys Glu Ile His Lys Tyr Ile Gln Asp Thr
                165                 170                 175

Ile Asn Phe Ile Asn Ser Asn Tyr Met Asn Asn Ile Thr Val Asn Glu
            180                 185                 190

Ile Ala Glu His Val Asn Leu Ser Arg Ser Tyr Leu Tyr Lys Met Phe
        195                 200                 205

Ile Lys Asn Leu Lys Ile Ser Pro Gln Lys Tyr Leu Ile Asn Leu Arg
    210                 215                 220

Met Tyr Lys Ala Thr Leu Leu Lys Asn Thr Lys Leu Pro Ile Gly
225                 230                 235                 240

Glu Ile Ala Asn Lys Val Gly Tyr Ala Asp Ser Leu Leu Phe Ser Lys
                245                 250                 255

Thr Phe Ser Lys Tyr Phe Ser Val Ser Pro Leu Asn Tyr Arg Asn Asn
                260                 265                 270

Lys Val Asn Lys Glu
            275

<210> SEQ ID NO 44
<211> LENGTH: 279
<212> TYPE: PRT
<213> ORGANISM: Artificial Sequence
<220> FEATURE:
<223> OTHER INFORMATION: N9YR91

<400> SEQUENCE: 44

Met Gln Ile Leu Trp Lys Lys Tyr Lys Asn Ile Asn Phe Asp Ser Asn
1               5                   10                  15

Leu Asp Glu Cys Gly Ile Glu Gln Gly Thr Pro Gly Thr Gly Tyr Lys
                20                  25                  30

Tyr Glu Val Val Lys Asn Ala Val Ile His Tyr Ile Ser Lys Gly Ser
            35                  40                  45

Gly Ile Phe Lys Ile Asn Asp Lys Ile Tyr Asn Leu Lys Arg Gly Asp
        50                  55                  60

Gly Phe Ile Leu Leu Lys Gly Met His Val Glu Tyr Ile Ser Ser Ile
65                  70                  75                  80

Asp Asp Pro Trp Lys Tyr Tyr Trp Val Gly Phe Ser Gly Lys Asn Ala
                85                  90                  95

Asn Glu Tyr Leu Lys Arg Thr Ser Ile Asp Thr Cys Ile Ile Asn
            100                 105                 110

Phe Ser Lys Lys Ser Lys Val Pro Asn Thr Ile Ile Asp Met Cys Asn
    115                 120                 125

Ile Ser Lys Lys Tyr Asn Gln Thr Ser Ser Asp Ile Leu Leu Leu
130                 135                 140

Ser Lys Leu His Leu Leu Leu Tyr Tyr Ile Ser Ser Glu Phe Pro Lys
145                 150                 155                 160

Ser Phe Lys Tyr Tyr Asn Asn Leu Ala His Thr Tyr Ile Gln Glu Ala
                165                 170                 175

Val Asp Phe Ile Asn Asn Tyr Met Lys Ser Ile Thr Val Gln Glu
            180                 185                 190

Val Ala Asn His Val Asn Leu Ser Arg Ser Tyr Leu Tyr Lys Met Phe
        195                 200                 205

Ile Lys Tyr Leu Gly Gln Ser Thr Gln Ser Tyr Leu Ile Asn Ile Arg
    210                 215                 220

Met Tyr Lys Ser Ser Leu Leu Leu Lys Glu Thr Asn Leu Ser Ile Leu
225                 230                 235                 240

Glu Ile Ala Asn Lys Val Gly Tyr Asp Asp Pro Gly Leu Phe Ser Lys
                245                 250                 255

Thr Phe Ser Lys His Phe Ser Met Ser Ala Ser Lys Tyr Arg Lys Ile
            260                 265                 270

Tyr Gln Lys Asn Lys Thr Asn
        275

<210> SEQ ID NO 45
<211> LENGTH: 279
<212> TYPE: PRT
<213> ORGANISM: Artificial Sequence
<220> FEATURE:
<223> OTHER INFORMATION: A0A174I591

<400> SEQUENCE: 45

Met Gln Ile Leu Trp Asn Lys Tyr Lys Ser Asn Asn Phe Glu Ala Asn
1               5                   10                  15

Leu Asp Glu Cys Gly Ile Glu Gln Gly Thr Pro Gly Ala Gly Tyr Asn
            20                  25                  30

Tyr Lys Val Glu Lys Asn Ala Val Ile His Tyr Ile Ser Lys Gly Ser
        35                  40                  45

Gly Thr Phe Lys Ile Asn Asp Lys Ile Tyr Thr Leu Lys Lys Gly Asp
    50                  55                  60

Gly Phe Ile Leu Leu Lys Asp Met Asn Val Glu Tyr Ile Pro Ser Ile
65                  70                  75                  80

Asp Asp Pro Trp Lys Tyr Tyr Trp Ile Gly Phe Ser Gly Gln Ser Leu
                85                  90                  95

Asn Glu Tyr Leu Lys Arg Thr Ser Ile Ile Asp Ser Cys Val Ile Asn
            100                 105                 110

Phe Ser Lys Lys Ser Lys Ile Pro Asn Leu Ile Ile Asp Met Cys Asn
        115                 120                 125

Ile Ser Lys Lys Tyr Asp Gln Thr Ser Ser Asp Ile Leu Leu Leu
    130                 135                 140

Ser Lys Leu His Leu Leu Leu Tyr Tyr Ile Ser Ser Glu Phe Pro Lys
145                 150                 155                 160

Ala Phe Lys Tyr Asn Asn Asn Leu Thr His Thr Tyr Ile Gln Glu Ala
                165                 170                 175

Thr Thr Phe Ile Asn Asn Asn Tyr Met Asn Pro Ile Thr Val Gln Glu
            180                 185                 190

Val Ala Asp His Val Asn Leu Ser Arg Ser Tyr Leu Tyr Lys Met Phe
        195                 200                 205

Ile Lys His Leu Gly Glu Ser Thr Gln Ser Tyr Leu Ile Asn Ile Arg
    210                 215                 220

Met Tyr Lys Ser Ser Ile Leu Leu Lys Glu Thr Ser Leu Ser Ile Ala
225                 230                 235                 240

Glu Ile Ala Asn Lys Val Gly Tyr Ser Asp Pro Leu Leu Phe Ser Lys
                245                 250                 255

Ile Phe Ser Lys His Phe Ser Met Ser Ala Ser Lys Tyr Arg Lys Ser
            260                 265                 270

His Gln Lys Asn Lys Lys Cys
        275

<210> SEQ ID NO 46
<211> LENGTH: 275

```
<212> TYPE: PRT
<213> ORGANISM: Artificial Sequence
<220> FEATURE:
<223> OTHER INFORMATION: A0A2A7ME67

<400> SEQUENCE: 46

Met Gln Ile Leu Trp Lys Lys Tyr Lys Ile Thr Asn Phe Glu Met Asn
1               5                   10                  15

Leu Asp Glu Cys Gly Ile Glu Gln Cys Thr Pro Gly Ile Lys Tyr Asn
            20                  25                  30

Tyr Glu Val Val Lys Asn Ser Val Ile His Tyr Ile Ser Glu Gly Glu
        35                  40                  45

Gly Thr Phe Lys Ile Asn Asn Gln Ile Phe Asp Leu Lys Lys Gly Asp
    50                  55                  60

Gly Phe Ile Leu Phe Lys Gly Met Asn Val Glu Tyr Thr Ala Ser Ile
65                  70                  75                  80

Asp Asn Pro Trp Lys Tyr Tyr Trp Val Gly Phe Ser Gly Thr Asn Ala
                85                  90                  95

Asn Glu Tyr Leu His Arg Ser Ser Ile Phe Asp Asn Tyr Ile Ile Asn
            100                 105                 110

Tyr Gln Ser Asn Ser Lys Ile Pro Ser Ile Ile Lys Asn Met Cys Ala
        115                 120                 125

Leu Ser Lys Thr Tyr Asp Gln Asn Ser Ser Asp Asp Ile Leu Leu Leu
    130                 135                 140

Asn Lys Leu Tyr Tyr Leu Leu Tyr Thr Ile Thr Gln Glu Phe Pro Lys
145                 150                 155                 160

Pro Phe Gln Leu Val Asn Asn Leu Thr His Thr Tyr Ile Gln Gln Ser
                165                 170                 175

Ile Asp Phe Ile Asn Ser Lys Tyr Ala Glu Lys Ile Thr Val Gln Gln
            180                 185                 190

Ile Ala Asp Asn Val Asn Leu Ser Arg Ser Tyr Leu Tyr Lys Leu Phe
        195                 200                 205

Ile Lys Tyr Leu Gly Glu Ser Pro Gln Lys Tyr Leu Leu Asn Leu Arg
    210                 215                 220

Met Tyr Lys Ala Thr Leu Leu Lys Glu Thr Asp Leu Ser Ile Ser
225                 230                 235                 240

Gln Ile Ser Ser Asn Ile Gly Tyr Asp Asp Pro Leu Phe Phe Ser Lys
            245                 250                 255

Thr Phe Ser Lys His Phe Ser Ile Ser Ala Ser Gln Tyr Arg Lys Leu
        260                 265                 270

Tyr Lys Lys
    275

<210> SEQ ID NO 47
<211> LENGTH: 274
<212> TYPE: PRT
<213> ORGANISM: Artificial Sequence
<220> FEATURE:
<223> OTHER INFORMATION: A0A2K4AZL9

<400> SEQUENCE: 47

Met Gln Leu Leu Trp Lys Met Phe Lys Lys Asn Gln Phe Glu Ala Asn
1               5                   10                  15

Ile Asp Glu Cys Gly Ile Glu Ile Gly Thr Pro Gln Gly Gly Tyr Gln
            20                  25                  30

Tyr Glu Val Thr Lys Pro Ala Val Leu His Val Val Met Ser Gly Thr
        35                  40                  45
```

Gly Thr Leu Thr Tyr Asn Gln Lys Lys Tyr Thr Leu Lys Pro Gly Asp
            50                  55                  60

Leu Phe Leu Leu Cys Arg Gly Met Lys Val His Tyr Glu Ser Thr Leu
 65                  70                  75                  80

Asp Glu Pro Trp Thr Tyr Tyr Trp Val Gly Phe Ser Gly Lys Leu Ala
                 85                  90                  95

Met Asp Tyr Leu Asn Arg Thr Thr Leu Tyr Glu Thr Arg Val Ile Gln
             100                 105                 110

Asn Gln Gln Thr Ser Thr Ile Arg Gln Ile Ile Tyr Gln Met Cys His
             115                 120                 125

Arg Ser Ile Asp Tyr Asn Pro Glu His Ser Asp Ile Gln His Met
            130                 135                 140

Arg Asp Leu Tyr Asp Leu Leu Tyr Ala Leu His Gln His Phe Pro Lys
145                 150                 155                 160

Pro Phe His Val Val Lys Asn Glu Lys Tyr Ser Asn Val Arg Glu Ala
                165                 170                 175

Ile Arg Tyr Ile Asn Asp Asn Tyr Met His Gly Ile Ser Ile His Asp
            180                 185                 190

Val Ala Lys His Val Asn Val Ser Arg Ser Tyr Leu Tyr Lys Met Phe
            195                 200                 205

Lys Lys His Ile Asp Gln Ser Pro Gln His Tyr Leu Ile His Ile Arg
210                 215                 220

Met Tyr His Ala Ser Gln Leu Phe Lys Asp Thr Asp Leu Gln Ser Gln
225                 230                 235                 240

Glu Ile Ala Asp Arg Val Gly Tyr Lys Asp Pro Leu Leu Phe Ser Arg
                245                 250                 255

Ala Phe Lys Lys His Phe Gly Ile Thr Ala Thr Gln Tyr Arg Glu Thr
            260                 265                 270

His Gln

<210> SEQ ID NO 48
<211> LENGTH: 286
<212> TYPE: PRT
<213> ORGANISM: Artificial Sequence
<220> FEATURE:
<223> OTHER INFORMATION: A0A166PPM9

<400> SEQUENCE: 48

Met Gln Leu Leu Trp Lys Met Phe Lys Lys Asn Gln Phe Glu Ala Asn
 1               5                  10                  15

Ile Asp Glu Cys Gly Ile Glu Ile Gly Thr Pro His Gly Gly Tyr Gln
             20                  25                  30

Tyr Glu Val Thr Lys Pro Ala Val Leu His Ile Val Met Ser Gly Thr
             35                  40                  45

Gly Thr Leu Thr Tyr Asn Gln Lys Lys Tyr Thr Leu Lys Pro Gly Asp
            50                  55                  60

Leu Phe Leu Leu Cys Arg Gly Met Asn Val His Tyr Glu Ser Thr Leu
 65                  70                  75                  80

Asp Glu Pro Trp Thr Tyr Tyr Trp Val Gly Phe Ser Gly Lys Leu Val
                 85                  90                  95

Phe Asp Tyr Leu Asn Arg Thr Ser Leu Tyr Glu Thr Arg Val Ile Gln
             100                 105                 110

Asn Gln Pro Thr Asn Thr Ile Arg Gln Ile Ile Tyr Arg Met Cys Gln
             115                 120                 125

```
Arg Ser Ile Glu Tyr Ala Thr Glu Asn Ser Asp Asp Ile Gln His Met
130                 135                 140

Arg Asp Leu Tyr Glu Leu Leu Tyr Glu Leu His Gln His Phe Pro Lys
145                 150                 155                 160

Pro Phe His Val Val Lys Asn Glu Arg Tyr Ser Asn Val Arg Glu Ala
            165                 170                 175

Ile Arg Tyr Ile Asn Asp Asn Tyr Met His Ala Ile Ser Ile Asn Asp
                180                 185                 190

Val Ala Lys His Val Asn Val Ser Arg Ser Tyr Leu Tyr Lys Met Phe
            195                 200                 205

Lys Lys His Ile Asp Gln Ser Pro Gln His Tyr Leu Ile His Ile Arg
210                 215                 220

Met Tyr His Ala Ser Gln Leu Phe Lys Glu Thr Asp Leu Gln Ser Gln
225                 230                 235                 240

Glu Ile Ala Asp Arg Val Gly Tyr Lys Asp Pro Leu Leu Phe Ser Arg
                245                 250                 255

Ala Phe Lys Lys His Phe Gly Val Thr Ala Thr Gln Tyr Arg Glu Glu
            260                 265                 270

Gln Gln Leu Arg Ile Glu Ser Thr Leu Asp Asn Gln Lys Arg
275                 280                 285

<210> SEQ ID NO 49
<211> LENGTH: 274
<212> TYPE: PRT
<213> ORGANISM: Artificial Sequence
<220> FEATURE:
<223> OTHER INFORMATION: A0A2T4R7G1

<400> SEQUENCE: 49

Met Gln Leu Leu Trp Lys Leu Phe Lys Arg Asn His Phe Glu Ala Asn
1               5                   10                  15

Ile Asp Glu Cys Gly Ile Glu Ile Gly Thr Pro Asn Val Ser Tyr Gln
                20                  25                  30

Tyr Thr Val Val Lys Pro Ala Val Leu His Ile Ile Val Ala Gly Thr
            35                  40                  45

Gly Ser Phe Thr Tyr Gln Gln Ser Thr Tyr Gln Leu Lys Ser Gly Asp
    50                  55                  60

Met Phe Leu Leu Gln Glu Gly Met His Val His Tyr Glu Ala Ser Ala
65                  70                  75                  80

Asp Asp Pro Trp Thr Tyr His Trp Val Gly Phe Ser Gly Asn Leu Ala
                85                  90                  95

Ile Asp Tyr Leu Lys Arg Thr Ser Leu Ile Asp Cys Pro Val Val Met
                100                 105                 110

Asn Lys Asp Thr Ser Asp Ile Ser Lys Val Met Tyr Gln Ile Cys Glu
            115                 120                 125

Arg Ala Ile Thr Tyr Glu Thr Ala Thr Ser Asp Asp Ile His His Leu
130                 135                 140

Ser Asp Leu Tyr Lys Leu Leu Phe Leu Ile Thr Gln Cys Ala Pro Lys
145                 150                 155                 160

Pro Phe Glu Lys Glu His Asn Glu Ile Tyr Ser Ser Val Gln Asp Ala
            165                 170                 175

Val Asp Tyr Met Asn Gln Asn Tyr Met Tyr Ala Ile Thr Ile Asp Asp
                180                 185                 190

Ile Ala Gln Tyr Ala Lys Val Ser Arg Ser Tyr Leu Tyr Lys Leu Phe
                195                 200                 205
```

```
Ile Lys Trp Met Asp Gln Ser Pro Gln Gln Tyr Leu Ile Tyr Leu Arg
    210                 215                 220
Leu Tyr His Ala Ser Ser Met Leu Lys Thr Thr Ser Lys Pro Ile Gln
225                 230                 235                 240
Asp Ile Ala Gln Ala Val Gly Tyr Ser Asp Pro Leu Leu Phe Ser Lys
                245                 250                 255
Ala Phe Arg Lys His Phe Asp Met Pro Pro Ser Thr Tyr Arg Lys Val
                260                 265                 270
Tyr Lys
```

<210> SEQ ID NO 50
<211> LENGTH: 274
<212> TYPE: PRT
<213> ORGANISM: Artificial Sequence
<220> FEATURE:
<223> OTHER INFORMATION: A0A2A4HCU9

<400> SEQUENCE: 50

```
Met Gln Leu Leu Trp Lys Met Phe Lys Lys Asn Gln Phe Glu Ala Asn
1               5                   10                  15
Ile Asp Glu Cys Gly Ile Glu Ile Gly Thr Pro Gln Arg Gly Tyr Gln
                20                  25                  30
Tyr Glu Val Thr Lys Pro Ala Val Leu His Val Val Met Ser Gly Thr
            35                  40                  45
Gly Thr Leu Thr Tyr Asn Gln Lys Lys Tyr Thr Leu Lys Pro Gly Asp
        50                  55                  60
Leu Phe Leu Leu Cys Arg Gly Met Asn Val His Tyr Glu Ser Thr Leu
65                  70                  75                  80
Asp Glu Pro Trp Thr Tyr Tyr Trp Val Gly Phe Ser Gly Lys Leu Val
                85                  90                  95
Phe Asp Tyr Leu Asn Arg Thr Ser Leu Tyr Glu Thr Arg Val Ile Gln
                100                 105                 110
Asn Gln Pro Thr Asn Ala Ile Arg Gln Ile Ile Tyr Arg Met Cys His
                115                 120                 125
Arg Ser Ile Glu Tyr Ala Thr Glu Asn Ser Asp Asp Ile Gln His Met
130                 135                 140
Arg Asp Leu Tyr Glu Leu Leu Tyr Glu Leu His Gln His Phe Pro Lys
145                 150                 155                 160
Pro Phe His Val Val Lys Asn Glu Lys Tyr Ser Asn Val Arg Glu Ala
                165                 170                 175
Ile Arg Tyr Met Asn Asp Asn Tyr Met His Ala Ile Ser Ile Asn Asp
                180                 185                 190
Val Ala Lys His Val Asn Val Ser Arg Ser Tyr Leu Tyr Lys Met Phe
                195                 200                 205
Lys Lys His Ile Asp Gln Ser Pro Gln His Tyr Leu Ile His Ile Arg
    210                 215                 220
Met Tyr His Ala Ser Gln Leu Phe Lys Glu Thr Asp Leu Gln Ser Gln
225                 230                 235                 240
Glu Ile Ala Asp Arg Val Gly Tyr Lys Asp Pro Leu Leu Phe Ser Arg
                245                 250                 255
Ala Phe Lys Lys His Phe Gly Val Thr Ala Thr Gln Tyr Arg Glu Glu
                260                 265                 270
His Gln
```

<210> SEQ ID NO 51

<211> LENGTH: 271
<212> TYPE: PRT
<213> ORGANISM: Artificial Sequence
<220> FEATURE:
<223> OTHER INFORMATION: A0A2T4MS83

<400> SEQUENCE: 51

```
Met Gln Leu Leu Trp Lys Leu Phe Lys Lys Asn His Phe Glu Ala Asn
1               5                   10                  15
Ile Asp Glu Cys Gly Ile Glu Ile Gly Thr Pro Asn Val Ser Tyr Gln
            20                  25                  30
Tyr Thr Val Val Lys Pro Ala Val Leu His Ile Ile Met Ser Gly Thr
        35                  40                  45
Gly Thr Phe Thr His Gln His Thr Ser Tyr Glu Leu Lys Ala Gly Asp
    50                  55                  60
Met Phe Leu Leu Arg Glu Gly Met Arg Val His Tyr Glu Ala Ser Thr
65                  70                  75                  80
Asp Asp Pro Trp Thr Tyr His Trp Val Gly Phe Ser Gly Asn Leu Ala
                85                  90                  95
Met Asp Tyr Leu Lys Arg Thr Thr Leu Ile Asp Cys Pro Val Val Leu
            100                 105                 110
Asn Gln Asp Thr Ser Lys Leu Ser Lys Leu Met Tyr Gln Ile Cys Glu
        115                 120                 125
Arg Ala Ile Thr Tyr Glu Thr Thr Ala Ser Asp Ile His His Leu
    130                 135                 140
Ser Asp Leu Tyr Lys Leu Leu Phe Leu Leu Thr Gln Leu Ser Pro Lys
145                 150                 155                 160
Pro Phe Glu Ser His Pro Asn Glu Ile Tyr Ser Ser Val Gln Ala Ala
                165                 170                 175
Val Asn Tyr Met Asn Gln His Tyr Met His Thr Ile Ser Ile Asp Asp
            180                 185                 190
Val Ala Gln His Ala Lys Val Ser Arg Ser Tyr Leu Tyr Lys Leu Phe
        195                 200                 205
Met Lys Trp Met Asp Gln Ser Pro Gln Gln Tyr Leu Val Tyr Leu Arg
    210                 215                 220
Leu Tyr His Ala Ser Ser Met Leu Lys Thr Thr Ser Lys Pro Ile Gln
225                 230                 235                 240
Glu Ile Ala Gln Asn Val Gly Tyr Asn Asp Pro Leu Leu Phe Ser Lys
                245                 250                 255
Ala Phe Arg Lys His Phe Asp Met Pro Pro Ser Thr Tyr Arg Lys
            260                 265                 270
```

<210> SEQ ID NO 52
<211> LENGTH: 279
<212> TYPE: PRT
<213> ORGANISM: Artificial Sequence
<220> FEATURE:
<223> OTHER INFORMATION: O33813

<400> SEQUENCE: 52

```
Met Gln Val Leu Trp Lys Lys Phe Gln Lys Lys Leu Ile Asp Ala Asn
1               5                   10                  15
Leu Ala Glu Cys Gly Ile Glu Ile Gly Val Pro Asn Val Gly Tyr Asn
            20                  25                  30
Tyr Thr Val Phe Gln Lys Ser Val Leu His Ile Val Thr Gln Gly Glu
        35                  40                  45
```

```
Gly Thr Phe Ser Tyr Ala Gly Glu Thr Tyr His Leu Thr Ala Gly Asp
 50                  55                  60

Ile Phe Leu Leu Glu Arg Gly Met Glu Val Glu Tyr Lys Pro Ser Phe
 65                  70                  75                  80

Ser Asn Pro Trp Thr Tyr Tyr Trp Val Gly Met Asn Gly Lys Gln Ile
                 85                  90                  95

Leu Asn Tyr Leu Ser Arg Cys Ser Ile Val Asp Ser His Val Ile Leu
            100                 105                 110

Gly Gln Asp Thr Thr Asp Ile Lys Asn Ile Ile Gln Leu Ile Cys Lys
        115                 120                 125

Leu Ser Gln Ser Ile Glu Ser Asn Asn Ser Asn Asp Ile Leu Ile Met
130                 135                 140

Gln Tyr Leu Tyr Gln Leu Val Tyr Thr Leu Gln Glu Lys Phe Pro Lys
145                 150                 155                 160

Ile Phe Ser Val Gln Val Asp Ile Val Asn Glu Asp Ile Gln His Ala
                165                 170                 175

Val Asp Phe Ile Asn Thr Asn Tyr Gln Lys His Ile Thr Val Glu Asp
            180                 185                 190

Val Ala Lys Ser Val Asn Ile Thr Arg Ser His Leu Tyr Lys Leu Phe
        195                 200                 205

Lys Lys Asn Leu Gly Cys Ser Pro Lys Glu Tyr Leu Thr Tyr Ile Arg
210                 215                 220

Met Tyr His Ala Ser Gln Leu Leu Ile His Thr Ser Thr Leu Ile Ser
225                 230                 235                 240

Asp Ile Ser Arg Gln Val Gly Tyr Lys Asp Pro Leu Leu Phe Ser Lys
                245                 250                 255

Asn Phe Thr Lys His Phe Glu Ile Ser Ala Ser Glu Tyr Arg His His
            260                 265                 270

Phe Ser Ile Asn Asn Lys Gln
        275

<210> SEQ ID NO 53
<211> LENGTH: 277
<212> TYPE: PRT
<213> ORGANISM: Artificial Sequence
<220> FEATURE:
<223> OTHER INFORMATION: A0A1D4LKB2

<400> SEQUENCE: 53

Met Gln Ile Leu Trp Lys Lys Phe Gln Lys Lys Leu Val Asp Ala Asn
 1                   5                  10                  15

Leu Ala Glu Cys Gly Ile Glu Ile Gly Ile Pro Asn Val Gly Tyr Asp
                 20                  25                  30

Tyr Thr Val Leu Gln Gln Ser Val Leu His Ile Val Thr Asp Gly Glu
            35                  40                  45

Gly Val Phe Lys Tyr Asn Asn Glu Ile Tyr His Leu Lys Lys Gly Asp
        50                  55                  60

Ile Phe Leu Leu Glu Arg Gly Met Ser Val Lys Tyr Met Pro Ser Phe
 65                  70                  75                  80

Ser Asn Pro Trp Thr Tyr Tyr Trp Val Gly Ile Asn Gly Lys Gln Leu
                 85                  90                  95

Leu Asn Tyr Leu Met Arg Ser Tyr Ile Val Asp Thr His Val Ile Ile
            100                 105                 110

Gly Lys Asp Thr Gln Asp Ile Lys Val Ile Ile Gln Lys Leu Cys Lys
        115                 120                 125
```

Leu Ala Lys Asp Ile Gln Ser Thr Asn Ser Asn Asp Ile Leu Ile Met
            130                 135                 140

Gln Tyr Leu Tyr Lys Leu Val Tyr Thr Phe Gln Asp Lys Phe Pro Lys
145                 150                 155                 160

Thr Phe Thr Val Pro Leu Asp Ile Val Asn Glu Asp Ile Gln His Ala
                165                 170                 175

Ile Glu Phe Ile Asn Thr His Tyr Gln Asn Gly Ile Thr Ile Thr Asp
            180                 185                 190

Val Thr Asn Ser Val Asn Met Ser Arg Ser Tyr Leu Tyr Lys Leu Phe
            195                 200                 205

Lys Lys His Leu Asn Cys Ser Pro Lys Ser Tyr Leu Thr Tyr Ile Arg
210                 215                 220

Met Tyr His Ala Ser Gln Leu Leu Ile Asn Ser Asn Leu Leu Val Ser
225                 230                 235                 240

Glu Ile Ser Gln Arg Val Gly Tyr Ser Asp Pro Leu Leu Phe Ser Lys
                245                 250                 255

Asn Phe Thr Lys His Phe Glu Ile Ser Ala Ser Ala Tyr Arg Phe His
            260                 265                 270

Phe Gln Gln Asn Lys
            275

<210> SEQ ID NO 54
<211> LENGTH: 314
<212> TYPE: PRT
<213> ORGANISM: Artificial Sequence
<220> FEATURE:
<223> OTHER INFORMATION: A0A133QVV5

<400> SEQUENCE: 54

Met Thr Leu Leu Ser Ile Phe Gln Lys Leu Tyr Asn Phe Val Lys Tyr
1               5                   10                  15

Thr Cys Tyr Asn Gly Ser Ile Ile Glu Arg Lys Arg Val Arg Gln Val
            20                  25                  30

Gln Val Phe Trp Thr Lys Leu Lys Lys Thr Ser Tyr Glu Ala Gln Val
        35                  40                  45

Asp Glu Cys Gly Lys Glu Asn Leu Tyr Val Gly Asn Gly Tyr Glu Tyr
    50                  55                  60

Glu Val Thr Lys Pro Ala Val Leu His Ile Val Thr Gln Gly Thr Gly
65                  70                  75                  80

Thr Phe Thr Val Asn Asp Thr Thr Tyr His Leu Lys Lys Gly Asp Val
                85                  90                  95

Phe Leu Leu Leu Lys Gly Met His Val Lys Tyr His Ala Thr Gly Glu
            100                 105                 110

Thr Pro Trp His Tyr Met Trp Val Gly Phe Ser Gly Thr His Ala Ile
            115                 120                 125

Ser Phe Ile Thr Arg Thr Ser Leu Ser Asp Glu Phe Val Leu Leu Asn
            130                 135                 140

Gln Asn Thr Glu Thr Leu Phe Lys Leu Ile Phe Lys Ile Cys Ile Leu
145                 150                 155                 160

Ala Asn Ser His Thr Pro Glu Asp Thr His Asp Ile Leu Leu Lys Ile
                165                 170                 175

Arg Leu Phe Glu Leu Leu Tyr Phe Leu Thr Gln Gln Asn Gln Lys Glu
            180                 185                 190

Ile Val Ile Pro Asp Gln Arg Glu Ala Thr Asp Leu Lys Asp Ala Leu
            195                 200                 205

```
Glu Tyr Phe Asn Asp Asn Phe Lys Ser Lys Asp Thr Thr Val Asp Asn
            210                 215                 220

Ala Ala Gln Val Ala Asn Met Ser Arg Ser Gln Leu Tyr Lys Arg Phe
225                 230                 235                 240

Lys Lys Gln Phe Gly Ala Ser Pro Ser Arg Tyr Leu Thr Asp Leu Arg
                245                 250                 255

Met Ala Phe Ala Ala Glu Gln Leu Lys Phe Thr Asn Lys Thr Val Gln
            260                 265                 270

Ala Ile Ala Asp Glu Leu Asn Tyr Asp Val Ser Leu Ala Phe Ser Lys
        275                 280                 285

Ala Phe Ser Lys Tyr Phe Asn Cys Pro Pro Thr Gln Tyr Arg Lys Asn
            290                 295                 300

Tyr Lys Ala Arg Lys Ala Leu Gln Ser Glu
305                 310

<210> SEQ ID NO 55
<211> LENGTH: 289
<212> TYPE: PRT
<213> ORGANISM: Artificial Sequence
<220> FEATURE:
<223> OTHER INFORMATION: A9QSR3

<400> SEQUENCE: 55

Met Glu Tyr Lys Glu Phe His Gln Asn Phe Leu Asp Ile Asn Leu Asp
1               5                   10                  15

Phe Val Gly Asn Glu Ala Thr Ile Pro Asn Phe Ser Phe Gly Pro Ala
            20                  25                  30

Ile Arg Glu Asn Tyr Val Ile His Tyr Ile Thr Ser Gly Ser Gly Arg
        35                  40                  45

Tyr Met Ile Tyr Gly Phe Glu His Gln Leu Lys Ala Gly Asp Cys Phe
    50                  55                  60

Ile Ile Pro Ala Asp Val Glu Thr Phe Tyr Gln Ser Asp Ala Leu Thr
65                  70                  75                  80

Pro Trp Ala Tyr Tyr Trp Leu Gly Leu Ser Gly His Val Val Asn Asp
                85                  90                  95

Leu Phe Ala Arg Thr Ala Leu Asp Asp Lys Gly Trp Ile Leu Glu Asn
            100                 105                 110

Val Ser Lys Thr Glu Phe Ile Glu His Phe Ser Lys Ile Gln Asn Leu
        115                 120                 125

Ile Ser Asp Asp Asp Lys Thr Val Asp Leu Asp Ile Gln Val Glu Leu
    130                 135                 140

Phe Ala Leu Met Lys Ser Leu Ile Thr Leu Phe Pro Lys Ser Ile Thr
145                 150                 155                 160

Glu His Lys Asn Gln Ser Asp Tyr Tyr Ala Glu Lys Ala Tyr Thr Phe
                165                 170                 175

Ile Asn Gln Asn Tyr Ser Gln Ser Ile Lys Ile Lys Asp Val Leu Ala
            180                 185                 190

His Val Met Ile Ser Arg Ala Tyr Leu Phe Thr Ile Phe Lys His Lys
        195                 200                 205

Tyr Gly Leu Ser Pro Gln Lys Tyr Leu Ile Asp Leu Arg Met Ala Lys
    210                 215                 220

Ala Ala Met Leu Leu Ile His Ser Asp Asn Leu Val Ser Gln Ile Ser
225                 230                 235                 240

Glu Ala Val Gly Phe Ser Asp Ser Leu Ser Phe Ser Ser Ala Phe Lys
                245                 250                 255
```

```
Lys Arg Tyr Gly Val Ser Pro Thr Lys Phe Lys Thr Gln Lys His Asp
            260                 265                 270

Asn Leu Met Leu Glu Thr Leu Asn Asn Met Asn Leu Asn Arg Leu Lys
        275                 280                 285

Lys

<210> SEQ ID NO 56
<211> LENGTH: 139
<212> TYPE: PRT
<213> ORGANISM: Artificial Sequence
<220> FEATURE:
<223> OTHER INFORMATION: A0A133MUX6 CBD

<400> SEQUENCE: 56

Asn Phe Glu Met Asn Val Asp Glu Cys Gly Ile Glu Gln Gly Ile Pro
1               5                   10                  15

Gly Leu Gly Tyr Asn Tyr Glu Val Leu Lys Asn Ala Val Ile His Tyr
            20                  25                  30

Val Thr Lys Gly Tyr Gly Thr Phe Lys Phe Asn Gly Lys Val Tyr Asn
        35                  40                  45

Leu Lys Gln Gly Asp Ile Phe Ile Leu Lys Gly Met Gln Val Glu
    50                  55                  60

Tyr Val Ala Ser Ile Asp Asp Pro Trp Glu Tyr Tyr Trp Ile Gly Phe
65                  70                  75                  80

Ser Gly Ser Asn Ala Asn Glu Tyr Leu Asn Arg Thr Ser Ile Thr Asp
                85                  90                  95

Ser Cys Val Ala Asn Cys Glu Glu Ser Lys Ile Pro Gln Ile Ile
            100                 105                 110

Leu Asn Met Cys Glu Ile Ser Lys Thr Tyr Asn Pro Ser Arg Ser Asp
        115                 120                 125

Asp Ile Leu Leu Leu Lys Glu Leu Tyr Ser Leu
    130                 135

<210> SEQ ID NO 57
<211> LENGTH: 139
<212> TYPE: PRT
<213> ORGANISM: Artificial Sequence
<220> FEATURE:
<223> OTHER INFORMATION: B1V7N0 CBD

<400> SEQUENCE: 57

Asn Phe Glu Met Asn Val Asp Glu Cys Gly Ile Glu Gln Gly Ile Pro
1               5                   10                  15

Gly Leu Gly Tyr Lys Tyr Glu Val Leu Lys Asn Ala Val Ile His Tyr
            20                  25                  30

Val Thr Lys Gly Tyr Gly Thr Phe Lys Phe Asn Gly Lys Val Tyr Thr
        35                  40                  45

Leu Lys Gln Gly Asp Ile Phe Ile Leu Lys Gly Met Gln Val Asp
    50                  55                  60

Tyr Val Ala Ser Ile Asp Asp Pro Trp Glu Tyr Tyr Trp Ile Gly Phe
65                  70                  75                  80

Ser Gly Ser Asn Ala Asn Glu Tyr Leu Asn Arg Thr Ser Ile Thr Asn
                85                  90                  95

Ser Cys Val Ala Asn Cys Glu Glu Ser Lys Ile Pro Gln Ile Ile
            100                 105                 110

Leu Asn Met Cys Glu Ile Ser Lys Thr Tyr Asn Pro Ser Arg Ser Asp
        115                 120                 125
```

Asp Ile Leu Leu Leu Lys Glu Leu Tyr Ser Leu
         130                 135

<210> SEQ ID NO 58
<211> LENGTH: 139
<212> TYPE: PRT
<213> ORGANISM: Artificial Sequence
<220> FEATURE:
<223> OTHER INFORMATION: A0A127EGD8 CBD

<400> SEQUENCE: 58

Asn Phe Glu Met Asn Val Asp Glu Cys Gly Ile Glu Gln Gly Ile Pro
1               5                   10                  15

Gly Leu Gly Tyr Lys Tyr Glu Val Leu Lys Asn Ala Val Ile His Tyr
            20                  25                  30

Val Thr Lys Gly Tyr Gly Thr Phe Lys Phe Asn Gly Lys Val Tyr Thr
        35                  40                  45

Leu Lys Gln Gly Asp Ile Phe Ile Leu Lys Gly Met Lys Val Glu
    50                  55                  60

Tyr Val Ala Ser Ile Asp Asp Pro Trp Glu Tyr Tyr Trp Ile Gly Phe
65                  70                  75                  80

Ser Gly Ser Asn Ala Asn Glu Tyr Leu Asn Arg Thr Ser Ile Thr Asn
                85                  90                  95

Ser Tyr Val Ala Asn Cys Glu Lys Asn Ser Lys Ile Pro Gln Ile Ile
            100                 105                 110

Leu Asn Met Cys Glu Ile Ser Lys Thr Tyr Asn Pro Ser Ser Ser Asp
        115                 120                 125

Asp Ile Leu Leu Leu Lys Glu Leu Tyr Ser Leu
    130                 135

<210> SEQ ID NO 59
<211> LENGTH: 139
<212> TYPE: PRT
<213> ORGANISM: Artificial Sequence
<220> FEATURE:
<223> OTHER INFORMATION: A0A1C6JUB7 CBD

<400> SEQUENCE: 59

Asn Phe Glu Met Asn Val Asp Glu Cys Gly Ile Glu Gln Gly Ile Pro
1               5                   10                  15

Gly Phe Gly Tyr Lys Tyr Glu Val Leu Lys Asn Ala Val Ile His Tyr
            20                  25                  30

Ile Ser Lys Gly Asn Gly Thr Phe Lys Phe Asn Asp Lys Val Tyr Asn
        35                  40                  45

Leu Lys Gln Gly Asp Val Phe Ile Leu Lys Gly Met Lys Val Glu
    50                  55                  60

Tyr Ile Ala Ser Ile Asp Asp Pro Trp Glu Tyr Tyr Trp Ile Gly Phe
65                  70                  75                  80

Ser Gly Ser Asn Ala Asn Glu Tyr Leu Asn Arg Thr Ser Ile Ile Asp
                85                  90                  95

Ser Tyr Ala Ala Asn Cys Lys Glu Asp Ser Lys Ile Pro Asp Ile Ile
            100                 105                 110

Ser Asn Met Cys Glu Ile Ser Lys Thr Tyr Asn Pro Ser Arg Ser Asp
        115                 120                 125

Asp Ile Leu Leu Leu Lys Glu Leu Tyr Ser Leu
    130                 135

```
<210> SEQ ID NO 60
<211> LENGTH: 139
<212> TYPE: PRT
<213> ORGANISM: Artificial Sequence
<220> FEATURE:
<223> OTHER INFORMATION: A0A174HYB7 CBD

<400> SEQUENCE: 60
```

Asn Phe Glu Met Asn Val Asp Glu Cys Gly Ile Glu Gln Gly Ile Pro
1               5                   10                  15

Gly Phe Gly Tyr Lys Tyr Glu Val Leu Lys Asn Ala Val Ile His Tyr
            20                  25                  30

Ile Ser Lys Gly Asn Gly Thr Phe Lys Phe Asn Asp Lys Val Tyr Asn
        35                  40                  45

Leu Lys Gln Gly Asp Val Phe Ile Leu Lys Gly Met Lys Val Glu
    50                  55                  60

Tyr Ile Ala Ser Ile Asp Asp Pro Trp Glu Tyr Tyr Trp Ile Gly Phe
65                  70                  75                  80

Ser Gly Ser Asn Ala Asn Glu Tyr Leu Asn Arg Thr Ser Ile Ile Asp
                85                  90                  95

Ser Tyr Ala Ala Lys Cys Lys Gly Asp Ser Lys Ile Pro Asp Ile Ile
            100                 105                 110

Ser Asn Met Cys Glu Ile Ser Lys Thr Tyr Asn Pro Ser Arg Ser Asp
        115                 120                 125

Asp Ile Leu Leu Leu Lys Glu Leu Tyr Ser Leu
    130                 135

```
<210> SEQ ID NO 61
<211> LENGTH: 139
<212> TYPE: PRT
<213> ORGANISM: Artificial Sequence
<220> FEATURE:
<223> OTHER INFORMATION: A0A1C6KY47 CBD

<400> SEQUENCE: 61
```

Asn Phe Glu Met Asn Val Asp Glu Cys Gly Ile Glu Gln Gly Ile Pro
1               5                   10                  15

Gly Phe Gly Tyr Lys Tyr Glu Val Leu Lys Asn Ser Val Ile His Tyr
            20                  25                  30

Ile Thr Lys Gly His Gly Thr Phe Lys Ile Asn Asp Lys Leu Tyr Asn
        35                  40                  45

Leu Gly Gln Gly Asp Val Phe Ile Leu Lys Gly Met Lys Val Glu
    50                  55                  60

Tyr Met Ala Ser Ile Asp Asp Pro Trp Glu Tyr Tyr Trp Ile Gly Phe
65                  70                  75                  80

Ser Gly Ser Asn Ala Asn Glu Tyr Leu Asn Arg Thr Ser Ile Ile Asp
                85                  90                  95

Ser Tyr Ala Ala Thr Cys Lys Glu Asp Ser Lys Ile Pro Cys Ile Ile
            100                 105                 110

Ser Asn Met Cys Glu Ile Ser Lys Thr Tyr Asn Pro Ser Cys Cys Asp
        115                 120                 125

Asp Ile Leu Leu Leu Lys Glu Leu Tyr Ser Leu
    130                 135

```
<210> SEQ ID NO 62
<211> LENGTH: 139
<212> TYPE: PRT
<213> ORGANISM: Artificial Sequence
<220> FEATURE:
```

<223> OTHER INFORMATION: A0A174LZQ7 CBD

<400> SEQUENCE: 62

Asn Phe Asp Ile Asn Leu Asp Glu Cys Gly Ile Glu His Gly Ile Pro
1               5                   10                  15

Gly Phe Gly Tyr Arg Tyr Lys Val Leu Lys Asn Ser Val Ile His Tyr
            20                  25                  30

Val Ile Arg Gly Tyr Gly Thr Phe Lys Val Asn Asp Lys Val Tyr Asn
        35                  40                  45

Leu Lys Glu Gly Asp Ile Phe Ile Leu Lys Gly Met Asp Val Glu
    50                  55                  60

Tyr Met Ala Ser Met Asp Asn Pro Trp Glu Tyr Cys Trp Ile Gly Phe
65                  70                  75                  80

Ser Gly Ser Lys Ala Asp Glu Tyr Leu Asn Arg Thr Ser Ile Ile Asp
                85                  90                  95

Ser His Val Ala Asn Cys Asn Glu Asn Ser Lys Ile Pro Cys Ile Ile
            100                 105                 110

Leu Asn Ile Cys Glu Ile Ser Lys Asn Tyr Asn Pro Ser Asn Ser Asp
        115                 120                 125

Asp Ile Leu Leu Leu Asn Glu Leu Tyr Ser Leu
    130                 135

<210> SEQ ID NO 63
<211> LENGTH: 139
<212> TYPE: PRT
<213> ORGANISM: Artificial Sequence
<220> FEATURE:
<223> OTHER INFORMATION: N9YR91 CBD

<400> SEQUENCE: 63

Asn Phe Asp Ser Asn Leu Asp Glu Cys Gly Ile Glu Gln Gly Thr Pro
1               5                   10                  15

Gly Thr Gly Tyr Lys Tyr Glu Val Val Lys Asn Ala Val Ile His Tyr
            20                  25                  30

Ile Ser Lys Gly Ser Gly Ile Phe Lys Ile Asn Asp Lys Ile Tyr Asn
        35                  40                  45

Leu Lys Arg Gly Asp Gly Phe Ile Leu Lys Gly Met His Val Glu
    50                  55                  60

Tyr Ile Ser Ser Ile Asp Asp Pro Trp Lys Tyr Tyr Trp Val Gly Phe
65                  70                  75                  80

Ser Gly Lys Asn Ala Asn Glu Tyr Leu Lys Arg Thr Ser Ile Ile Asp
                85                  90                  95

Thr Cys Ile Ile Asn Phe Ser Lys Lys Ser Lys Val Pro Asn Thr Ile
            100                 105                 110

Ile Asp Met Cys Asn Ile Ser Lys Lys Tyr Asn Gln Thr Ser Ser Asp
        115                 120                 125

Asp Ile Leu Leu Leu Ser Lys Leu His Leu Leu
    130                 135

<210> SEQ ID NO 64
<211> LENGTH: 139
<212> TYPE: PRT
<213> ORGANISM: Artificial Sequence
<220> FEATURE:
<223> OTHER INFORMATION: A0A174I591 CBD

<400> SEQUENCE: 64

Asn Phe Glu Ala Asn Leu Asp Glu Cys Gly Ile Glu Gln Gly Thr Pro
1               5                   10                  15

Gly Ala Gly Tyr Asn Tyr Lys Val Glu Lys Asn Ala Val Ile His Tyr
            20                  25                  30

Ile Ser Lys Gly Ser Gly Thr Phe Lys Ile Asn Asp Lys Ile Tyr Thr
        35                  40                  45

Leu Lys Lys Gly Asp Gly Phe Ile Leu Lys Asp Met Asn Val Glu
    50                  55                  60

Tyr Ile Pro Ser Ile Asp Asp Pro Trp Lys Tyr Tyr Trp Ile Gly Phe
65                  70                  75                  80

Ser Gly Gln Ser Leu Asn Glu Tyr Leu Lys Arg Thr Ser Ile Ile Asp
            85                  90                  95

Ser Cys Val Ile Asn Phe Ser Lys Lys Ser Lys Ile Pro Asn Leu Ile
                100                 105                 110

Ile Asp Met Cys Asn Ile Ser Lys Lys Tyr Asp Gln Thr Ser Ser Asp
            115                 120                 125

Asp Ile Leu Leu Leu Ser Lys Leu His Leu Leu
        130                 135

<210> SEQ ID NO 65
<211> LENGTH: 139
<212> TYPE: PRT
<213> ORGANISM: Artificial Sequence
<220> FEATURE:
<223> OTHER INFORMATION: A0A2A7ME67 CBD

<400> SEQUENCE: 65

Asn Phe Glu Met Asn Leu Asp Glu Cys Gly Ile Glu Gln Cys Thr Pro
1               5                   10                  15

Gly Ile Lys Tyr Asn Tyr Glu Val Val Lys Asn Ser Val Ile His Tyr
            20                  25                  30

Ile Ser Glu Gly Glu Gly Thr Phe Lys Ile Asn Asn Gln Ile Phe Asp
        35                  40                  45

Leu Lys Lys Gly Asp Gly Phe Ile Leu Phe Lys Gly Met Asn Val Glu
    50                  55                  60

Tyr Thr Ala Ser Ile Asp Asn Pro Trp Lys Tyr Tyr Trp Val Gly Phe
65                  70                  75                  80

Ser Gly Thr Asn Ala Asn Glu Tyr Leu His Arg Ser Ser Ile Phe Asp
            85                  90                  95

Asn Tyr Ile Ile Asn Tyr Gln Ser Asn Ser Lys Ile Pro Ser Ile Ile
                100                 105                 110

Lys Asn Met Cys Ala Leu Ser Lys Thr Tyr Asp Gln Asn Ser Ser Asp
            115                 120                 125

Asp Ile Leu Leu Leu Asn Lys Leu Tyr Tyr Leu
        130                 135

<210> SEQ ID NO 66
<211> LENGTH: 139
<212> TYPE: PRT
<213> ORGANISM: Artificial Sequence
<220> FEATURE:
<223> OTHER INFORMATION: A0A2K4AZL9 CBD

<400> SEQUENCE: 66

Gln Phe Glu Ala Asn Ile Asp Glu Cys Gly Ile Glu Ile Gly Thr Pro
1               5                   10                  15

```
Gln Gly Gly Tyr Gln Tyr Glu Val Thr Lys Pro Ala Val Leu His Val
                20                  25                  30

Val Met Ser Gly Thr Gly Thr Leu Thr Tyr Asn Gln Lys Lys Tyr Thr
            35                  40                  45

Leu Lys Pro Gly Asp Leu Phe Leu Leu Cys Arg Gly Met Lys Val His
 50                  55                  60

Tyr Glu Ser Thr Leu Asp Glu Pro Trp Thr Tyr Tyr Trp Val Gly Phe
 65                  70                  75                  80

Ser Gly Lys Leu Ala Met Asp Tyr Leu Asn Arg Thr Thr Leu Tyr Glu
                85                  90                  95

Thr Arg Val Ile Gln Asn Gln Thr Ser Thr Ile Arg Gln Ile Ile
            100                 105                 110

Tyr Gln Met Cys His Arg Ser Ile Asp Tyr Asn Pro Glu His Ser Asp
            115                 120                 125

Asp Ile Gln His Met Arg Asp Leu Tyr Asp Leu
        130                 135

<210> SEQ ID NO 67
<211> LENGTH: 139
<212> TYPE: PRT
<213> ORGANISM: Artificial Sequence
<220> FEATURE:
<223> OTHER INFORMATION: A0A166PPM9 CBD

<400> SEQUENCE: 67

Gln Phe Glu Ala Asn Ile Asp Glu Cys Gly Ile Glu Ile Gly Thr Pro
1               5                   10                  15

His Gly Gly Tyr Gln Tyr Glu Val Thr Lys Pro Ala Val Leu His Ile
                20                  25                  30

Val Met Ser Gly Thr Gly Thr Leu Thr Tyr Asn Gln Lys Lys Tyr Thr
            35                  40                  45

Leu Lys Pro Gly Asp Leu Phe Leu Leu Cys Arg Gly Met Asn Val His
 50                  55                  60

Tyr Glu Ser Thr Leu Asp Glu Pro Trp Thr Tyr Tyr Trp Val Gly Phe
 65                  70                  75                  80

Ser Gly Lys Leu Val Phe Asp Tyr Leu Asn Arg Thr Ser Leu Tyr Glu
                85                  90                  95

Thr Arg Val Ile Gln Asn Gln Pro Thr Asn Thr Ile Arg Gln Ile Ile
            100                 105                 110

Tyr Arg Met Cys Gln Arg Ser Ile Glu Tyr Ala Thr Glu Asn Ser Asp
            115                 120                 125

Asp Ile Gln His Met Arg Asp Leu Tyr Glu Leu
        130                 135

<210> SEQ ID NO 68
<211> LENGTH: 139
<212> TYPE: PRT
<213> ORGANISM: Artificial Sequence
<220> FEATURE:
<223> OTHER INFORMATION: A0A2T4R7G1 CBD

<400> SEQUENCE: 68

His Phe Glu Ala Asn Ile Asp Glu Cys Gly Ile Glu Ile Gly Thr Pro
1               5                   10                  15

Asn Val Ser Tyr Gln Tyr Thr Val Val Lys Pro Ala Val Leu His Ile
                20                  25                  30
```

-continued

```
Ile Val Ala Gly Thr Gly Ser Phe Thr Tyr Gln Gln Ser Thr Tyr Gln
            35                  40                  45

Leu Lys Ser Gly Asp Met Phe Leu Leu Gln Glu Gly Met His Val His
 50                  55                  60

Tyr Glu Ala Ser Ala Asp Asp Pro Trp Thr Tyr His Trp Val Gly Phe
 65                  70                  75                  80

Ser Gly Asn Leu Ala Ile Asp Tyr Leu Lys Arg Thr Ser Leu Ile Asp
                85                  90                  95

Cys Pro Val Val Met Asn Lys Asp Thr Ser Asp Ile Ser Lys Val Met
                100                 105                 110

Tyr Gln Ile Cys Glu Arg Ala Ile Thr Tyr Glu Thr Ala Thr Ser Asp
            115                 120                 125

Asp Ile His His Leu Ser Asp Leu Tyr Lys Leu
        130                 135

<210> SEQ ID NO 69
<211> LENGTH: 139
<212> TYPE: PRT
<213> ORGANISM: Artificial Sequence
<220> FEATURE:
<223> OTHER INFORMATION: A0A2A4HCU9 CBD

<400> SEQUENCE: 69

Gln Phe Glu Ala Asn Ile Asp Glu Cys Gly Ile Glu Ile Gly Thr Pro
 1               5                  10                  15

Gln Arg Gly Tyr Gln Tyr Glu Val Thr Lys Pro Ala Val Leu His Val
            20                  25                  30

Val Met Ser Gly Thr Gly Thr Leu Thr Tyr Asn Gln Lys Lys Tyr Thr
        35                  40                  45

Leu Lys Pro Gly Asp Leu Phe Leu Leu Cys Arg Gly Met Asn Val His
 50                  55                  60

Tyr Glu Ser Thr Leu Asp Glu Pro Trp Thr Tyr Tyr Trp Val Gly Phe
 65                  70                  75                  80

Ser Gly Lys Leu Val Phe Asp Tyr Leu Asn Arg Thr Ser Leu Tyr Glu
                85                  90                  95

Thr Arg Val Ile Gln Asn Gln Pro Thr Asn Ala Ile Arg Gln Ile Ile
                100                 105                 110

Tyr Arg Met Cys His Arg Ser Ile Glu Tyr Ala Thr Glu Asn Ser Asp
            115                 120                 125

Asp Ile Gln His Met Arg Asp Leu Tyr Glu Leu
        130                 135

<210> SEQ ID NO 70
<211> LENGTH: 139
<212> TYPE: PRT
<213> ORGANISM: Artificial Sequence
<220> FEATURE:
<223> OTHER INFORMATION: A0A2T4MS83 CBD

<400> SEQUENCE: 70

His Phe Glu Ala Asn Ile Asp Glu Cys Gly Ile Glu Ile Gly Thr Pro
 1               5                  10                  15

Asn Val Ser Tyr Gln Tyr Thr Val Val Lys Pro Ala Val Leu His Ile
            20                  25                  30

Ile Met Ser Gly Thr Gly Thr Phe Thr His Gln His Thr Ser Tyr Glu
        35                  40                  45
```

```
Leu Lys Ala Gly Asp Met Phe Leu Arg Glu Gly Met Arg Val His
    50                  55                  60

Tyr Glu Ala Ser Thr Asp Pro Trp Thr Tyr His Trp Val Gly Phe
65                  70                  75                  80

Ser Gly Asn Leu Ala Met Asp Tyr Leu Lys Arg Thr Thr Leu Ile Asp
                85                  90                  95

Cys Pro Val Val Leu Asn Gln Asp Thr Ser Lys Leu Ser Lys Leu Met
            100                 105                 110

Tyr Gln Ile Cys Glu Arg Ala Ile Thr Tyr Glu Thr Thr Ala Ser Asp
        115                 120                 125

Asp Ile His His Leu Ser Asp Leu Tyr Lys Leu
    130                 135
```

<210> SEQ ID NO 71
<211> LENGTH: 139
<212> TYPE: PRT
<213> ORGANISM: Artificial Sequence
<220> FEATURE:
<223> OTHER INFORMATION: O33813 CBD

<400> SEQUENCE: 71

```
Leu Ile Asp Ala Asn Leu Ala Glu Cys Gly Ile Glu Ile Gly Val Pro
1               5                   10                  15

Asn Val Gly Tyr Asn Tyr Thr Val Phe Gln Lys Ser Val Leu His Ile
                20                  25                  30

Val Thr Gln Gly Glu Gly Thr Phe Ser Tyr Ala Gly Glu Thr Tyr His
            35                  40                  45

Leu Thr Ala Gly Asp Ile Phe Leu Leu Glu Arg Gly Met Glu Val Glu
    50                  55                  60

Tyr Lys Pro Ser Phe Ser Asn Pro Trp Thr Tyr Tyr Trp Val Gly Met
65                  70                  75                  80

Asn Gly Lys Gln Ile Leu Asn Tyr Leu Ser Arg Cys Ser Ile Val Asp
                85                  90                  95

Ser His Val Ile Leu Gly Gln Asp Thr Thr Asp Ile Lys Asn Ile Ile
            100                 105                 110

Gln Leu Ile Cys Lys Leu Ser Gln Ser Ile Glu Ser Asn Asn Ser Asn
        115                 120                 125

Asp Ile Leu Ile Met Gln Tyr Leu Tyr Gln Leu
    130                 135
```

<210> SEQ ID NO 72
<211> LENGTH: 139
<212> TYPE: PRT
<213> ORGANISM: Artificial Sequence
<220> FEATURE:
<223> OTHER INFORMATION: A0A1D4LKB2 CBD

<400> SEQUENCE: 72

```
Leu Val Asp Ala Asn Leu Ala Glu Cys Gly Ile Glu Ile Gly Ile Pro
1               5                   10                  15

Asn Val Gly Tyr Asp Tyr Thr Val Leu Gln Gln Ser Val Leu His Ile
                20                  25                  30

Val Thr Asp Gly Glu Gly Val Phe Lys Tyr Asn Asn Glu Ile Tyr His
            35                  40                  45

Leu Lys Lys Gly Asp Ile Phe Leu Leu Glu Arg Gly Met Ser Val Lys
    50                  55                  60
```

```
Tyr Met Pro Ser Phe Ser Asn Pro Trp Thr Tyr Tyr Trp Val Gly Ile
 65                  70                  75                  80

Asn Gly Lys Gln Leu Leu Asn Tyr Leu Met Arg Ser Tyr Ile Val Asp
             85                  90                  95

Thr His Val Ile Ile Gly Lys Asp Thr Gln Asp Ile Lys Val Ile Ile
            100                 105                 110

Gln Lys Leu Cys Lys Leu Ala Lys Asp Ile Gln Ser Thr Asn Ser Asn
            115                 120                 125

Asp Ile Leu Ile Met Gln Tyr Leu Tyr Lys Leu
            130                 135
```

<210> SEQ ID NO 73
<211> LENGTH: 139
<212> TYPE: PRT
<213> ORGANISM: Artificial Sequence
<220> FEATURE:
<223> OTHER INFORMATION: A0A133QVV5 CBD

<400> SEQUENCE: 73

```
Asn Phe Val Lys Tyr Thr Cys Tyr Asn Gly Ser Ile Ile Glu Arg Lys
 1               5                  10                  15

Arg Val Arg Gln Val Gln Val Phe Trp Thr Lys Leu Lys Lys Thr Ser
             20                  25                  30

Tyr Glu Ala Gln Val Asp Glu Cys Gly Lys Glu Asn Leu Tyr Val Gly
         35                  40                  45

Asn Gly Tyr Glu Tyr Glu Val Thr Lys Pro Ala Val Leu His Ile Val
     50                  55                  60

Thr Gln Gly Thr Gly Thr Phe Val Asn Asp Thr Thr Tyr His Leu
 65                  70                  75                  80

Lys Lys Gly Asp Val Phe Leu Leu Lys Gly Met His Val Lys Tyr
             85                  90                  95

His Ala Thr Gly Glu Thr Pro Trp His Tyr Met Trp Val Gly Phe Ser
            100                 105                 110

Gly Thr His Ala Ile Ser Phe Ile Thr Arg Thr Ser Leu Ser Asp Glu
            115                 120                 125

Phe Val Leu Leu Asn Gln Asn Thr Glu Thr Leu
            130                 135
```

<210> SEQ ID NO 74
<211> LENGTH: 139
<212> TYPE: PRT
<213> ORGANISM: Artificial Sequence
<220> FEATURE:
<223> OTHER INFORMATION: A9QSR3

<400> SEQUENCE: 74

```
Asp Ile Asn Leu Asp Phe Val Gly Asn Glu Ala Thr Ile Pro Asn Phe
 1               5                  10                  15

Ser Phe Gly Pro Ala Ile Arg Glu Asn Tyr Val Ile His Tyr Ile Thr
             20                  25                  30

Ser Gly Ser Gly Arg Tyr Met Ile Tyr Gly Phe Glu His Gln Leu Lys
         35                  40                  45

Ala Gly Asp Cys Phe Ile Ile Pro Ala Asp Val Glu Thr Phe Tyr Gln
     50                  55                  60

Ser Asp Ala Leu Thr Pro Trp Ala Tyr Tyr Trp Leu Gly Leu Ser Gly
 65                  70                  75                  80
```

-continued

```
His Val Val Asn Asp Leu Phe Ala Arg Thr Ala Leu Asp Asp Lys Gly
                85                  90                  95

Trp Ile Leu Glu Asn Val Ser Lys Thr Glu Phe Ile Glu His Phe Ser
                100                 105                 110

Lys Ile Gln Asn Leu Ile Ser Asp Asp Asp Lys Thr Val Asp Leu Asp
            115                 120                 125

Ile Gln Val Glu Leu Phe Ala Leu Met Lys Ser
        130                 135
```